US011939385B2

(12) United States Patent
Vrljic et al.

(10) Patent No.: US 11,939,385 B2
(45) Date of Patent: Mar. 26, 2024

(54) ACTIVATABLE ANTIBODIES AND METHODS OF USE THEREOF

(71) Applicant: ALX Oncology Inc., South San Francisco, CA (US)

(72) Inventors: Marija Vrljic, San Mateo, CA (US); Jaume Pons, San Francisco, CA (US)

(73) Assignee: ALX ONCOLOGY INC., South San Francisco, CA (US)

( * ) Notice: Subject to any disclaimer, the term of this patent is extended or adjusted under 35 U.S.C. 154(b) by 149 days.

(21) Appl. No.: 16/613,774

(22) PCT Filed: May 15, 2018

(86) PCT No.: PCT/US2018/032806
§ 371 (c)(1),
(2) Date: Nov. 14, 2019

(87) PCT Pub. No.: WO2018/213335
PCT Pub. Date: Nov. 22, 2018

(65) Prior Publication Data
US 2020/0062851 A1 Feb. 27, 2020

Related U.S. Application Data

(60) Provisional application No. 62/507,129, filed on May 16, 2017.

(51) Int. Cl.
| | | |
|---|---|---|
| C07K 16/28 | (2006.01) | |
| A61K 39/00 | (2006.01) | |
| A61P 35/00 | (2006.01) | |
| C07K 14/47 | (2006.01) | |
| C07K 14/52 | (2006.01) | |
| C07K 14/54 | (2006.01) | |
| C07K 16/32 | (2006.01) | |

(52) U.S. Cl.
CPC .......... *C07K 16/2863* (2013.01); *A61P 35/00* (2018.01); *C07K 14/47* (2013.01); *C07K 14/52* (2013.01); *C07K 14/5428* (2013.01); *C07K 14/5434* (2013.01); *C07K 16/2818* (2013.01); *C07K 16/32* (2013.01); *A61K 2039/505* (2013.01); *C07K 2317/31* (2013.01); *C07K 2317/41* (2013.01); *C07K 2317/55* (2013.01); *C07K 2317/62* (2013.01); *C07K 2317/76* (2013.01); *C07K 2319/01* (2013.01); *C07K 2319/30* (2013.01); *C07K 2319/50* (2013.01)

(58) Field of Classification Search
CPC ............ C07K 16/2863; C07K 16/2818; C07K 16/32; C07K 2317/31; C07K 2317/41; C07K 2317/55; C07K 2317/62; C07K 2319/01
See application file for complete search history.

(56) References Cited

U.S. PATENT DOCUMENTS

| | | | |
|---|---|---|---|
| 8,987,418 B2 | 3/2015 | Ghayur et al. | |
| 9,109,026 B2 | 8/2015 | Ghayur et al. | |
| 9,840,554 B2 | 12/2017 | Gu et al. | |
| 10,077,298 B2 | 9/2018 | Corper et al. | |
| 10,077,315 B2 | 9/2018 | Vu et al. | |
| 2010/0178292 A1* | 7/2010 | Wang | A61P 35/00 530/387.5 |
| 2010/0233079 A1 | 9/2010 | Jakob et al. | |
| 2013/0122020 A1 | 5/2013 | Liu | |
| 2013/0230543 A1 | 9/2013 | Pons | |
| 2014/0356385 A1 | 12/2014 | Dennler | |
| 2015/0087810 A1 | 3/2015 | Moore | |
| 2015/0284713 A1 | 10/2015 | Fischer | |
| 2015/0344549 A1* | 12/2015 | Muir | C12P 21/06 435/188 |
| 2016/0185875 A1* | 6/2016 | Cheng | A61P 35/00 424/133.1 |
| 2018/0125988 A1* | 5/2018 | Yang | A61K 47/6803 |
| 2019/0016819 A1* | 1/2019 | Li | A61K 39/3955 |

FOREIGN PATENT DOCUMENTS

| | | |
|---|---|---|
| AU | 2013202755 B2 | 5/2016 |
| AU | 2014274215 B2 | 2/2019 |
| NO | 2014193973 A3 | 2/2015 |
| WO | 198704462 A1 | 7/1987 |
| WO | 2007024715 A2 | 3/2007 |
| WO | 2007024715 A3 | 10/2008 |
| WO | 2010081173 A2 | 7/2010 |
| WO | 2010081173 A3 | 11/2010 |
| WO | 2012025530 A1 | 3/2012 |
| WO | WO-2012025525 A1 * | 3/2012 ......... C07K 16/2896 |
| WO | 2014193973 A2 | 12/2014 |
| WO | 2015162563 A1 | 10/2015 |
| WO | 2016046778 A2 | 3/2016 |
| WO | 2016046778 A3 | 5/2016 |
| WO | 2018107125 A1 | 6/2018 |

OTHER PUBLICATIONS

Khew et al, Biomaterials 21 (2010) 4600-4608. (Year: 2010).*
(Continued)

*Primary Examiner* — Meera Natarajan
*Assistant Examiner* — Cheom-Gil Cheong
(74) *Attorney, Agent, or Firm* — MORRISON & FOERSTER LLP

(57) ABSTRACT

The present application provides activatable antibodies comprising an antibody comprising an antigen-binding domain (ABD), wherein the ABD comprises a heavy chain variable region (VH) and a light chain variable region (VL), wherein the N-terminus of the VH is fused to a first polypeptide shield moiety (S1), and the N-terminus of the VL is fused to a second polypeptide shield moiety (S2), wherein S1 comprises a first disease-sensing releasable moiety (DS1) and/or S2 comprises a second disease-sensing releasable moiety (DS2), wherein association of S1 with S2 blocks binding of the ABD to its target, and wherein the ABD does not specifically bind to S1, S2, or association thereof. Composition, methods of treatment using the activatable antibodies, and methods of preparation thereof are further provided.

9 Claims, 22 Drawing Sheets
Specification includes a Sequence Listing.

(56) References Cited

OTHER PUBLICATIONS

Yusuke Tanaka et al, Org. Biomol. Chem., 2007, 5, 1764-1770. (Year: 2007).*
Tsutomu Tanaka et al., FEBS Letters 579 (2005) 2092-2096. (Year: 2005).*
DeCoux et al., Journal of Molecular and Cellular Cardiology 77 (2014) 64-72. (Year: 2014).*
Almagro, J. et al. (Jan. 1, 2008). "Humanization of Antibodies," Frontiers in Bioscience 13:1619-1633.
Chothia, C. et al. (1987). "Canonical Structures for the Hypervariable Regions of Immunoglobulins," J. Mol. Biol. 196:901-917.
Clackson, T. et al. (Aug. 15, 1991). "Making Antibody Fragments Using Phage Display Libraries," Nature 352:624-628.
Doi, T. et al. (Oct. 14, 1994). "The Histidine Interruption of an α-Helical Coiled Coil Allosterically Mediates a pH-dependent Ligand Dissociation from Macrophage Scavenger Receptors," J. Biol. Chem. 269(41):25598-25604.
Endo, Y. et al. (2003). "High-Throughput, Genome-Scale Protein Production Method Based On The Wheat Germ Cell-Free Expression System," Biotechnol. Adv. 21:695-713.
Garlatti, V. et al. (Dec. 7, 2007). "Structural Basis For Innate Immune Sensing By M-Ficolin and Its Control By a pH-Dependent Conformational Switch," J. Biol. Chem. 282:35814-35820.
Gout, E. et al. (Feb. 26, 2010). "Carbohydrate Recognition Properties of Human Ficolins: Glycan Array Screening Reveals The Sialic Acid Binding Specificity Of M-Ficolin," J. Biol. Chem. 285(9):6612-6622.
Icard, P. et al. (Dec. 2012, e-pub. Jul. 25, 2012). "A Global View Of The Biochemical Pathways Involved In The Regulation Of The Metabolism Of Cancer Cells," Biochim. Biophys. Acta. 1826:423-433.
International Preliminary Report on Patentability, dated Nov. 19, 2019, for PCT Application No. PCT/US2018/032806, filed May 15, 2018, 6 pages.
International Search Report and Written Opinion, dated Sep. 4, 2018, for PCT Application No. PCT/US2018/032806, filed May 15, 2018, 14 pages.
Ishii, K et al. (Oct. 8, 2015). "pH-Dependent Assembly and Segregation of The Coiled-Coil Segments of Yeast Putative Cargo Receptors Emp46p and Emp47p," PLoS ONE 10(10):e014028, 10 pages.
Johnsson, N. et al. (Oct. 1994). "Split Ubiquitin As A Sensor Of Protein Interactions in vivo," Proc. Natl. Acad. Sci. USA 91:10340-10344.
Junutula, J.R. et al. (2008), "Site-specific conjugation of cytotoxic drug to an antibody improves the therapeutic index," Nat Biotechnol. 26(8):925-932.
Kabat, E.A. et al. (1991). Sequences of Proteins of Immunological Interest, 5th ed., Public Health Service, National Institutes of Health, Bethesda, MD. TOC, 21 pages.
Keresztessy, Z. et al. (2006). "Phage Display Selection Of Efficient Glutamine-Donor Substrate Peptides For Transglutaminase 2," Protein Science 15:2466-2480.
Khew, S.T. et al. (Jun. 2010, e-pub. Mar. 11, 2010). "Characterization Of Amine Donor And Acceptor Sites For Tissue Type Transglutaminase Using A Sequence From The C-Terminus Of Human Fibrillin-1 And The N-Terminus Of Osteonectin," Biomaterials 31(2010) 4600-4608.
Kindt, T.J. et al. (2007). "Antigens And Antibodies," Chapter 4 In Kuby Immunology 6th Ed., W.H. Freeman And Co., p. 91, 14 pages.
Li, L. et al. (Jan. 2014). "Structural Analysis and Optimization of the Covalent Association between SpyCatcher and a Peptide Tag," J Mol Biol. 426(2):309-317, 15 pages.
Liu, C.C. et al. (2010, e-pub. Mar. 18, 2010). "Adding New Chemistries to the Genetic Code," Annual Review of Biochemistry 79:413-444.
Onuoha, S.C. et al. (Oct. 2015). "Rational Design of Antirheumatic Prodrugs Specific for Sites of Inflammation," Arthritis & Rheumatology 67(10):2661-2672.
Portolano, S. et al. (Feb. 1, 1993). "Lack of Promiscuity in Autoantigen-Specific H and L Chain Combinations as Revealed by Human H And L Chain 'Roulette'," The Journal of Immunology 150(3):880-887.
Remington's Pharmaceutical Sciences. (1980). 16th edition, Osol, A. Ed, pp. 1-2, (Table of Contents Only).
Running Deer, J. et al. (May-Jun. 2004, e-pub. Mar. 10, 2004). "High-Level Expression Of Proteins In Mammalian Cells Using Transcription Regulatory Sequences From The Chinese Hamster EF-1Alpha Gene," Biotechnol. Prog. 20(3):880-889.
Sambrook, J. et al. (2001). Molecular Cloning: A Laboratory Manual Cold Spring Harbor Laboratory Press, Cold Spring Harbor,N. Y., 3rd ed., 1 page, Table of Contents.
Sevenich, L. et al. (2014). "Pericellular Proteolysis In Cancer," Genes & Dev. 28:2331-2347.
Sitaraman et al., "High-throughput protein expression using cell-free system," Methods Mol. Biol. (2009) 498:229-44.
Spirin, A.S. (Oct. 2004). "High-Throughput Cell-Free Systems For Synthesis Of Functionally Active Proteins," Trends Biotechnol. 22(10):538-545.
Sugimura, Y et al. (Jun. 30, 2006). "Screening for the Preferred Substrate Sequence of Transglutaminase Using a Phage-displayed Peptide Library: Identification Of Peptide Substrates For Tgase 2 And Factor XIIIa," J. Biol. Chem. 281(26):17699-17706.
Tanaka, T et al. (2005, e-pub. Mar. 10, 2005). "N-Terminal Glycine-Specific Protein Conjugation Catalyzed By Microbial Transglutaminase," FEBS Letters 579:2092-2096.
Tanio, M. et al. (2008). "Trimeric Structure and Conformational Equilibrium Of M-Ficolin Fibrinogen-Like Domain," J. Synchrotron Rad. 15:243-245.
Tarli, L. et al. (Jul. 1, 1999). "A High-Affinity Human Antibody That Targets Tumoral Blood Vessels," Blood 94 (1):192-198.
Turanov, A. et al. (2013, e-pub. May 28, 2013). "UGA Codon Position-Dependent Incorporation Of Selenocysteine Into Mammalian Selenoproteins," Nucleic Acids Res. 41(14):6952-6959.
Zakeri, B. et al. (2012, e-pub. Feb. 24, 2012). "Peptide Tag Forming a Rapid Covalent Bond to a Protein, Through Engineering a Bacterial Adhesin," PNAS 109:E690-E697.
Zdanov, A. et al. (Jun. 15, 1995). "Crystal Structure Of Interleukin-10 Reveals The Functional Dimer With An Unexpected Topological Similarity To Interferon γ," Structure 3:591-601.
Digiammarino, E. et al. (Sep.-Oct. 2011, e-pub. Sep. 1, 2011). "Ligand Association Rates to the Inner-Variable-Domain of a Dual-Variable-Domain Immunoglobulin are Significantly Impacted by Linker Design," MAbs. 3(5):487-494.
Wu, C. et al. (Nov. 2007; e-pub. Oct. 14, 2007). "Simultaneous Targeting of Multiple Disease Mediators by a Dual-Variable-Domain Immunoglobulin," Nat. Biotechnol. 25(11):1290-1297.

* cited by examiner

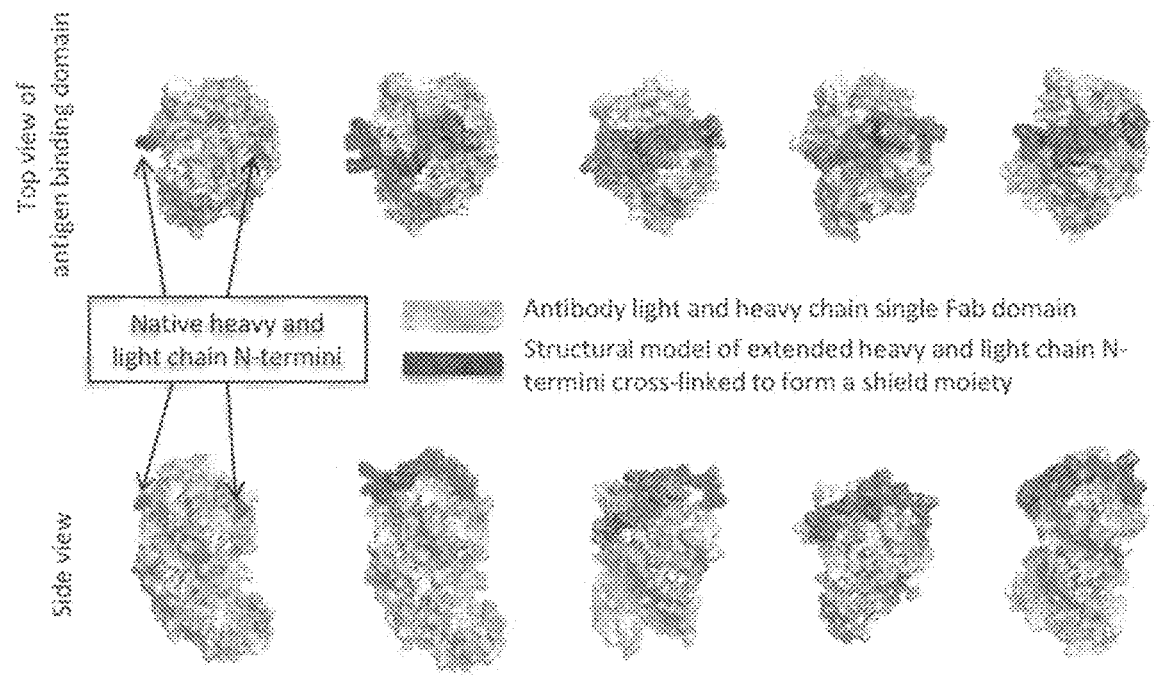

FIG. 9B

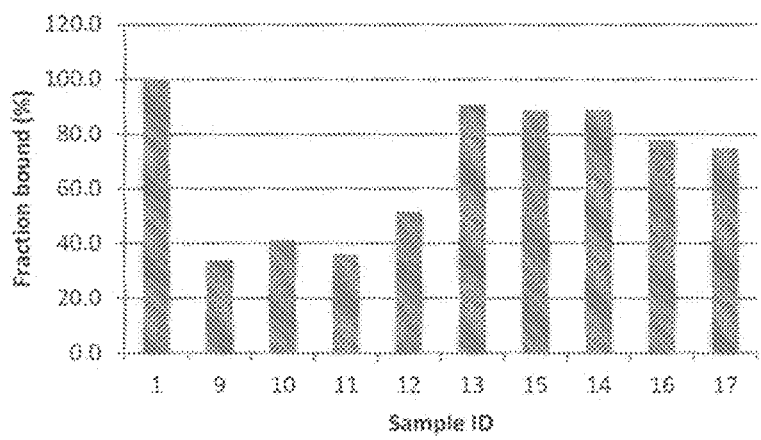

| Sample ID | Sample description |
|---|---|
| 1 | anti-EGFR antibody control (Cetuximab) |
| 9 | Activatable EGFR Ab 3 with shield -condition 3 |
| 10 | Activatable EGFR Ab 3 with shield -condition 4 |
| 11 | Activatable EGFR Ab 4 with shield -condition 3 |
| 12 | Activatable EGFR Ab 4 with shield -condition 4 |
| 13 | Activatable EGFR Ab 3 with shield -condition 3 and matriptase |
| 14 | Activatable EGFR Ab 3 with shield -condition 4 and matriptase |
| 15 | Activatable EGFR Ab 4 with shield -condition 3 and matriptase |
| 16 | Activatable EGFR Ab 4 with shield -condition 4 and matriptase |
| 17 | Activatable EGFR Ab 4 with shield -condition 5 and uPA |

| Sample ID | Sample description |
|---|---|
| 1 | anti-EGFR antibody control (Cetuximab) |
| 2 | Activatable EGFR Ab 1 before shield formation |
| 3 | Activatable EGFR Ab 1 with shield |
| 4 | Activatable EGFR Ab 1 with shield and matriptase |

| Lane # | Sample description |
|---|---|
| 1 | Activatable mCTLA-4 Fab without shield |
| 2 | Activatable mCTLA-4 Fab with shield |
| 3 | Activatable mCTLA-4 Fab with shield and matriptase |
| 4 | Activatable mCTLA-4 Fab with shield and MMP9 |

SEQUENCE LISTING

<160> NUMBER OF SEQ ID NOS: 241

<210> SEQ ID NO 1
<211> LENGTH: 4
<212> TYPE: PRT
<213> ORGANISM: Artificial Sequence
<220> FEATURE:
<223> OTHER INFORMATION: Synthetic Construct

<400> SEQUENCE: 1

Leu Leu Gln Gly
1

<210> SEQ ID NO 2
<211> LENGTH: 3
<212> TYPE: PRT
<213> ORGANISM: Artificial Sequence
<220> FEATURE:
<223> OTHER INFORMATION: Synthetic Construct

<400> SEQUENCE: 2

Gly Lys Gly
1

<210> SEQ ID NO 3
<211> LENGTH: 2
<212> TYPE: PRT
<213> ORGANISM: Artificial Sequence
<220> FEATURE:
<223> OTHER INFORMATION: Synthetic Construct

<400> SEQUENCE: 3

Ser Cys
1

<210> SEQ ID NO 4
<211> LENGTH: 83
<212> TYPE: PRT
<213> ORGANISM: Artificial Sequence
<220> FEATURE:
<223> OTHER INFORMATION: Synthetic Construct

<400> SEQUENCE: 4

Asp Ser Ala Thr His Ile Lys Phe Ser Lys Arg Asp Glu Asp Gly Lys
1               5                   10                  15

Glu Leu Ala Gly Ala Thr Met Glu Leu Arg Asp Ser Ser Gly Lys Thr
            20                  25                  30

Ile Ser Thr Trp Ile Ser Asp Gly Gln Val Lys Asp Phe Tyr Leu Tyr
        35                  40                  45

Pro Gly Lys Tyr Thr Phe Val Glu Thr Ala Ala Pro Asp Gly Tyr Glu
    50                  55                  60

Val Ala Thr Ala Ile Thr Phe Thr Val Asn Glu Gln Gly Gln Val Thr
65                  70                  75                  80

Val Asn Gly

<210> SEQ ID NO 5
<211> LENGTH: 13
<212> TYPE: PRT
<213> ORGANISM: Artificial Sequence
<220> FEATURE:
<223> OTHER INFORMATION: Synthetic Construct

<400> SEQUENCE: 5

Ala His Ile Val Met Val Ala Ala Tyr Lys Pro Thr Lys

-continued

<210> SEQ ID NO 6
<211> LENGTH: 34
<212> TYPE: PRT
<213> ORGANISM: Artificial Sequence
<220> FEATURE:
<223> OTHER INFORMATION: Synthetic Construct

<400> SEQUENCE: 6

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu

<210> SEQ ID NO 7
<211> LENGTH: 42
<212> TYPE: PRT
<213> ORGANISM: Artificial Sequence
<220> FEATURE:
<223> OTHER INFORMATION: Synthetic Construct

<400> SEQUENCE: 7

Gly Ile Pro Pro Asp Gln Gln Arg Leu Ile Phe Ala Gly Lys Gln Leu
1               5                   10                  15

Glu Asp Gly Arg Thr Leu Ser Asp Tyr Asn Ile Gln Lys Glu Ser Thr
            20                  25                  30

Leu His Leu Val Leu Arg Leu Arg Gly Gly
            35                  40

<210> SEQ ID NO 8
<211> LENGTH: 160
<212> TYPE: PRT
<213> ORGANISM: Artificial Sequence
<220> FEATURE:
<223> OTHER INFORMATION: Synthetic Construct

<400> SEQUENCE: 8

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
            35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
            115                 120                 125

Asn Lys Leu Gln Glu Lys Gly Ile Tyr Lys Ala Met Ser Glu Phe Asp
        130                 135                 140

Ile Phe Ile Asn Tyr Ile Glu Ala Tyr Met Thr Met Lys Ile Arg Asn
145                 150                 155                 160

<210> SEQ ID NO 9
<211> LENGTH: 70
<212> TYPE: PRT
<213> ORGANISM: Artificial Sequence
<220> FEATURE:
<223> OTHER INFORMATION: Synthetic Construct

<400> SEQUENCE: 9

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
    50                  55                  60

Lys Lys Leu Leu Glu Ser
65                  70

<210> SEQ ID NO 10
<211> LENGTH: 78
<212> TYPE: PRT
<213> ORGANISM: Artificial Sequence
<220> FEATURE:
<223> OTHER INFORMATION: Synthetic Construct

<400> SEQUENCE: 10

Ala Gly Pro Ala Ala Ala Val Leu Arg Glu Leu Arg Cys Val Cys Leu
1               5                   10                  15

Gln Thr Thr Gln Gly Val His Pro Lys Met Ile Ser Asn Leu Gln Val
            20                  25                  30

Phe Ala Ile Gly Pro Gln Cys Ser Lys Val Glu Val Val Ala Ser Leu
        35                  40                  45

Lys Asn Gly Lys Glu Ile Cys Leu Asp Pro Glu Ala Pro Phe Leu Lys
    50                  55                  60

Lys Val Ile Gln Lys Ile Leu Asp Gly Gly Asn Lys Glu Asn
65                  70                  75

<210> SEQ ID NO 11
<211> LENGTH: 219
<212> TYPE: PRT
<213> ORGANISM: Artificial Sequence
<220> FEATURE:
<223> OTHER INFORMATION: Synthetic Construct

<400> SEQUENCE: 11

Met Cys Pro Ala Arg Ser Leu Leu Leu Val Ala Thr Leu Val Leu Leu
1               5                   10                  15

Asp His Leu Ser Leu Ala Arg Asn Leu Pro Val Ala Thr Pro Asp Pro
            20                  25                  30

Gly Met Phe Pro Cys Leu His His Ser Gln Asn Leu Leu Arg Ala Val
        35                  40                  45

Ser Asn Met Leu Gln Lys Ala Arg Gln Thr Leu Glu Phe Tyr Pro Cys
    50                  55                  60

Thr Ser Glu Glu Ile Asp His Glu Asp Ile Thr Lys Asp Lys Thr Ser
65                  70                  75                  80

Thr Val Glu Ala Cys Leu Pro Leu Glu Leu Thr Lys Asn Glu Ser Cys
                85                  90                  95

Leu Asn Ser Arg Glu Thr Ser Phe Ile Thr Asn Gly Ser Cys Leu Ala

```
              100                 105                 110
Ser Arg Lys Thr Ser Phe Met Met Ala Leu Cys Leu Ser Ser Ile Tyr
            115                 120                 125

Glu Asp Leu Lys Met Tyr Gln Val Glu Phe Lys Thr Met Asn Ala Lys
        130                 135                 140

Leu Leu Met Asp Pro Lys Arg Gln Ile Phe Leu Asp Gln Asn Met Leu
145                 150                 155                 160

Ala Val Ile Asp Glu Leu Met Gln Ala Leu Asn Phe Asn Ser Glu Thr
                165                 170                 175

Val Pro Gln Lys Ser Ser Leu Glu Gly Pro Asp Phe Tyr Lys Thr Lys
            180                 185                 190

Ile Lys Leu Cys Ile Leu Leu His Ala Phe Arg Ile Arg Ala Val Thr
        195                 200                 205

Ile Asp Arg Val Met Ser Tyr Leu Asn Ala Ser
    210                 215

<210> SEQ ID NO 12
<211> LENGTH: 328
<212> TYPE: PRT
<213> ORGANISM: Artificial Sequence
<220> FEATURE:
<223> OTHER INFORMATION: Synthetic Construct

<400> SEQUENCE: 12

Met Cys His Gln Gln Leu Val Ile Ser Trp Phe Ser Leu Val Phe Leu
1               5                  10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
```

```
                    245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320

Glu Trp Ala Ser Val Pro Cys Ser
                325

<210> SEQ ID NO 13
<211> LENGTH: 30
<212> TYPE: PRT
<213> ORGANISM: Artificial Sequence
<220> FEATURE:
<223> OTHER INFORMATION: Synthetic Construct

<400> SEQUENCE: 13

Glu Asn Lys Gln Val Glu Glu Ile Leu Arg Leu Glu Lys Glu Ile Glu
1               5                   10                  15

Asp Leu Gln Arg Met Lys Glu Gln Gln Glu Leu Ser Leu Thr
            20                  25                  30

<210> SEQ ID NO 14
<211> LENGTH: 61
<212> TYPE: PRT
<213> ORGANISM: Artificial Sequence
<220> FEATURE:
<223> OTHER INFORMATION: Synthetic Construct

<400> SEQUENCE: 14

Gly Ala Met Asp Pro Glu Phe Thr Lys Asn Ala Leu Asn Val Val Lys
1               5                   10                  15

Asn Asp Leu Ile Ala Lys Val Asp Gln Leu Ser Gly Glu Gln Glu Val
            20                  25                  30

Leu Arg Gly Glu Leu Glu Ala Ala Lys Gln Ala Lys Val Lys Leu Glu
        35                  40                  45

Asn Arg Ile Lys Glu Leu Glu Glu Glu Leu Lys Arg Val
    50                  55                  60

<210> SEQ ID NO 15
<211> LENGTH: 80
<212> TYPE: PRT
<213> ORGANISM: Artificial Sequence
<220> FEATURE:
<223> OTHER INFORMATION: Synthetic Construct

<400> SEQUENCE: 15

Gly Ser Met Thr Ile Ser Asn Met Glu Ala Asp Met Asn Arg Leu Leu
1               5                   10                  15

Lys Gln Arg Glu Glu Leu Thr Lys Arg Arg Glu Lys Leu Ser Lys Arg
            20                  25                  30

Arg Glu Lys Ile Val Lys Glu Asn Gly Glu Gly Asp Lys Asn Val Ala
        35                  40                  45

Asn Ile Asn Glu Glu Met Glu Ser Leu Thr Ala Asn Ile Asp Tyr Ile
    50                  55                  60

Asn Asp Ser Ile Ser Asp Cys Gln Ala Asn Ile Met Gln Met Glu Glu
65                  70                  75                  80
```

<210> SEQ ID NO 16
<211> LENGTH: 51
<212> TYPE: PRT
<213> ORGANISM: Artificial Sequence
<220> FEATURE:
<223> OTHER INFORMATION: Synthetic Construct

<400> SEQUENCE: 16

Gly Ser Asp Tyr Glu Phe Leu Lys Ser Trp Thr Val Glu Asp Leu Gln
1               5                   10                  15

Lys Arg Leu Leu Ala Leu Asp Pro Met Met Glu Gln Glu Ile Glu Glu
            20                  25                  30

Ile Arg Gln Lys Tyr Gln Ser Lys Arg Gln Pro Ile Leu Asp Ala Ile
        35                  40                  45

Glu Ala Lys
    50

<210> SEQ ID NO 17
<211> LENGTH: 55
<212> TYPE: PRT
<213> ORGANISM: Artificial Sequence
<220> FEATURE:
<223> OTHER INFORMATION: Synthetic Construct

<400> SEQUENCE: 17

Gly Ser Glu Val Glu Trp Asp Ala Phe Ser Ile Pro Glu Leu Gln Asn
1               5                   10                  15

Phe Leu Thr Ile Leu Glu Lys Glu Glu Gln Asp Lys Ile Gln Gln Val
            20                  25                  30

Gln Lys Lys Tyr Asp Lys Phe Arg Gln Lys Leu Glu Glu Ala Leu Arg
        35                  40                  45

Glu Ser Gln Gly Lys Pro Gly
    50                  55

<210> SEQ ID NO 18
<211> LENGTH: 14
<212> TYPE: PRT
<213> ORGANISM: Artificial Sequence
<220> FEATURE:
<223> OTHER INFORMATION: Synthetic Construct

<400> SEQUENCE: 18

Ser Asn Tyr Ser Met Val Asn Thr Thr Asn Met Thr Ser Ala
1               5                   10

<210> SEQ ID NO 19
<211> LENGTH: 8
<212> TYPE: PRT
<213> ORGANISM: Artificial Sequence
<220> FEATURE:
<223> OTHER INFORMATION: Synthetic Construct

<400> SEQUENCE: 19

Leu Ser Gly Arg Ser Asp Asn His
1               5

<210> SEQ ID NO 20
<211> LENGTH: 218
<212> TYPE: PRT
<213> ORGANISM: Artificial Sequence
<220> FEATURE:
<223> OTHER INFORMATION: Synthetic Construct

<400> SEQUENCE: 20

```
Gln Ser Cys Ala Thr Gly Pro Arg Asn Cys Lys Asp Leu Leu Asp Arg
1               5                   10                  15

Gly Tyr Phe Arg Ser Gly Trp His Thr Ile Tyr Leu Pro Asp Cys Arg
            20                  25                  30

Pro Leu Thr Val Leu Cys Asp Met Asp Thr Asp Gly Gly Trp Thr
        35                  40                  45

Val Phe Gln Arg Arg Met Asp Gly Ser Val Asp Phe Tyr Arg Asp Trp
    50                  55                  60

Ala Ala Tyr Lys Gln Gly Phe Gly Ser Gln Leu Gly Glu Phe Trp Leu
65                  70                  75                  80

Gly Asn Asp Asn Ile His Ala Leu Thr Ala Gln Gly Ser Ser Glu Leu
                85                  90                  95

Arg Thr Asp Leu Val Asp Phe Glu Gly Asn His Gln Phe Ala Lys Tyr
            100                 105                 110

Lys Ser Phe Lys Val Ala Asp Glu Ala Glu Lys Tyr Lys Leu Val Leu
            115                 120                 125

Gly Ala Phe Val Gly Gly Ser Ala Gly Asn Ser Leu Thr Gly His Asn
        130                 135                 140

Asn Asn Phe Phe Ser Thr Lys Asp Gln Asp Asn Asp Val Ser Ser Ser
145                 150                 155                 160

Asn Cys Ala Glu Lys Phe Gln Gly Ala Trp Trp Tyr Ala Asp Cys His
                165                 170                 175

Ala Ser Asn Leu Asn Gly Leu Tyr Leu Met Gly Pro His Glu Ser Tyr
            180                 185                 190

Ala Asn Gly Ile Asn Trp Ser Ala Ala Lys Gly Tyr Lys Tyr Ser Tyr
            195                 200                 205

Lys Val Ser Glu Met Lys Val Arg Pro Ala
            210                 215
```

<210> SEQ ID NO 21
<211> LENGTH: 460
<212> TYPE: PRT
<213> ORGANISM: Artificial Sequence
<220> FEATURE:
<223> OTHER INFORMATION: Synthetic Construct

<400> SEQUENCE: 21

```
Leu Leu Gln Gly Leu Ser Gly Arg Ser Asp Asn His Gln Val Gln Leu
1               5                   10                  15

Lys Gln Ser Gly Pro Gly Leu Val Gln Pro Ser Gln Ser Leu Ser Ile
            20                  25                  30

Thr Cys Thr Val Ser Gly Phe Ser Leu Thr Asn Tyr Gly Val His Trp
            35                  40                  45

Val Arg Gln Ser Pro Gly Lys Gly Leu Glu Trp Leu Gly Val Ile Trp
    50                  55                  60

Ser Gly Gly Asn Thr Asp Tyr Asn Thr Pro Phe Thr Ser Arg Leu Ser
65                  70                  75                  80

Ile Asn Lys Asp Asn Ser Lys Ser Gln Val Phe Phe Lys Met Asn Ser
                85                  90                  95

Leu Gln Ser Glu Asp Thr Ala Ile Tyr Tyr Cys Ala Arg Ala Leu Thr
            100                 105                 110

Tyr Tyr Asp Tyr Glu Phe Ala Tyr Trp Gly Gln Gly Thr Leu Val Thr
            115                 120                 125

Val Ser Ala Ala Ser Thr Lys Gly Pro Ser Val Phe Pro Leu Ala Pro
```

```
            130                 135                 140
Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
                180                 185                 190

Leu Tyr Ser Leu Ser Ser Val Val Thr Val Pro Ser Ser Ser Leu Gly
            195                 200                 205

Thr Gln Thr Tyr Ile Cys Asn Val Asn His Lys Pro Ser Asn Thr Lys
210                 215                 220

Val Asp Lys Lys Val Glu Pro Lys Ser Cys Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
                260                 265                 270

Val Thr Cys Val Val Val Asp Val Ser His Glu Asp Pro Glu Val Lys
            275                 280                 285

Phe Asn Trp Tyr Val Asp Gly Val Glu Val His Asn Ala Lys Thr Lys
290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
                340                 345                 350

Ala Lys Gly Gln Pro Arg Glu Pro Gln Val Tyr Thr Leu Pro Pro Ser
            355                 360                 365

Arg Asp Glu Leu Thr Lys Asn Gln Val Ser Leu Thr Cys Leu Val Lys
370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
                420                 425                 430

Gln Gly Asn Val Phe Ser Cys Ser Val Met His Glu Ala Leu His Asn
            435                 440                 445

His Tyr Thr Gln Lys Ser Leu Ser Leu Ser Pro Gly
450                 455                 460

<210> SEQ ID NO 22
<211> LENGTH: 225
<212> TYPE: PRT
<213> ORGANISM: Artificial Sequence
<220> FEATURE:
<223> OTHER INFORMATION: Synthetic Construct

<400> SEQUENCE: 22

Gly Lys Gly Leu Ser Gly Arg Ser Asp Asn His Asp Ile Leu Leu Thr
1               5                   10                  15

Gln Ser Pro Val Ile Leu Ser Val Ser Pro Gly Glu Arg Val Ser Phe
            20                  25                  30

Ser Cys Arg Ala Ser Gln Ser Ile Gly Thr Asn Ile His Trp Tyr Gln
```

```
                35                  40                  45
Gln Arg Thr Asn Gly Ser Pro Arg Leu Leu Ile Lys Tyr Ala Ser Glu
 50                  55                  60

Ser Ile Ser Gly Ile Pro Ser Arg Phe Ser Gly Ser Gly Ser Gly Thr
 65                  70                  75                  80

Asp Phe Thr Leu Ser Ile Asn Ser Val Glu Ser Glu Asp Ile Ala Asp
                 85                  90                  95

Tyr Tyr Cys Gln Gln Asn Asn Asn Trp Pro Thr Thr Phe Gly Ala Gly
            100                 105                 110

Thr Lys Leu Glu Leu Lys Arg Thr Val Ala Ala Pro Ser Val Phe Ile
        115                 120                 125

Phe Pro Pro Ser Asp Glu Gln Leu Lys Ser Gly Thr Ala Ser Val Val
130                 135                 140

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
                165                 170                 175

Gln Asp Ser Lys Asp Ser Thr Tyr Ser Leu Ser Ser Thr Leu Thr Leu
            180                 185                 190

Ser Lys Ala Asp Tyr Glu Lys His Lys Val Tyr Ala Cys Glu Val Thr
        195                 200                 205

His Gln Gly Leu Ser Ser Pro Val Thr Lys Ser Phe Asn Arg Gly Glu
210                 215                 220

Cys
225

<210> SEQ ID NO 23
<211> LENGTH: 464
<212> TYPE: PRT
<213> ORGANISM: Artificial Sequence
<220> FEATURE:
<223> OTHER INFORMATION: Synthetic Construct

<400> SEQUENCE: 23

Leu Leu Gln Gly Leu Ser Gly Arg Ser Asp Asn His Gly Gly Gly Ser
 1               5                  10                  15

Gln Val Gln Leu Lys Gln Ser Gly Pro Gly Leu Val Gln Pro Ser Gln
             20                  25                  30

Ser Leu Ser Ile Thr Cys Thr Val Ser Gly Phe Ser Leu Thr Asn Tyr
         35                  40                  45

Gly Val His Trp Val Arg Gln Ser Pro Gly Lys Gly Leu Glu Trp Leu
     50                  55                  60

Gly Val Ile Trp Ser Gly Gly Asn Thr Asp Tyr Asn Thr Pro Phe Thr
 65                  70                  75                  80

Ser Arg Leu Ser Ile Asn Lys Asp Asn Ser Lys Ser Gln Val Phe Phe
                 85                  90                  95

Lys Met Asn Ser Leu Gln Ser Glu Asp Thr Ala Ile Tyr Tyr Cys Ala
            100                 105                 110

Arg Ala Leu Thr Tyr Tyr Asp Tyr Glu Phe Ala Tyr Trp Gly Gln Gly
        115                 120                 125

Thr Leu Val Thr Val Ser Ala Ala Ser Thr Lys Gly Pro Ser Val Phe
130                 135                 140

Pro Leu Ala Pro Ser Ser Lys Ser Thr Ser Gly Gly Thr Ala Ala Leu
145                 150                 155                 160

Gly Cys Leu Val Lys Asp Tyr Phe Pro Glu Pro Val Thr Val Ser Trp
```

```
                165                 170                 175
Asn Ser Gly Ala Leu Thr Ser Gly Val His Thr Phe Pro Ala Val Leu
            180                 185                 190

Gln Ser Ser Gly Leu Tyr Ser Leu Ser Ser Val Val Thr Val Pro Ser
            195                 200                 205

Ser Ser Leu Gly Thr Gln Thr Tyr Ile Cys Asn Val Asn His Lys Pro
        210                 215                 220

Ser Asn Thr Lys Val Asp Lys Lys Val Glu Pro Lys Ser Cys Asp Lys
225                 230                 235                 240

Thr His Thr Cys Pro Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365

Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

<210> SEQ ID NO 24
<211> LENGTH: 229
<212> TYPE: PRT
<213> ORGANISM: Artificial Sequence
<220> FEATURE:
<223> OTHER INFORMATION: Synthetic Construct

<400> SEQUENCE: 24

Gly Lys Gly Leu Ser Gly Arg Ser Asp Asn His Gly Gly Gly Ser Asp
1               5                   10                  15

Ile Leu Leu Thr Gln Ser Pro Val Ile Leu Ser Val Ser Pro Gly Glu
            20                  25                  30

Arg Val Ser Phe Ser Cys Arg Ala Ser Gln Ser Ile Gly Thr Asn Ile
        35                  40                  45

His Trp Tyr Gln Gln Arg Thr Asn Gly Ser Pro Arg Leu Leu Ile Lys
    50                  55                  60

Tyr Ala Ser Glu Ser Ile Ser Gly Ile Pro Ser Arg Phe Ser Gly Ser
```

```
                65                  70                  75                  80
Gly Ser Gly Thr Asp Phe Thr Leu Ser Ile Asn Ser Val Glu Ser Glu
                    85                  90                  95

Asp Ile Ala Asp Tyr Tyr Cys Gln Gln Asn Asn Asn Trp Pro Thr Thr
                100                 105                 110

Phe Gly Ala Gly Thr Lys Leu Glu Leu Lys Arg Thr Val Ala Ala Pro
            115                 120                 125

Ser Val Phe Ile Phe Pro Pro Ser Asp Glu Gln Leu Lys Ser Gly Thr
        130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg Gly Glu Cys
225

<210> SEQ ID NO 25
<211> LENGTH: 460
<212> TYPE: PRT
<213> ORGANISM: Artificial Sequence
<220> FEATURE:
<223> OTHER INFORMATION: Synthetic Construct

<400> SEQUENCE: 25

Ser Cys Leu Ser Gly Arg Ser Asp Asn His Gly Gly Gln Val Gln Leu
1               5                   10                  15

Lys Gln Ser Gly Pro Gly Leu Val Gln Pro Ser Gln Ser Leu Ser Ile
            20                  25                  30

Thr Cys Thr Val Ser Gly Phe Ser Leu Thr Asn Tyr Gly Val His Trp
        35                  40                  45

Val Arg Gln Ser Pro Gly Lys Gly Leu Glu Trp Leu Gly Val Ile Trp
    50                  55                  60

Ser Gly Gly Asn Thr Asp Tyr Asn Thr Pro Phe Thr Ser Arg Leu Ser
65                  70                  75                  80

Ile Asn Lys Asp Asn Ser Lys Ser Gln Val Phe Phe Lys Met Asn Ser
                85                  90                  95

Leu Gln Ser Glu Asp Thr Ala Ile Tyr Tyr Cys Ala Arg Ala Leu Thr
            100                 105                 110

Tyr Tyr Asp Tyr Glu Phe Ala Tyr Trp Gly Gln Gly Thr Leu Val Thr
        115                 120                 125

Val Ser Ala Ala Ser Thr Lys Gly Pro Ser Val Phe Pro Leu Ala Pro
    130                 135                 140

Ser Ser Lys Ser Thr Ser Gly Gly Thr Ala Ala Leu Gly Cys Leu Val
145                 150                 155                 160

Lys Asp Tyr Phe Pro Glu Pro Val Thr Val Ser Trp Asn Ser Gly Ala
                165                 170                 175

Leu Thr Ser Gly Val His Thr Phe Pro Ala Val Leu Gln Ser Ser Gly
            180                 185                 190

Leu Tyr Ser Leu Ser Ser Val Val Thr Val Pro Ser Ser Ser Leu Gly
```

```
                     195                 200                 205
Thr Gln Thr Tyr Ile Cys Asn Val Asn His Lys Pro Ser Asn Thr Lys
    210                 215                 220

Val Asp Lys Lys Val Glu Pro Lys Ser Ser Asp Lys Thr His Thr Cys
225                 230                 235                 240

Pro Pro Cys Pro Ala Pro Glu Leu Leu Gly Gly Pro Ser Val Phe Leu
                245                 250                 255

Phe Pro Pro Lys Pro Lys Asp Thr Leu Met Ile Ser Arg Thr Pro Glu
            260                 265                 270

Val Thr Cys Val Val Val Asp Val Ser His Glu Asp Pro Glu Val Lys
        275                 280                 285

Phe Asn Trp Tyr Val Asp Gly Val Glu Val His Asn Ala Lys Thr Lys
    290                 295                 300

Pro Arg Glu Glu Gln Tyr Asn Ser Thr Tyr Arg Val Val Ser Val Leu
305                 310                 315                 320

Thr Val Leu His Gln Asp Trp Leu Asn Gly Lys Glu Tyr Lys Cys Lys
                325                 330                 335

Val Ser Asn Lys Ala Leu Pro Ala Pro Ile Glu Lys Thr Ile Ser Lys
            340                 345                 350

Ala Lys Gly Gln Pro Arg Glu Pro Gln Val Tyr Thr Leu Pro Pro Ser
        355                 360                 365

Arg Asp Glu Leu Thr Lys Asn Gln Val Ser Leu Thr Cys Leu Val Lys
    370                 375                 380

Gly Phe Tyr Pro Ser Asp Ile Ala Val Glu Trp Glu Ser Asn Gly Gln
385                 390                 395                 400

Pro Glu Asn Asn Tyr Lys Thr Thr Pro Pro Val Leu Asp Ser Asp Gly
                405                 410                 415

Ser Phe Phe Leu Tyr Ser Lys Leu Thr Val Asp Lys Ser Arg Trp Gln
            420                 425                 430

Gln Gly Asn Val Phe Ser Cys Ser Val Met His Glu Ala Leu His Asn
        435                 440                 445

His Tyr Thr Gln Lys Ser Leu Ser Leu Ser Pro Gly
    450                 455                 460

<210> SEQ ID NO 26
<211> LENGTH: 226
<212> TYPE: PRT
<213> ORGANISM: Artificial Sequence
<220> FEATURE:
<223> OTHER INFORMATION: Synthetic Construct

<400> SEQUENCE: 26

Ser Cys Leu Ser Gly Arg Ser Asp Asn His Gly Gly Asp Ile Leu Leu
1               5                   10                  15

Thr Gln Ser Pro Val Ile Leu Ser Val Ser Pro Gly Glu Arg Val Ser
            20                  25                  30

Phe Ser Cys Arg Ala Ser Gln Ser Ile Gly Thr Asn Ile His Trp Tyr
        35                  40                  45

Gln Gln Arg Thr Asn Gly Ser Pro Arg Leu Leu Ile Lys Tyr Ala Ser
    50                  55                  60

Glu Ser Ile Ser Gly Ile Pro Ser Arg Phe Ser Gly Ser Gly Ser Gly
65                  70                  75                  80

Thr Asp Phe Thr Leu Ser Ile Asn Ser Val Glu Ser Glu Asp Ile Ala
                85                  90                  95

Asp Tyr Tyr Cys Gln Gln Asn Asn Asn Trp Pro Thr Thr Phe Gly Ala
```

```
            100                 105                 110
Gly Thr Lys Leu Glu Leu Lys Arg Thr Val Ala Ala Pro Ser Val Phe
            115                 120                 125

Ile Phe Pro Pro Ser Asp Glu Gln Leu Lys Ser Gly Thr Ala Ser Val
            130                 135                 140

Val Cys Leu Leu Asn Asn Phe Tyr Pro Arg Glu Ala Lys Val Gln Trp
145                 150                 155                 160

Lys Val Asp Asn Ala Leu Gln Ser Gly Asn Ser Gln Glu Ser Val Thr
                165                 170                 175

Glu Gln Asp Ser Lys Asp Ser Thr Tyr Ser Leu Ser Ser Thr Leu Thr
            180                 185                 190

Leu Ser Lys Ala Asp Tyr Glu Lys His Lys Val Tyr Ala Cys Glu Val
            195                 200                 205

Thr His Gln Gly Leu Ser Ser Pro Val Thr Lys Ser Phe Asn Arg Gly
            210                 215                 220

Glu Ser
225

<210> SEQ ID NO 27
<211> LENGTH: 462
<212> TYPE: PRT
<213> ORGANISM: Artificial Sequence
<220> FEATURE:
<223> OTHER INFORMATION: Synthetic Construct

<400> SEQUENCE: 27

Ser Cys Leu Ser Gly Arg Ser Asp Asn His Gly Gly Ser Gln Val
1               5                   10                  15

Gln Leu Lys Gln Ser Gly Pro Gly Leu Val Gln Pro Ser Gln Ser Leu
            20                  25                  30

Ser Ile Thr Cys Thr Val Ser Gly Phe Ser Leu Thr Asn Tyr Gly Val
            35                  40                  45

His Trp Val Arg Gln Ser Pro Gly Lys Gly Leu Glu Trp Leu Gly Val
        50                  55                  60

Ile Trp Ser Gly Gly Asn Thr Asp Tyr Asn Thr Pro Phe Thr Ser Arg
65                  70                  75                  80

Leu Ser Ile Asn Lys Asp Asn Ser Lys Ser Gln Val Phe Phe Lys Met
                85                  90                  95

Asn Ser Leu Gln Ser Glu Asp Thr Ala Ile Tyr Tyr Cys Ala Arg Ala
            100                 105                 110

Leu Thr Tyr Tyr Asp Tyr Glu Phe Ala Tyr Trp Gly Gln Gly Thr Leu
            115                 120                 125

Val Thr Val Ser Ala Ala Ser Thr Lys Gly Pro Ser Val Phe Pro Leu
            130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
            195                 200                 205

Leu Gly Thr Gln Thr Tyr Ile Cys Asn Val Asn His Lys Pro Ser Asn
            210                 215                 220

Thr Lys Val Asp Lys Lys Val Glu Pro Lys Ser Ser Asp Lys Thr His
```

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
        260                 265                 270

Val Lys Phe Asn Trp Tyr Val Asp Gly Val Glu Val His Asn Ala Lys
    275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
        340                 345                 350

Pro Ser Arg Asp Glu Leu Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
            405                 410                 415

Trp Gln Gln Gly Asn Val Phe Ser Cys Ser Val Met His Glu Ala Leu
        420                 425                 430

His Asn His Tyr Thr Gln Lys Ser Leu Ser Leu Ser Pro Gly
    435                 440                 445

<210> SEQ ID NO 28
<211> LENGTH: 228
<212> TYPE: PRT
<213> ORGANISM: Artificial Sequence
<220> FEATURE:
<223> OTHER INFORMATION: Synthetic Construct

<400> SEQUENCE: 28

Ser Cys Leu Ser Gly Arg Ser Asp Asn His Gly Gly Gly Ser Asp Ile
1               5                   10                  15

Leu Leu Thr Gln Ser Pro Val Ile Leu Ser Val Ser Pro Gly Glu Arg
            20                  25                  30

Val Ser Phe Ser Cys Arg Ala Ser Gln Ser Ile Gly Thr Asn Ile His
        35                  40                  45

Trp Tyr Gln Gln Arg Thr Asn Gly Ser Pro Arg Leu Leu Ile Lys Tyr
    50                  55                  60

Ala Ser Glu Ser Ile Ser Gly Ile Pro Ser Arg Phe Ser Gly Ser Gly
65                  70                  75                  80

Ser Gly Thr Asp Phe Thr Leu Ser Ile Asn Ser Val Glu Ser Glu Asp
            85                  90                  95

Ile Ala Asp Tyr Tyr Cys Gln Gln Asn Asn Asn Trp Pro Thr Thr Phe
        100                 105                 110

Gly Ala Gly Thr Lys Leu Glu Leu Lys Arg Thr Val Ala Ala Pro Ser
    115                 120                 125

Val Phe Ile Phe Pro Pro Ser Asp Glu Gln Leu Lys Ser Gly Thr Ala

```
                130                 135                 140
Ser Val Val Cys Leu Leu Asn Asn Phe Tyr Pro Arg Glu Ala Lys Val
145                 150                 155                 160

Gln Trp Lys Val Asp Asn Ala Leu Gln Ser Gly Asn Ser Gln Glu Ser
                165                 170                 175

Val Thr Glu Gln Asp Ser Lys Asp Ser Thr Tyr Ser Leu Ser Ser Thr
                180                 185                 190

Leu Thr Leu Ser Lys Ala Asp Tyr Glu Lys His Lys Val Tyr Ala Cys
                195                 200                 205

Glu Val Thr His Gln Gly Leu Ser Ser Pro Val Thr Lys Ser Phe Asn
                210                 215                 220

Arg Gly Glu Ser
225

<210> SEQ ID NO 29
<211> LENGTH: 239
<212> TYPE: PRT
<213> ORGANISM: Artificial Sequence
<220> FEATURE:
<223> OTHER INFORMATION: Synthetic Construct

<400> SEQUENCE: 29

Leu Leu Gln Gly Leu Ser Gly Arg Ser Asp Asn His Gly Gly Gly Ser
1               5                   10                  15

Glu Val Gln Leu Val Glu Ser Gly Gly Gly Leu Val Gln Pro Gly Gly
                20                  25                  30

Ser Leu Arg Leu Ser Cys Ala Ala Ser Gly Phe Asn Ile Lys Asp Thr
                35                  40                  45

Tyr Ile His Trp Val Arg Gln Ala Pro Gly Lys Gly Leu Glu Trp Val
50                  55                  60

Ala Arg Ile Tyr Pro Thr Asn Gly Tyr Thr Arg Tyr Ala Asp Ser Val
65                  70                  75                  80

Lys Gly Arg Phe Thr Ile Ser Ala Asp Thr Ser Lys Asn Thr Ala Tyr
                85                  90                  95

Leu Gln Met Asn Ser Leu Arg Ala Glu Asp Thr Ala Val Tyr Tyr Cys
                100                 105                 110

Ser Arg Trp Gly Gly Asp Gly Phe Tyr Ala Met Asp Tyr Trp Gly Gln
                115                 120                 125

Gly Thr Leu Val Thr Val Ser Ser Ala Ser Thr Lys Gly Pro Ser Val
                130                 135                 140

Phe Pro Leu Ala Pro Ser Ser Lys Ser Thr Ser Gly Gly Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
                195                 200                 205

Ser Ser Ser Leu Gly Thr Gln Thr Tyr Ile Cys Asn Val Asn His Lys
                210                 215                 220

Pro Ser Asn Thr Lys Val Asp Lys Lys Val Glu Pro Lys Ser Cys
225                 230                 235

<210> SEQ ID NO 30
<211> LENGTH: 229
<212> TYPE: PRT
```

```
<213> ORGANISM: Artificial Sequence
<220> FEATURE:
<223> OTHER INFORMATION: Synthetic Construct

<400> SEQUENCE: 30

Gly Lys Gly Leu Ser Gly Arg Ser Asp Asn His Gly Gly Ser Asp
1               5                   10                  15

Ile Gln Met Thr Gln Ser Pro Ser Ser Leu Ser Ala Ser Val Gly Asp
                20                  25                  30

Arg Val Thr Ile Thr Cys Arg Ala Ser Gln Asp Val Asn Thr Ala Val
            35                  40                  45

Ala Trp Tyr Gln Gln Lys Pro Gly Lys Ala Pro Lys Leu Leu Ile Tyr
50                  55                  60

Ser Ala Ser Phe Leu Tyr Ser Gly Val Pro Ser Arg Phe Ser Gly Ser
65                  70                  75                  80

Arg Ser Gly Thr Asp Phe Thr Leu Thr Ile Ser Ser Leu Gln Pro Glu
                85                  90                  95

Asp Phe Ala Thr Tyr Tyr Cys Gln Gln His Tyr Thr Thr Pro Pro Thr
            100                 105                 110

Phe Gly Gln Gly Thr Lys Val Glu Ile Lys Arg Thr Val Ala Ala Pro
        115                 120                 125

Ser Val Phe Ile Phe Pro Pro Ser Asp Glu Gln Leu Lys Ser Gly Thr
130                 135                 140

Ala Ser Val Val Cys Leu Leu Asn Asn Phe Tyr Pro Arg Glu Ala Lys
145                 150                 155                 160

Val Gln Trp Lys Val Asp Asn Ala Leu Gln Ser Gly Asn Ser Gln Glu
                165                 170                 175

Ser Val Thr Glu Gln Asp Ser Lys Asp Ser Thr Tyr Ser Leu Ser Ser
            180                 185                 190

Thr Leu Thr Leu Ser Lys Ala Asp Tyr Glu Lys His Lys Val Tyr Ala
        195                 200                 205

Cys Glu Val Thr His Gln Gly Leu Ser Ser Pro Val Thr Lys Ser Phe
    210                 215                 220

Asn Arg Gly Glu Cys
225

<210> SEQ ID NO 31
<211> LENGTH: 237
<212> TYPE: PRT
<213> ORGANISM: Artificial Sequence
<220> FEATURE:
<223> OTHER INFORMATION: Synthetic Construct

<400> SEQUENCE: 31

Leu Leu Gln Gly Leu Ser Gly Arg Ser Asp Asn His Gly Gly Gly Ser
1               5                   10                  15

Gln Val Gln Leu Val Glu Ser Gly Gly Gly Val Val Gln Pro Gly Arg
                20                  25                  30

Ser Leu Arg Leu Ser Cys Ala Ala Ser Gly Phe Thr Phe Ser Ser Tyr
            35                  40                  45

Thr Met His Trp Val Arg Gln Ala Pro Gly Lys Gly Leu Glu Trp Val
50                  55                  60

Thr Phe Ile Ser Tyr Asp Gly Asn Asn Lys Tyr Tyr Ala Asp Ser Val
65                  70                  75                  80

Lys Gly Arg Phe Thr Ile Ser Arg Asp Asn Ser Lys Asn Thr Leu Tyr
                85                  90                  95
```

```
Leu Gln Met Asn Ser Leu Arg Ala Glu Asp Thr Ala Ile Tyr Tyr Cys
            100                 105                 110

Ala Arg Thr Gly Trp Leu Gly Pro Phe Asp Tyr Trp Gly Gln Gly Thr
            115                 120                 125

Leu Val Thr Val Ser Ser Ala Ser Thr Lys Gly Pro Ser Val Phe Pro
130                 135                 140

Leu Ala Pro Ser Ser Lys Ser Thr Ser Gly Gly Thr Ala Ala Leu Gly
145                 150                 155                 160

Cys Leu Val Lys Asp Tyr Phe Pro Glu Pro Val Thr Val Ser Trp Asn
            165                 170                 175

Ser Gly Ala Leu Thr Ser Gly Val His Thr Phe Pro Ala Val Leu Gln
            180                 185                 190

Ser Ser Gly Leu Tyr Ser Leu Ser Ser Val Val Thr Val Pro Ser Ser
            195                 200                 205

Ser Leu Gly Thr Gln Thr Tyr Ile Cys Asn Val Asn His Lys Pro Ser
            210                 215                 220

Asn Thr Lys Val Asp Lys Arg Val Glu Pro Lys Ser Cys
225                 230                 235

<210> SEQ ID NO 32
<211> LENGTH: 230
<212> TYPE: PRT
<213> ORGANISM: Artificial Sequence
<220> FEATURE:
<223> OTHER INFORMATION: Synthetic Construct

<400> SEQUENCE: 32

Gly Lys Gly Leu Ser Gly Arg Ser Asp Asn His Gly Gly Gly Ser Glu
1               5                   10                  15

Ile Val Leu Thr Gln Ser Pro Gly Thr Leu Ser Leu Ser Pro Gly Glu
            20                  25                  30

Arg Ala Thr Leu Ser Cys Arg Ala Ser Gln Ser Val Gly Ser Ser Tyr
            35                  40                  45

Leu Ala Trp Tyr Gln Gln Lys Pro Gly Gln Ala Pro Arg Leu Leu Ile
    50                  55                  60

Tyr Gly Ala Phe Ser Arg Ala Thr Gly Ile Pro Asp Arg Phe Ser Gly
65                  70                  75                  80

Ser Gly Ser Gly Thr Asp Phe Thr Leu Thr Ile Ser Arg Leu Glu Pro
            85                  90                  95

Glu Asp Phe Ala Val Tyr Tyr Cys Gln Gln Tyr Gly Ser Ser Pro Trp
            100                 105                 110

Thr Phe Gly Gln Gly Thr Lys Val Glu Ile Lys Arg Thr Val Ala Ala
            115                 120                 125

Pro Ser Val Phe Ile Phe Pro Pro Ser Asp Glu Gln Leu Lys Ser Gly
130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
            165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
            195                 200                 205

Ala Cys Glu Val Thr His Gln Gly Leu Ser Ser Pro Val Thr Lys Ser
210                 215                 220
```

Phe Asn Arg Gly Glu Cys
225                 230

<210> SEQ ID NO 33
<211> LENGTH: 234
<212> TYPE: PRT
<213> ORGANISM: Artificial Sequence
<220> FEATURE:
<223> OTHER INFORMATION: Synthetic Construct

<400> SEQUENCE: 33

Leu Leu Gln Gly Leu Ser Gly Arg Ser Asp Asn His Gly Gly Gly Ser
1               5                   10                  15

Gln Val Gln Leu Val Gln Ser Gly Val Glu Val Lys Lys Pro Gly Ala
            20                  25                  30

Ser Val Lys Val Ser Cys Lys Ala Ser Gly Tyr Thr Phe Thr Asn Tyr
        35                  40                  45

Tyr Met Tyr Trp Val Arg Gln Ala Pro Gly Gln Gly Leu Glu Trp Met
    50                  55                  60

Gly Gly Ile Asn Pro Ser Asn Gly Gly Thr Asn Phe Asn Glu Lys Phe
65                  70                  75                  80

Lys Asn Arg Val Thr Leu Thr Thr Asp Ser Ser Thr Thr Thr Ala Tyr
                85                  90                  95

Met Glu Leu Lys Ser Leu Gln Phe Asp Asp Thr Ala Val Tyr Tyr Cys
            100                 105                 110

Ala Arg Arg Asp Tyr Arg Phe Asp Met Gly Phe Asp Tyr Trp Gly Gln
        115                 120                 125

Gly Thr Thr Val Thr Val Ser Ser Ala Ser Thr Lys Gly Pro Ser Val
    130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
            180                 185                 190

Leu Gln Ser Ser Gly Leu Tyr Ser Leu Ser Ser Val Val Thr Val Pro
        195                 200                 205

Ser Ser Ser Leu Gly Thr Lys Thr Tyr Thr Cys Asn Val Asp His Lys
    210                 215                 220

Pro Ser Asn Thr Lys Val Asp Lys Arg Val
225                 230

<210> SEQ ID NO 34
<211> LENGTH: 233
<212> TYPE: PRT
<213> ORGANISM: Artificial Sequence
<220> FEATURE:
<223> OTHER INFORMATION: Synthetic Construct

<400> SEQUENCE: 34

Gly Lys Gly Leu Ser Gly Arg Ser Asp Asn His Gly Gly Gly Ser Glu
1               5                   10                  15

Ile Val Leu Thr Gln Ser Pro Ala Thr Leu Ser Leu Ser Pro Gly Glu
            20                  25                  30

Arg Ala Thr Leu Ser Cys Arg Ala Ser Lys Gly Val Ser Thr Ser Gly
        35                  40                  45

Tyr Ser Tyr Leu His Trp Tyr Gln Gln Lys Pro Gly Gln Ala Pro Arg
    50                  55                  60

```
Leu Leu Ile Tyr Leu Ala Ser Tyr Leu Glu Ser Gly Val Pro Ala Arg
 65                  70                  75                  80

Phe Ser Gly Ser Gly Ser Gly Thr Asp Phe Thr Leu Thr Ile Ser Ser
                 85                  90                  95

Leu Glu Pro Glu Asp Phe Ala Val Tyr Tyr Cys Gln His Ser Arg Asp
            100                 105                 110

Leu Pro Leu Thr Phe Gly Gly Gly Thr Lys Val Glu Ile Lys Arg Thr
            115                 120                 125

Val Ala Ala Pro Ser Val Phe Ile Phe Pro Pro Ser Asp Glu Gln Leu
130                 135                 140

Lys Ser Gly Thr Ala Ser Val Val Cys Leu Leu Asn Asn Phe Tyr Pro
145                 150                 155                 160

Arg Glu Ala Lys Val Gln Trp Lys Val Asp Asn Ala Leu Gln Ser Gly
                165                 170                 175

Asn Ser Gln Glu Ser Val Thr Glu Gln Asp Ser Lys Asp Ser Thr Tyr
            180                 185                 190

Ser Leu Ser Ser Thr Leu Thr Leu Ser Lys Ala Asp Tyr Glu Lys His
            195                 200                 205

Lys Val Tyr Ala Cys Glu Val Thr His Gln Gly Leu Ser Ser Pro Val
210                 215                 220

Thr Lys Ser Phe Asn Arg Gly Glu Cys
225                 230
```

<210> SEQ ID NO 35
<211> LENGTH: 114
<212> TYPE: PRT
<213> ORGANISM: Artificial Sequence
<220> FEATURE:
<223> OTHER INFORMATION: Synthetic Construct

<400> SEQUENCE: 35

```
Glu Val Gln Leu Leu Glu Ser Gly Gly Gly Leu Val Gln Pro Gly Gly
 1                5                  10                  15

Ser Leu Arg Leu Ser Cys Ala Ala Ser Gly Phe Thr Phe Ser Ser Phe
                 20                  25                  30

Ser Met Ser Trp Val Arg Gln Ala Pro Gly Lys Gly Leu Glu Trp Val
             35                  40                  45

Ser Ser Ile Ser Gly Ser Ser Gly Thr Thr Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys Pro Phe Pro Tyr Phe Asp Tyr Trp Gly Gln Gly Thr Leu Val
            100                 105                 110

Thr Val
```

<210> SEQ ID NO 36
<211> LENGTH: 107
<212> TYPE: PRT
<213> ORGANISM: Artificial Sequence
<220> FEATURE:
<223> OTHER INFORMATION: Synthetic Construct

<400> SEQUENCE: 36

```
Glu Ile Val Leu Thr Gln Ser Pro Gly Thr Leu Ser Leu Ser Pro Gly
 1                5                  10                  15
```

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Thr Gly Arg Ile Pro
                85                  90                  95

Pro Thr Phe Gly Gln Gly Thr Lys Val Glu Ile
            100                 105

<210> SEQ ID NO 37
<211> LENGTH: 616
<212> TYPE: PRT
<213> ORGANISM: Artificial Sequence
<220> FEATURE:
<223> OTHER INFORMATION: Synthetic Construct

<400> SEQUENCE: 37

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Leu Ser Gly Arg Ser Asp Asn His Gln Val Gln Leu Lys Gln Ser Gly
                165                 170                 175

Pro Gly Leu Val Gln Pro Ser Gln Ser Leu Ser Ile Thr Cys Thr Val
            180                 185                 190

Ser Gly Phe Ser Leu Thr Asn Tyr Gly Val His Trp Val Arg Gln Ser
        195                 200                 205

Pro Gly Lys Gly Leu Glu Trp Leu Gly Val Ile Trp Ser Gly Gly Asn
    210                 215                 220

Thr Asp Tyr Asn Thr Pro Phe Thr Ser Arg Leu Ser Ile Asn Lys Asp
225                 230                 235                 240

Asn Ser Lys Ser Gln Val Phe Phe Lys Met Asn Ser Leu Gln Ser Glu
                245                 250                 255

Asp Thr Ala Ile Tyr Tyr Cys Ala Arg Ala Leu Thr Tyr Tyr Asp Tyr
            260                 265                 270

Glu Phe Ala Tyr Trp Gly Gln Gly Thr Leu Val Thr Val Ser Ala Ala
            275                 280                 285

Ser Thr Lys Gly Pro Ser Val Phe Pro Leu Ala Pro Ser Ser Lys Ser
        290                 295                 300

Thr Ser Gly Gly Thr Ala Ala Leu Gly Cys Leu Val Lys Asp Tyr Phe
305                 310                 315                 320

Pro Glu Pro Val Thr Val Ser Trp Asn Ser Gly Ala Leu Thr Ser Gly
                325                 330                 335

Val His Thr Phe Pro Ala Val Leu Gln Ser Ser Gly Leu Tyr Ser Leu
            340                 345                 350

Ser Ser Val Val Thr Val Pro Ser Ser Ser Leu Gly Thr Gln Thr Tyr
        355                 360                 365

Ile Cys Asn Val Asn His Lys Pro Ser Asn Thr Lys Val Asp Lys Lys
    370                 375                 380

Val Glu Pro Lys Ser Cys Asp Lys Thr His Thr Cys Pro Pro Cys Pro
385                 390                 395                 400

Ala Pro Glu Leu Leu Gly Gly Pro Ser Val Phe Leu Phe Pro Pro Lys
                405                 410                 415

Pro Lys Asp Thr Leu Met Ile Ser Arg Thr Pro Glu Val Thr Cys Val
            420                 425                 430

Val Val Asp Val Ser His Glu Asp Pro Glu Val Lys Phe Asn Trp Tyr
        435                 440                 445

Val Asp Gly Val Glu Val His Asn Ala Lys Thr Lys Pro Arg Glu Glu
    450                 455                 460

Gln Tyr Asn Ser Thr Tyr Arg Val Val Ser Val Leu Thr Val Leu His
465                 470                 475                 480

Gln Asp Trp Leu Asn Gly Lys Glu Tyr Lys Cys Lys Val Ser Asn Lys
                485                 490                 495

Ala Leu Pro Ala Pro Ile Glu Lys Thr Ile Ser Lys Ala Lys Gly Gln
            500                 505                 510

Pro Arg Glu Pro Gln Val Tyr Thr Leu Pro Pro Ser Arg Asp Glu Leu
        515                 520                 525

Thr Lys Asn Gln Val Ser Leu Thr Cys Leu Val Lys Gly Phe Tyr Pro
    530                 535                 540

Ser Asp Ile Ala Val Glu Trp Glu Ser Asn Gly Gln Pro Glu Asn Asn
545                 550                 555                 560

Tyr Lys Thr Thr Pro Pro Val Leu Asp Ser Asp Gly Ser Phe Phe Leu
                565                 570                 575

Tyr Ser Lys Leu Thr Val Asp Lys Ser Arg Trp Gln Gln Gly Asn Val
            580                 585                 590

Phe Ser Cys Ser Val Met His Glu Ala Leu His Asn His Tyr Thr Gln
        595                 600                 605

Lys Ser Leu Ser Leu Ser Pro Gly
    610                 615

<210> SEQ ID NO 38
<211> LENGTH: 382
<212> TYPE: PRT
<213> ORGANISM: Artificial Sequence
<220> FEATURE:
<223> OTHER INFORMATION: Synthetic Construct

<400> SEQUENCE: 38

Ser Pro Gly Gln Gly Thr Gln Ser Glu Asn Ser Cys Thr His Phe Pro
1               5                   10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
 50                  55                  60

Leu Ser Glu Met Ile Gln Phe Tyr Leu Glu Glu Val Met Pro Gln Ala
 65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
130                 135                 140

Ile Phe Ile Asn Tyr Ile Glu Ala Tyr Met Thr Met Lys Ile Arg Asn
145                 150                 155                 160

Leu Ser Gly Arg Ser Asp Asn His Asp Ile Leu Leu Thr Gln Ser Pro
                165                 170                 175

Val Ile Leu Ser Val Ser Pro Gly Glu Arg Val Ser Phe Ser Cys Arg
            180                 185                 190

Ala Ser Gln Ser Ile Gly Thr Asn Ile His Trp Tyr Gln Gln Arg Thr
        195                 200                 205

Asn Gly Ser Pro Arg Leu Leu Ile Lys Tyr Ala Ser Glu Ser Ile Ser
210                 215                 220

Gly Ile Pro Ser Arg Phe Ser Gly Ser Gly Ser Gly Thr Asp Phe Thr
225                 230                 235                 240

Leu Ser Ile Asn Ser Val Glu Ser Glu Asp Ile Ala Asp Tyr Tyr Cys
                245                 250                 255

Gln Gln Asn Asn Asn Trp Pro Thr Thr Phe Gly Ala Gly Thr Lys Leu
            260                 265                 270

Glu Leu Lys Arg Thr Val Ala Ala Pro Ser Val Phe Ile Phe Pro Pro
        275                 280                 285

Ser Asp Glu Gln Leu Lys Ser Gly Thr Ala Ser Val Val Cys Leu Leu
290                 295                 300

Asn Asn Phe Tyr Pro Arg Glu Ala Lys Val Gln Trp Lys Val Asp Asn
305                 310                 315                 320

Ala Leu Gln Ser Gly Asn Ser Gln Glu Ser Val Thr Glu Gln Asp Ser
                325                 330                 335

Lys Asp Ser Thr Tyr Ser Leu Ser Ser Thr Leu Thr Leu Ser Lys Ala
            340                 345                 350

Asp Tyr Glu Lys His Lys Val Tyr Ala Cys Glu Val Thr His Gln Gly
        355                 360                 365

Leu Ser Ser Pro Val Thr Lys Ser Phe Asn Arg Gly Glu Cys
370                 375                 380

<210> SEQ ID NO 39
<211> LENGTH: 490
<212> TYPE: PRT
<213> ORGANISM: Artificial Sequence
<220> FEATURE:
<223> OTHER INFORMATION: Synthetic Construct

<400> SEQUENCE: 39

```
Met Gln Ile Phe Val Lys Thr Leu Thr Gly Lys Thr Ile Thr Leu Glu
1               5                   10                  15
Val Glu Pro Ser Asp Thr Ile Glu Asn Val Lys Ala Lys Ile Gln Asp
            20                  25                  30
Lys Glu Leu Ser Gly Arg Ser Asp Asn His Gln Val Gln Leu Lys Gln
        35                  40                  45
Ser Gly Pro Gly Leu Val Gln Pro Ser Gln Ser Leu Ser Ile Thr Cys
    50                  55                  60
Thr Val Ser Gly Phe Ser Leu Thr Asn Tyr Gly Val His Trp Val Arg
65                  70                  75                  80
Gln Ser Pro Gly Lys Gly Leu Glu Trp Leu Gly Val Ile Trp Ser Gly
            85                  90                  95
Gly Asn Thr Asp Tyr Asn Thr Pro Phe Thr Ser Arg Leu Ser Ile Asn
        100                 105                 110
Lys Asp Asn Ser Lys Ser Gln Val Phe Phe Lys Met Asn Ser Leu Gln
    115                 120                 125
Ser Glu Asp Thr Ala Ile Tyr Tyr Cys Ala Arg Ala Leu Thr Tyr Tyr
    130                 135                 140
Asp Tyr Glu Phe Ala Tyr Trp Gly Gln Gly Thr Leu Val Thr Val Ser
145                 150                 155                 160
Ala Ala Ser Thr Lys Gly Pro Ser Val Phe Pro Leu Ala Pro Ser Ser
            165                 170                 175
Lys Ser Thr Ser Gly Gly Thr Ala Ala Leu Gly Cys Leu Val Lys Asp
        180                 185                 190
Tyr Phe Pro Glu Pro Val Thr Val Ser Trp Asn Ser Gly Ala Leu Thr
    195                 200                 205
Ser Gly Val His Thr Phe Pro Ala Val Leu Gln Ser Ser Gly Leu Tyr
    210                 215                 220
Ser Leu Ser Ser Val Val Thr Val Pro Ser Ser Ser Leu Gly Thr Gln
225                 230                 235                 240
Thr Tyr Ile Cys Asn Val Asn His Lys Pro Ser Asn Thr Lys Val Asp
            245                 250                 255
Lys Lys Val Glu Pro Lys Ser Cys Asp Lys Thr His Thr Cys Pro Pro
        260                 265                 270
Cys Pro Ala Pro Glu Leu Leu Gly Gly Pro Ser Val Phe Leu Phe Pro
    275                 280                 285
Pro Lys Pro Lys Asp Thr Leu Met Ile Ser Arg Thr Pro Glu Val Thr
    290                 295                 300
Cys Val Val Val Asp Val Ser His Glu Asp Pro Glu Val Lys Phe Asn
305                 310                 315                 320
Trp Tyr Val Asp Gly Val Glu Val His Asn Ala Lys Thr Lys Pro Arg
            325                 330                 335
Glu Glu Gln Tyr Asn Ser Thr Tyr Arg Val Val Ser Val Leu Thr Val
        340                 345                 350
Leu His Gln Asp Trp Leu Asn Gly Lys Glu Tyr Lys Cys Lys Val Ser
    355                 360                 365
Asn Lys Ala Leu Pro Ala Pro Ile Glu Lys Thr Ile Ser Lys Ala Lys
    370                 375                 380
Gly Gln Pro Arg Glu Pro Gln Val Tyr Thr Leu Pro Pro Ser Arg Asp
385                 390                 395                 400
Glu Leu Thr Lys Asn Gln Val Ser Leu Thr Cys Leu Val Lys Gly Phe
            405                 410                 415
```

```
Tyr Pro Ser Asp Ile Ala Val Glu Trp Glu Ser Asn Gly Gln Pro Glu
            420                 425                 430

Asn Asn Tyr Lys Thr Thr Pro Pro Val Leu Asp Ser Asp Gly Ser Phe
        435                 440                 445

Phe Leu Tyr Ser Lys Leu Thr Val Asp Lys Ser Arg Trp Gln Gln Gly
450                 455                 460

Asn Val Phe Ser Cys Ser Val Met His Glu Ala Leu His Asn His Tyr
465                 470                 475                 480

Thr Gln Lys Ser Leu Ser Leu Ser Pro Gly
            485                 490

<210> SEQ ID NO 40
<211> LENGTH: 264
<212> TYPE: PRT
<213> ORGANISM: Artificial Sequence
<220> FEATURE:
<223> OTHER INFORMATION: Synthetic Construct

<400> SEQUENCE: 40

Gly Ile Pro Pro Asp Gln Gln Arg Leu Ile Phe Ala Gly Lys Gln Leu
1               5                   10                  15

Glu Asp Gly Arg Thr Leu Ser Asp Tyr Asn Ile Gln Lys Glu Ser Thr
            20                  25                  30

Leu His Leu Val Leu Arg Leu Arg Gly Gly Leu Ser Gly Arg Ser Asp
        35                  40                  45

Asn His Asp Ile Leu Leu Thr Gln Ser Pro Val Ile Leu Ser Val Ser
    50                  55                  60

Pro Gly Glu Arg Val Ser Phe Ser Cys Arg Ala Ser Gln Ser Ile Gly
65                  70                  75                  80

Thr Asn Ile His Trp Tyr Gln Gln Arg Thr Asn Gly Ser Pro Arg Leu
            85                  90                  95

Leu Ile Lys Tyr Ala Ser Glu Ser Ile Ser Gly Ile Pro Ser Arg Phe
        100                 105                 110

Ser Gly Ser Gly Ser Gly Thr Asp Phe Thr Leu Ser Ile Asn Ser Val
    115                 120                 125

Glu Ser Glu Asp Ile Ala Asp Tyr Tyr Cys Gln Gln Asn Asn Asn Trp
130                 135                 140

Pro Thr Thr Phe Gly Ala Gly Thr Lys Leu Glu Leu Lys Arg Thr Val
145                 150                 155                 160

Ala Ala Pro Ser Val Phe Ile Phe Pro Pro Ser Asp Glu Gln Leu Lys
            165                 170                 175

Ser Gly Thr Ala Ser Val Val Cys Leu Leu Asn Asn Phe Tyr Pro Arg
        180                 185                 190

Glu Ala Lys Val Gln Trp Lys Val Asp Asn Ala Leu Gln Ser Gly Asn
    195                 200                 205

Ser Gln Glu Ser Val Thr Glu Gln Asp Ser Lys Asp Ser Thr Tyr Ser
210                 215                 220

Leu Ser Ser Thr Leu Thr Leu Ser Lys Ala Asp Tyr Glu Lys His Lys
225                 230                 235                 240

Val Tyr Ala Cys Glu Val Thr His Gln Gly Leu Ser Ser Pro Val Thr
            245                 250                 255

Lys Ser Phe Asn Arg Gly Glu Cys
        260

<210> SEQ ID NO 41
<211> LENGTH: 526
```

```
<212> TYPE: PRT
<213> ORGANISM: Artificial Sequence
<220> FEATURE:
<223> OTHER INFORMATION: Synthetic Construct

<400> SEQUENCE: 41

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
        35                  40                  45

Arg Lys Ile Cys Leu Asp Leu Gln Ala Pro Leu Tyr Lys Lys Ile Ile
    50                  55                  60

Lys Lys Leu Leu Glu Ser Leu Ser Gly Arg Ser Asp Asn His Gln Val
65                  70                  75                  80

Gln Leu Lys Gln Ser Gly Pro Gly Leu Val Gln Pro Ser Gln Ser Leu
                85                  90                  95

Ser Ile Thr Cys Thr Val Ser Gly Phe Ser Leu Thr Asn Tyr Gly Val
            100                 105                 110

His Trp Val Arg Gln Ser Pro Gly Lys Gly Leu Glu Trp Leu Gly Val
        115                 120                 125

Ile Trp Ser Gly Gly Asn Thr Asp Tyr Asn Thr Pro Phe Thr Ser Arg
    130                 135                 140

Leu Ser Ile Asn Lys Asp Asn Ser Lys Ser Gln Val Phe Phe Lys Met
145                 150                 155                 160

Asn Ser Leu Gln Ser Glu Asp Thr Ala Ile Tyr Tyr Cys Ala Arg Ala
                165                 170                 175

Leu Thr Tyr Tyr Asp Tyr Glu Phe Ala Tyr Trp Gly Gln Gly Thr Leu
            180                 185                 190

Val Thr Val Ser Ala Ala Ser Thr Lys Gly Pro Ser Val Phe Pro Leu
        195                 200                 205

Ala Pro Ser Ser Lys Ser Thr Ser Gly Gly Thr Ala Ala Leu Gly Cys
    210                 215                 220

Leu Val Lys Asp Tyr Phe Pro Glu Pro Val Thr Val Ser Trp Asn Ser
225                 230                 235                 240

Gly Ala Leu Thr Ser Gly Val His Thr Phe Pro Ala Val Leu Gln Ser
                245                 250                 255

Ser Gly Leu Tyr Ser Leu Ser Ser Val Val Thr Val Pro Ser Ser Ser
            260                 265                 270

Leu Gly Thr Gln Thr Tyr Ile Cys Asn Val Asn His Lys Pro Ser Asn
        275                 280                 285

Thr Lys Val Asp Lys Lys Val Glu Pro Lys Ser Cys Asp Lys Thr His
    290                 295                 300

Thr Cys Pro Pro Cys Pro Ala Pro Glu Leu Leu Gly Gly Pro Ser Val
305                 310                 315                 320

Phe Leu Phe Pro Pro Lys Pro Lys Asp Thr Leu Met Ile Ser Arg Thr
                325                 330                 335

Pro Glu Val Thr Cys Val Val Val Asp Val Ser His Glu Asp Pro Glu
            340                 345                 350

Val Lys Phe Asn Trp Tyr Val Asp Gly Val Glu Val His Asn Ala Lys
        355                 360                 365

Thr Lys Pro Arg Glu Glu Gln Tyr Asn Ser Thr Tyr Arg Val Val Ser
    370                 375                 380
```

```
Val Leu Thr Val Leu His Gln Asp Trp Leu Asn Gly Lys Glu Tyr Lys
385                 390                 395                 400

Cys Lys Val Ser Asn Lys Ala Leu Pro Ala Pro Ile Glu Lys Thr Ile
            405                 410                 415

Ser Lys Ala Lys Gly Gln Pro Arg Glu Pro Gln Val Tyr Thr Leu Pro
            420                 425                 430

Pro Ser Arg Asp Glu Leu Thr Lys Asn Gln Val Ser Leu Thr Cys Leu
            435                 440                 445

Val Lys Gly Phe Tyr Pro Ser Asp Ile Ala Val Glu Trp Glu Ser Asn
            450                 455                 460

Gly Gln Pro Glu Asn Asn Tyr Lys Thr Thr Pro Pro Val Leu Asp Ser
465                 470                 475                 480

Asp Gly Ser Phe Phe Leu Tyr Ser Lys Leu Thr Val Asp Lys Ser Arg
            485                 490                 495

Trp Gln Gln Gly Asn Val Phe Ser Cys Ser Val Met His Glu Ala Leu
            500                 505                 510

His Asn His Tyr Thr Gln Lys Ser Leu Ser Leu Ser Pro Gly
            515                 520                 525

<210> SEQ ID NO 42
<211> LENGTH: 292
<212> TYPE: PRT
<213> ORGANISM: Artificial Sequence
<220> FEATURE:
<223> OTHER INFORMATION: Synthetic Construct

<400> SEQUENCE: 42

Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
            35                  40                  45

Arg Lys Ile Cys Leu Asp Leu Gln Ala Pro Leu Tyr Lys Lys Ile Ile
        50                  55                  60

Lys Lys Leu Leu Glu Ser Leu Ser Gly Arg Ser Asp Asn His Asp Ile
65                  70                  75                  80

Leu Leu Thr Gln Ser Pro Val Ile Leu Ser Val Ser Pro Gly Glu Arg
            85                  90                  95

Val Ser Phe Ser Cys Arg Ala Ser Gln Ser Ile Gly Thr Asn Ile His
            100                 105                 110

Trp Tyr Gln Gln Arg Thr Asn Gly Ser Pro Arg Leu Leu Ile Lys Tyr
            115                 120                 125

Ala Ser Glu Ser Ile Ser Gly Ile Pro Ser Arg Phe Ser Gly Ser Gly
130                 135                 140

Ser Gly Thr Asp Phe Thr Leu Ser Ile Asn Ser Val Glu Ser Glu Asp
145                 150                 155                 160

Ile Ala Asp Tyr Tyr Cys Gln Gln Asn Asn Asn Trp Pro Thr Thr Phe
            165                 170                 175

Gly Ala Gly Thr Lys Leu Glu Leu Lys Arg Thr Val Ala Ala Pro Ser
            180                 185                 190

Val Phe Ile Phe Pro Pro Ser Asp Glu Gln Leu Lys Ser Gly Thr Ala
            195                 200                 205

Ser Val Val Cys Leu Leu Asn Asn Phe Tyr Pro Arg Glu Ala Lys Val
210                 215                 220
```

```
Gln Trp Lys Val Asp Asn Ala Leu Gln Ser Gly Asn Ser Gln Glu Ser
225                 230                 235                 240

Val Thr Glu Gln Asp Ser Lys Asp Ser Thr Tyr Ser Leu Ser Ser Thr
            245                 250                 255

Leu Thr Leu Ser Lys Ala Asp Tyr Glu Lys His Lys Val Tyr Ala Cys
            260                 265                 270

Glu Val Thr His Gln Gly Leu Ser Ser Pro Val Thr Lys Ser Phe Asn
            275                 280                 285

Arg Gly Glu Cys
    290

<210> SEQ ID NO 43
<211> LENGTH: 486
<212> TYPE: PRT
<213> ORGANISM: Artificial Sequence
<220> FEATURE:
<223> OTHER INFORMATION: Synthetic Construct

<400> SEQUENCE: 43

Glu Asn Lys Gln Val Glu Ile Leu Arg Leu Lys Glu Ile Glu
1               5                   10                  15

Asp Leu Gln Arg Met Lys Glu Gln Glu Leu Ser Leu Thr Leu Ser
            20                  25                  30

Gly Arg Ser Asp Asn His Gln Val Gln Leu Lys Gln Ser Gly Pro Gly
        35                  40                  45

Leu Val Gln Pro Ser Gln Ser Leu Ser Ile Thr Cys Thr Val Ser Gly
    50                  55                  60

Phe Ser Leu Thr Asn Tyr Gly Val His Trp Val Arg Gln Ser Pro Gly
65                  70                  75                  80

Lys Gly Leu Glu Trp Leu Gly Val Ile Trp Ser Gly Gly Asn Thr Asp
                85                  90                  95

Tyr Asn Thr Pro Phe Thr Ser Arg Leu Ser Ile Asn Lys Asp Asn Ser
            100                 105                 110

Lys Ser Gln Val Phe Phe Lys Met Asn Ser Leu Gln Ser Glu Asp Thr
        115                 120                 125

Ala Ile Tyr Tyr Cys Ala Arg Ala Leu Thr Tyr Tyr Asp Tyr Glu Phe
    130                 135                 140

Ala Tyr Trp Gly Gln Gly Thr Leu Val Thr Val Ser Ala Ala Ser Thr
145                 150                 155                 160

Lys Gly Pro Ser Val Phe Pro Leu Ala Pro Ser Ser Lys Ser Thr Ser
                165                 170                 175

Gly Gly Thr Ala Ala Leu Gly Cys Leu Val Lys Asp Tyr Phe Pro Glu
            180                 185                 190

Pro Val Thr Val Ser Trp Asn Ser Gly Ala Leu Thr Ser Gly Val His
        195                 200                 205

Thr Phe Pro Ala Val Leu Gln Ser Ser Gly Leu Tyr Ser Leu Ser Ser
    210                 215                 220

Val Val Thr Val Pro Ser Ser Ser Leu Gly Thr Gln Thr Tyr Ile Cys
225                 230                 235                 240

Asn Val Asn His Lys Pro Ser Asn Thr Lys Val Asp Lys Lys Val Glu
                245                 250                 255

Pro Lys Ser Cys Asp Lys Thr His Thr Cys Pro Pro Cys Pro Ala Pro
            260                 265                 270

Glu Leu Leu Gly Gly Pro Ser Val Phe Leu Phe Pro Pro Lys Pro Lys
        275                 280                 285
```

```
Asp Thr Leu Met Ile Ser Arg Thr Pro Glu Val Cys Val Val
    290                 295                 300

Asp Val Ser His Glu Asp Pro Glu Val Lys Phe Asn Trp Tyr Val Asp
305                 310                 315                 320

Gly Val Glu Val His Asn Ala Lys Thr Lys Pro Arg Glu Gln Tyr
                325                 330                 335

Asn Ser Thr Tyr Arg Val Val Ser Val Leu Thr Val Leu His Gln Asp
                340                 345                 350

Trp Leu Asn Gly Lys Glu Tyr Lys Cys Lys Val Ser Asn Lys Ala Leu
                355                 360                 365

Pro Ala Pro Ile Glu Lys Thr Ile Ser Lys Ala Lys Gly Gln Pro Arg
370                 375                 380

Glu Pro Gln Val Tyr Thr Leu Pro Pro Ser Arg Asp Glu Leu Thr Lys
385                 390                 395                 400

Asn Gln Val Ser Leu Thr Cys Leu Val Lys Gly Phe Tyr Pro Ser Asp
                405                 410                 415

Ile Ala Val Glu Trp Glu Ser Asn Gly Gln Pro Glu Asn Asn Tyr Lys
                420                 425                 430

Thr Thr Pro Pro Val Leu Asp Ser Asp Gly Ser Phe Phe Leu Tyr Ser
                435                 440                 445

Lys Leu Thr Val Asp Lys Ser Arg Trp Gln Gln Gly Asn Val Phe Ser
450                 455                 460

Cys Ser Val Met His Glu Ala Leu His Asn His Tyr Thr Gln Lys Ser
465                 470                 475                 480

Leu Ser Leu Ser Pro Gly
                485

<210> SEQ ID NO 44
<211> LENGTH: 252
<212> TYPE: PRT
<213> ORGANISM: Artificial Sequence
<220> FEATURE:
<223> OTHER INFORMATION: Synthetic Construct

<400> SEQUENCE: 44

Glu Asn Lys Gln Val Glu Glu Ile Leu Arg Leu Glu Lys Glu Ile Glu
1               5                   10                  15

Asp Leu Gln Arg Met Lys Glu Gln Glu Leu Ser Leu Thr Leu Ser
                20                  25                  30

Gly Arg Ser Asp Asn His Asp Ile Leu Leu Thr Gln Ser Pro Val Ile
            35                  40                  45

Leu Ser Val Ser Pro Gly Glu Arg Val Ser Phe Ser Cys Arg Ala Ser
    50                  55                  60

Gln Ser Ile Gly Thr Asn Ile His Trp Tyr Gln Gln Arg Thr Asn Gly
65                  70                  75                  80

Ser Pro Arg Leu Leu Ile Lys Tyr Ala Ser Glu Ser Ile Ser Gly Ile
                85                  90                  95

Pro Ser Arg Phe Ser Gly Ser Gly Ser Gly Thr Asp Phe Thr Leu Ser
                100                 105                 110

Ile Asn Ser Val Glu Ser Glu Asp Ile Ala Asp Tyr Tyr Cys Gln Gln
            115                 120                 125

Asn Asn Asn Trp Pro Thr Thr Phe Gly Ala Gly Thr Lys Leu Glu Leu
        130                 135                 140

Lys Arg Thr Val Ala Ala Pro Ser Val Phe Ile Phe Pro Pro Ser Asp
145                 150                 155                 160
```

```
Glu Gln Leu Lys Ser Gly Thr Ala Ser Val Val Cys Leu Leu Asn Asn
                165                 170                 175

Phe Tyr Pro Arg Glu Ala Lys Val Gln Trp Lys Val Asp Asn Ala Leu
            180                 185                 190

Gln Ser Gly Asn Ser Gln Glu Ser Val Thr Glu Gln Asp Ser Lys Asp
        195                 200                 205

Ser Thr Tyr Ser Leu Ser Ser Thr Leu Thr Leu Ser Lys Ala Asp Tyr
    210                 215                 220

Glu Lys His Lys Val Tyr Ala Cys Glu Val Thr His Gln Gly Leu Ser
225                 230                 235                 240

Ser Pro Val Thr Lys Ser Phe Asn Arg Gly Glu Cys
                245                 250
```

<210> SEQ ID NO 45
<211> LENGTH: 572
<212> TYPE: PRT
<213> ORGANISM: Artificial Sequence
<220> FEATURE:
<223> OTHER INFORMATION: Synthetic Construct

<400> SEQUENCE: 45

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Phe
            20                  25                  30

Ser Met Ser Trp Val Arg Gln Ala Pro Gly Lys Gly Leu Glu Trp Val
        35                  40                  45

Ser Ser Ile Ser Gly Ser Ser Gly Thr Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Leu Ser Gly Arg Ser Asp Asn His Val Gln Leu Val Glu Ser
        115                 120                 125

Gly Gly Gly Val Val Gln Pro Gly Arg Ser Leu Arg Leu Ser Cys Ala
    130                 135                 140

Ala Ser Gly Phe Thr Phe Ser Ser Tyr Gly Met His Trp Val Arg Gln
145                 150                 155                 160

Ala Pro Gly Lys Gly Leu Glu Trp Val Ala Val Ile Trp Tyr Asp Gly
                165                 170                 175

Ser Asn Lys Tyr Tyr Ala Asp Ser Val Lys Gly Arg Phe Thr Ile Ser
            180                 185                 190

Arg Asp Asn Ser Lys Asn Thr Leu Tyr Leu Gln Met Asn Ser Leu Arg
        195                 200                 205

Ala Glu Asp Thr Ala Val Tyr Tyr Cys Ala Arg Asp Pro Arg Gly Ala
    210                 215                 220

Thr Leu Tyr Tyr Tyr Tyr Tyr Gly Met Asp Val Trp Gly Gln Gly Thr
225                 230                 235                 240

Thr Val Thr Val Ser Ser Ala Ser Thr Lys Gly Pro Ser Val Phe Pro
                245                 250                 255

Leu Ala Pro Cys Ser Arg Ser Thr Ser Glu Ser Thr Ala Ala Leu Gly
            260                 265                 270
```

```
Cys Leu Val Lys Asp Tyr Phe Pro Glu Pro Val Thr Val Ser Trp Asn
            275                 280                 285

Ser Gly Ala Leu Thr Ser Gly Val His Thr Phe Pro Ala Val Leu Gln
        290                 295                 300

Ser Ser Gly Leu Tyr Ser Leu Ser Ser Val Val Thr Val Pro Ser Ser
305                 310                 315                 320

Asn Phe Gly Thr Gln Thr Tyr Thr Cys Asn Val Asp His Lys Pro Ser
                325                 330                 335

Asn Thr Lys Val Asp Lys Thr Val Glu Arg Lys Cys Cys Val Glu Cys
            340                 345                 350

Pro Pro Cys Pro Ala Pro Pro Val Ala Gly Pro Ser Val Phe Leu Phe
        355                 360                 365

Pro Pro Lys Pro Lys Asp Thr Leu Met Ile Ser Arg Thr Pro Glu Val
370                 375                 380

Thr Cys Val Val Val Asp Val Ser His Glu Asp Pro Glu Val Gln Phe
385                 390                 395                 400

Asn Trp Tyr Val Asp Gly Val Glu Val His Asn Ala Lys Thr Lys Pro
                405                 410                 415

Arg Glu Glu Gln Phe Asn Ser Thr Phe Arg Val Val Ser Val Leu Thr
            420                 425                 430

Val Val His Gln Asp Trp Leu Asn Gly Lys Glu Tyr Lys Cys Lys Val
        435                 440                 445

Ser Asn Lys Gly Leu Pro Ala Pro Ile Glu Lys Thr Ile Ser Lys Thr
450                 455                 460

Lys Gly Gln Pro Arg Glu Pro Gln Val Tyr Thr Leu Pro Pro Ser Arg
465                 470                 475                 480

Glu Glu Met Thr Lys Asn Gln Val Ser Leu Thr Cys Leu Val Lys Gly
                485                 490                 495

Phe Tyr Pro Ser Asp Ile Ala Val Glu Trp Glu Ser Asn Gly Gln Pro
            500                 505                 510

Glu Asn Asn Tyr Lys Thr Thr Pro Pro Met Leu Asp Ser Asp Gly Ser
        515                 520                 525

Phe Phe Leu Tyr Ser Lys Leu Thr Val Asp Lys Ser Arg Trp Gln Gln
530                 535                 540

Gly Asn Val Phe Ser Cys Ser Val Met His Glu Ala Leu His Asn His
545                 550                 555                 560

Tyr Thr Gln Lys Ser Leu Ser Leu Ser Pro Gly Lys
                565                 570

<210> SEQ ID NO 46
<211> LENGTH: 328
<212> TYPE: PRT
<213> ORGANISM: Artificial Sequence
<220> FEATURE:
<223> OTHER INFORMATION: Synthetic Construct

<400> SEQUENCE: 46

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Tyr Ala Ser Ser Arg Ala Thr Gly Ile Pro Asp Arg Phe Ser
    50                  55                  60
```

-continued

```
Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Thr Gly Arg Ile Pro
                 85                  90                  95

Pro Thr Phe Gly Gln Gly Thr Lys Val Glu Ile Leu Ser Gly Arg Ser
            100                 105                 110

Asp Asn His Ile Gln Met Thr Gln Ser Pro Ser Ser Leu Ser Ala Ser
        115                 120                 125

Val Gly Asp Arg Val Thr Ile Thr Cys Arg Ala Ser Gln Ser Ile Asn
    130                 135                 140

Ser Tyr Leu Asp Trp Tyr Gln Gln Lys Pro Gly Lys Ala Pro Lys Leu
145                 150                 155                 160

Leu Ile Tyr Ala Ala Ser Ser Leu Gln Ser Gly Val Pro Ser Arg Phe
                165                 170                 175

Ser Gly Ser Gly Ser Gly Thr Asp Phe Thr Leu Thr Ile Ser Ser Leu
            180                 185                 190

Gln Pro Glu Asp Phe Ala Thr Tyr Tyr Cys Gln Gln Tyr Tyr Ser Thr
        195                 200                 205

Pro Phe Thr Phe Gly Pro Gly Thr Lys Val Glu Ile Lys Arg Thr Val
    210                 215                 220

Ala Ala Pro Ser Val Phe Ile Phe Pro Pro Ser Asp Glu Gln Leu Lys
225                 230                 235                 240

Ser Gly Thr Ala Ser Val Val Cys Leu Leu Asn Asn Phe Tyr Pro Arg
                245                 250                 255

Glu Ala Lys Val Gln Trp Lys Val Asp Asn Ala Leu Gln Ser Gly Asn
            260                 265                 270

Ser Gln Glu Ser Val Thr Glu Gln Asp Ser Lys Asp Ser Thr Tyr Ser
        275                 280                 285

Leu Ser Ser Thr Leu Thr Leu Ser Lys Ala Asp Tyr Glu Lys His Lys
    290                 295                 300

Val Tyr Ala Cys Glu Val Thr His Gln Gly Leu Ser Ser Pro Val Thr
305                 310                 315                 320

Lys Ser Phe Asn Arg Gly Glu Cys
                325

<210> SEQ ID NO 47
<211> LENGTH: 666
<212> TYPE: PRT
<213> ORGANISM: Artificial Sequence
<220> FEATURE:
<223> OTHER INFORMATION: Synthetic Construct

<400> SEQUENCE: 47

Gln Ser Cys Ala Thr Gly Pro Arg Asn Cys Lys Asp Leu Leu Asp Arg
 1               5                  10                  15

Gly Tyr Phe Arg Ser Gly Trp His Thr Ile Tyr Leu Pro Asp Cys Arg
                20                  25                  30

Pro Leu Thr Val Leu Cys Asp Met Asp Thr Asp Gly Gly Gly Trp Thr
            35                  40                  45

Val Phe Gln Arg Arg Met Asp Gly Ser Val Asp Phe Tyr Arg Asp Trp
    50                  55                  60

Ala Ala Tyr Lys Gln Gly Phe Gly Ser Gln Leu Gly Glu Phe Trp Leu
 65                 70                  75                  80

Gly Asn Asp Asn Ile His Ala Leu Thr Ala Gln Gly Ser Ser Glu Leu
                85                  90                  95
```

-continued

```
Arg Thr Asp Leu Val Asp Phe Glu Gly Asn His Gln Phe Ala Lys Tyr
                100                 105                 110
Lys Ser Phe Lys Val Ala Asp Glu Ala Glu Lys Tyr Lys Leu Val Leu
            115                 120                 125
Gly Ala Phe Val Gly Gly Ser Ala Gly Asn Ser Leu Thr Gly His Asn
        130                 135                 140
Asn Asn Phe Phe Ser Thr Lys Asp Gln Asp Asn Asp Val Ser Ser Ser
145                 150                 155                 160
Asn Cys Ala Glu Lys Phe Gln Gly Ala Trp Trp Tyr Ala Asp Cys His
                165                 170                 175
Ala Ser Asn Leu Asn Gly Leu Tyr Leu Met Gly Pro His Glu Ser Tyr
            180                 185                 190
Ala Asn Gly Ile Asn Trp Ser Ala Ala Lys Gly Tyr Lys Tyr Ser Tyr
        195                 200                 205
Lys Val Ser Glu Met Lys Val Arg Pro Ala Gln Val Gln Leu Lys Gln
    210                 215                 220
Ser Gly Pro Gly Leu Val Gln Pro Ser Gln Ser Leu Ser Ile Thr Cys
225                 230                 235                 240
Thr Val Ser Gly Phe Ser Leu Thr Asn Tyr Gly Val His Trp Val Arg
                245                 250                 255
Gln Ser Pro Gly Lys Gly Leu Glu Trp Leu Gly Val Ile Trp Ser Gly
            260                 265                 270
Gly Asn Thr Asp Tyr Asn Thr Pro Phe Thr Ser Arg Leu Ser Ile Asn
        275                 280                 285
Lys Asp Asn Ser Lys Ser Gln Val Phe Phe Lys Met Asn Ser Leu Gln
    290                 295                 300
Ser Glu Asp Thr Ala Ile Tyr Tyr Cys Ala Arg Ala Leu Thr Tyr Tyr
305                 310                 315                 320
Asp Tyr Glu Phe Ala Tyr Trp Gly Gln Gly Thr Leu Val Thr Val Ser
                325                 330                 335
Ala Ala Ser Thr Lys Gly Pro Ser Val Phe Pro Leu Ala Pro Ser Ser
            340                 345                 350
Lys Ser Thr Ser Gly Gly Thr Ala Ala Leu Gly Cys Leu Val Lys Asp
        355                 360                 365
Tyr Phe Pro Glu Pro Val Thr Val Ser Trp Asn Ser Gly Ala Leu Thr
    370                 375                 380
Ser Gly Val His Thr Phe Pro Ala Val Leu Gln Ser Ser Gly Leu Tyr
385                 390                 395                 400
Ser Leu Ser Ser Val Val Thr Val Pro Ser Ser Ser Leu Gly Thr Gln
                405                 410                 415
Thr Tyr Ile Cys Asn Val Asn His Lys Pro Ser Asn Thr Lys Val Asp
            420                 425                 430
Lys Lys Val Glu Pro Lys Ser Cys Asp Lys Thr His Thr Cys Pro Pro
        435                 440                 445
Cys Pro Ala Pro Glu Leu Leu Gly Gly Pro Ser Val Phe Leu Phe Pro
    450                 455                 460
Pro Lys Pro Lys Asp Thr Leu Met Ile Ser Arg Thr Pro Glu Val Thr
465                 470                 475                 480
Cys Val Val Val Asp Val Ser His Glu Asp Pro Glu Val Lys Phe Asn
                485                 490                 495
Trp Tyr Val Asp Gly Val Glu Val His Asn Ala Lys Thr Lys Pro Arg
            500                 505                 510
Glu Glu Gln Tyr Asn Ser Thr Tyr Arg Val Val Ser Val Leu Thr Val
```

```
                 515                 520                 525
Leu His Gln Asp Trp Leu Asn Gly Lys Glu Tyr Lys Cys Lys Val Ser
             530                 535                 540

Asn Lys Ala Leu Pro Ala Pro Ile Glu Lys Thr Ile Ser Lys Ala Lys
545                 550                 555                 560

Gly Gln Pro Arg Glu Pro Gln Val Tyr Thr Leu Pro Pro Ser Arg Asp
                565                 570                 575

Glu Leu Thr Lys Asn Gln Val Ser Leu Thr Cys Leu Val Lys Gly Phe
            580                 585                 590

Tyr Pro Ser Asp Ile Ala Val Glu Trp Glu Ser Asn Gly Gln Pro Glu
                595                 600                 605

Asn Asn Tyr Lys Thr Thr Pro Pro Val Leu Asp Ser Asp Gly Ser Phe
            610                 615                 620

Phe Leu Tyr Ser Lys Leu Thr Val Asp Lys Ser Arg Trp Gln Gln Gly
625                 630                 635                 640

Asn Val Phe Ser Cys Ser Val Met His Glu Ala Leu His Asn His Tyr
                645                 650                 655

Thr Gln Lys Ser Leu Ser Leu Ser Pro Gly
            660                 665

<210> SEQ ID NO 48
<211> LENGTH: 227
<212> TYPE: PRT
<213> ORGANISM: Artificial Sequence
<220> FEATURE:
<223> OTHER INFORMATION: Synthetic Construct

<400> SEQUENCE: 48

Ser Asn Tyr Ser Met Val Asn Thr Thr Asn Met Thr Ser Asp Ile Leu
1               5                   10                  15

Leu Thr Gln Ser Pro Val Ile Leu Ser Val Ser Pro Gly Glu Arg Val
            20                  25                  30

Ser Phe Ser Cys Arg Ala Ser Gln Ser Ile Gly Thr Asn Ile His Trp
        35                  40                  45

Tyr Gln Gln Arg Thr Asn Gly Ser Pro Arg Leu Leu Ile Lys Tyr Ala
    50                  55                  60

Ser Glu Ser Ile Ser Gly Ile Pro Ser Arg Phe Ser Gly Ser Gly Ser
65                  70                  75                  80

Gly Thr Asp Phe Thr Leu Ser Ile Asn Ser Val Glu Ser Glu Asp Ile
                85                  90                  95

Ala Asp Tyr Tyr Cys Gln Gln Asn Asn Asn Trp Pro Thr Thr Phe Gly
            100                 105                 110

Ala Gly Thr Lys Leu Glu Leu Lys Arg Thr Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
```

210                 215                 220
Gly Glu Cys
225

<210> SEQ ID NO 49
<211> LENGTH: 674
<212> TYPE: PRT
<213> ORGANISM: Artificial Sequence
<220> FEATURE:
<223> OTHER INFORMATION: Synthetic Construct

<400> SEQUENCE: 49

Gln Ser Cys Ala Thr Gly Pro Arg Asn Cys Lys Asp Leu Leu Asp Arg
1               5                   10                  15

Gly Tyr Phe Arg Ser Gly Trp His Thr Ile Tyr Leu Pro Asp Cys Arg
                20                  25                  30

Pro Leu Thr Val Leu Cys Asp Met Asp Thr Asp Gly Gly Gly Trp Thr
            35                  40                  45

Val Phe Gln Arg Arg Met Asp Gly Ser Val Asp Phe Tyr Arg Asp Trp
    50                  55                  60

Ala Ala Tyr Lys Gln Gly Phe Gly Ser Gln Leu Gly Glu Phe Trp Leu
65                  70                  75                  80

Gly Asn Asp Asn Ile His Ala Leu Thr Ala Gln Gly Ser Ser Glu Leu
                85                  90                  95

Arg Thr Asp Leu Val Asp Phe Glu Gly Asn His Gln Phe Ala Lys Tyr
            100                 105                 110

Lys Ser Phe Lys Val Ala Asp Glu Ala Glu Lys Tyr Lys Leu Val Leu
        115                 120                 125

Gly Ala Phe Val Gly Gly Ser Ala Gly Asn Ser Leu Thr Gly His Asn
130                 135                 140

Asn Asn Phe Phe Ser Thr Lys Asp Gln Asp Asn Asp Val Ser Ser Ser
145                 150                 155                 160

Asn Cys Ala Glu Lys Phe Gln Gly Ala Trp Trp Tyr Ala Asp Cys His
                165                 170                 175

Ala Ser Asn Leu Asn Gly Leu Tyr Leu Met Gly Pro His Glu Ser Tyr
            180                 185                 190

Ala Asn Gly Ile Asn Trp Ser Ala Ala Lys Gly Tyr Lys Tyr Ser Tyr
        195                 200                 205

Lys Val Ser Glu Met Lys Val Arg Pro Ala Leu Ser Gly Arg Ser Asp
    210                 215                 220

Asn His Gln Val Gln Leu Lys Gln Ser Gly Pro Gly Leu Val Gln Pro
225                 230                 235                 240

Ser Gln Ser Leu Ser Ile Thr Cys Thr Val Ser Gly Phe Ser Leu Thr
                245                 250                 255

Asn Tyr Gly Val His Trp Val Arg Gln Ser Pro Gly Lys Gly Leu Glu
            260                 265                 270

Trp Leu Gly Val Ile Trp Ser Gly Gly Asn Thr Asp Tyr Asn Thr Pro
        275                 280                 285

Phe Thr Ser Arg Leu Ser Ile Asn Lys Asp Asn Ser Lys Ser Gln Val
    290                 295                 300

Phe Phe Lys Met Asn Ser Leu Gln Ser Glu Asp Thr Ala Ile Tyr Tyr
305                 310                 315                 320

Cys Ala Arg Ala Leu Thr Tyr Tyr Asp Tyr Glu Phe Ala Tyr Trp Gly
                325                 330                 335

Gln Gly Thr Leu Val Thr Val Ser Ala Ala Ser Thr Lys Gly Pro Ser

```
                340                 345                 350
Val Phe Pro Leu Ala Pro Ser Ser Lys Ser Thr Ser Gly Gly Thr Ala
            355                 360                 365

Ala Leu Gly Cys Leu Val Lys Asp Tyr Phe Pro Glu Pro Val Thr Val
    370                 375                 380

Ser Trp Asn Ser Gly Ala Leu Thr Ser Gly Val His Thr Phe Pro Ala
385                 390                 395                 400

Val Leu Gln Ser Ser Gly Leu Tyr Ser Leu Ser Ser Val Val Thr Val
                405                 410                 415

Pro Ser Ser Ser Leu Gly Thr Gln Thr Tyr Ile Cys Asn Val Asn His
            420                 425                 430

Lys Pro Ser Asn Thr Lys Val Asp Lys Lys Val Glu Pro Lys Ser Cys
        435                 440                 445

Asp Lys Thr His Thr Cys Pro Pro Cys Pro Ala Pro Glu Leu Leu Gly
    450                 455                 460

Gly Pro Ser Val Phe Leu Phe Pro Pro Lys Pro Lys Asp Thr Leu Met
465                 470                 475                 480

Ile Ser Arg Thr Pro Glu Val Thr Cys Val Val Val Asp Val Ser His
                485                 490                 495

Glu Asp Pro Glu Val Lys Phe Asn Trp Tyr Val Asp Gly Val Glu Val
            500                 505                 510

His Asn Ala Lys Thr Lys Pro Arg Glu Glu Gln Tyr Asn Ser Thr Tyr
        515                 520                 525

Arg Val Val Ser Val Leu Thr Val Leu His Gln Asp Trp Leu Asn Gly
    530                 535                 540

Lys Glu Tyr Lys Cys Lys Val Ser Asn Lys Ala Leu Pro Ala Pro Ile
545                 550                 555                 560

Glu Lys Thr Ile Ser Lys Ala Lys Gly Gln Pro Arg Glu Pro Gln Val
                565                 570                 575

Tyr Thr Leu Pro Pro Ser Arg Asp Glu Leu Thr Lys Asn Gln Val Ser
            580                 585                 590

Leu Thr Cys Leu Val Lys Gly Phe Tyr Pro Ser Asp Ile Ala Val Glu
        595                 600                 605

Trp Glu Ser Asn Gly Gln Pro Glu Asn Asn Tyr Lys Thr Thr Pro Pro
    610                 615                 620

Val Leu Asp Ser Asp Gly Ser Phe Phe Leu Tyr Ser Lys Leu Thr Val
625                 630                 635                 640

Asp Lys Ser Arg Trp Gln Gln Gly Asn Val Phe Ser Cys Ser Val Met
                645                 650                 655

His Glu Ala Leu His Asn His Tyr Thr Gln Lys Ser Leu Ser Leu Ser
            660                 665                 670

Pro Gly

<210> SEQ ID NO 50
<211> LENGTH: 235
<212> TYPE: PRT
<213> ORGANISM: Artificial Sequence
<220> FEATURE:
<223> OTHER INFORMATION: Synthetic Construct

<400> SEQUENCE: 50

Ser Asn Tyr Ser Met Val Asn Thr Thr Asn Met Thr Ser Leu Ser Gly
1               5                   10                  15

Arg Ser Asp Asn His Asp Ile Leu Leu Thr Gln Ser Pro Val Ile Leu
            20                  25                  30
```

```
Ser Val Ser Pro Gly Glu Arg Val Ser Phe Ser Cys Arg Ala Ser Gln
        35                  40                  45
Ser Ile Gly Thr Asn Ile His Trp Tyr Gln Gln Arg Thr Asn Gly Ser
    50                  55                  60
Pro Arg Leu Leu Ile Lys Tyr Ala Ser Glu Ser Ile Ser Gly Ile Pro
65                  70                  75                  80
Ser Arg Phe Ser Gly Ser Gly Ser Gly Thr Asp Phe Thr Leu Ser Ile
                85                  90                  95
Asn Ser Val Glu Ser Glu Asp Ile Ala Asp Tyr Tyr Cys Gln Gln Asn
            100                 105                 110
Asn Asn Trp Pro Thr Thr Phe Gly Ala Gly Thr Lys Leu Glu Leu Lys
        115                 120                 125
Arg Thr Val Ala Ala Pro Ser Val Phe Ile Phe Pro Pro Ser Asp Glu
130                 135                 140
Gln Leu Lys Ser Gly Thr Ala Ser Val Val Cys Leu Leu Asn Asn Phe
145                 150                 155                 160
Tyr Pro Arg Glu Ala Lys Val Gln Trp Lys Val Asp Asn Ala Leu Gln
                165                 170                 175
Ser Gly Asn Ser Gln Glu Ser Val Thr Glu Gln Asp Ser Lys Asp Ser
            180                 185                 190
Thr Tyr Ser Leu Ser Ser Thr Leu Thr Leu Ser Lys Ala Asp Tyr Glu
        195                 200                 205
Lys His Lys Val Tyr Ala Cys Glu Val Thr His Gln Gly Leu Ser Ser
    210                 215                 220
Pro Val Thr Lys Ser Phe Asn Arg Gly Glu Cys
225                 230                 235

<210> SEQ ID NO 51
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 3
<223> OTHER INFORMATION: Xaa = Any Amino Acid

<400> SEQUENCE: 51

Xaa Lys Xaa
1

<210> SEQ ID NO 52
<211> LENGTH: 4
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 4
<223> OTHER INFORMATION: Xaa = Any Amino Acid

<400> SEQUENCE: 52

Xaa Xaa Gln Xaa
1

<210> SEQ ID NO 53
<211> LENGTH: 8
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Gly or Pro
<220> FEATURE:
<221> NAME/KEY: VARIANT
<222> LOCATION: 5
<223> OTHER INFORMATION: Xaa = Ala, Gly, Pro, or absent
<220> FEATURE:
<221> NAME/KEY: VARIANT
<222> LOCATION: 6
<223> OTHER INFORMATION: Xaa = Ala, Gly, Lys, Pro, or absent
<220> FEATURE:
<221> NAME/KEY: VARIANT
<222> LOCATION: 7
<223> OTHER INFORMATION: Xaa = Gly, Lys, or absent
<220> FEATURE:
<221> NAME/KEY: VARIANT
<222> LOCATION: 8
<223> OTHER INFORMATION: Xaa = Lys or absent

<400> SEQUENCE: 53

Leu Leu Gln Xaa Xaa Xaa Xaa Xaa
1               5

<210> SEQ ID NO 54
<211> LENGTH: 11
<212> TYPE: PRT
<213> ORGANISM: Artificial Sequence
<220> FEATURE:
<223> OTHER INFORMATION: Synthetic Construct

<400> SEQUENCE: 54

Val Leu Asn Leu Ala Gln Ser Lys Asn Phe His
1               5                   10

<210> SEQ ID NO 55
<211> LENGTH: 11
<212> TYPE: PRT
<213> ORGANISM: Artificial Sequence
<220> FEATURE:
<223> OTHER INFORMATION: Synthetic Construct

<400> SEQUENCE: 55

Ala Pro Ala Leu Gln Pro Thr Gln Gly Ala Met
1               5                   10

<210> SEQ ID NO 56
<211> LENGTH: 9
<212> TYPE: PRT
<213> ORGANISM: Artificial Sequence
<220> FEATURE:
<223> OTHER INFORMATION: Synthetic Construct

<400> SEQUENCE: 56

Ile Pro Lys Glu Gln Lys Tyr Ser Phe
1               5

<210> SEQ ID NO 57
<211> LENGTH: 13
<212> TYPE: PRT
<213> ORGANISM: Artificial Sequence
<220> FEATURE:
<223> OTHER INFORMATION: Synthetic Construct

<400> SEQUENCE: 57

Met Gly Gly Ser Pro Leu Ala Gln Ser His Gly Gly Ser
1               5                   10
```

<210> SEQ ID NO 58
<211> LENGTH: 15
<212> TYPE: PRT
<213> ORGANISM: Artificial Sequence
<220> FEATURE:
<223> OTHER INFORMATION: Synthetic Construct

<400> SEQUENCE: 58

Lys Glu Thr Ala Ala Ala Lys Phe Glu Arg Gln His Met Asp Ser
1               5                   10                  15

<210> SEQ ID NO 59
<211> LENGTH: 12
<212> TYPE: PRT
<213> ORGANISM: Artificial Sequence
<220> FEATURE:
<223> OTHER INFORMATION: Synthetic Construct

<400> SEQUENCE: 59

Thr Glu Tyr Gly Leu Phe Gln Ile Asn Asn Asp Ser
1               5                   10

<210> SEQ ID NO 60
<211> LENGTH: 6
<212> TYPE: PRT
<213> ORGANISM: Artificial Sequence
<220> FEATURE:
<223> OTHER INFORMATION: Synthetic Construct

<400> SEQUENCE: 60

Ala Pro Gln Gln Glu Ala
1               5

<210> SEQ ID NO 61
<211> LENGTH: 7
<212> TYPE: PRT
<213> ORGANISM: Artificial Sequence
<220> FEATURE:
<223> OTHER INFORMATION: Synthetic Construct

<400> SEQUENCE: 61

Glu Asp Gly Phe Phe Lys Ile
1               5

<210> SEQ ID NO 62
<211> LENGTH: 9
<212> TYPE: PRT
<213> ORGANISM: Artificial Sequence
<220> FEATURE:
<223> OTHER INFORMATION: Synthetic Construct

<400> SEQUENCE: 62

Glu Glu Gln Tyr Asn Ser Thr Tyr Arg
1               5

<210> SEQ ID NO 63
<211> LENGTH: 34
<212> TYPE: PRT
<213> ORGANISM: Artificial Sequence
<220> FEATURE:
<223> OTHER INFORMATION: Synthetic Construct

<400> SEQUENCE: 63

Lys Leu Glu Ala Leu Glu Gly Lys Leu Glu Ala Leu Glu Lys Leu Glu
1               5                   10                  15

```
Ala Leu Glu Gly Lys Leu Glu Ala Leu Gly Lys Leu Glu Ala Leu
            20                  25                  30

Glu Gly

<210> SEQ ID NO 64
<211> LENGTH: 30
<212> TYPE: PRT
<213> ORGANISM: Artificial Sequence
<220> FEATURE:
<223> OTHER INFORMATION: Synthetic Construct

<400> SEQUENCE: 64

Asp Asn Ile Glu Gln Lys Ile Asp Asp Ile Asp His Glu Ile Ala Asp
1               5                   10                  15

Leu Gln Ala Lys Arg Thr Arg Lys Val Gln Gln His Pro Arg
            20                  25                  30

<210> SEQ ID NO 65
<211> LENGTH: 30
<212> TYPE: PRT
<213> ORGANISM: Artificial Sequence
<220> FEATURE:
<223> OTHER INFORMATION: Synthetic Construct

<400> SEQUENCE: 65

Arg Pro His Gln Gln Val Leu Arg Thr Arg Lys Ala Gln Leu Asp Ala
1               5                   10                  15

Ile Glu His Asp Ile Asp Asp Ile Lys Gln Glu Ile Asn Asp
            20                  25                  30

<210> SEQ ID NO 66
<211> LENGTH: 11
<212> TYPE: PRT
<213> ORGANISM: Artificial Sequence
<220> FEATURE:
<223> OTHER INFORMATION: Synthetic Construct

<400> SEQUENCE: 66

Arg Arg Arg Arg Arg Arg Arg Arg Arg Arg Arg
1               5                   10

<210> SEQ ID NO 67
<211> LENGTH: 11
<212> TYPE: PRT
<213> ORGANISM: Artificial Sequence
<220> FEATURE:
<223> OTHER INFORMATION: Synthetic Construct

<400> SEQUENCE: 67

Glu Glu Glu Glu Glu Glu Glu Glu Glu Glu Glu
1               5                   10

<210> SEQ ID NO 68
<211> LENGTH: 3
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: Xaa = Any Amino Acid except Pro
<220> FEATURE:
<221> NAME/KEY: VARIANT
<222> LOCATION: 3
<223> OTHER INFORMATION: Xaa = Ser, Thr, or Cys
```

```
<400> SEQUENCE: 68

Asn Xaa Xaa
1

<210> SEQ ID NO 69
<211> LENGTH: 20
<212> TYPE: PRT
<213> ORGANISM: Artificial Sequence
<220> FEATURE:
<223> OTHER INFORMATION: Synthetic Construct

<400> SEQUENCE: 69

Val Asn Asn Thr Ile Val Trp Thr Asn Ser Ser Leu Asn Gln Asn Met
1               5                   10                  15

Thr Asn Gly Thr
            20

<210> SEQ ID NO 70
<211> LENGTH: 15
<212> TYPE: PRT
<213> ORGANISM: Artificial Sequence
<220> FEATURE:
<223> OTHER INFORMATION: Synthetic Construct

<400> SEQUENCE: 70

Phe Asn Gln Thr Gln Pro Glu Arg Gly Asp Asn Asn Leu Thr Arg
1               5                   10                  15

<210> SEQ ID NO 71
<211> LENGTH: 11
<212> TYPE: PRT
<213> ORGANISM: Artificial Sequence
<220> FEATURE:
<223> OTHER INFORMATION: Synthetic Construct

<400> SEQUENCE: 71

Gly Asn Ser Thr His Ser Arg Asn Asn Ser Tyr
1               5                   10

<210> SEQ ID NO 72
<211> LENGTH: 9
<212> TYPE: PRT
<213> ORGANISM: Artificial Sequence
<220> FEATURE:
<223> OTHER INFORMATION: Synthetic Construct

<400> SEQUENCE: 72

Glu Glu Gln Tyr Asn Ser Thr Tyr Arg
1               5

<210> SEQ ID NO 73
<211> LENGTH: 9
<212> TYPE: PRT
<213> ORGANISM: Artificial Sequence
<220> FEATURE:
<223> OTHER INFORMATION: Synthetic Construct

<400> SEQUENCE: 73

Glu Glu Gln Tyr Asn Ser Thr Phe Arg
1               5

<210> SEQ ID NO 74
<211> LENGTH: 3
<212> TYPE: PRT
<213> ORGANISM: Artificial Sequence
<220> FEATURE:
```

```
<223> OTHER INFORMATION: Synthetic Construct

<400> SEQUENCE: 74

Gly Gly Gly
1

<210> SEQ ID NO 75
<211> LENGTH: 4
<212> TYPE: PRT
<213> ORGANISM: Artificial Sequence
<220> FEATURE:
<223> OTHER INFORMATION: Synthetic Construct

<400> SEQUENCE: 75

Gly Gly Gly Gly
1

<210> SEQ ID NO 76
<211> LENGTH: 3
<212> TYPE: PRT
<213> ORGANISM: Artificial Sequence
<220> FEATURE:
<223> OTHER INFORMATION: Synthetic Construct

<400> SEQUENCE: 76

Leu Gln Gly
1

<210> SEQ ID NO 77
<211> LENGTH: 5
<212> TYPE: PRT
<213> ORGANISM: Artificial Sequence
<220> FEATURE:
<223> OTHER INFORMATION: Synthetic Construct

<400> SEQUENCE: 77

Leu Leu Gln Gly Gly
1               5

<210> SEQ ID NO 78
<211> LENGTH: 6
<212> TYPE: PRT
<213> ORGANISM: Artificial Sequence
<220> FEATURE:
<223> OTHER INFORMATION: Synthetic Construct

<400> SEQUENCE: 78

Leu Ser Leu Ser Gln Gly
1               5

<210> SEQ ID NO 79
<211> LENGTH: 8
<212> TYPE: PRT
<213> ORGANISM: Artificial Sequence
<220> FEATURE:
<223> OTHER INFORMATION: Synthetic Construct

<400> SEQUENCE: 79

Gly Gly Gly Leu Leu Gln Gly Gly
1               5

<210> SEQ ID NO 80
<211> LENGTH: 5
<212> TYPE: PRT
<213> ORGANISM: Artificial Sequence
<220> FEATURE:
<223> OTHER INFORMATION: Synthetic Construct
```

```
<400> SEQUENCE: 80

Gly Leu Leu Gln Gly
1               5

<210> SEQ ID NO 81
<211> LENGTH: 3
<212> TYPE: PRT
<213> ORGANISM: Artificial Sequence
<220> FEATURE:
<223> OTHER INFORMATION: Synthetic Construct

<400> SEQUENCE: 81

Leu Leu Gln
1

<210> SEQ ID NO 82
<211> LENGTH: 10
<212> TYPE: PRT
<213> ORGANISM: Artificial Sequence
<220> FEATURE:
<223> OTHER INFORMATION: Synthetic Construct

<400> SEQUENCE: 82

Gly Ser Pro Leu Ala Gln Ser His Gly Gly
1               5                   10

<210> SEQ ID NO 83
<211> LENGTH: 7
<212> TYPE: PRT
<213> ORGANISM: Artificial Sequence
<220> FEATURE:
<223> OTHER INFORMATION: Synthetic Construct

<400> SEQUENCE: 83

Gly Leu Leu Gln Gly Gly Gly
1               5

<210> SEQ ID NO 84
<211> LENGTH: 6
<212> TYPE: PRT
<213> ORGANISM: Artificial Sequence
<220> FEATURE:
<223> OTHER INFORMATION: Synthetic Construct

<400> SEQUENCE: 84

Gly Leu Leu Gln Gly Gly
1               5

<210> SEQ ID NO 85
<211> LENGTH: 4
<212> TYPE: PRT
<213> ORGANISM: Artificial Sequence
<220> FEATURE:
<223> OTHER INFORMATION: Synthetic Construct

<400> SEQUENCE: 85

Gly Leu Leu Gln
1

<210> SEQ ID NO 86
<211> LENGTH: 8
<212> TYPE: PRT
<213> ORGANISM: Artificial Sequence
<220> FEATURE:
<223> OTHER INFORMATION: Synthetic Construct
```

```
<400> SEQUENCE: 86

Leu Leu Gln Leu Leu Gln Gly Ala
1               5

<210> SEQ ID NO 87
<211> LENGTH: 5
<212> TYPE: PRT
<213> ORGANISM: Artificial Sequence
<220> FEATURE:
<223> OTHER INFORMATION: Synthetic Construct

<400> SEQUENCE: 87

Leu Leu Gln Gly Ala
1               5

<210> SEQ ID NO 88
<211> LENGTH: 7
<212> TYPE: PRT
<213> ORGANISM: Artificial Sequence
<220> FEATURE:
<223> OTHER INFORMATION: Synthetic Construct

<400> SEQUENCE: 88

Leu Leu Gln Tyr Gln Gly Ala
1               5

<210> SEQ ID NO 89
<211> LENGTH: 6
<212> TYPE: PRT
<213> ORGANISM: Artificial Sequence
<220> FEATURE:
<223> OTHER INFORMATION: Synthetic Construct

<400> SEQUENCE: 89

Leu Leu Gln Gly Ser Gly
1               5

<210> SEQ ID NO 90
<211> LENGTH: 6
<212> TYPE: PRT
<213> ORGANISM: Artificial Sequence
<220> FEATURE:
<223> OTHER INFORMATION: Synthetic Construct

<400> SEQUENCE: 90

Leu Leu Gln Tyr Gln Gly
1               5

<210> SEQ ID NO 91
<211> LENGTH: 7
<212> TYPE: PRT
<213> ORGANISM: Artificial Sequence
<220> FEATURE:
<223> OTHER INFORMATION: Synthetic Construct

<400> SEQUENCE: 91

Leu Leu Gln Leu Leu Gln Gly
1               5

<210> SEQ ID NO 92
<211> LENGTH: 5
<212> TYPE: PRT
<213> ORGANISM: Artificial Sequence
<220> FEATURE:
<223> OTHER INFORMATION: Synthetic Construct

<400> SEQUENCE: 92
```

Ser Leu Leu Gln Gly
1               5

<210> SEQ ID NO 93
<211> LENGTH: 5
<212> TYPE: PRT
<213> ORGANISM: Artificial Sequence
<220> FEATURE:
<223> OTHER INFORMATION: Synthetic Construct

<400> SEQUENCE: 93

Leu Leu Gln Leu Gln
1               5

<210> SEQ ID NO 94
<211> LENGTH: 6
<212> TYPE: PRT
<213> ORGANISM: Artificial Sequence
<220> FEATURE:
<223> OTHER INFORMATION: Synthetic Construct

<400> SEQUENCE: 94

Leu Leu Gln Leu Leu Gln
1               5

<210> SEQ ID NO 95
<211> LENGTH: 5
<212> TYPE: PRT
<213> ORGANISM: Artificial Sequence
<220> FEATURE:
<223> OTHER INFORMATION: Synthetic Construct

<400> SEQUENCE: 95

Leu Leu Gln Gly Arg
1               5

<210> SEQ ID NO 96
<211> LENGTH: 6
<212> TYPE: PRT
<213> ORGANISM: Artificial Sequence
<220> FEATURE:
<223> OTHER INFORMATION: Synthetic Construct

<400> SEQUENCE: 96

Leu Leu Gln Gly Pro Pro
1               5

<210> SEQ ID NO 97
<211> LENGTH: 6
<212> TYPE: PRT
<213> ORGANISM: Artificial Sequence
<220> FEATURE:
<223> OTHER INFORMATION: Synthetic Construct

<400> SEQUENCE: 97

Leu Leu Gln Gly Pro Ala
1               5

<210> SEQ ID NO 98
<211> LENGTH: 8
<212> TYPE: PRT
<213> ORGANISM: Artificial Sequence
<220> FEATURE:
<223> OTHER INFORMATION: Synthetic Construct

<400> SEQUENCE: 98

Gly Gly Leu Leu Gln Gly Pro Pro
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic Construct

<400> SEQUENCE: 99

Gly Gly Leu Leu Gln Gly Ala
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic Construct

<400> SEQUENCE: 100

Leu Leu Gln Gly Pro Gly Lys
1               5

<210> SEQ ID NO 101
<211> LENGTH: 6
<212> TYPE: PRT
<213> ORGANISM: Artificial Sequence
<220> FEATURE:
<223> OTHER INFORMATION: Synthetic Construct

<400> SEQUENCE: 101

Leu Leu Gln Gly Pro Gly
1               5

<210> SEQ ID NO 102
<211> LENGTH: 5
<212> TYPE: PRT
<213> ORGANISM: Artificial Sequence
<220> FEATURE:
<223> OTHER INFORMATION: Synthetic Construct

<400> SEQUENCE: 102

Leu Leu Gln Gly Pro
1               5

<210> SEQ ID NO 103
<211> LENGTH: 4
<212> TYPE: PRT
<213> ORGANISM: Artificial Sequence
<220> FEATURE:
<223> OTHER INFORMATION: Synthetic Construct

<400> SEQUENCE: 103

Leu Leu Gln Pro
1

<210> SEQ ID NO 104
<211> LENGTH: 6
<212> TYPE: PRT
<213> ORGANISM: Artificial Sequence
<220> FEATURE:
<223> OTHER INFORMATION: Synthetic Construct

<400> SEQUENCE: 104

Leu Leu Gln Pro Gly Lys

```
<210> SEQ ID NO 105
<211> LENGTH: 7
<212> TYPE: PRT
<213> ORGANISM: Artificial Sequence
<220> FEATURE:
<223> OTHER INFORMATION: Synthetic Construct

<400> SEQUENCE: 105

Leu Leu Gln Ala Pro Gly Lys
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic Construct

<400> SEQUENCE: 106

Leu Leu Gln Gly Ala Pro Gly
1               5

<210> SEQ ID NO 107
<211> LENGTH: 6
<212> TYPE: PRT
<213> ORGANISM: Artificial Sequence
<220> FEATURE:
<223> OTHER INFORMATION: Synthetic Construct

<400> SEQUENCE: 107

Leu Leu Gln Gly Ala Pro
1               5

<210> SEQ ID NO 108
<211> LENGTH: 6
<212> TYPE: PRT
<213> ORGANISM: Artificial Sequence
<220> FEATURE:
<223> OTHER INFORMATION: Synthetic Construct

<400> SEQUENCE: 108

Leu Leu Gln Leu Gln Gly
1               5

<210> SEQ ID NO 109
<211> LENGTH: 5
<212> TYPE: PRT
<213> ORGANISM: Artificial Sequence
<220> FEATURE:
<223> OTHER INFORMATION: Synthetic Construct

<400> SEQUENCE: 109

Leu Leu Gln Gly Ala
1               5

<210> SEQ ID NO 110
<211> LENGTH: 3
<212> TYPE: PRT
<213> ORGANISM: Artificial Sequence
<220> FEATURE:
<223> OTHER INFORMATION: Synthetic Construct

<400> SEQUENCE: 110

Leu Gln Gly
1
```

```
<210> SEQ ID NO 111
<211> LENGTH: 7
<212> TYPE: PRT
<213> ORGANISM: Artificial Sequence
<220> FEATURE:
<223> OTHER INFORMATION: Synthetic Construct

<400> SEQUENCE: 111

Gly Gly Leu Leu Gln Gly Ala
1               5

<210> SEQ ID NO 112
<211> LENGTH: 6
<212> TYPE: PRT
<213> ORGANISM: Artificial Sequence
<220> FEATURE:
<223> OTHER INFORMATION: Synthetic Construct

<400> SEQUENCE: 112

Leu Leu Gln Gly Pro Ala
1               5

<210> SEQ ID NO 113
<211> LENGTH: 6
<212> TYPE: PRT
<213> ORGANISM: Artificial Sequence
<220> FEATURE:
<223> OTHER INFORMATION: Synthetic Construct

<400> SEQUENCE: 113

Leu Leu Gln Gly Pro Pro
1               5

<210> SEQ ID NO 114
<211> LENGTH: 8
<212> TYPE: PRT
<213> ORGANISM: Artificial Sequence
<220> FEATURE:
<223> OTHER INFORMATION: Synthetic Construct

<400> SEQUENCE: 114

Gly Gly Leu Leu Gln Gly Pro Pro
1               5

<210> SEQ ID NO 115
<211> LENGTH: 6
<212> TYPE: PRT
<213> ORGANISM: Artificial Sequence
<220> FEATURE:
<223> OTHER INFORMATION: Synthetic Construct

<400> SEQUENCE: 115

Leu Leu Gln Gly Trp Gly
1               5

<210> SEQ ID NO 116
<211> LENGTH: 4
<212> TYPE: PRT
<213> ORGANISM: Artificial Sequence
<220> FEATURE:
<223> OTHER INFORMATION: Synthetic Construct

<400> SEQUENCE: 116

Leu Leu Gln Gly
1
```

```
<210> SEQ ID NO 117
<211> LENGTH: 6
<212> TYPE: PRT
<213> ORGANISM: Artificial Sequence
<220> FEATURE:
<223> OTHER INFORMATION: Synthetic Construct

<400> SEQUENCE: 117

Leu Leu Gln Tyr Gln Gly
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic Construct

<400> SEQUENCE: 118

Leu Leu Gln Leu Leu Gln Gly
1               5

<210> SEQ ID NO 119
<211> LENGTH: 6
<212> TYPE: PRT
<213> ORGANISM: Artificial Sequence
<220> FEATURE:
<223> OTHER INFORMATION: Synthetic Construct

<400> SEQUENCE: 119

Leu Leu Gln Leu Gln Gly
1               5

<210> SEQ ID NO 120
<211> LENGTH: 6
<212> TYPE: PRT
<213> ORGANISM: Artificial Sequence
<220> FEATURE:
<223> OTHER INFORMATION: Synthetic Construct

<400> SEQUENCE: 120

Leu Leu Gln Leu Leu Gln
1               5

<210> SEQ ID NO 121
<211> LENGTH: 5
<212> TYPE: PRT
<213> ORGANISM: Artificial Sequence
<220> FEATURE:
<223> OTHER INFORMATION: Synthetic Construct

<400> SEQUENCE: 121

Leu Leu Gln Leu Gln
1               5

<210> SEQ ID NO 122
<211> LENGTH: 5
<212> TYPE: PRT
<213> ORGANISM: Artificial Sequence
<220> FEATURE:
<223> OTHER INFORMATION: Synthetic Construct

<400> SEQUENCE: 122

Leu Leu Gln Gly Arg
1               5
```

```
<210> SEQ ID NO 123
<211> LENGTH: 7
<212> TYPE: PRT
<213> ORGANISM: Artificial Sequence
<220> FEATURE:
<223> OTHER INFORMATION: Synthetic Construct

<400> SEQUENCE: 123

Leu Leu Gln Tyr Gln Gly Ala
1               5

<210> SEQ ID NO 124
<211> LENGTH: 5
<212> TYPE: PRT
<213> ORGANISM: Artificial Sequence
<220> FEATURE:
<223> OTHER INFORMATION: Synthetic Construct

<400> SEQUENCE: 124

Ser Leu Leu Gln Gly
1               5

<210> SEQ ID NO 125
<211> LENGTH: 8
<212> TYPE: PRT
<213> ORGANISM: Artificial Sequence
<220> FEATURE:
<223> OTHER INFORMATION: Synthetic Construct

<400> SEQUENCE: 125

Leu Leu Gln Leu Leu Gln Gly Ala
1               5

<210> SEQ ID NO 126
<211> LENGTH: 6
<212> TYPE: PRT
<213> ORGANISM: Artificial Sequence
<220> FEATURE:
<223> OTHER INFORMATION: Synthetic Construct

<400> SEQUENCE: 126

Leu Leu Gln Gly Pro Pro
1               5

<210> SEQ ID NO 127
<211> LENGTH: 6
<212> TYPE: PRT
<213> ORGANISM: Artificial Sequence
<220> FEATURE:
<223> OTHER INFORMATION: Synthetic Construct

<400> SEQUENCE: 127

Gln Val Gln Leu Lys Glu
1               5

<210> SEQ ID NO 128
<211> LENGTH: 5
<212> TYPE: PRT
<213> ORGANISM: Artificial Sequence
<220> FEATURE:
<223> OTHER INFORMATION: Synthetic Construct

<400> SEQUENCE: 128

Val Gln Leu Lys Glu
1               5

<210> SEQ ID NO 129
```

```
<211> LENGTH: 7
<212> TYPE: PRT
<213> ORGANISM: Artificial Sequence
<220> FEATURE:
<223> OTHER INFORMATION: Synthetic Construct

<400> SEQUENCE: 129

Gly Gly Leu Leu Gln Gly Gly
1               5

<210> SEQ ID NO 130
<211> LENGTH: 6
<212> TYPE: PRT
<213> ORGANISM: Artificial Sequence
<220> FEATURE:
<223> OTHER INFORMATION: Synthetic Construct

<400> SEQUENCE: 130

Thr Val Gln Gln Glu Leu
1               5

<210> SEQ ID NO 131
<211> LENGTH: 7
<212> TYPE: PRT
<213> ORGANISM: Artificial Sequence
<220> FEATURE:
<223> OTHER INFORMATION: Synthetic Construct

<400> SEQUENCE: 131

Gly Gln Gln Gln Thr Pro Tyr
1               5

<210> SEQ ID NO 132
<211> LENGTH: 7
<212> TYPE: PRT
<213> ORGANISM: Artificial Sequence
<220> FEATURE:
<223> OTHER INFORMATION: Synthetic Construct

<400> SEQUENCE: 132

Gly Leu Gln Gln Ala Ser Val
1               5

<210> SEQ ID NO 133
<211> LENGTH: 7
<212> TYPE: PRT
<213> ORGANISM: Artificial Sequence
<220> FEATURE:
<223> OTHER INFORMATION: Synthetic Construct

<400> SEQUENCE: 133

Trp Gln Thr Pro Met Asn Ser
1               5

<210> SEQ ID NO 134
<211> LENGTH: 12
<212> TYPE: PRT
<213> ORGANISM: Artificial Sequence
<220> FEATURE:
<223> OTHER INFORMATION: Synthetic Construct

<400> SEQUENCE: 134

Trp Gln His Pro Leu His Asp Trp Phe Asp Leu Val
1               5                   10

<210> SEQ ID NO 135
<211> LENGTH: 12
```

```
<212> TYPE: PRT
<213> ORGANISM: Artificial Sequence
<220> FEATURE:
<223> OTHER INFORMATION: Synthetic Construct

<400> SEQUENCE: 135

Phe Gln Gln Pro Leu Asp Pro Trp Thr Ser Pro Ile
1               5                   10

<210> SEQ ID NO 136
<211> LENGTH: 12
<212> TYPE: PRT
<213> ORGANISM: Artificial Sequence
<220> FEATURE:
<223> OTHER INFORMATION: Synthetic Construct

<400> SEQUENCE: 136

His Gln Ser Tyr Val Asp Pro Trp Met Leu Asp His
1               5                   10

<210> SEQ ID NO 137
<211> LENGTH: 12
<212> TYPE: PRT
<213> ORGANISM: Artificial Sequence
<220> FEATURE:
<223> OTHER INFORMATION: Synthetic Construct

<400> SEQUENCE: 137

Arg Glu Gln Leu Tyr Leu Asp Tyr Asn Val Phe Ser
1               5                   10

<210> SEQ ID NO 138
<211> LENGTH: 13
<212> TYPE: PRT
<213> ORGANISM: Artificial Sequence
<220> FEATURE:
<223> OTHER INFORMATION: Synthetic Construct

<400> SEQUENCE: 138

Met Trp Gln Lys Leu Pro Leu Val Val His Trp Pro Thr
1               5                   10

<210> SEQ ID NO 139
<211> LENGTH: 12
<212> TYPE: PRT
<213> ORGANISM: Artificial Sequence
<220> FEATURE:
<223> OTHER INFORMATION: Synthetic Construct

<400> SEQUENCE: 139

Thr His Met Tyr Gln Ser Ile Tyr Val Pro Asp Ile
1               5                   10

<210> SEQ ID NO 140
<211> LENGTH: 12
<212> TYPE: PRT
<213> ORGANISM: Artificial Sequence
<220> FEATURE:
<223> OTHER INFORMATION: Synthetic Construct

<400> SEQUENCE: 140

Leu Leu Gln Gly Leu Ser Gly Arg Ser Asp Asn His
1               5                   10

<210> SEQ ID NO 141
<211> LENGTH: 11
<212> TYPE: PRT
```

<213> ORGANISM: Artificial Sequence
<220> FEATURE:
<223> OTHER INFORMATION: Synthetic Construct

<400> SEQUENCE: 141

Gly Lys Gly Leu Ser Gly Arg Ser Asp Asn His
1               5                   10

<210> SEQ ID NO 142
<211> LENGTH: 16
<212> TYPE: PRT
<213> ORGANISM: Artificial Sequence
<220> FEATURE:
<223> OTHER INFORMATION: Synthetic Construct

<400> SEQUENCE: 142

Leu Leu Gln Gly Leu Ser Gly Arg Ser Asp Asn His Gly Gly Gly Ser
1               5                   10                  15

<210> SEQ ID NO 143
<211> LENGTH: 15
<212> TYPE: PRT
<213> ORGANISM: Artificial Sequence
<220> FEATURE:
<223> OTHER INFORMATION: Synthetic Construct

<400> SEQUENCE: 143

Gly Lys Gly Leu Ser Gly Arg Ser Asp Asn His Gly Gly Gly Ser
1               5                   10                  15

<210> SEQ ID NO 144
<211> LENGTH: 10
<212> TYPE: PRT
<213> ORGANISM: Artificial Sequence
<220> FEATURE:
<223> OTHER INFORMATION: Synthetic Construct

<400> SEQUENCE: 144

Ser Cys Leu Ser Gly Arg Ser Asp Asn His
1               5                   10

<210> SEQ ID NO 145
<211> LENGTH: 12
<212> TYPE: PRT
<213> ORGANISM: Artificial Sequence
<220> FEATURE:
<223> OTHER INFORMATION: Synthetic Construct

<400> SEQUENCE: 145

Ser Cys Leu Ser Gly Arg Ser Asp Asn His Gly Gly
1               5                   10

<210> SEQ ID NO 146
<211> LENGTH: 14
<212> TYPE: PRT
<213> ORGANISM: Artificial Sequence
<220> FEATURE:
<223> OTHER INFORMATION: Synthetic Construct

<400> SEQUENCE: 146

Ser Cys Leu Ser Gly Arg Ser Asp Asn His Gly Gly Gly Ser
1               5                   10

<210> SEQ ID NO 147
<211> LENGTH: 6
<212> TYPE: PRT
<213> ORGANISM: Artificial Sequence

```
<220> FEATURE:
<223> OTHER INFORMATION: Synthetic Construct

<400> SEQUENCE: 147

Arg Gln Ala Arg Val Val
1               5

<210> SEQ ID NO 148
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Gly or Lys

<400> SEQUENCE: 148

Xaa Ser Gly Arg Ser Ala
1               5

<210> SEQ ID NO 149
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Arg
<220> FEATURE:
<221> NAME/KEY: VARIANT
<222> LOCATION: 2, 3, 7
<223> OTHER INFORMATION: Xaa = Any Amino Acid
<220> FEATURE:
<221> NAME/KEY: VARIANT
<222> LOCATION: 4
<223> OTHER INFORMATION: Xaa = Arg
<220> FEATURE:
<221> NAME/KEY: VARIANT
<222> LOCATION: 5
<223> OTHER INFORMATION: Xaa = Lys
<220> FEATURE:
<221> NAME/KEY: VARIANT
<222> LOCATION: 6
<223> OTHER INFORMATION: Xaa = Val
<220> FEATURE:
<221> NAME/KEY: VARIANT
<222> LOCATION: 8
<223> OTHER INFORMATION: Xaa = Gly

<400> SEQUENCE: 149

Xaa Xaa Xaa Xaa Xaa Xaa Xaa Xaa
1               5

<210> SEQ ID NO 150
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Lys or Arg
<220> FEATURE:
<221> NAME/KEY: VARIANT
<222> LOCATION: 2
<223> OTHER INFORMATION: Xaa = Arg, Lys, His, or Gln
<220> FEATURE:
<221> NAME/KEY: VARIANT
```

<222> LOCATION: 3
<223> OTHER INFORMATION: Xaa = Gly, Ala, or Ser
<220> FEATURE:
<221> NAME/KEY: VARIANT
<222> LOCATION: 4
<223> OTHER INFORMATION: Xaa = Arg or Lys
<220> FEATURE:
<221> NAME/KEY: VARIANT
<222> LOCATION: 5
<223> OTHER INFORMATION: Xaa = Ala

<400> SEQUENCE: 150

Xaa Xaa Xaa Xaa Xaa
1               5

<210> SEQ ID NO 151
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Leu, Ile, Ala, or Lys
<220> FEATURE:
<221> NAME/KEY: VARIANT
<222> LOCATION: 2
<223> OTHER INFORMATION: Xaa = Ser, Gly, or Gln
<220> FEATURE:
<221> NAME/KEY: VARIANT
<222> LOCATION: 3
<223> OTHER INFORMATION: Xaa = Lys, Leu, Ala, Gly, or Ser
<220> FEATURE:
<221> NAME/KEY: VARIANT
<222> LOCATION: 4
<223> OTHER INFORMATION: Xaa = Arg
<220> FEATURE:
<221> NAME/KEY: VARIANT
<222> LOCATION: 5
<223> OTHER INFORMATION: Xaa = Ser, Lys, Gly, Ala, or Val
<220> FEATURE:
<221> NAME/KEY: VARIANT
<222> LOCATION: 6
<223> OTHER INFORMATION: Xaa = Ala, Val, or Leu
<220> FEATURE:
<221> NAME/KEY: VARIANT
<222> LOCATION: 7
<223> OTHER INFORMATION: Xaa = Asn
<220> FEATURE:
<221> NAME/KEY: VARIANT
<222> LOCATION: 8
<223> OTHER INFORMATION: Xaa = His, Gly, Val, or Leu

<400> SEQUENCE: 151

Xaa Xaa Xaa Xaa Xaa Xaa Xaa Xaa
1               5

<210> SEQ ID NO 152
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Arg or Lys
<220> FEATURE:
<221> NAME/KEY: VARIANT
<222> LOCATION: 2
<223> OTHER INFORMATION: Xaa = Gly, Ala, Ser, Thr, Cys, Val, Leu, Ile,
      Met, Pro, Phe, Tyr, Trp, Asp, Glu, Asn, or Gln
<220> FEATURE:
<221> NAME/KEY: VARIANT

```
<222> LOCATION: 3
<223> OTHER INFORMATION: Xaa = Ser
<220> FEATURE:
<221> NAME/KEY: VARIANT
<222> LOCATION: 4
<223> OTHER INFORMATION: Xaa = Arg
<220> FEATURE:
<221> NAME/KEY: VARIANT
<222> LOCATION: 5
<223> OTHER INFORMATION: Xaa = Ala

<400> SEQUENCE: 152

Xaa Xaa Xaa Xaa Xaa
1               5

<210> SEQ ID NO 153
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Gly, Ala, Ser, Thr, Cys, Val, Leu, Ile,
      Met, Pro, Phe, Tyr, Trp, Asp, Glu, Asn, or Gln
<220> FEATURE:
<221> NAME/KEY: VARIANT
<222> LOCATION: 2
<223> OTHER INFORMATION: Xaa = Arg or Lys
<220> FEATURE:
<221> NAME/KEY: VARIANT
<222> LOCATION: 3
<223> OTHER INFORMATION: Xaa = Ser
<220> FEATURE:
<221> NAME/KEY: VARIANT
<222> LOCATION: 4
<223> OTHER INFORMATION: Xaa = Arg
<220> FEATURE:
<221> NAME/KEY: VARIANT
<222> LOCATION: 5
<223> OTHER INFORMATION: Xaa = Ala

<400> SEQUENCE: 153

Xaa Xaa Xaa Xaa Xaa
1               5

<210> SEQ ID NO 154
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Asp, Val, or Ala

<400> SEQUENCE: 154

Leu Ser Gly Arg Ser Xaa Asn His
1               5

<210> SEQ ID NO 155
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 5, 6, 7, 8
<223> OTHER INFORMATION: Xaa = Any Amino Acid
<220> FEATURE:
```

```
<221> NAME/KEY: VARIANT
<222> LOCATION: 4
<223> OTHER INFORMATION: Xaa = Asn

<400> SEQUENCE: 155

Xaa Xaa Xaa Xaa Xaa Xaa Xaa Xaa
1               5

<210> SEQ ID NO 156
<211> LENGTH: 4
<212> TYPE: PRT
<213> ORGANISM: Artificial Sequence
<220> FEATURE:
<223> OTHER INFORMATION: Synthetic Construct

<400> SEQUENCE: 156

Ala Ala Asn Leu
1

<210> SEQ ID NO 157
<211> LENGTH: 4
<212> TYPE: PRT
<213> ORGANISM: Artificial Sequence
<220> FEATURE:
<223> OTHER INFORMATION: Synthetic Construct

<400> SEQUENCE: 157

Ala Thr Asn Leu
1

<210> SEQ ID NO 158
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Leu, Ile, Ala, or Lys
<220> FEATURE:
<221> NAME/KEY: VARIANT
<222> LOCATION: 2
<223> OTHER INFORMATION: Xaa = Ser, Gly, or Gln
<220> FEATURE:
<221> NAME/KEY: VARIANT
<222> LOCATION: 3
<223> OTHER INFORMATION: Xaa = Lys, Leu, Ala, Gly, or Ser
<220> FEATURE:
<221> NAME/KEY: VARIANT
<222> LOCATION: 4
<223> OTHER INFORMATION: Xaa = Arg
<220> FEATURE:
<221> NAME/KEY: VARIANT
<222> LOCATION: 5
<223> OTHER INFORMATION: Xaa = Ser, Lys, Gly, Ala, or Val
<220> FEATURE:
<221> NAME/KEY: VARIANT
<222> LOCATION: 6
<223> OTHER INFORMATION: Xaa = Ala, Val, or Leu
<220> FEATURE:
<221> NAME/KEY: VARIANT
<222> LOCATION: 7
<223> OTHER INFORMATION: Xaa = Asn
<220> FEATURE:
<221> NAME/KEY: VARIANT
<222> LOCATION: 8
<223> OTHER INFORMATION: Xaa = His, Gly, Val, or Leu

<400> SEQUENCE: 158

Xaa Xaa Xaa Xaa Xaa Xaa Xaa Xaa
1               5
```

<210> SEQ ID NO 159
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Gly or Lys

<400> SEQUENCE: 159

Xaa Ser Gly Arg Ser Ala
1               5

<210> SEQ ID NO 160
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 5, 7, 8
<223> OTHER INFORMATION: Xaa = Any Amino Acid
<220> FEATURE:
<221> NAME/KEY: VARIANT
<222> LOCATION: 2
<223> OTHER INFORMATION: Xaa = Ser
<220> FEATURE:
<221> NAME/KEY: VARIANT
<222> LOCATION: 3
<223> OTHER INFORMATION: Xaa = Gly or Ser
<220> FEATURE:
<221> NAME/KEY: VARIANT
<222> LOCATION: 4
<223> OTHER INFORMATION: Xaa = Arg or Lys
<220> FEATURE:
<221> NAME/KEY: VARIANT
<222> LOCATION: 6
<223> OTHER INFORMATION: Xaa = Arg or Val

<400> SEQUENCE: 160

Xaa Xaa Xaa Xaa Xaa Xaa Xaa Xaa
1               5

<210> SEQ ID NO 161
<211> LENGTH: 5
<212> TYPE: PRT
<213> ORGANISM: Artificial Sequence
<220> FEATURE:
<223> OTHER INFORMATION: Synthetic Construct

<400> SEQUENCE: 161

Ser Gly Arg Ser Ala
1               5

<210> SEQ ID NO 162
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Leu, Ile, Ala, or Lys
<220> FEATURE:
<221> NAME/KEY: VARIANT
<222> LOCATION: 2
<223> OTHER INFORMATION: Xaa = Ser, Gly, or Gln

```
<220> FEATURE:
<221> NAME/KEY: VARIANT
<222> LOCATION: 3
<223> OTHER INFORMATION: Xaa = Lys, Leu, Ala, Gly, or Ser
<220> FEATURE:
<221> NAME/KEY: VARIANT
<222> LOCATION: 4
<223> OTHER INFORMATION: Xaa = Arg
<220> FEATURE:
<221> NAME/KEY: VARIANT
<222> LOCATION: 5
<223> OTHER INFORMATION: Xaa = Ser, Lys, Gly, Ala, or Val
<220> FEATURE:
<221> NAME/KEY: VARIANT
<222> LOCATION: 6
<223> OTHER INFORMATION: Xaa = Ala, Val, or Leu
<220> FEATURE:
<221> NAME/KEY: VARIANT
<222> LOCATION: 7
<223> OTHER INFORMATION: Xaa = Asn
<220> FEATURE:
<221> NAME/KEY: VARIANT
<222> LOCATION: 8
<223> OTHER INFORMATION: Xaa = His, Gly, Val, or Leu

<400> SEQUENCE: 162

Xaa Xaa Xaa Xaa Xaa Xaa Xaa Xaa
1               5

<210> SEQ ID NO 163
<211> LENGTH: 13
<212> TYPE: PRT
<213> ORGANISM: Artificial Sequence
<220> FEATURE:
<223> OTHER INFORMATION: Synthetic Construct

<400> SEQUENCE: 163

Arg Lys Ser Ser Ile Ile Ile Arg Met Arg Asp Trp Leu
1               5                   10

<210> SEQ ID NO 164
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 4
<223> OTHER INFORMATION: Xaa = Lys or Arg

<400> SEQUENCE: 164

Pro Arg Phe Xaa Ile Ile Gly Gly
1               5

<210> SEQ ID NO 165
<211> LENGTH: 7
<212> TYPE: PRT
<213> ORGANISM: Artificial Sequence
<220> FEATURE:
<223> OTHER INFORMATION: Synthetic Construct

<400> SEQUENCE: 165

Ser Arg Pro Leu Ala Leu Arg
1               5

<210> SEQ ID NO 166
<211> LENGTH: 7
<212> TYPE: PRT
<213> ORGANISM: Artificial Sequence
<220> FEATURE:
```

<223> OTHER INFORMATION: Synthetic Construct

<400> SEQUENCE: 166

Ser Arg Pro Ala Asn Leu Arg
1               5

<210> SEQ ID NO 167
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Ser, Val, or Arg
<220> FEATURE:
<221> NAME/KEY: VARIANT
<222> LOCATION: 2
<223> OTHER INFORMATION: Xaa = Any Amino Acid
<220> FEATURE:
<221> NAME/KEY: VARIANT
<222> LOCATION: 3
<223> OTHER INFORMATION: Xaa = Pro or Ala
<220> FEATURE:
<221> NAME/KEY: VARIANT
<222> LOCATION: 4
<223> OTHER INFORMATION: Xaa = Leu, Met, Ala, Arg, or Tyr
<220> FEATURE:
<221> NAME/KEY: VARIANT
<222> LOCATION: 5
<223> OTHER INFORMATION: Xaa = Ala, Ser, Asn, Gly, His, or Met
<220> FEATURE:
<221> NAME/KEY: VARIANT
<222> LOCATION: 6
<223> OTHER INFORMATION: Xaa = Leu
<220> FEATURE:
<221> NAME/KEY: VARIANT
<222> LOCATION: 7
<223> OTHER INFORMATION: Xaa = Arg, Leu, Gln, or Met

<400> SEQUENCE: 167

Xaa Xaa Xaa Xaa Xaa Xaa Xaa
1               5

<210> SEQ ID NO 168
<211> LENGTH: 8
<212> TYPE: PRT
<213> ORGANISM: Artificial Sequence
<220> FEATURE:
<223> OTHER INFORMATION: Synthetic Construct

<400> SEQUENCE: 168

Asp Val Ala Gln Phe Val Leu Thr
1               5

<210> SEQ ID NO 169
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 3, 4, 6, 7, 8
<223> OTHER INFORMATION: Xaa = Any Amino Acid
<220> FEATURE:
<221> NAME/KEY: VARIANT
<222> LOCATION: 2
<223> OTHER INFORMATION: Xaa = Pro or Ala
<220> FEATURE:
<221> NAME/KEY: VARIANT
<222> LOCATION: 5

```
<223> OTHER INFORMATION: Xaa = Leu or Ile

<400> SEQUENCE: 169

Xaa Xaa Xaa Xaa Xaa Xaa Xaa Xaa
1               5

<210> SEQ ID NO 170
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Val or Trp

<400> SEQUENCE: 170

His Arg Pro Arg Gly Xaa Thr Asn
1               5

<210> SEQ ID NO 171
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 3, 4, 6, 7, 8
<223> OTHER INFORMATION: Xaa = Any Amino Acid
<220> FEATURE:
<221> NAME/KEY: VARIANT
<222> LOCATION: 2
<223> OTHER INFORMATION: Xaa = Pro
<220> FEATURE:
<221> NAME/KEY: VARIANT
<222> LOCATION: 5
<223> OTHER INFORMATION: Xaa = Leu or Ile

<400> SEQUENCE: 171

Xaa Xaa Xaa Xaa Xaa Xaa Xaa Xaa
1               5

<210> SEQ ID NO 172
<211> LENGTH: 6
<212> TYPE: PRT
<213> ORGANISM: Artificial Sequence
<220> FEATURE:
<223> OTHER INFORMATION: Synthetic Construct

<400> SEQUENCE: 172

Pro Leu Gly Leu Ala Gly
1               5

<210> SEQ ID NO 173
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 6
<223> OTHER INFORMATION: Xaa = Val or Trp

<400> SEQUENCE: 173

His Arg Pro Arg Gly Xaa Thr Asn
1               5
```

```
<210> SEQ ID NO 174
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 7
<223> OTHER INFORMATION: Xaa = Gly
<220> FEATURE:
<221> NAME/KEY: VARIANT
<222> LOCATION: 2
<223> OTHER INFORMATION: Xaa = Pro or Ala
<220> FEATURE:
<221> NAME/KEY: VARIANT
<222> LOCATION: 3, 6, 8
<223> OTHER INFORMATION: Xaa = Any Amino Acid
<220> FEATURE:
<221> NAME/KEY: VARIANT
<222> LOCATION: 4
<223> OTHER INFORMATION: Xaa = Gly or Ala
<220> FEATURE:
<221> NAME/KEY: VARIANT
<222> LOCATION: 5
<223> OTHER INFORMATION: Xaa = Leu

<400> SEQUENCE: 174

Xaa Xaa Xaa Xaa Xaa Xaa Xaa Xaa
1               5

<210> SEQ ID NO 175
<211> LENGTH: 8
<212> TYPE: PRT
<213> ORGANISM: Artificial Sequence
<220> FEATURE:
<223> OTHER INFORMATION: Synthetic Construct

<400> SEQUENCE: 175

Gly Pro Leu Gly Ile Ala Gly Gln
1               5

<210> SEQ ID NO 176
<211> LENGTH: 6
<212> TYPE: PRT
<213> ORGANISM: Artificial Sequence
<220> FEATURE:
<223> OTHER INFORMATION: Synthetic Construct

<400> SEQUENCE: 176

Pro Val Gly Leu Ile Gly
1               5

<210> SEQ ID NO 177
<211> LENGTH: 8
<212> TYPE: PRT
<213> ORGANISM: Artificial Sequence
<220> FEATURE:
<223> OTHER INFORMATION: Synthetic Construct

<400> SEQUENCE: 177

His Pro Val Gly Leu Leu Ala Arg
1               5

<210> SEQ ID NO 178
<211> LENGTH: 6
<212> TYPE: PRT
<213> ORGANISM: Artificial Sequence
<220> FEATURE:
<223> OTHER INFORMATION: Synthetic Construct
```

<400> SEQUENCE: 178

Pro Leu Gly Leu Trp Ala
1               5

<210> SEQ ID NO 179
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = His, Lys, Arg, or Val
<220> FEATURE:
<221> NAME/KEY: VARIANT
<222> LOCATION: 2
<223> OTHER INFORMATION: Xaa = Arg, Met, Thr, Val, Tyr, or Ala
<220> FEATURE:
<221> NAME/KEY: VARIANT
<222> LOCATION: 3
<223> OTHER INFORMATION: Xaa = Pro or Val
<220> FEATURE:
<221> NAME/KEY: VARIANT
<222> LOCATION: 4
<223> OTHER INFORMATION: Xaa = Arg, Ser, or Ala
<220> FEATURE:
<221> NAME/KEY: VARIANT
<222> LOCATION: 5
<223> OTHER INFORMATION: Xaa = Gly, Ala, Ser, Asn, or Trp
<220> FEATURE:
<221> NAME/KEY: VARIANT
<222> LOCATION: 6
<223> OTHER INFORMATION: Xaa = Val, Trp, Leu, or Tyr
<220> FEATURE:
<221> NAME/KEY: VARIANT
<222> LOCATION: 7
<223> OTHER INFORMATION: Xaa = Thr, Arg, Tyr, or Ile

<400> SEQUENCE: 179

Xaa Xaa Xaa Xaa Xaa Xaa Xaa
1               5

<210> SEQ ID NO 180
<211> LENGTH: 5
<212> TYPE: PRT
<213> ORGANISM: Artificial Sequence
<220> FEATURE:
<223> OTHER INFORMATION: Synthetic Construct

<400> SEQUENCE: 180

Ser Ser Lys Leu Gln
1               5

<210> SEQ ID NO 181
<211> LENGTH: 7
<212> TYPE: PRT
<213> ORGANISM: Artificial Sequence
<220> FEATURE:
<223> OTHER INFORMATION: Synthetic Construct

<400> SEQUENCE: 181

Ser Arg Lys Ser Gln Gln Tyr
1               5

<210> SEQ ID NO 182
<211> LENGTH: 7
<212> TYPE: PRT
<213> ORGANISM: Artificial Sequence
<220> FEATURE:

```
<223> OTHER INFORMATION: Synthetic Construct

<400> SEQUENCE: 182

Gly Gln Lys Gly Gln His Tyr
1               5

<210> SEQ ID NO 183
<211> LENGTH: 7
<212> TYPE: PRT
<213> ORGANISM: Artificial Sequence
<220> FEATURE:
<223> OTHER INFORMATION: Synthetic Construct

<400> SEQUENCE: 183

Lys Gly Ile Ser Ser Gln Tyr
1               5

<210> SEQ ID NO 184
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Ser or Ile
<220> FEATURE:
<221> NAME/KEY: VARIANT
<222> LOCATION: 2
<223> OTHER INFORMATION: Xaa = Ser or Gln
<220> FEATURE:
<221> NAME/KEY: VARIANT
<222> LOCATION: 3, 7, 8
<223> OTHER INFORMATION: Xaa = Any Amino Acid
<220> FEATURE:
<221> NAME/KEY: VARIANT
<222> LOCATION: 4
<223> OTHER INFORMATION: Xaa = Tyr, Gln, or Glu
<220> FEATURE:
<221> NAME/KEY: VARIANT
<222> LOCATION: 5, 6
<223> OTHER INFORMATION: Xaa = Ser

<400> SEQUENCE: 184

Xaa Xaa Xaa Xaa Xaa Xaa Xaa Xaa
1               5

<210> SEQ ID NO 185
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 3
<223> OTHER INFORMATION: Xaa = Tyr or Phe
<220> FEATURE:
<221> NAME/KEY: VARIANT
<222> LOCATION: 6
<223> OTHER INFORMATION: Xaa = Gly or Ser

<400> SEQUENCE: 185

Ser Ser Xaa Tyr Ser Xaa
1               5

<210> SEQ ID NO 186
<211> LENGTH: 8
<212> TYPE: PRT
<213> ORGANISM: Artificial Sequence
```

```
<220> FEATURE:
<223> OTHER INFORMATION: Synthetic Construct
<220> FEATURE:
<221> NAME/KEY: VARIANT
<222> LOCATION: 1, 2, 3, 5, 6, 7, 8
<223> OTHER INFORMATION: Xaa = Any Amino Acid
<220> FEATURE:
<221> NAME/KEY: VARIANT
<222> LOCATION: 4
<223> OTHER INFORMATION: Xaa = Val, Ile, Ala, or Thr

<400> SEQUENCE: 186

Xaa Xaa Xaa Xaa Xaa Xaa Xaa Xaa
1               5

<210> SEQ ID NO 187
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Arg or Met
<220> FEATURE:
<221> NAME/KEY: VARIANT
<222> LOCATION: 3
<223> OTHER INFORMATION: Xaa = Ala or His

<400> SEQUENCE: 187

Xaa Glu Xaa Val Val Tyr
1               5

<210> SEQ ID NO 188
<211> LENGTH: 6
<212> TYPE: PRT
<213> ORGANISM: Artificial Sequence
<220> FEATURE:
<223> OTHER INFORMATION: Synthetic Construct

<400> SEQUENCE: 188

Val Ala Asp Cys Ala Gln
1               5

<210> SEQ ID NO 189
<211> LENGTH: 9
<212> TYPE: PRT
<213> ORGANISM: Artificial Sequence
<220> FEATURE:
<223> OTHER INFORMATION: Synthetic Construct

<400> SEQUENCE: 189

Ala Pro Glu Glu Ile Met Asp Arg Gln
1               5

<210> SEQ ID NO 190
<211> LENGTH: 16
<212> TYPE: PRT
<213> ORGANISM: Artificial Sequence
<220> FEATURE:
<223> OTHER INFORMATION: Synthetic Construct

<400> SEQUENCE: 190

Ile Val Ser Ala Arg Met Ala Pro Glu Glu Ile Ile Met Asp Arg Gln
1               5                   10                  15

<210> SEQ ID NO 191
<211> LENGTH: 12
```

-continued

```
<212> TYPE: PRT
<213> ORGANISM: Artificial Sequence
<220> FEATURE:
<223> OTHER INFORMATION: Synthetic Construct

<400> SEQUENCE: 191

Gly Ile Ala Thr Phe Cys Met Leu Met Pro Glu Gln
1               5                   10

<210> SEQ ID NO 192
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 5, 6, 7, 8
<223> OTHER INFORMATION: Xaa = Any Amino Acid
<220> FEATURE:
<221> NAME/KEY: VARIANT
<222> LOCATION: 2, 3
<223> OTHER INFORMATION: Xaa = Tyr
<220> FEATURE:
<221> NAME/KEY: VARIANT
<222> LOCATION: 4
<223> OTHER INFORMATION: Xaa = Val, Thr, or Ala

<400> SEQUENCE: 192

Xaa Xaa Xaa Xaa Xaa Xaa Xaa Xaa
1               5

<210> SEQ ID NO 193
<211> LENGTH: 6
<212> TYPE: PRT
<213> ORGANISM: Artificial Sequence
<220> FEATURE:
<223> OTHER INFORMATION: Synthetic Construct

<400> SEQUENCE: 193

Val Ala Asp Cys Ala Gln
1               5

<210> SEQ ID NO 194
<211> LENGTH: 9
<212> TYPE: PRT
<213> ORGANISM: Artificial Sequence
<220> FEATURE:
<223> OTHER INFORMATION: Synthetic Construct

<400> SEQUENCE: 194

Ala Pro Glu Glu Ile Met Asp Arg Gln
1               5

<210> SEQ ID NO 195
<211> LENGTH: 16
<212> TYPE: PRT
<213> ORGANISM: Artificial Sequence
<220> FEATURE:
<223> OTHER INFORMATION: Synthetic Construct

<400> SEQUENCE: 195

Ile Val Ser Ala Arg Met Ala Pro Glu Glu Ile Ile Met Asp Arg Gln
1               5                   10                  15

<210> SEQ ID NO 196
<211> LENGTH: 12
<212> TYPE: PRT
<213> ORGANISM: Artificial Sequence
```

<220> FEATURE:
<223> OTHER INFORMATION: Synthetic Construct

<400> SEQUENCE: 196

Gly Ile Ala Thr Phe Cys Met Leu Met Pro Glu Gln
1               5                   10

<210> SEQ ID NO 197
<211> LENGTH: 4
<212> TYPE: PRT
<213> ORGANISM: Artificial Sequence
<220> FEATURE:
<223> OTHER INFORMATION: Synthetic Construct

<400> SEQUENCE: 197

Ile Glu Gly Arg
1

<210> SEQ ID NO 198
<211> LENGTH: 4
<212> TYPE: PRT
<213> ORGANISM: Artificial Sequence
<220> FEATURE:
<223> OTHER INFORMATION: Synthetic Construct

<400> SEQUENCE: 198

Ile Asp Gly Arg
1

<210> SEQ ID NO 199
<211> LENGTH: 7
<212> TYPE: PRT
<213> ORGANISM: Artificial Sequence
<220> FEATURE:
<223> OTHER INFORMATION: Synthetic Construct

<400> SEQUENCE: 199

Gly Gly Ser Ile Asp Gly Arg
1               5

<210> SEQ ID NO 200
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Ala or Ile
<220> FEATURE:
<221> NAME/KEY: VARIANT
<222> LOCATION: 2, 7
<223> OTHER INFORMATION: Xaa = Any Amino Acid
<220> FEATURE:
<221> NAME/KEY: VARIANT
<222> LOCATION: 3
<223> OTHER INFORMATION: Xaa = Gly, Pro, or Phe
<220> FEATURE:
<221> NAME/KEY: VARIANT
<222> LOCATION: 4
<223> OTHER INFORMATION: Xaa = Arg
<220> FEATURE:
<221> NAME/KEY: VARIANT
<222> LOCATION: 5
<223> OTHER INFORMATION: Xaa = Thr, Ser, or Ile
<220> FEATURE:
<221> NAME/KEY: VARIANT
<222> LOCATION: 6
<223> OTHER INFORMATION: Xaa = Val or Phe
<220> FEATURE:

```
<221> NAME/KEY: VARIANT
<222> LOCATION: 8
<223> OTHER INFORMATION: Xaa = Gly

<400> SEQUENCE: 200

Xaa Xaa Xaa Xaa Xaa Xaa Xaa Xaa
1               5

<210> SEQ ID NO 201
<211> LENGTH: 7
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 3, 5, 7
<223> OTHER INFORMATION: Xaa = Any Amino Acid

<400> SEQUENCE: 201

Xaa Xaa Xaa Gly Xaa Gly Xaa
1               5

<210> SEQ ID NO 202
<211> LENGTH: 8
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1, 2, 5, 6, 7, 8
<223> OTHER INFORMATION: Xaa = Any Amino Acid
<220> FEATURE:
<221> NAME/KEY: VARIANT
<222> LOCATION: 3
<223> OTHER INFORMATION: Xaa = Leu, Pro, or Val
<220> FEATURE:
<221> NAME/KEY: VARIANT
<222> LOCATION: 4
<223> OTHER INFORMATION: Xaa = Glu or Ala

<400> SEQUENCE: 202

Xaa Xaa Xaa Xaa Xaa Xaa Xaa Xaa
1               5

<210> SEQ ID NO 203
<211> LENGTH: 30
<212> TYPE: PRT
<213> ORGANISM: Artificial Sequence
<220> FEATURE:
<223> OTHER INFORMATION: Synthetic Construct

<400> SEQUENCE: 203

Trp Glu Ala Ala Leu Ala Glu Ala Leu Ala Glu Ala Leu Ala Glu His
1               5                   10                  15

Leu Ala Glu Ala Leu Ala Glu Ala Leu Glu Ala Leu Ala Ala
            20                  25                  30

<210> SEQ ID NO 204
<211> LENGTH: 2
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 2
<223> OTHER INFORMATION: citrulline
```

```
<400> SEQUENCE: 204

Val Xaa
1

<210> SEQ ID NO 205
<211> LENGTH: 3
<212> TYPE: PRT
<213> ORGANISM: Artificial Sequence
<220> FEATURE:
<223> OTHER INFORMATION: Synthetic Construct

<400> SEQUENCE: 205

Gly Gly Ser
1

<210> SEQ ID NO 206
<211> LENGTH: 5
<212> TYPE: PRT
<213> ORGANISM: Artificial Sequence
<220> FEATURE:
<223> OTHER INFORMATION: Synthetic Construct

<400> SEQUENCE: 206

Gly Gly Gly Gly Ser
1               5

<210> SEQ ID NO 207
<211> LENGTH: 4
<212> TYPE: PRT
<213> ORGANISM: Artificial Sequence
<220> FEATURE:
<223> OTHER INFORMATION: Synthetic Construct

<400> SEQUENCE: 207

Gly Gly Ser Gly
1

<210> SEQ ID NO 208
<211> LENGTH: 4
<212> TYPE: PRT
<213> ORGANISM: Artificial Sequence
<220> FEATURE:
<223> OTHER INFORMATION: Synthetic Construct

<400> SEQUENCE: 208

Ser Gly Gly Gly
1

<210> SEQ ID NO 209
<211> LENGTH: 4
<212> TYPE: PRT
<213> ORGANISM: Artificial Sequence
<220> FEATURE:
<223> OTHER INFORMATION: Synthetic Construct

<400> SEQUENCE: 209

Gly Ser Gly Ser
1

<210> SEQ ID NO 210
<211> LENGTH: 6
<212> TYPE: PRT
<213> ORGANISM: Artificial Sequence
<220> FEATURE:
<223> OTHER INFORMATION: Synthetic Construct

<400> SEQUENCE: 210
```

```
<210> SEQ ID NO 211
<211> LENGTH: 8
<212> TYPE: PRT
<213> ORGANISM: Artificial Sequence
<220> FEATURE:
<223> OTHER INFORMATION: Synthetic Construct

<400> SEQUENCE: 211

Gly Ser Gly Ser Gly Ser Gly Ser
1               5

<210> SEQ ID NO 212
<211> LENGTH: 10
<212> TYPE: PRT
<213> ORGANISM: Artificial Sequence
<220> FEATURE:
<223> OTHER INFORMATION: Synthetic Construct

<400> SEQUENCE: 212

Gly Ser Gly Ser Gly Ser Gly Ser Gly Ser
1               5                   10

<210> SEQ ID NO 213
<211> LENGTH: 12
<212> TYPE: PRT
<213> ORGANISM: Artificial Sequence
<220> FEATURE:
<223> OTHER INFORMATION: Synthetic Construct

<400> SEQUENCE: 213

Gly Ser Gly Ser Gly Ser Gly Ser Gly Ser Gly Ser
1               5                   10

<210> SEQ ID NO 214
<211> LENGTH: 6
<212> TYPE: PRT
<213> ORGANISM: Artificial Sequence
<220> FEATURE:
<223> OTHER INFORMATION: Synthetic Construct

<400> SEQUENCE: 214

Gly Gly Ser Gly Gly Ser
1               5

<210> SEQ ID NO 215
<211> LENGTH: 9
<212> TYPE: PRT
<213> ORGANISM: Artificial Sequence
<220> FEATURE:
<223> OTHER INFORMATION: Synthetic Construct

<400> SEQUENCE: 215

Gly Gly Ser Gly Gly Ser Gly Gly Ser
1               5

<210> SEQ ID NO 216
<211> LENGTH: 12
<212> TYPE: PRT
<213> ORGANISM: Artificial Sequence
<220> FEATURE:
<223> OTHER INFORMATION: Synthetic Construct

<400> SEQUENCE: 216
```

(The first line visible at top of page, continuing SEQ ID NO 210:)

```
Gly Ser Gly Ser Gly Ser
1               5
```

Gly Gly Ser Gly Gly Ser Gly Gly Ser Gly Gly Ser
1               5                   10

<210> SEQ ID NO 217
<211> LENGTH: 8
<212> TYPE: PRT
<213> ORGANISM: Artificial Sequence
<220> FEATURE:
<223> OTHER INFORMATION: Synthetic Construct

<400> SEQUENCE: 217

Gly Gly Ser Gly Gly Gly Ser Gly
1               5

<210> SEQ ID NO 218
<211> LENGTH: 12
<212> TYPE: PRT
<213> ORGANISM: Artificial Sequence
<220> FEATURE:
<223> OTHER INFORMATION: Synthetic Construct

<400> SEQUENCE: 218

Gly Gly Ser Gly Gly Gly Ser Gly Gly Gly Ser Gly
1               5                   10

<210> SEQ ID NO 219
<211> LENGTH: 5
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (1)..(5)
<223> OTHER INFORMATION: Can be present in repeat of at least one and up
      to 10

<400> SEQUENCE: 219

Gly Gly Gly Gly Ser
1               5

<210> SEQ ID NO 220
<211> LENGTH: 3
<212> TYPE: PRT
<213> ORGANISM: Artificial Sequence
<220> FEATURE:
<223> OTHER INFORMATION: Synthetic Construct

<400> SEQUENCE: 220

Pro Ala Ser
1

<210> SEQ ID NO 221
<211> LENGTH: 6
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: (2)..(6)
<223> OTHER INFORMATION: Can be present in repeat of at least one and up
      to 10

<400> SEQUENCE: 221

Ala Glu Ala Ala Ala Lys
1               5

```
<210> SEQ ID NO 222
<211> LENGTH: 2
<212> TYPE: PRT
<213> ORGANISM: Artificial Sequence
<220> FEATURE:
<223> OTHER INFORMATION: Synthetic Construct
<220> FEATURE:
<221> NAME/KEY: VARIANT
<222> LOCATION: 1
<223> OTHER INFORMATION: Xaa = Any Amino Acid, preferably Ala, Lys, or
      Glu
<220> FEATURE:
<221> NAME/KEY: VARIANT
<222> LOCATION: (1)..(2)
<223> OTHER INFORMATION: Can be present in repeat of at least one and up
      to 10

<400> SEQUENCE: 222

Xaa Pro
1

<210> SEQ ID NO 223
<211> LENGTH: 4
<212> TYPE: PRT
<213> ORGANISM: Artificial Sequence
<220> FEATURE:
<223> OTHER INFORMATION: Synthetic Construct

<400> SEQUENCE: 223

Gly Gly Gly Ser
1

<210> SEQ ID NO 224
<211> LENGTH: 232
<212> TYPE: PRT
<213> ORGANISM: Artificial Sequence
<220> FEATURE:
<223> OTHER INFORMATION: Synthetic Construct

<400> SEQUENCE: 224
```

Leu Leu Gln Gly Pro Leu Gly Leu Ala Gly Gly Ser Gly Gly Gly Ser
1               5                   10                  15

Glu Ala Lys Leu Gln Glu Ser Gly Pro Val Leu Val Lys Pro Gly Ala
            20                  25                  30

Ser Val Lys Met Ser Cys Lys Ala Ser Gly Tyr Thr Phe Thr Asp Tyr
        35                  40                  45

Tyr Met Asn Trp Val Lys Gln Ser His Gly Lys Ser Leu Glu Trp Ile
    50                  55                  60

Gly Val Ile Asn Pro Tyr Asn Gly Asp Thr Ser Tyr Asn Gln Lys Phe
65                  70                  75                  80

Lys Gly Lys Ala Thr Leu Thr Val Asp Lys Ser Ser Ser Thr Ala Tyr
                85                  90                  95

Met Glu Leu Asn Ser Leu Thr Ser Glu Asp Ser Ala Val Tyr Tyr Cys
            100                 105                 110

Ala Arg Tyr Tyr Gly Ser Trp Phe Ala Tyr Trp Gly Gln Gly Thr Leu
        115                 120                 125

Ile Thr Val Ser Thr Ala Lys Thr Thr Pro Pro Ser Val Tyr Pro Leu
    130                 135                 140

Ala Pro Gly Cys Gly Asp Thr Thr Gly Ser Ser Val Thr Leu Gly Cys
145                 150                 155                 160

Leu Val Lys Gly Tyr Phe Pro Glu Ser Val Thr Val Thr Trp Asn Ser
                165                 170                 175

Gly Ser Leu Ser Ser Ser Val His Thr Phe Pro Ala Leu Leu Gln Ser

```
                   180                 185                 190
Gly Leu Tyr Thr Met Ser Ser Val Thr Val Pro Ser Ser Thr Trp
            195                 200                 205

Pro Ser Glu Thr Val Thr Cys Ser Val Ala His Pro Ala Ser Ser Thr
            210                 215                 220

Thr Val Asp Lys Lys Leu Glu Pro
225                 230

<210> SEQ ID NO 225
<211> LENGTH: 234
<212> TYPE: PRT
<213> ORGANISM: Artificial Sequence
<220> FEATURE:
<223> OTHER INFORMATION: Synthetic Construct

<400> SEQUENCE: 225

Gly Lys Gly Leu Ser Gly Arg Ser Asp Asn His Gly Gly Ser Asp
1               5                   10                  15

Ile Val Met Thr Gln Thr Thr Leu Ser Leu Pro Val Ser Leu Gly Asp
            20                  25                  30

Gln Ala Ser Ile Ser Cys Arg Ser Ser Gln Ser Ile Val His Ser Asn
        35                  40                  45

Gly Asn Thr Tyr Leu Glu Trp Tyr Leu Gln Lys Pro Gly Gln Ser Pro
    50                  55                  60

Lys Leu Leu Ile Tyr Lys Val Ser Asn Arg Phe Ser Gly Val Pro Asp
65                  70                  75                  80

Arg Phe Ser Gly Ser Gly Ser Gly Thr Asp Phe Thr Leu Lys Ile Ser
                85                  90                  95

Arg Val Glu Ala Glu Asp Leu Gly Val Tyr Tyr Cys Phe Gln Gly Ser
            100                 105                 110

His Val Pro Tyr Thr Phe Gly Gly Gly Thr Lys Leu Glu Ile Lys Arg
        115                 120                 125

Ala Asp Ala Ala Pro Thr Val Ser Ile Phe Pro Pro Ser Ser Glu Gln
    130                 135                 140

Leu Thr Ser Gly Gly Ala Ser Val Val Cys Phe Leu Asn Asn Phe Tyr
145                 150                 155                 160

Pro Lys Asp Ile Asn Val Lys Trp Lys Ile Asp Gly Ser Glu Arg Gln
                165                 170                 175

Asn Gly Val Leu Asn Ser Trp Thr Asp Gln Asn Ser Lys Asp Ser Thr
            180                 185                 190

Tyr Ser Met Ser Ser Thr Leu Thr Leu Thr Lys Asp Glu Tyr Glu Arg
        195                 200                 205

His Asn Ser Tyr Thr Cys Glu Ala Thr His Lys Thr Ser Thr Ser Pro
    210                 215                 220

Ile Val Lys Ser Phe Asn Arg Asn Glu Cys
225                 230

<210> SEQ ID NO 226
<211> LENGTH: 6
<212> TYPE: PRT
<213> ORGANISM: Artificial Sequence
<220> FEATURE:
<223> OTHER INFORMATION: Synthetic Construct

<400> SEQUENCE: 226

Gly Ser Gly Gly Gly Ser
1               5
```

<210> SEQ ID NO 227
<211> LENGTH: 16
<212> TYPE: PRT
<213> ORGANISM: Artificial Sequence
<220> FEATURE:
<223> OTHER INFORMATION: Synthetic Construct

<400> SEQUENCE: 227

Leu Leu Gln Gly Pro Leu Gly Leu Ala Gly Gly Ser Gly Gly Gly Ser
1               5                   10                  15

<210> SEQ ID NO 228
<211> LENGTH: 120
<212> TYPE: PRT
<213> ORGANISM: Artificial Sequence
<220> FEATURE:
<223> OTHER INFORMATION: Synthetic Construct

<400> SEQUENCE: 228

Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Tyr Met Tyr Trp Val Arg Gln Ala Pro Gly Gln Gly Leu Glu Trp Met
            35                  40                  45

Gly Gly Ile Asn Pro Ser Asn Gly Gly Thr Asn Phe Asn Glu Lys Phe
        50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser
        115                 120

<210> SEQ ID NO 229
<211> LENGTH: 111
<212> TYPE: PRT
<213> ORGANISM: Artificial Sequence
<220> FEATURE:
<223> OTHER INFORMATION: Synthetic Construct

<400> SEQUENCE: 229

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
                20                  25                  30

Gly Tyr Ser Tyr Leu His Trp Tyr Gln Gln Lys Pro Gly Gln Ala Pro
            35                  40                  45

Arg Leu Leu Ile Tyr Leu Ala Ser Tyr Leu Glu Ser Gly Val Pro Ala
        50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
                85                  90                  95

Asp Leu Pro Leu Thr Phe Gly Gly Gly Thr Lys Val Glu Ile Lys
            100                 105                 110

-continued

```
<210> SEQ ID NO 230
<211> LENGTH: 119
<212> TYPE: PRT
<213> ORGANISM: Artificial Sequence
<220> FEATURE:
<223> OTHER INFORMATION: Synthetic Construct

<400> SEQUENCE: 230

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Thr Asn Tyr
            20                  25                  30

Gly Val His Trp Val Arg Gln Ser Pro Gly Lys Gly Leu Glu Trp Leu
        35                  40                  45

Gly Val Ile Trp Ser Gly Gly Asn Thr Asp Tyr Asn Thr Pro Phe Thr
    50                  55                  60

Ser Arg Leu Ser Ile Asn Lys Asp Asn Ser Lys Ser Gln Val Phe Phe
65                  70                  75                  80

Lys Met Asn Ser Leu Gln Ser Glu Asp Thr Ala Ile Tyr Tyr Cys Ala
                85                  90                  95

Arg Ala Leu Thr Tyr Tyr Asp Tyr Glu Phe Ala Tyr Trp Gly Gln Gly
            100                 105                 110

Thr Leu Val Thr Val Ser Ala
        115

<210> SEQ ID NO 231
<211> LENGTH: 107
<212> TYPE: PRT
<213> ORGANISM: Artificial Sequence
<220> FEATURE:
<223> OTHER INFORMATION: Synthetic Construct

<400> SEQUENCE: 231

Asp Ile Leu Leu Thr Gln Ser Pro Val Ile Leu Ser Val Ser Pro Gly
1               5                   10                  15

Glu Arg Val Ser Phe Ser Cys Arg Ala Ser Gln Ser Ile Gly Thr Asn
            20                  25                  30

Ile His Trp Tyr Gln Gln Arg Thr Asn Gly Ser Pro Arg Leu Leu Ile
        35                  40                  45

Lys Tyr Ala Ser Glu Ser Ile Ser Gly Ile Pro Ser Arg Phe Ser Gly
    50                  55                  60

Ser Gly Ser Gly Thr Asp Phe Thr Leu Ser Ile Asn Ser Val Glu Ser
65                  70                  75                  80

Glu Asp Ile Ala Asp Tyr Tyr Cys Gln Gln Asn Asn Asn Trp Pro Thr
                85                  90                  95

Thr Phe Gly Ala Gly Thr Lys Leu Glu Leu Lys
            100                 105

<210> SEQ ID NO 232
<211> LENGTH: 125
<212> TYPE: PRT
<213> ORGANISM: Artificial Sequence
<220> FEATURE:
<223> OTHER INFORMATION: Synthetic Construct

<400> SEQUENCE: 232

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30
```

Gly Met His Trp Val Arg Gln Ala Pro Gly Lys Gly Leu Glu Trp Val
            35                  40                  45

Ala Val Ile Trp Tyr Asp Gly Ser Asn Lys Tyr Tyr Ala Asp Ser Val
 50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
            85                  90                  95

Ala Arg Asp Pro Arg Gly Ala Thr Leu Tyr Tyr Tyr Tyr Gly Met
            100                 105                 110

Asp Val Trp Gly Gln Gly Thr Thr Val Thr Val Ser Ser
            115                 120                 125

<210> SEQ ID NO 233
<211> LENGTH: 107
<212> TYPE: PRT
<213> ORGANISM: Artificial Sequence
<220> FEATURE:
<223> OTHER INFORMATION: Synthetic Construct

<400> SEQUENCE: 233

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Asn Ser Tyr
            20                  25                  30

Leu Asp Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
 50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ser Thr Pro Phe
            85                  90                  95

Thr Phe Gly Pro Gly Thr Lys Val Glu Ile Lys
            100                 105

<210> SEQ ID NO 234
<211> LENGTH: 120
<212> TYPE: PRT
<213> ORGANISM: Artificial Sequence
<220> FEATURE:
<223> OTHER INFORMATION: Synthetic Construct

<400> SEQUENCE: 234

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
 50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
            85                  90                  95

Ser Arg Trp Gly Gly Asp Gly Phe Tyr Ala Met Asp Tyr Trp Gly Gln

```
                    100                 105                 110

Gly Thr Leu Val Thr Val Ser Ser
        115                 120

<210> SEQ ID NO 235
<211> LENGTH: 107
<212> TYPE: PRT
<213> ORGANISM: Artificial Sequence
<220> FEATURE:
<223> OTHER INFORMATION: Synthetic Construct

<400> SEQUENCE: 235

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 236
<211> LENGTH: 118
<212> TYPE: PRT
<213> ORGANISM: Artificial Sequence
<220> FEATURE:
<223> OTHER INFORMATION: Synthetic Construct

<400> SEQUENCE: 236

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
            20                  25                  30

Thr Met His Trp Val Arg Gln Ala Pro Gly Lys Gly Leu Glu Trp Val
        35                  40                  45

Thr Phe Ile Ser Tyr Asp Gly Asn Asn Lys Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Ile Tyr Tyr Cys
                85                  90                  95

Ala Arg Thr Gly Trp Leu Gly Pro Phe Asp Tyr Trp Gly Gln Gly Thr
            100                 105                 110

Leu Val Thr Val Ser Ser
        115

<210> SEQ ID NO 237
<211> LENGTH: 108
<212> TYPE: PRT
<213> ORGANISM: Artificial Sequence
<220> FEATURE:
<223> OTHER INFORMATION: Synthetic Construct

<400> SEQUENCE: 237
```

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Gly Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Phe Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Trp Thr Phe Gly Gln Gly Thr Lys Val Glu Ile Lys
            100                 105
```

<210> SEQ ID NO 238
<211> LENGTH: 117
<212> TYPE: PRT
<213> ORGANISM: Artificial Sequence
<220> FEATURE:
<223> OTHER INFORMATION: Synthetic Construct

<400> SEQUENCE: 238

```
Glu Ala Lys Leu Gln Glu Ser Gly Pro Val Leu Val Lys Pro Gly Ala
1               5                   10                  15

Ser Val Lys Met Ser Cys Lys Ala Ser Gly Tyr Thr Phe Thr Asp Tyr
            20                  25                  30

Tyr Met Asn Trp Val Lys Gln Ser His Gly Lys Ser Leu Glu Trp Ile
        35                  40                  45

Gly Val Ile Asn Pro Tyr Asn Gly Asp Thr Ser Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Asn Ser Leu Thr Ser Glu Asp Ser Ala Val Tyr Tyr Cys
                85                  90                  95

Ala Arg Tyr Tyr Gly Ser Trp Phe Ala Tyr Trp Gly Gln Gly Thr Leu
            100                 105                 110

Ile Thr Val Ser Thr
        115
```

<210> SEQ ID NO 239
<211> LENGTH: 112
<212> TYPE: PRT
<213> ORGANISM: Artificial Sequence
<220> FEATURE:
<223> OTHER INFORMATION: Synthetic Construct

<400> SEQUENCE: 239

```
Asp Ile Val Met Thr Gln Thr Thr Leu Ser Leu Pro Val Ser Leu Gly
1               5                   10                  15

Asp Gln Ala Ser Ile Ser Cys Arg Ser Ser Gln Ser Ile Val His Ser
            20                  25                  30

Asn Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Leu Gly Val Tyr Tyr Cys Phe Gln Gly
                        85                  90                  95
Ser His Val Pro Tyr Thr Phe Gly Gly Gly Thr Lys Leu Glu Ile Lys
            100                 105                 110

<210> SEQ ID NO 240
<211> LENGTH: 7
<212> TYPE: PRT
<213> ORGANISM: Artificial Sequence
<220> FEATURE:
<223> OTHER INFORMATION: Synthetic Construct

<400> SEQUENCE: 240

Lys Ser Arg Thr Thr Asn Gly
1               5

<210> SEQ ID NO 241
<211> LENGTH: 8
<212> TYPE: PRT
<213> ORGANISM: Artificial Sequence
<220> FEATURE:
<223> OTHER INFORMATION: Synthetic Construct

<400> SEQUENCE: 241

Lys Gly Ser Arg Thr Thr Asn Gly
1               5
```

ACTIVATABLE ANTIBODIES AND METHODS OF USE THEREOF

CROSS-REFERENCE TO RELATED APPLICATION

This application is a National Phase application under 35 U.S.C. § 371 of International Application No. PCT/US2018/032806, filed May 15, 2018, which claims priority to U.S. Provisional Application No. 62/507,129, filed on May 16, 2017, the contents of which are hereby incorporated by reference in their entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 781282000100SEQLIST.txt, date recorded: Nov. 8, 2019, size: 158 KB).

FIELD OF THE INVENTION

The present invention relates to activatable antibodies and methods of use thereof.

BACKGROUND OF THE INVENTION

Antibodies have successfully been used as therapeutic and diagnostic agents for a variety of diseases. A native antibody acts by binding to a specific target. However, antibody targets can be expressed in both diseased (e.g. tumor) tissues and normal tissues. When antibodies bind to targets expressed in normal tissues of a patient, the patient can experience undesirable, toxic side-effects, which can range from mild to severe or even life-threatening degree of intensity. Such side effects can lead to a decreased effective dosage of the antibody, which can lower its therapeutic efficacy. The antibody treatment may even be discontinued due to the side effects, which, in some cases, renders the antibody therapeutic unavailable to human patients. Thus, there exists an unmet need to engineer antibodies that preferentially bind to targets on diseased cells and tissues.

BRIEF SUMMARY OF THE INVENTION

The present application provides activatable antibodies, methods of preparing the activatable antibodies, and method of treating a disease in an individual using the activatable antibodies.

In one aspect of the present application, there is provided an activatable antibody comprising an antibody comprising an antigen-binding domain (ABD), wherein the ABD comprises a heavy chain variable region (VH) and a light chain variable region (VL), wherein the N-terminus of the VH is fused to a first polypeptide shield moiety (S1), and the N-terminus of the VL is fused to a second polypeptide shield moiety (S2), wherein S1 comprises a first disease-sensing releasable moiety (DS1) and/or S2 comprises a second disease-sensing releasable moiety (DS2), wherein association of S1 with S2 blocks binding of the ABD to its target, and wherein the ABD does not specifically bind to S1, S2, or association thereof. In some embodiments, the activatable antibody comprises a first polypeptide comprising, from N-terminus to C-terminus, S1-VH; and a second polypeptide comprising, from N-terminus to C-terminus. S2-VL, wherein S1 and S2 are associated covalently or non-covalently.

In some embodiments, S comprises DS1 and S2 does not comprise DS2. In some embodiments, S2 comprises DS2 and S1 does not comprise DS1. In some embodiments, S1 comprises DS1, and S2 comprises DS2. In some embodiments, DS1 is identical to DS2. In some embodiments, DS1 is different from DS2.

In some embodiments according to any one of the activatable antibodies described above, the association between S1 and S2 spans a length greater than about 35 Å. In some embodiments, S1 and/or S2 comprise at least 7 amino acid residues (such as at least 10 amino acid residues). In some embodiments, each of S1 and S2 is a polypeptide no more than about 50 amino acids long. In some embodiments, S1 and/or S2 are oligopeptides.

In some embodiments according to any one of the activatable antibodies described above, the association between S1 and S2 is covalent. In some embodiments, S1 comprises a first association moiety (B), and S2 comprises a second association moiety (C), and wherein B and C are conjugated to each other via a covalent bond. In some embodiments, the association between S1 and S2 is non-covalent. In some embodiments, S1 comprises a first association moiety (B), and S2 comprises a second association moiety (C), and wherein B and C interact with each other non-covalently.

In some embodiments according to any one of the activatable antibodies described above, wherein association between S1 and S2 is covalent, B and C are conjugated to each other via an isopeptide bond. In some embodiments, the isopeptide bond is formed between an acyl donor and an acyl acceptor by a transglutaminase. In some embodiments, B comprises the amino acid sequence of SEQ ID NO: 1, and C comprises the amino acid sequence of SEQ ID NO: 2. In some embodiments, B comprises the amino acid sequence of SEQ ID NO: 2, and C comprises the amino acid sequence of SEQ ID NO: 1.

In some embodiments according to any one of the activatable antibodies described above, wherein the association between S1 and S2 is covalent, B and C are cysteines, and wherein B and C are conjugated to each other via a disulfide bond. In some embodiments, each of B and C comprises the amino acid sequence of SEQ ID NO: 3.

In some embodiments according to any one of the activatable antibodies described above, wherein the association between S1 and S2 is covalent, B is a first unnatural amino acid residue, and C is a second unnatural amino acid residue. In some embodiments, B and C are selenocysteines, and wherein B and C are conjugated to each other via a diselenide bond.

In some embodiments according to any one of the activatable antibodies described above, wherein the association between S1 and S2 is non-covalent, B and C are two complementary halves of a split-protein. In some embodiments, the split-protein is selected from the group consisting of GFP. Ubiquitin, CnaB2, interleukins, and chemokines. In some embodiments, wherein: (a) one of B and C comprises the amino acid sequence of SEQ ID NO: 4 and the other comprises the amino acid sequence of SEQ ID NO: 5, or (b) one of B and C comprises the amino acid sequence of SEQ ID NO: 6 and the other comprises the amino acid sequence of SEQ ID NO: 7. In some embodiments, B and C associate to form a therapeutic protein.

In some embodiments according to any one of the activatable antibodies described above, wherein the association between S1 and S2 is non-covalent, B and C are monomeric subunits of a dimeric protein. In some embodiments, the dimeric protein is selected from the group consisting of HIV protease, relaxin-2, Myo10, STIL, Troponin C, defensin-5, IL-10, DHBN domain of human BLM helicase, Insulin, human copper chaperone, KIX domain of human RECQL5, galectin-1, TNF-alpha, human neutrophil peptide 1, CXCL5, CXCL4, ILT1-immunoglobulin-like transcript, and IL-12. In some embodiments, the dimeric protein is a homodimer. In some embodiments, each of B and C comprises an amino acid sequence selected from the group consisting of SEQ ID NOs: 8-10. In some embodiments, the dimeric protein is a heterodimer. In some embodiments, one of B and C comprises the amino acid sequence of SEQ ID NO: 11 and the other comprises the amino acid sequence of SEQ ID NO: 12. In some embodiments, B and C associate to form a therapeutic protein.

In some embodiments according to any one of the activatable antibodies described above, wherein the association between S1 and S2 is non-covalent, B and C are complementary binding peptides. In some embodiments, B and C associate to form a parallel coiled-coil homodimer. In some embodiments, each of B and C comprises an amino acid sequence selected from the group consisting of SEQ ID NO: 13-15. In some embodiments. B and C associate to form an anti-parallel coiled-coil heterodimer. In some embodiments, one of B and C comprises the amino acid sequence of SEQ ID NO: 16 and the other comprises the amino acid sequence of SEQ ID NO: 17. In some embodiments, B and C associate to form a therapeutic protein.

In some embodiments according to any one of the activatable antibodies described above, wherein the association between S1 and S2 is non-covalent, one of B and C is a second VH, and the other is a second VL, and wherein B and C associate to form an Fv. In some embodiments, each of B and C comprises a cysteine, and wherein B is further conjugated to C via a disulfide bond. In some embodiments, B and C associate to form a therapeutic protein.

In some embodiments according to any one of the activatable antibodies described above, wherein the association between S1 and S2 is non-covalent, one of B and C is a glycan linked to a glycosylation peptide sequence, and the other is a glycan-binding protein (such as lectin, ficolin, or ERGIC-53). In some embodiments, the glycosylation peptide sequence comprises the amino acid sequence of SEQ ID NO: 18. In some embodiments, the glycan-binding protein is M-ficolin.

In some embodiments according to any one of the activatable antibodies described above, DS1 and/or DS2 comprises a peptide substrate specific for an enzyme that is expressed at a diseased site. In some embodiments, DS1 and/or DS2 is a tumor-sensing releasable moiety. In some embodiments, DS1 and/or DS2 comprises a peptide substrate cleavable by a tumor-specific protease. In some embodiments, the tumor-specific protease is selected from the group consisting of matriptase, legumain, uPA, matrix metalloproteases, MMP1, MMP2, MMP9, gelatinase, PSA, human neutrophil elastase, proteinase 3, pro-urokinase. Factor Xa, cathepsin K and cathepsin B. In some embodiments, the DS1 and/or DS2 comprises the amino acid sequence of SEQ ID NO: 19, 172, 240 or 241. In some embodiments, DS1 and/or DS2 comprises at least two peptide substrates each specific for an enzyme that is expressed at a diseased site. In some embodiments, DS1 and/or DS2 comprises a pH-sensitive protein or peptide, e.g., a protein or peptide that undergoes conformational change at acidic pH.

In some embodiments according to any one of the activatable antibodies described above, DS1 and/or DS2 comprises a flexible peptide linker.

In some embodiments according to any one of the activatable antibodies described above, the antibody comprises two or more antigen-binding domains. In some embodiments, the two or more antigen-binding domains bind to the same target. In some embodiments, the two or more antigen-binding domains bind to different targets. In some embodiments, the antibody is a bispecific antibody. In some embodiments, the antibody comprises a heavy chain constant domain fused to the C-terminus of VH, and a light chain constant domain fused to the C-terminus of VL. In some embodiments, the antibody is a Fab or a (Fab)$_2$. In some embodiments, the antibody comprises an immunoglobulin Fc region. In some embodiments, the antibody is a full length antibody. In some embodiments, the antibody is an antibody-drug conjugate (ADC).

In some embodiments according to any one of the activatable antibodies described above, the ABD specifically binds to a target selected from the molecules shown in Table 8, such as EGFR, CTLA-4, PD-1, CD-71 or PD-L1. In some embodiments, the ABD is derived from a therapeutic antibody selected from the antibodies shown in Table 9, such as Cetuximab, Trastuzumab, Tremelimumab, Ipilimumab, Nivolumab, Pembrolizumab, or Atezolizumab.

In some embodiments according to any one of the activatable antibodies described above, disruption (such as cleavage or conformational change) of DS1 and/or DS2 unblocks the binding of the ABD to its target.

In some embodiments, there is provided a vector for expressing any one of the activatable antibodies described above, comprising: (a) a first nucleic acid encoding a heavy chain comprising S1 fused to the N-terminus of the VH; and (b) a second nucleic acid encoding a light chain comprising S2 fused to the N-terminus of the VL. In some embodiments, there is provided a host cell comprising the vector.

In some embodiments, there is provided a method of preparing an activatable antibody, comprising: (a) culturing the host cell described under a condition that produces a fusion antibody comprising the heavy chain and the light chain; and (b) isolating the fusion antibody, thereby providing the activatable antibody. In some embodiments, the method further comprises treating the fusion antibody with a reducing agent followed by an oxidation agent. In some embodiments, the method further comprises treating the fusion antibody with a transglutaminase. In some embodiments, the method further comprises treating the fusion antibody with a glycosylase. In some embodiments, there is provided a composition comprising the fusion antibody prepared in step (b) of the any one of methods described above.

Also provided is a pharmaceutical composition comprising any one of the activatable antibodies described above and a pharmaceutically acceptable carrier.

Another aspect of the present application provides a method of treating a disease in an individual, comprising administering to the individual an effective amount of any one of the pharmaceutical compositions described above, wherein DS1 and/or DS2 are disrupted at a diseased site, thereby unblocking binding of the ABD to its target at the diseased site. In some embodiments, the disease is a cancer. In some embodiments, the cancer is selected from the group consisting of bladder cancer, brain cancer, breast cancer, cervical cancer, colorectal cancer, esophageal cancer, kidney cancer, leukemia, liver cancer, lung cancer, melanoma, non- Hodgkin's lymphoma, ovarian cancer, pancreatic cancer, prostate cancer, skin cancer, thyroid cancer and uterine cancer.

These and other aspects and advantages of the present invention will become apparent from the subsequent detailed description and the appended claims. It is to be understood that one, some, or all of the properties of the various embodiments described herein may be combined to form other embodiments of the present invention.

All references cited herein, including patent applications, patent publications, and Genbank Accession numbers are herein incorporated by reference, as if each individual reference were specifically and individually indicated to be incorporated by reference in its entirety.

BRIEF DESCRIPTION OF THE DRAWINGS

FIG. 3A shows positions of the heavy chain and light chain N-termini relative to the antigen binding site in the crystal structure of a Fab of Pembrolizumab (PDB ID: 5JXE).

FIG. 3B shows a structural model of an exemplary steric shield based on the crystal structure of a Fab of Pembrolizumab (PDB ID: 5JXE). A structural model of the peptide SCLSGRSDNHGG (SEQ ID NO: 145) was added to the native N-termini of both the heavy and light chains, and the peptides were joined by modeling Cys-Cys disulfide bridge formation.

FIG. 3C shows a structural model of an exemplary steric shield based on the crystal structure of a Fab of Cetuximab (PDB ID: 1YY9). A structural model of the peptide LLQGLSGRSDNH (SEQ ID NO: 140) was added to the native N-terminus of the heavy chain, a structural model of the peptide GKGLSGRSDNH (SEQ ID NO: 141) was added to the native N-terminus of the light chain, and the peptides were joined by modeling transglutaminase-mediated crosslinking.

FIG. 3D shows a structural model of an exemplary steric shield based on the crystal structure of a diabody of Hu5F9 (PDB ID: 5IWL). A structural model of the peptide LLQGLSGRSDNH (SEQ ID NO: 140) was added to the native N-terminus of the heavy chain, and a structural model of the peptide GKGLSGRSDNH (SEQ ID NO: 141) was added to the native N-terminus of the light chain, and the peptides were joined by modeling transglutaminase-mediated crosslinking.

FIG. 3E shows a structural model of an exemplary steric shield based on the crystal structure of Trastuzumab (PDB ID: IN8Z). A structural model of the peptide LLQGLSGRSDNH (SEQ ID NO: 140) was added to the native N-terminus of the heavy chain, and a structural model of the peptide GKGLSGRSDNH (SEQ ID NO: 141) was added to the native N-terminus of the light chain, and the peptides were joined by modeling transglutaminase-mediated crosslinking.

FIG. 9B shows a bar graph of SPR data illustrating EGFR binding to two exemplary activatable anti-EGFR antibodies (activatable EGFR Ab 3 and 4). The data demonstrated that the steric shields formed by Cys-Cys disulfide bridges in the activatable antibodies substantially reduced their EGFR binding activities, and removal of the steric shields from the activatable antibodies restored their EGFR binding activities.

DETAILED DESCRIPTION OF THE INVENTION

Figure 1A:
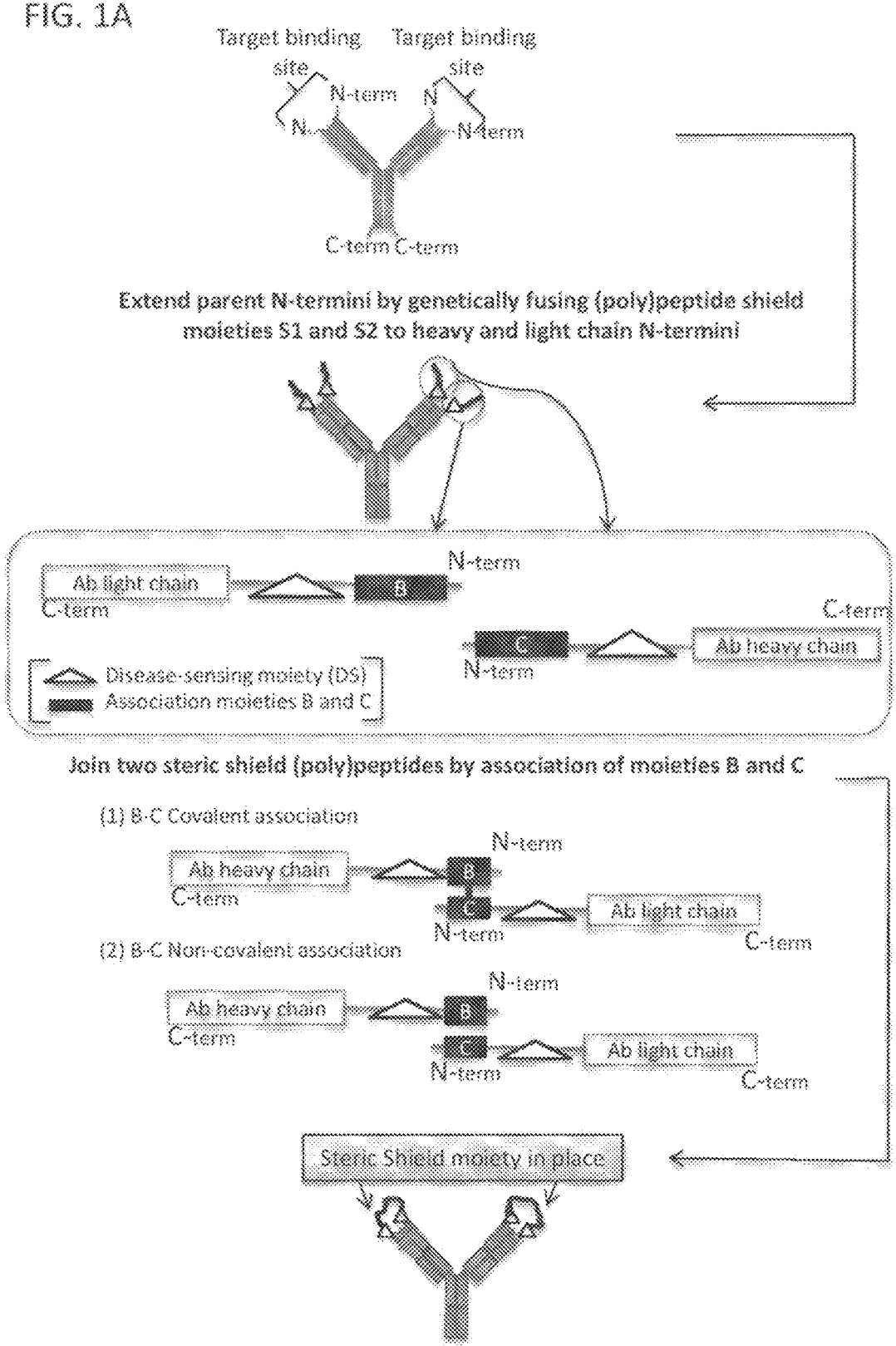
FIG. 1A is a schematic diagram illustrating generation of exemplary activatable antibodies. Each activatable antibody has a steric shield covering its target-binding site(s).

The present application provides an activatable antibody having steric shield(s) that block the antigen binding site(s) of an antibody (including an antibody fragment) so that in the inactive state, the antibody is unable to bind to its antigen. The steric shield is generated by covalent or non-covalent association of two polypeptide shield moieties that extend from the N-termini of the heavy chain variable region (VH) and the light chain variable region (VL) of the antibody across an antigen binding site. One or both of the polypeptide shield moieties contain a disease-sensing releasable moiety that can be preferentially disrupted (such as cleaved or deformed) at a diseased site, resulting in release of the steric shield from the antigen binding site, and activation of the activatable antibody at the diseased site. In some embodiments, the steric shield itself is a therapeutic agent, which can act independently on its own target upon activation of the activatable antibody.

The design of the activatable antibodies described in the present application is applicable to any therapeutic antibodies. The activatable antibodies can be prepared by the following steps: the polypeptide shield moieties can be introduced into a therapeutic antibody by genetic engineering, and the steric shield can be formed during protein expression, or via a simple transglutaminase-catalyzed or oxidation/reduction step post protein expression. The activatable antibodies described herein can improve the pharmacokinetics and reduce unwanted side-effects of traditional therapeutic antibodies, and enable antibody therapy for previously unavailable targets due to excessive on-target off-tumor (or other diseased tissue) binding activities.

Accordingly, one aspect of the present application provides an activatable antibody comprising an antibody comprising an antigen-binding domain (ABD), wherein the ABD comprises a heavy chain variable region (VH) and a light chain variable region (VL), wherein the N-terminus of the VH is fused to a first polypeptide shield moiety (S1), and the N-terminus of the VL is fused to a second polypeptide shield moiety (S2), wherein S1 comprises a first disease-sensing releasable moiety (DS1) and/or S2 comprises a second disease-sensing releasable moiety (DS2), wherein association of S1 with S2 blocks binding of the ABD to its target, and wherein the ABD does not specifically bind to S1, S2, or association thereof. In some embodiments, each of S1 and S2 is a polypeptide no more than about 50 amino acids long. In some embodiments, S1 comprises a first association moiety (B), and S2 comprises a second association moiety (C), wherein B and C interact with each other non-covalently, and wherein B and C do not associate to form a second antigen-binding domain (e.g., an Fv).

Further provided are nucleic acids and vectors comprising a sequence encoding the activatable antibody described herein, host cells comprising the nucleic acids or vectors, and methods of producing the activatable antibodies. Further provided herein are methods of treating a disease using the activatable antibodies, and compositions (such as pharmaceutical compositions) comprising the activatable antibodies, medicine, kits, and articles of manufacture useful for the methods described herein.

I. Definitions

Terms are used herein as generally used in the art, unless otherwise defined as follows.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

The term antibody includes, but is not limited to, fragments that are capable of binding antigen, such as Fv, Fab, Fab', and (Fab')$_2$. Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-combining sites and is still capable of cross-linking antigen. The term antibody also includes, but is not limited to, chimeric antibodies, humanized antibodies, and antibodies of various species such as mouse, human, cynomolgus monkey, etc.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

The term "hypervariable region" or "HVR." as used herein, refers to each of the regions of an antibody variable domain which are hypervariable in sequence. HVRs may form structurally defined loops ("hypervariable loops"). Generally, native four-chain antibodies comprise six HVRs: three in the VH (H1, H2, H3), and three in the VL (L1, L2, L3). HVRs generally comprise amino acid residues from the hypervariable loops and/or from the "complementarity determining regions" (CDRs), CDRs being of highest sequence variability and/or involved in antigen recognition. Exemplary hypervariable loops occur at amino acid residues 26-32 (L1), 50-52 (L2), 91-96 (L3), 26-32 (H1), 53-55 (H2), and 96-101 (H3). (Chothia and Lesk, J. Mol. Biol. 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., Sequences of Proteins of Immunological Interest, 5th Ed. Public Health Service, National Institutes of Health, Bethesda, MD (1991)) With the exception of CDR1 in VH, CDRs generally comprise the amino acid residues that form the hypervariable loops. CDRs also comprise "specificity determining residues," or "SDRs." which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, Front Biosci. 13:1619-1633 (2008)). Unless otherwise indicated, HVR residues and other residues in the variable domain (e.g., FR residues) are numbered herein according to Kabat et al., supra. Use of the term "or" herein is not meant to imply that alternatives are mutually exclusive.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four framework regions (FRs) and three hypervariable regions (HVRs), arranged from amino-terminus to carboxy-terminus in the following order: FR1, HVR1, FR2, HVR2, FR3, HVR3, FR4. (See, e.g., Kindt et al. Kuby Immunology, 6th ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., J. Immunol. 150:880-887 (1993); Clarkson et al., Nature 352:624-628 (1991).

The term "heavy chain constant region" as used herein refers to a region comprising at least three heavy chain constant domains, CH1, CH2, and CH3, and a hinge region between CH1 and CH2. Non-limiting exemplary heavy chain constant regions include γ, δ, and α. Non-limiting exemplary heavy chain constant regions also include ε and μ. Each heavy constant region corresponds to an antibody isotype. For example, an antibody comprising a γ constant region is an IgG antibody, an antibody comprising a δ constant region is an IgD antibody, and an antibody comprising an α constant region is an IgA antibody. Further, an antibody comprising a μ constant region is an IgM antibody, and an antibody comprising an ε constant region is an IgE antibody. Certain isotypes can be further subdivided into subclasses. For example, IgG antibodies include, but are not limited to, IgG1 (comprising a $\gamma_1$ constant region), IgG2 (comprising a $\gamma_2$ constant region), IgG3 (comprising a $\gamma_3$ constant region), and IgG4 (comprising a $\gamma_4$ constant region) antibodies; IgA antibodies include, but are not limited to, IgA1 (comprising an $\alpha_1$ constant region) and IgA2 (comprising an $\alpha_2$ constant region) antibodies; and IgM antibodies include, but are not limited to, IgM1 and IgM2.

The term "heavy chain" as used herein refers to a polypeptide comprising at least a heavy chain variable region, with or without a leader sequence. In some embodiments, a heavy chain comprises at least a portion of a heavy chain constant region. The term "full-length heavy chain" as used herein refers to a polypeptide comprising a heavy chain variable region and a heavy chain constant region, with or without a leader sequence.

The term "light chain constant region" as used herein refers to a region comprising a light chain constant domain, CL. Non-limiting exemplary light chain constant regions include λ and κ.

The term "light chain" as used herein refers to a polypeptide comprising at least a light chain variable region, with or without a leader sequence. In some embodiments, a light chain comprises at least a portion of a light chain constant region. The term "full-length light chain" as used herein refers to a polypeptide comprising a light chain variable region and a light chain constant region, with or without a leader sequence.

"Affinity" refers to the strength of the sum total of noncovalent interactions between a single binding site of a molecule (e.g., an antibody) and its binding partner (e.g., an antigen). The affinity of a molecule X for its partner Y can generally be represented by the dissociation constant ($K_d$). Affinity can be measured by common methods known in the art, including those described herein.

The term "binds", "specifically binds to" or is "specific for" refers to measurable and reproducible interactions such as binding between a target and an antibody, which is determinative of the presence of the target in the presence of a heterogeneous population of molecules including biological molecules. For example, an antibody that binds to or specifically binds to a target (which can be an epitope) is an antibody that binds this target with greater affinity, avidity, more readily, and/or with greater duration than it binds to other targets. In some embodiments, the extent of binding of an antibody to an unrelated target is less than about 10% of the binding of the antibody to the target as measured, e.g., by a radioimmunoassay (RIA). In some embodiments, an antibody that specifically binds to a target has a dissociation constant (Kd) of ≤1 μM, ≤100 nM, ≤10 nM, ≤1 nM, or ≤0.1 nM. In some embodiments, an antibody specifically binds to an epitope on a protein that is conserved among the protein from different species. In another embodiment, specific binding can include, but does not require exclusive binding.

The term "multispecific" as used in conjunction with an antibody refers to an antibody having polyepitopic specificity (i.e., is capable of specifically binding to two, three, or more, different epitopes on one biological molecule or is capable of specifically binding to epitopes on two, three, or more, different biological molecules).

An "affinity matured" antibody refers to an antibody with one or more alterations in one or more hypervariable regions (HVRs) compared to a parent antibody which does not possess such alterations, such alterations resulting in an improvement in the affinity of the antibody for antigen. In some examples, an affinity matured antibody refers to an antibody with one or more alterations in one or more complementarity determining regions (CDRs) compared to a parent antibody which does not possess such alterations, such alterations resulting in an improvement in the affinity of the antibody for antigen.

A "chimeric antibody" as used herein refers to an antibody in which a portion of the heavy and/or light chain is derived from a particular source or species, while the remainder of the heavy and/or light chain is derived from a different source or species. In some embodiments, a chimeric antibody refers to an antibody comprising at least one variable region from a first species (such as mouse, rat, cynomolgus monkey, etc.) and at least one constant region from a second species (such as human, cynomolgus monkey, etc.). In some embodiments, a chimeric antibody comprises at least one mouse variable region and at least one human constant region. In some embodiments, a chimeric antibody comprises at least one cynomolgus variable region and at least one human constant region. In some embodiments, all of the variable regions of a chimeric antibody are from a first species and all of the constant regions of the chimeric antibody are from a second species.

A "humanized antibody" as used herein refers to an antibody in which at least one amino acid in a framework region of a non-human variable region has been replaced with the corresponding amino acid from a human variable region. In some embodiments, a humanized antibody comprises at least one human constant region or fragment thereof. In some embodiments, a humanized antibody is an Fab, a (Fab')$_2$, etc.

An "HVR-grafted antibody" as used herein refers to a humanized antibody in which one or more hypervariable regions (HVRs) of a first (non-human) species have been grafted onto the framework regions (FRs) of a second (human) species. In some examples, a "CDR-grafted antibody" as used herein refers to a humanized antibody in which one or more complementarity determining regions (CDRs) of a first (non-human) species have been grafted onto the framework regions (FRs) of a second (human) species.

A "human antibody" as used herein refers to antibodies produced in humans, antibodies produced in non-human animals that comprise human immunoglobulin genes, such as XENOMOUSE®, and antibodies selected using in vitro methods, such as phage display, wherein the antibody repertoire is based on a human immunoglobulin sequence.

The terms "nucleic acid molecule", "nucleic acid" and "polynucleotide" may be used interchangeably, and refer to a polymer of nucleotides. Such polymers of nucleotides may contain natural and/or unnatural nucleotides, and include, but are not limited to, DNA, RNA, and PNA. "Nucleic acid sequence" refers to the linear sequence of nucleotides that comprise the nucleic acid molecule or polynucleotide.

The terms "polypeptide" and "peptide" are used interchangeably to refer to a polymer of amino acid residues, and are not limited to a minimum length. Such polymers of amino acid residues may contain natural or unnatural amino acid residues. Both full-length proteins and fragments thereof are encompassed by the definition. The terms also include post-expression modifications of the polypeptide, for example, glycosylation, sialylation, acetylation, phosphorylation, and the like. Furthermore, a "polypeptide" includes modifications, such as deletions, additions, and substitutions (generally conservative in nature), to the native sequence, as long as the polypeptide maintains the desired activity. These modifications may be deliberate, as through site-directed mutagenesis, or may be accidental, such as through mutations of hosts which produce the proteins or errors due to PCR amplification.

The term "fusion" refers to genetically joining two polypeptide fragments to provide a single continuous polypeptide ("fusion polypeptide"). The two polypeptide fragments may be directly joined to each other, or joined via another polypeptide disposed therebetween. Routine recombinant DNA techniques or chemical gene synthesis can be used to provide nucleic acids that genetically encode a fusion polypeptide.

The term "conjugation" refers to chemically joining two chemical groups or moieties together via one or more covalent bonds formed therebetween.

The term "leader sequence" refers to a sequence of amino acid residues located at the N-terminus of a polypeptide that facilitates secretion of a polypeptide from a mammalian cell. A leader sequence may be cleaved upon export of the polypeptide from the mammalian cell, forming a mature protein. Leader sequences may be natural or synthetic, and they may be heterologous or homologous to the protein to which they are attached.

A "native sequence" polypeptide comprises a polypeptide having the same amino acid sequence as a polypeptide found in nature. Thus, a native sequence polypeptide can have the amino acid sequence of naturally occurring polypeptide from any mammal. Such native sequence polypeptide can be isolated from nature or can be produced by recombinant or synthetic means. The term "native sequence" polypeptide specifically encompasses naturally occurring truncated or secreted forms of the polypeptide (e.g., an extracellular domain sequence), naturally occurring variant forms (e.g., alternatively spliced forms) and naturally occurring allelic variants of the polypeptide.

A polypeptide "variant" means a biologically active polypeptide having at least about 80% amino acid sequence identity with the native sequence polypeptide after aligning the sequences and introducing gaps, if necessary, to achieve the maximum percent sequence identity, and not considering any conservative substitutions as part of the sequence identity. Such variants include, for instance, polypeptides wherein one or more amino acid residues are added, or deleted, at the N- or C-terminus of the polypeptide. In some embodiments, a variant will have at least about 80% amino acid sequence identity. In some embodiments, a variant will have at least about 90% amino acid sequence identity. In some embodiments, a variant will have at least about 95% amino acid sequence identity with the native sequence polypeptide.

As used herein, "Percent (%) amino acid sequence identity" and "homology" with respect to a peptide, polypeptide or antibody sequence are defined as the percentage of amino acid residues in a candidate sequence that are identical with the amino acid residues in the specific peptide or polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or MEGALIGN™ (DNASTAR) software. Those skilled in the art can determine appropriate parameters for measuring alignment, including any algorithms needed to achieve maximal alignment over the full length of the sequences being compared.

An amino acid substitution may include but are not limited to the replacement of one amino acid in a polypeptide with another amino acid. Exemplary substitutions are shown in Table 1. Amino acid substitutions may be introduced into an antibody of interest and the products screened for a desired activity, e.g., retained/improved antigen binding, decreased immunogenicity, or improved ADCC or CDC.

TABLE 1

Exemplary Amino Acid Substitutions.

| Original Residue | Exemplary Substitutions |
| --- | --- |
| Ala (A) | Val; Leu; Ile |
| Arg (R) | Lys; Gln; Asn |
| Asn (N) | Gln; His; Asp, Lys; Arg |
| Asp (D) | Glu; Asn |
| Cys (C) | Ser; Ala |
| Gln (Q) | Asn; Glu |
| Glu (E) | Asp; Gln |
| Gly (G) | Ala |
| His (H) | Asn; Gln; Lys; Arg |
| Ile (I) | Leu; Val; Met; Ala; Phe; Norleucine |
| Leu (L) | Norleucine; Ile; Val; Met; Ala; Phe |
| Lys (K) | Arg; Gln; Asn |
| Met (M) | Leu; Phe; Ile |
| Phe (F) | Trp; Leu; Val; Ile; Ala; Tyr |
| Pro (P) | Ala |
| Ser (S) | Thr |
| Thr (T) | Val; Ser |
| Trp (W) | Tyr; Phe |
| Tyr (Y) | Trp; Phe; Thr; Ser |
| Val (V) | Ile; Leu; Met; Phe; Ala; Norleucine |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "vector" is used to describe a polynucleotide that may be engineered to contain a cloned polynucleotide or polynucleotides that may be propagated in a host cell. A vector may include one or more of the following elements:

an origin of replication, one or more regulatory sequences (such as, for example, promoters and/or enhancers) that regulate the expression of the polypeptide of interest, and/or one or more selectable marker genes (such as, for example, antibiotic resistance genes and genes that may be used in colorimetric assays, e.g., j-galactosidase). The term "expression vector" refers to a vector that is used to express a polypeptide of interest in a host cell.

A "host cell" refers to a cell that may be or has been a recipient of a vector or isolated polynucleotide. Host cells may be prokaryotic cells or eukaryotic cells. Exemplary eukaryotic cells include mammalian cells, such as primate or non-primate animal cells; fungal cells, such as yeast; plant cells; and insect cells. Non-limiting exemplary mammalian cells include, but are not limited to, NSO cells, PER.C6® cells (Crucell), and 293 and CHO cells, and their derivatives, such as 293-6E and DG44 cells, respectively. The term "cell" includes the primary subject cell and its progeny.

The term "isolated" as used herein refers to a molecule that has been separated from at least some of the components with which it is typically found in nature or produced. For example, a polypeptide is referred to as "isolated" when it is separated from at least some of the components of the cell in which it was produced. Where a polypeptide is secreted by a cell after expression, physically separating the supernatant containing the polypeptide from the cell that produced it is considered to be "isolating" the polypeptide. Similarly, a polynucleotide is referred to as "isolated" when it is not part of the larger polynucleotide (such as, for example, genomic DNA or mitochondrial DNA, in the case of a DNA polynucleotide) in which it is typically found in nature, or is separated from at least some of the components of the cell in which it was produced, e.g., in the case of an RNA polynucleotide. Thus, a DNA polynucleotide that is contained in a vector inside a host cell may be referred to as "isolated".

The terms "individual" or "subject" are used interchangeably herein to refer to an animal; for example a mammal. In some embodiments, methods of treating mammals, including, but not limited to, humans, rodents, simians, felines, canines, equines, bovines, porcines, ovines, caprines, mammalian laboratory animals, mammalian farm animals, mammalian sport animals, and mammalian pets, are provided. In some examples, an "individual" or "subject" refers to an individual or subject in need of treatment for a disease or disorder.

As used herein, "treatment" is an approach for obtaining beneficial or desired clinical results. "Treatment" as used herein, covers any administration or application of a therapeutic for disease in a mammal, including a human. For purposes of this invention, beneficial or desired clinical results include, but are not limited to, any one or more of: alleviation of one or more symptoms, diminishment of extent of disease, preventing or delaying spread (e.g., metastasis, for example metastasis to the lung or to the lymph node) of disease, preventing or delaying recurrence of disease, delay or slowing of disease progression, amelioration of the disease state, inhibiting the disease or progression of the disease, inhibiting or slowing the disease or its progression, arresting its development, and remission (whether partial or total). Also encompassed by "treatment" is a reduction of pathological consequence of a proliferative disease. The methods of the invention contemplate any one or more of these aspects of treatment.

In the context of cancer, the term "treating" includes any or all of: inhibiting growth of cancer cells, inhibiting replication of cancer cells, lessening of overall tumor burden and ameliorating one or more symptoms associated with the disease.

The terms "inhibition" or "inhibit" refer to a decrease or cessation of any phenotypic characteristic or to the decrease or cessation in the incidence, degree, or likelihood of that characteristic. To "reduce" or "inhibit" is to decrease, reduce or arrest an activity, function, and/or amount as compared to a reference. In some embodiments, by "reduce" or "inhibit" is meant the ability to cause an overall decrease of 20% or greater. In another embodiment, by "reduce" or "inhibit" is meant the ability to cause an overall decrease of 50% or greater. In yet another embodiment, by "reduce" or "inhibit" is meant the ability to cause an overall decrease of 75%, 85%, 90%, 95%, or greater.

As used herein, "delaying development of a disease" means to defer, hinder, slow, retard, stabilize, suppress and/or postpone development of the disease (such as cancer). This delay can be of varying lengths of time, depending on the history of the disease and/or individual being treated. As is evident to one skilled in the art, a sufficient or significant delay can, in effect, encompass prevention, in that the individual does not develop the disease. For example, a late stage cancer, such as development of metastasis, may be delayed.

"Preventing," as used herein, includes providing prophylaxis with respect to the occurrence or recurrence of a disease in a subject that may be predisposed to the disease but has not yet been diagnosed with the disease.

As used herein, to "suppress" a function or activity is to reduce the function or activity when compared to otherwise same conditions except for a condition or parameter of interest, or alternatively, as compared to another condition. For example, an antibody which suppresses tumor growth reduces the rate of growth of the tumor compared to the rate of growth of the tumor in the absence of the antibody.

An "effective amount" refers to an amount of an agent or drug effective to treat a disease or disorder in a subject. In the case of cancer, the effective amount of the agent may reduce the number of cancer cells; reduce the tumor size; inhibit (i.e., slow to some extent and preferably stop) cancer cell infiltration into peripheral organs; inhibit (i.e., slow to some extent and preferably stop) tumor metastasis; inhibit, to some extent, tumor growth; and/or relieve to some extent one or more of the symptoms associated with the cancer. As is understood in the clinical context, an effective amount of a drug, compound, or pharmaceutical composition may or may not be achieved in conjunction with another drug, compound, or pharmaceutical composition. Thus, an "effective amount" may be considered in the context of administering one or more therapeutic agents, and a single agent may be considered to be given in an effective amount if, in conjunction with one or more other agents, a desirable result may be or is achieved.

The terms "pharmaceutical formulation" and "pharmaceutical composition" refer to a preparation which is in such form as to permit the biological activity of the active ingredient(s) to be effective, and which contains no additional components which are unacceptably toxic to a subject to which the formulation would be administered. Such formulations may be sterile.

A "pharmaceutically acceptable carrier" refers to a non-toxic solid, semisolid, or liquid filler, diluent, encapsulating material, formulation auxiliary, or carrier conventional in the art for use with a therapeutic agent that together comprise a "pharmaceutical composition" for administration to a subject. A pharmaceutically acceptable carrier is non-toxic to recipients at the dosages and concentrations employed and is compatible with other ingredients of the formulation. The pharmaceutically acceptable carrier is appropriate for the formulation employed.

A "sterile" formulation is aseptic or essentially free from living microorganisms and their spores.

The term "package insert" is used to refer to instructions customarily included in commercial packages of therapeutic products, that contain information about the indications, usage, dosage, administration, combination therapy, contraindications and/or warnings concerning the use of such therapeutic products.

An "article of manufacture" is any manufacture (e.g., a package or container) or kit comprising at least one reagent, e.g., a medicament for treatment of a disease or disorder (e.g., cancer), or a probe for specifically detecting a biomarker described herein. In some embodiments, the manufacture or kit is promoted, distributed, or sold as a unit for performing the methods described herein.

It is understood that embodiments of the invention described herein include "consisting" and/or "consisting essentially of" embodiments.

Reference to "about" a value or parameter herein includes (and describes) variations that are directed to that value or parameter per se. For example, description referring to "about X" includes description of "X".

As used herein, reference to "not" a value or parameter generally means and describes "other than" a value or parameter. For example, the method is not used to treat cancer of type X means the method is used to treat cancer of types other than X.

The term "about X-Y" used herein has the same meaning as "about X to about Y."

As used herein and in the appended claims, the singular forms "a," "or," and "the" include plural referents unless the context clearly dictates otherwise.

II. Activatable Antibodies

The present application provides activatable antibodies comprising one or more antigen-binding domains having their antigen-binding sites reversibly blocked by a steric shield. As used herein, "steric shield" refers to the covalent and/or non-covalent association between two polypeptide shield moieties (e.g., S1 and S2) that are fused to the N-termini of the heavy chain variable region (VH) and the light chain variable region (VL) across an antigen-binding site in the activatable antibody. One or each of the polypeptide shield moieties comprises a disease-sensing releasable moiety (e.g., DS1 or DS2), which is disrupted at a diseased site to release the steric block from the antigen-binding site. Thus, the switch between the inactive and active state of activatable antibody is provided by the presence of the disease-sensing releasable moiety. For example, in some embodiments, the disease-sensing releasable moiety is a tumor-sensing releasable moiety that can sense the presence of a tumor-specific reagent, such as tumor-specific protease or acidic pH, wherein in the absence of the tumor-specific reagent, the tumor-sensing releasable moiety stays intact, but in the presence of the tumor-specific reagent, the tumor-sensing releasable moiety falls apart, thus causing separation of the steric shield from the antigen binding site. The term "activatable" refers to antibody that can exist in two states: "inactive" state where target binding is reduced due to presence of associated shield moieties S1 and S2, and "active" state where target binding is increased due to disruption (e.g. cleavage) of associated S1 and S2 shield moieties. Experimentally measured "affinity" of activatable antibody and its target depends on relative fractions in a composition of "inactive" and "active" states present. As the fraction of "active" state increases measured "affinity" increases, and conversely, as the fraction of the "inactive" state increases, measured affinity decreases. Ratio of the "active" and "inactive" states is controlled by the agents (e.g. proteases) that disrupt (e.g. cleave) disease-sensing moieties DS1 and DS2. The affinity of an activatable antibody composition after disruption of associated S1 and/or S2 shield moieties may be about 5×, 10×, 20×, 30×, 40×, 50×, 60×, 70×, 80×, 90×, 100×, 200×, 500×, or 1000× higher than the affinity of the activatable antibody composition before disruption of associated S1 and/or S2 shield moieties. Affinities may be measured in vitro using target proteins or cells expressing target proteins.

In some embodiments, the activatable antibody is used as a pro-drug for specific delivery of a therapeutic antibody to a diseased site. Such activatable antibody has preferential activities at a diseased site (e.g. at a tumor site) than at non-diseased sites, wherein the therapeutic antibody can only bind to its target at the diseased site in the absence of the steric shield, and not to the same target in normal tissues in the presence of the steric shield. In some embodiments, the steric shield is itself a therapeutic agent such that upon activation of the activatable antibody in the diseased site, both the therapeutic antibody and the released steric shield become active therapeutic agents that can act independently or synergistically on targets in the diseased site. The present application further provides methods for generating a steric shield that blocks one or more binding site in a therapeutic antibody, thereby providing a pro-drug of the therapeutic antibody.

A native antibody comprises two polypeptide chains, known as the heavy chain and the light chain. The N-termini of the heavy chain variable region (VH) and the light chain variable region (VL) are positioned in close proximity to each antigen binding site. Inventors of the present application discovered that connection of the N-termini of the VH and VL via various genetically encoded shield moieties described herein result in steric shielding of the antigen binding site, thereby providing a universal strategy for inactivating the antigen-binding site(s) in any antibody (including antigen binding fragments). Inventors further engineered disease-tissue specific sensor(s) in the steric shield connecting the two N-termini such that in the presence of a disease specific element that interacts with the sensor moiety, the steric shield falls apart, allowing the steric shield to diffuse out of the way of the antigen binding sites, thus restoring the antibody's ability to bind its target(s).

Thus, in some embodiments, there is provided an activatable antibody comprising an antibody comprising an antigen-binding domain (ABD), wherein the ABD comprises a heavy chain variable region (VH) and a light chain variable region (VL), wherein the N-terminus of the VH is fused to a first polypeptide shield moiety (S1), and the N-terminus of the VL is fused to a second polypeptide shield moiety (S2), wherein S1 comprises a first disease-sensing releasable moiety (DS1) and S2 comprises a second disease-sensing releasable moiety (DS2), wherein association of S1 with S2 blocks binding of the ABD to its target, and wherein the ABD does not specifically bind to S1, S2, or association thereof. In some embodiments, S1 further comprises a first association moiety B, and S2 further comprises a second association moiety C, wherein B and C associate with each other covalently and/or non-covalently. In some embodiments, disruption (e.g., cleavage) of DS1 and/or DS2 unblocks the binding of the ABD to its target. In some embodiments, DS1 and/or DS2 comprise a peptide substrates specific for an enzyme (e.g., protease) that is expressed at a diseased site. In some embodiments, DS1 and/or DS2 comprises a pH-sensitive protein or peptide.

In some embodiments, there is provided an activatable antibody comprising an antibody comprising an antigen-binding domain (ABD), wherein the ABD comprises a heavy chain variable region (VH) and a light chain variable region (VL), wherein the N-terminus of the VH is fused to a first polypeptide shield moiety (S1), and the N-terminus of the VL is fused to a second polypeptide shield moiety (S2), wherein S1 comprises a disease-sensing releasable moiety (DS1), wherein association of S1 with S2 blocks binding of the ABD to its target, and wherein the ABD does not specifically bind to S1, S2, or association thereof. In some embodiments, S1 comprises a first association moiety B, and S2 comprises a second association moiety C, wherein B and C associate with each other covalently and/or non-covalently. In some embodiments, disruption (e.g., cleavage) of DS1 unblocks the binding of the ABD to its target. In some embodiments, DS1 comprises a peptide substrates specific for an enzyme (e.g., protease) that is expressed at a diseased site. In some embodiments, DS1 comprises a pH-sensitive protein or peptide.

In some embodiments, there is provided an activatable antibody comprising an antibody comprising an antigen-binding domain (ABD), wherein the ABD comprises a heavy chain variable region (VH) and a light chain variable region (VL), wherein the N-terminus of the VH is fused to a first polypeptide shield moiety (S1), and the N-terminus of the VL is fused to a second polypeptide shield moiety (S2), wherein S2 comprises a disease-sensing releasable moiety (DS2), wherein association of S1 with S2 blocks binding of the ABD to its target, and wherein the ABD does not specifically bind to S1, S2, or association thereof. In some embodiments, S1 comprises a first association moiety B, and S2 comprises a second association moiety C, wherein B and C associate with each other covalently and/or non-covalently. In some embodiments, disruption (e.g., cleavage) of DS2 unblocks the binding of the ABD to its target. In some embodiments, DS2 comprises a peptide substrates specific for an enzyme (e.g., protease) that is expressed at a diseased site. In some embodiments, DS2 comprises a pH-sensitive protein or peptide.

In some embodiments, there is provided a fusion antibody comprising an antibody comprising an antigen-binding domain (ABD), wherein the ABD comprises a heavy chain variable region (VH) and a light chain variable region (VL), wherein the N-terminus of the VH is fused to a first polypeptide shield moiety (S1), and the N-terminus of the VL is fused to a second polypeptide shield moiety (S2), wherein S1 comprises a first disease-sensing releasable moiety (DS1) and/or S2 comprises a second disease-sensing releasable moiety (DS2), wherein S1 is capable of associating with S2 but S1 is not associated with S2, wherein the association between S1 and S2 blocks binding of the ABD to its target, and wherein the ABD does not specifically bind to S1, S2, or association thereof.

In some embodiments, there is provided an activatable antibody comprising an antibody comprising an antigen-binding domain (ABD), wherein the ABD comprises a heavy chain variable region (VH) and a light chain variable region (VL), wherein the N-terminus of the VH is fused to a first polypeptide shield moiety (S1), and the N-terminus of the VL is fused to a second polypeptide shield moiety (S2), wherein each of S1 and S2 is a polypeptide no more than about 50 amino acids long, wherein S1 comprises a first disease-sensing releasable moiety (DS1) and/or S2 comprises a second disease-sensing releasable moiety (DS2), wherein association of S1 with S2 blocks binding of the ABD to its target, and wherein the ABD does not specifically bind to S1, S2, or association thereof.

In some embodiments, there is provided an activatable antibody comprising an antibody comprising an antigen-binding domain (ABD), wherein the ABD comprises a heavy chain variable region (VH) and a light chain variable region (VL), wherein the N-terminus of the VH is fused to a first polypeptide shield moiety (S1), and the N-terminus of the VL is fused to a second polypeptide shield moiety (S2), wherein S1 comprises a first disease-sensing releasable moiety (DS1) and/or S2 comprises a second disease-sensing releasable moiety (DS2), wherein S1 comprises a first association moiety (B), and S2 comprises a second association moiety (C), wherein B and C interact with each other non-covalently, wherein B and C do not associate to form a second antigen-binding domain (e.g., an Fv), and wherein association of S1 with S2 blocks binding of the ABD to its target, and wherein the ABD does not specifically bind to S1, S2, or association thereof.

In some embodiments, the activatable antibody binds with higher affinity to its antigen on diseased cells or at a diseased site than on non-diseased cells. In some embodiments, the activatable antibody binds to its antigen under conditions characteristic for the diseased site (e.g. at the site of or inside a tumor). In some embodiments, the activatable antibody binds with higher affinity in the presence of diseased-site specific proteases. In some embodiments, the activatable antibody binds to its target with higher affinity under acidic pH (e.g. less than around pH 7.0) than at normal pH. In some embodiments, the activatable antibody binds to its target with higher affinity under hypoxic conditions (e.g. compared to normal physiological conditions at non-diseased site).

S1 and S2 are polypeptides that can have the same sequences or different sequences. S1 and S2 can comprise any natural or unnatural amino acid residues, including post-translational modifications, such as glycosylation, phosphorylation, etc. In some embodiments, S1 and S2 are oligopeptides. In some embodiments, S1 and S2 are protein domains or fragments. In some embodiments, one of S1 and S2 is an oligopeptide, and the other is a protein. In some embodiments, S1 and/or S2 comprises at least about any one of 5, 10, 15, 20, 25, 30, 50, 100, 150, 200 or more amino acid residues. In some embodiments, S1 and/or S2 is an oligopeptide of about any one of 10, 11, 12, 13, 14, 15, 16, 17, 18, 19, 20, 21, 22, 23, 24, 25, 26, 27, 28, 29, 30 amino acids long. In some embodiments, S1 and/or S2 is an oligopeptide having no more than about any one of 50, 45, 40, 35, 30, 29, 28, 27, 26, 25, 24, 23, 22, 21, 20, 19, 18, 17, 16, 15, 14, 13, 12, 11, or no amino acids. In some embodiments, S1 and/or S2 is a protein, domain or fragment thereof no more than about any one of 300, 250, 200, 100, or 50 amino acids long.

Upon association between B and C, the resulting S1-S2 steric shield is of sufficient length to span the distance between the N-termini of the VH and VL of the antibody component. This steric shield hoovers over the antigen binding site at a distance that prevents antigen binding until it is released via disruption of the disease-sensing releasable moieties DS1 and/or DS2 (e.g., FIG. 1B). In some embodiments, the association between S1 and S2 spans the entire length between the N-termini of the VH and VL. In some embodiments, the association between S1 and S2 spans a length greater than about any one of 35 Å, 40 Å, 45 Å, 50 Å, 55 Å, 60 Å, 65 Å, 70 Å, 75 Å, or 80 Å. In some embodiments, the association between S1 and S2 spans a length that is no more than about any one of 80 Å, 75 Å, 70 Å, 65 Å, 60 Å, 55 Å, 50 Å, 45 Å, 40 Å, or 35 Å.

As used herein, the "N-terminus" of a polypeptide refers to the first N-terminal amino acid of the polypeptide. In some embodiments, S1 is fused to the N-terminus of a native VH, and/or S2 is fused to the N-terminus of a native VL. In some embodiments, S1 is fused to the N-terminus of an engineered VH, and/or S2 is fused to the N-terminus of an engineered VL. In some embodiments, an engineered VH or VL has an amino acid variation in any one or more of the N-terminal residues 1-5 in the FR1 region of the VH or VL, including, but not limited to substitution, deletion, and/or insertion, which do no substantially reduce the binding affinity of VH, VL or the antigen-binding domain to its target antigen. For example, the binding affinity is reduced by less than any of 50%, 40%, 30%, 20%, and 10% as compared to the binding affinity of the antigen-binding domain without the amino acid variation.

Non-limiting exemplary schematics of the activatable antibody are shown in the formula below, wherein $L_1$, $L_2$, $L_3$, and $L_4$ are optional peptide linkers, and "-" between B and C indicate covalent and/or non-covalent interactions.

A. Covalent Association

In some embodiments, the association between S1 and S2 is covalent. In some embodiments, S1 comprises a first association moiety (B), and S2 comprises a second association moiety (C), and wherein B and C are conjugated to each other via a covalent bond. See, for example, FIG. 2A. In some embodiments, B further interacts with C non-covalently, such as with any one of the non-covalent interactions described in Section B. B and C can be genetically encoded and engineered into the activatable antibodies. The conjugation between B and C can be formed during expression of the antibody, or by treating the expressed fusion protein comprising the heavy chain and light chain polypeptides of the activatable antibody with an enzyme (e.g., transglutaminase) or chemical reagents (such as reduction and oxidation reagents) to allow the formation (or re-formation) of one or more covalent bonds between B and C.

Non-limiting examples of B and C that allow covalent association between S1 and S2 are described in Sections 1-3 below.

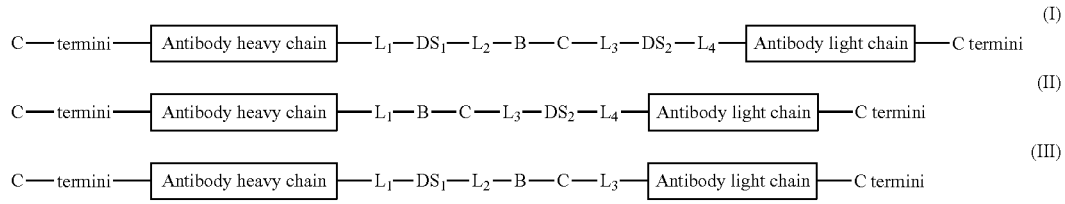

In some embodiments, B and C are residues or chemical groups as part of or attached to DS1, DS2, or the peptide linkers. In some embodiments, B is a polypeptide that extends from DS1, and C is a polypeptide extending from DS2. In some embodiments, one of B and C is a polypeptide extending from DS1 or DS2, and the other is a residue or chemical group as part of or attached to DS1, DS2 or the peptide linkers.

In some embodiments, B and C are complementary interaction moieties that are different from each other. In other embodiments, B and C are the same. In some embodiments, B and C are conjugated to each other by a covalent bond, such as a disulfide bond, diselenide bond, or isopeptide bond (e.g., via transglutamination). In some embodiments, B and C are protein domains or fragments, or complementary binding peptides that associate with each other non-covalently. In some embodiments, B and C associate with each other by both covalent and non-covalent interactions.

The various components of the activatable antibody, including modes of association between B and C (or S1 and S2), the disease-sensing releasable moieties (DS1 and DS2), peptide linkers, and the antibody component, are described in sections A-E below. One of skill in the art would readily appreciate that any one, some, or all properties described herein for each component can be combined in any suitable manner to form embodiments of the present invention.

1. Transglutamination

In some embodiments, B and C are conjugated to each other via an isopeptide bond. In some embodiments, B and C are conjugated to each other by a transglutamination reaction. In some embodiments, the transglutamination reaction is catalyzed by a transglutaminase. For example, see the schematics in FIG. 1A and FIG. 2A. Transglutaminases transfer the γ-glutaminyl of an acyl donor glutamine from a polypeptide to an acyl acceptor amine group, such as primary amine or the ε-amino group of lysine, resulting in an isopeptide bond connecting the acyl donor glutamine and the acyl acceptor residue. In some embodiments, the transglutaminase preferentially recognizes a peptide sequence that harbors an amino acid residue having an acyl acceptor group, and a peptide sequence that harbors an amino acid residue having an acyl donor group. The amino acid residue having the acyl acceptor group is referred herein as the "acyl acceptor residue" (e.g., lysing, N-terminal glycine) and the amino acid residue having the acyl donor group is referred herein as the "acyl donor residue" (e.g., glutamine). In some embodiments, B comprises an amino acid sequence comprising an acyl donor residue, and C comprises an amino acid sequence comprising an acyl acceptor residue, and wherein B and C are conjugated to each other by a transglutaminase. In some embodiments, C comprises an amino acid sequence comprising an acyl acceptor residue, and B comprises an amino acid sequence comprising an acyl donor residue, and wherein B and C are conjugated to each other by a transglutaminase.

Exemplary acyl donor and acyl acceptor residue containing sequences are shown in Table 2.

TABLE 2

Exemplary acyl donor and acyl acceptor sequences.

| SEQ ID NO | Type | Sequence |
|---|---|---|
| 52 | Acyl donor | XXQX, wherein X is any natural or unnatural amino acid |
| 53 | | LLQX$_1$X$_2$X$_3$X$_4$X$_5$, wherein X$_1$ is G or P, wherein X$_2$ is A, G, P, or absent, wherein X$_3$ is A, G, K, P, or absent, wherein X$_4$ is G, K, or absent, and wherein X$_5$ is K or absent |
| 1 | | LLQG |
| 54 | | VLNLAQSKNFH (Human Interleukin-2) |
| 55 | | APALQPTQGAM (Filgrastim) |
| 56 | | IPKEQKYSF (Human growth hormone) |
| 57 | | MGGSPLAQSHGGS (Myoglobin) |
| 58 | | KETAAAKFERQHMDS (S-tag) |
| 59 | | TEYGLFQINNDS (a-lactalbumin) |
| 60 | | APQQEA (Human osteonectin) |
| 61 | | EDGFFKI (Human fibrillin-1) |
| 62 | | EEQYNSTYR (IgG) |
| 51 | Acyl acceptor | X$_1$KX$_2$, wherein X$_1$ and X$_2$ are any natural or unnatural amino acids |
| 2 | | GKG |
| 74 | | GGG |
| 75 | | GGGG |

In some embodiments, the acyl donor residue is a glutamine (Q). In some embodiments, the sequence comprising the acyl donor residue is XXQX (SEQ ID NO: 52), wherein X is any natural or unnatural amino acid. In some embodiments, the sequence comprising the acyl donor residue is LLQX$_1$X$_2$X$_3$X$_4$X$_5$ (SEQ ID NO: 53), wherein X$_1$ is G or P, wherein X$_2$ is A, G, P, or absent, wherein X$_3$ is A, G, K, P, or absent, wherein X$_4$ is G, K, or absent, and wherein X$_5$ is K or absent. In some embodiments, the sequence comprising the acyl donor residue is LLQG (SEQ ID NO: 1). In some embodiments, the sequence comprising the acyl donor residue is any one of native transglutaminase acyl donor substrates found in naturally-occurring proteins, such as any one of SEQ ID NOs: 54-62. In some embodiments, the sequence comprising the acyl donor residue is any one of LQG (SEQ ID NO: 76), LLQGG (SEQ ID NO: 77), LSLSQG (SEQ ID NO: 78), GGGLLQGG (SEQ ID NO: 79), GLLQG (SEQ ID NO: 80), LLQ (SEQ ID NO: 81), GSPLAQSHGG (SEQ ID NO: 82), GLLQGGG (SEQ ID NO: 83), GLLQGG (SEQ ID NO: 84), GLLQ (SEQ ID NO: 85), LLQLLQGA (SEQ ID NO: 86), LLQGA (SEQ ID NO: 87), LLQYQGA (SEQ ID NO: 88), LLQGSG (SEQ ID NO: 89), LLQYQG (SEQ ID NO: 90), LLQLLQG (SEQ ID NO: 91), SLLQG (SEQ ID NO: 92), LLQLQ (SEQ ID NO: 93), LLQLLQ (SEQ ID NO: 94), LLQGR (SEQ ID NO: 95), LLQGPP (SEQ ID NO: 96), LLQGPA (SEQ ID NO: 97), GGLLQGPP (SEQ ID NO: 98), GGLLQGA (SEQ ID NO: 99), LLQGPGK (SEQ ID NO: 100), LLQGPG (SEQ ID NO: 101), LLQGP (SEQ ID NO: 102), LLQP (SEQ ID NO: 103), LLQPGK (SEQ ID NO: 104), LLQAPGK (SEQ ID NO: 105), LLQGAPG (SEQ ID NO: 106), LLQGAP (SEQ ID NO: 107), LLQLQG (SEQ ID NO: 108), LLQGA (SEQ ID NO: 109), LQG (SEQ ID NO: 110), GGLLQGA (SEQ ID NO: 111), LLQPGA (SEQ ID NO: 112), LLQGPP (SEQ ID NO: 113), GGLLQGPP (SEQ ID NO: 114), LLQGWG (SEQ ID NO: 115), LLQG (SEQ ID NO: 116), LLQYQG (SEQ ID NO: 117), LLQLLQG (SEQ ID NO: 118), LLQLQG (SEQ ID NO: 119), LLQLLQ (SEQ ID NO: 120), LLQLQ (SEQ ID NO: 121), LLQGR (SEQ ID NO: 122), LLQYQGA (SEQ ID NO: 123), SLLQG (SEQ ID NO: 124), LLQLLQGA (SEQ ID NO: 125), LLQGPP (SEQ ID NO: 126), QVQLKE (SEQ ID NO: 127), VQLKE (SEQ ID NO: 128), GGLLQGG (SEQ ID NO: 129), TVQQEL (SEQ ID NO: 130), GQQQTPY (SEQ ID NO: 131), GLQQASV (SEQ ID NO: 132), WQTPMNS (SEQ ID NO: 133), WQHPLHDWFDLV (SEQ ID NO: 134), FQQPLDPWTSPI (SEQ ID NO: 135), HQSYVDPWMLDH (SEQ ID NO: 136), REQLYLDYNVFS (SEQ ID NO: 137), MWQKLPLVVHWPT (SEQ ID NO: 138), or THMYQSIYVPDI (SEQ ID NO: 139). See, for example, US20130230543A1, US20130122020A1, WO02015/162563, US20150284713A1, US20140356385A1, Keresztessy Z et al. 2006 Protein Science 15: 2466-2480; and Sugimura Y et al. 2006 J Biol. Chem. 281.17699-17706; Biomaterials 31(2010) 4600-4608.

In some embodiments, the acyl acceptor residue is lysine (K). In some embodiments, the sequence comprising the acyl acceptor residue is X$_1$KX$_2$ (SEQ ID NO:51), wherein X$_1$ and X$_2$ are any natural or unnatural amino acids. In some embodiments, the sequence comprising the acyl acceptor residue is GKG (SEQ ID NO: 2). In some embodiments, the acyl acceptor residue is an N-terminal glycine. In some embodiments, the sequence comprising the acyl acceptor residue is GGG (SEQ ID NO: 74) or GGGG (SEQ ID NO:75). Also, see e.g., Tanaka T et al. 2005. FEBS Letters 579, 2092-2096.

In some embodiments, B comprises the amino acid sequence of SEQ ID NO:2 and C comprises the amino acid sequence of SEQ ID NO: 1, or B comprises the amino acid sequence of SEQ ID NO:2 and C comprises the amino acid sequence of SEQ ID NO:1. In some embodiments, B comprises the amino acid sequence LLQGLSGRSDNH (SEQ ID NO: 140) and C comprises the amino acid sequence GKGLSGRSDNH (SEQ ID NO:141), or B comprises the amino acid sequence of SEQ ID NO: 141 and C comprises the amino acid sequence of SEQ ID NO: 140. In some embodiments, S11 comprises the amino acid sequence LLQGLSGRSDNHGGGS (SEQ ID NO: 142) and S2 comprises the amino acid sequence GKGLSGRSDNHGGGS (SEQ ID NO: 143), or S1 comprises the amino acid sequence of SEQ ID NO: 143 and S2 comprises the amino acid sequence of SEQ ID NO: 142. In some embodiments, S11 comprises the amino acid sequence LLQG-PLGLAGGSGGGS (SEQ ID NO: 227) and S2 comprises the amino acid sequence GKGLSGRSDNHGGGS (SEQ ID NO: 143), or S1 comprises the amino acid sequence of SEQ ID NO: 143 and S2 comprises the amino acid sequence of SEQ ID NO: 227.

In some embodiments, the activatable antibody comprises a first polypeptide comprising the amino acid sequence of SEQ ID NO: 21, and a second polypeptide comprising the amino acid sequence of SEQ ID NO: 22, wherein amino acid residue 3 (Q) in SEQ ID NO: 21 is conjugated to amino acid residue 2 (K) of SEQ ID NO: 22 via isopeptide bond. In some embodiments, the activatable antibody comprises a first polypeptide comprising the amino acid sequence of SEQ ID NO: 23, and a second polypeptide comprising the amino acid sequence of SEQ ID NO: 24, wherein amino acid residue 3 (Q) in SEQ ID NO: 23 is conjugated to amino acid residue 2 (K) of SEQ ID NO: 24 via isopeptide bond. In some embodiments, the activatable antibody comprises a first polypeptide comprising the amino acid sequence of SEQ ID NO: 29, and a second polypeptide comprising the amino acid sequence of SEQ ID NO: 30, wherein amino acid residue 3 (Q) in SEQ ID NO: 29 is conjugated to amino acid residue 2 (K) of SEQ ID NO: 30 via isopeptide bond. In some embodiments, the activatable antibody comprises a first polypeptide comprising the amino acid sequence of SEQ ID NO: 31, and a second polypeptide comprising the amino acid sequence of SEQ ID NO: 32, wherein amino acid residue 3 (Q) in SEQ ID NO: 31 is conjugated to amino acid residue 2 (K) of SEQ ID NO: 32 via isopeptide bond. In some embodiments, the activatable antibody comprises a first polypeptide comprising the amino acid sequence of SEQ ID NO: 33, and a second polypeptide comprising the amino acid sequence of SEQ ID NO: 34, wherein amino acid residue 3 (Q) in SEQ ID NO: 33 is conjugated to amino acid residue 2 (K) of SEQ ID NO: 34 via isopeptide bond. In some embodiments, the activatable antibody comprises a first polypeptide comprising the amino acid sequence of SEQ ID NO: 224, and a second polypeptide comprising the amino acid sequence of SEQ ID NO: 225, wherein amino acid residue 3 (Q) in SEQ ID NO: 224 is conjugated to amino acid residue 2 (K) of SEQ ID NO: 225 via isopeptide bond.

The transglutaminase used in the present application can be obtained or made from a variety of sources. See, e.g., US20130230543A1. In some embodiments, the transglutaminase is a naturally-occurring transglutaminase. In some embodiments, the transglutaminase is a calcium dependent transglutaminase which requires calcium to induce enzyme conformational changes and allow enzyme activity. For example, transglutaminase can be derived from guinea pig liver and obtained through commercial sources (e.g., Sigma-Aldrich (St Louis, Mo.) and MP Biomedicals (Irvine, Calif.)). In some embodiments, the transglutaminase is a calcium independent transglutaminase which does not require calcium to induce enzyme conformational changes and allow enzyme activity. In some embodiments, the transglutaminase is a microbial transglutaminase derived from a microbial genome, such as transglutaminase from *Streptoverticillium* or *Streptomices* (e.g., *Streptomyces mobarensis* or *Streptoverticillium mobarensis*). Commercially available calcium independent transglutaminase such as ACTIVA™ (Ajinomoto, Japan) is suitable for the present invention. In some embodiments, the transglutaminase is a mammalian protein (e.g., human transglutaminase), a bacterial protein, a plant protein, a fungi protein (e.g., *Oomycetes* and *Actinomicetes transglutaminases*), or a prokaryotic protein. In some embodiments, the transglutaminase is from *Micrococcus, Clostridium, Turolpsis, Rhizopus, Monascus,* or *Bacillus*.

In some embodiments, the transglutaminase is a recombinant protein produced using recombinant techniques known to persons skilled in the art. In some embodiments, the transglutaminase is an engineered transglutaminase. In some embodiments, the transglutaminase is a purified protein. For example, the purified transglutaminase is least about 50% pure. In some embodiments, the purified transglutaminase is at least about any of 50%, 55%, 60%, 65%, 70%, 75%, 80%, 85%, 90%, 95%, 96%, 97%, 98%, 99%, or 100% pure.

2. Cys-Cys Disulfide Bond

Figure 1B:
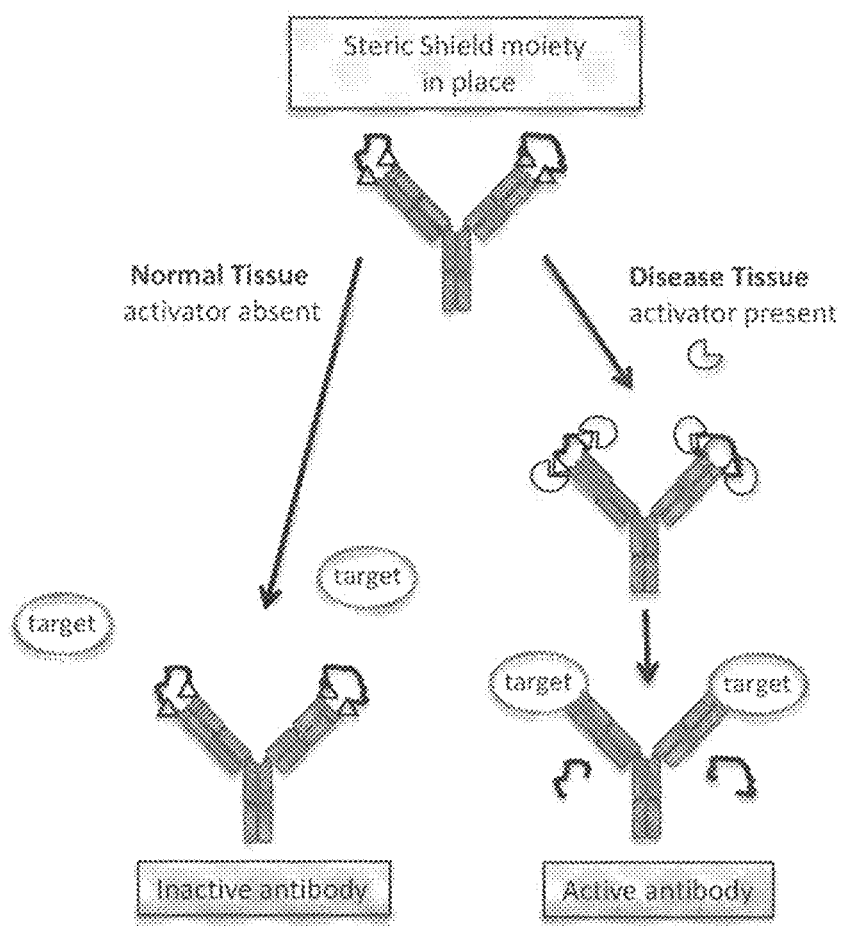
FIG. 1B is a schematic diagram illustrating behavior of an exemplary activatable antibody in normal and diseased tissues.
Figure 2A:
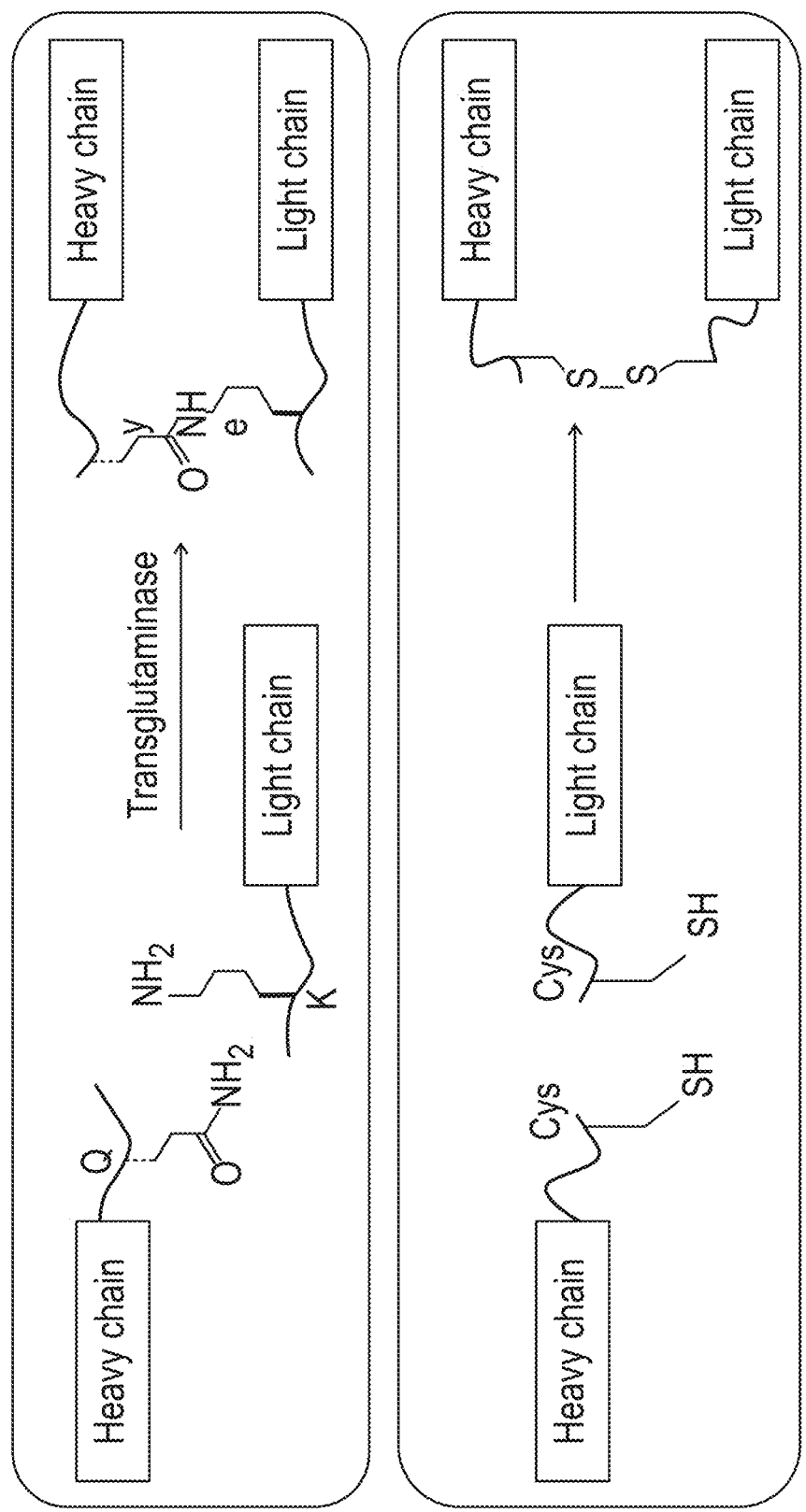
FIG. 2A shows covalent interactions that can be used to generate steric shields in exemplary activatable antibodies, including transglutaminase-catalyzed isopeptide bond formation and Cys-Cys disulfide bridge formation.

In some embodiments, B and C are conjugated to each other by one or more (such as any of 1, 2, 3, or more) cysteine-cysteine disulfide bonds (see, e.g., the schematics in FIG. 1A and FIG. 2A). In some embodiments, B and C comprise an amino acid sequence comprising cysteine, and wherein B and C are conjugated to each other via a disulfide bond. In some embodiments, cysteines that form the disulfide bond are within DS1 and DS2 or peptide linkers in S1 and S2 respectively. In some embodiments, B and C are cysteine-containing peptides that are conjugated to each other via one or more Cys-Cys disulfide bonds. B and C can be the same cysteine-containing peptides, or different cysteine-containing peptides. In some embodiments, each of B and C comprises the amino acid sequence SC (SEQ ID NO: 3).

In some embodiments, each of B and C contains a single cysteine. In some embodiments, each of B and C has any of 2, 3, or more cysteines. In some embodiments, B and C do not comprise cysteines that do not form disulfide bonds.

In some embodiments, DS1 and/or DS2 comprises a peptide substrate specific for an enzyme (e.g., protease) that is expressed at a disease site. In some embodiments, each of S1 and S2 comprises the amino acid sequence of SEQ ID NO: 3. In some embodiments, each of S1 and S2 comprises the amino acid sequence SCLSGRSDNH (SEQ ID NO: 144). In some embodiments, each of S1 and S2 comprises the amino acid sequence SCLSGRSDNHGG (SEQ ID NO: 145). In some embodiments, each of S1 and S2 comprises the amino acid sequence SCLSGRSDNHGGGS (SEQ ID NO: 146).

In some embodiments, the activatable antibody comprises a first polypeptide comprising the amino acid sequence of SEQ ID NO: 25, and a second polypeptide comprising the amino acid sequence of SEQ ID NO: 26, wherein amino acid residue 2 (C) of SEQ ID NO: 25 is conjugated to amino acid residue 2 (C) of SEQ ID NO: 26 via Cys-Cys disulfide bond. In some embodiments, the activatable antibody comprises a first polypeptide comprising the amino acid sequence of SEQ ID NO: 27, and a second polypeptide comprising the amino acid sequence of SEQ ID NO: 28, wherein amino acid residue 2 (C) of SEQ ID NO: 27 is conjugated to amino acid residue 2 (C) of SEQ ID NO: 28 via Cys-Cys disulfide bond.

3. Unnatural Amino Acid Conjugation

As used herein, "unnatural amino acids" include any amino acids that do not occur or rarely occur in naturally produced proteins or polypeptides; that is, any amino acids that do not belong to the twenty conventional amino acids listed in the column "Original Residues" of Table 1 are considered "unnatural amino acids" for the purpose of this invention. In some embodiments, B and C comprise unnatural amino acids that are conjugated to each other via a covalent bond. In some embodiments, one of B and C comprises an unnatural amino acid, and the other comprises a natural amino acid, and wherein B and C are conjugated to each other via a covalent bond.

In some embodiments, B and C comprise selenocysteines which are conjugated via a diselenide bond. In some embodiments, one of B and C comprises a selenocysteine and the other comprises a cysteine, wherein the selenocysteine and the cysteine forms a Se—S bond. Selenocysteine can be incorporated into proteins using any known methods in the art. For example, selenocysteine can be encoded by the UGA codon in an mRNA if a special stem-loop structure is present in the mRNA (Turanov A et al. 2013. Nucleic Acids Res. 41(14): 6952-6959).

Figure 10:
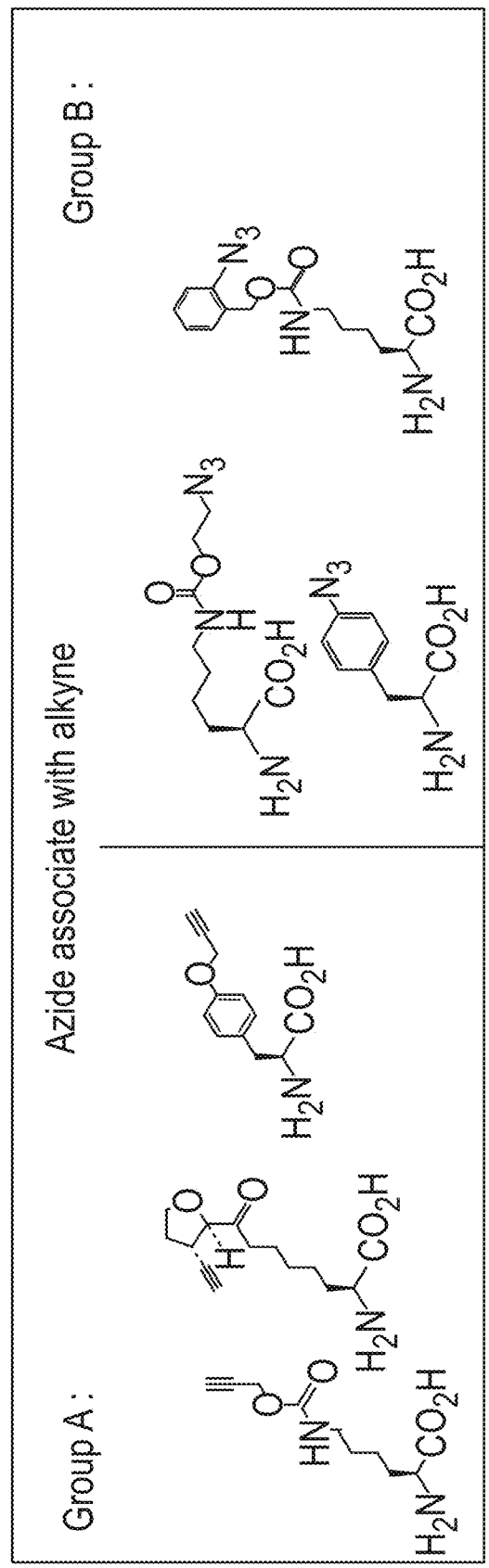
FIG. 10 shows classes of unnatural amino acids that can be incorporated as unnatural amino acid pairs or unnatural-natural amino acid pairs to serve as association moieties B and C, thereby allowing association between polypeptide shield moieties S1 and S2.

In some embodiments, B and C comprise an unnatural amino acid pair carrying side chains with orthogonal chemistries, such as those shown in FIG. 10. In some embodiments, one of B and C comprises an unnatural amino acid carrying an azide side chain, and the other comprises an unnatural amino acid carrying an alkyne group, wherein B and C are conjugated to each other via click-chemistry. In some embodiments, one of B and C comprises any one of the unnatural amino acids in group A of FIG. 10, and the other comprises any one of the unnatural amino acids in group B of FIG. 10. For example, B comprises p-Propargyloxyphenylalanine and C comprises p-Azidophenylalanine. Other orthogonal unnatural amino acid pairs known in the art can also be used in the present application. See, for example, Liu C C and Schultz P G. 2010. Annual Review of Biochemistry. 79: 413-444. Unnatural amino acids can be genetically incorporated into proteins expressed in mammalian or *E. coli* expression systems using known approaches in the art. See, for example, Liu C C and Schultz P G. 2010. Annual Review of Biochemistry. 79: 413-444.

B. Non-Covalent Association

In some exemplary activatable antibodies, the association between S1 and S2 is non-covalent. In some embodiments, wherein S1 comprises a first association moiety (B), and S2 comprises a second association moiety (C), and wherein B and C interact with each other non-covalently. In some embodiments, B is further conjugated to C covalently, such as with any one of the manners described in Section A.

Figure 2B:
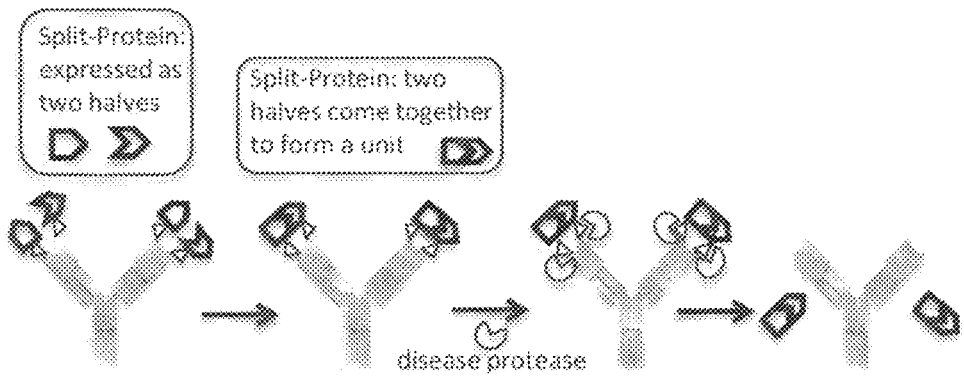
FIG. 2B shows non-covalent interactions between two half fragments of a split-protein that generate a steric shield in an exemplary activatable antibody.
Figure 2C:
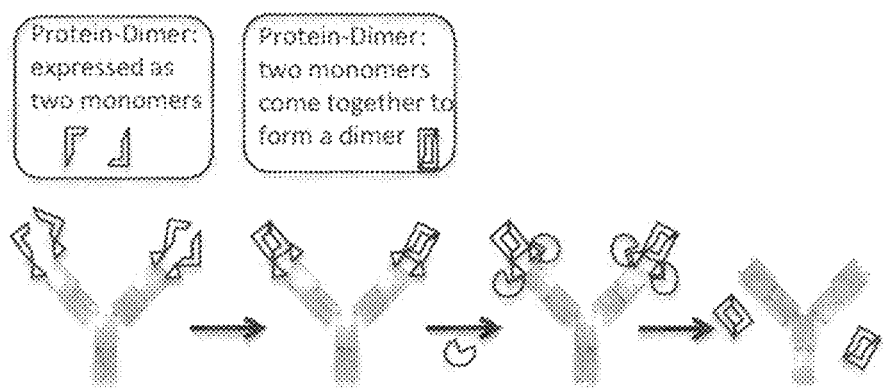
FIG. 2C shows non-covalent interactions between two monomeric subunits of a protein dimer that generate a steric shield in an exemplary activatable antibody.
Figure 2D:
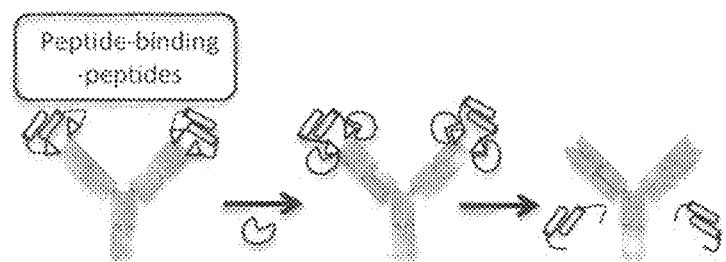
FIG. 2D shows non-covalent interactions between two peptides binding to one another, which generate a steric shield in an exemplary activatable antibody.
Figure 2E:
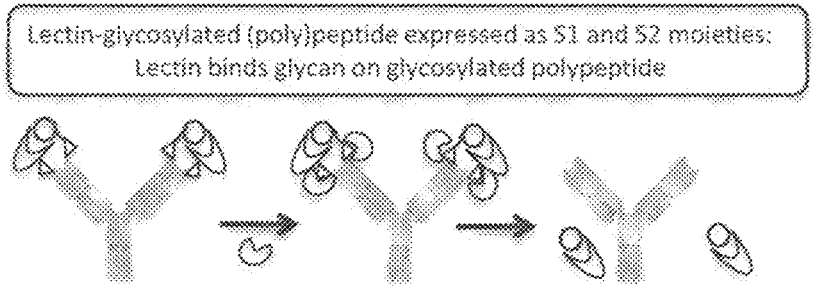
FIG. 2E shows non-covalent interactions between a glycan-binding protein (such as lectin) binding to a glycan in a glycosylated polypeptide shield moiety, which generate a steric shield in an exemplary activatable antibody.

In some embodiments, B and C are proteins, domains or fragments, or complementary binding peptides. For example, B and C can each be a half fragment of a split-protein, a monomeric subunit of a protein dimer, one of a pair of complementary binding peptides, or one of VH and VL of an Fv fragment. B and C can be genetically encoded and engineered into the activatable antibodies using any known methods for producing antibody fusion proteins known in the art. B and C can form a functional protein or protein domain thereby providing the steric shield in the activatable antibody. See, e.g., FIGS. 2B-2D. In some embodiments, one of B and C is a protein (e.g., lectin), and the other is a naturally occurring chemical moiety (e.g., glycan) that the protein binds to. See, e.g., FIG. 2E. The naturally occurring chemical moiety can be post-translationally added onto the polypeptide either during antibody expression or in vitro using an enzyme, thereby allowing formation of the non-covalent association between B and C.

The distance spanned by the folded S1 and S2 is sufficiently short to prevent antigen binding by the ABD in the activatable antibody. This distance can be controlled by the number of residues of disease-sensing releasable moieties DS1 and DS2 that act as releasable linkers between the N-termini of VH and VL of the antibody and the C-termini of the folded B and C moieties. This distance can be adjusted according to antigen binding efficiency data, e.g., assessed using surface plasmon resonance methods as described in Example 9.

Non-limiting examples of B and C that allow non-covalent association between S1 and S2 are described in sections 1-5 below.

1. Split-Protein

In some embodiments, B and C are two complementary halves of a split-protein. Single-domain proteins can be split into two polypeptides that associate to form a whole protein. These two half fragments can be fused to the N-termini of VH and VL of the ABD respectively. The two half fragments associate non-covalently to form a steric shield comprising a whole protein, thereby joining the N-termini of the VH and VL of the ABD. See, e.g., FIG. 2B.

In some embodiments, the split-protein is selected from the group consisting of GFP, Ubiquitin, CnaB2, interleukins, and chemokines. In some embodiments, S comprises the amino acid sequence of SEQ ID NO: 4 and S2 comprises the amino acid sequence of SEQ ID NO: 5, or S2 comprises the amino acid sequence of SEQ ID NO: 4 and S1 comprises the amino acid sequence of SEQ ID NO: 5. In some embodiments, S1 comprises the amino acid sequence of SEQ ID NO: 6 and S2 comprises the amino acid sequence of SEQ ID NO: 7, or S2 comprises the amino acid sequence of SEQ ID NO: 6 and S1 comprises the amino acid sequence of SEQ ID NO: 7.

In some embodiments, the activatable antibody comprises a first polypeptide comprising the amino acid sequence of SEQ ID NO: 39, and a second polypeptide comprising the amino acid sequence of SEQ ID NO: 40.

Any split-proteins known in the art can be used in the present application, including, but not limited to those listed in Table 3 below. Split-proteins have previously used to study protein-protein interactions. For example, GFP, Ubiquitin, CnaB2 domain from FbaB of *Streptococcus pyaogenes*, interleukins, and chemokines (such as CC: CXC; C; CX3C families) have been designed as split-proteins. See, for example, Johnsson, N. & Varshavsky, A. 1994. Proc. Natl. Acad. Sci. USA 91, 10340-10344; Zakeri B et al. 2012. PNA. 109:690-697: Li L et al. 2014. J Mol Biol. 426:309-317.

TABLE 3

Exemplary half fragments of split-proteins.

| SEQ ID NO | Source | Sequence |
|---|---|---|
| 4 | CnaB2 split-protein | DSATHIKFSKRDEDGKELAGATMELRDSSGKTISTWISDGQVKDF YLYPGKYTFVE TAAPDGYEVATAITFTVNEQGQVTVNG (SpyCatcher) |

TABLE 3-continued

Exemplary half fragments of split-proteins.

| SEQ ID NO | Source | Sequence |
|---|---|---|
| 5 | | AHIVMVAAYKPTK (Spytag) |
| 6 | Ubiquitin split-protein | MQIFVKTLTGKTITLEVEPSDTIENVKAKIQDKE (Cub) |
| 7 | | GIPPDQQRLIFAGKQLEDGRTLSDYNIQKESTLHLVLRLRGG (Nub) |

2. Dimeric Protein

In some embodiments, B and C are two monomeric subunits of a protein dimer. In some embodiments, B and C have the same sequence. In some embodiments, B and C are associated to form a homodimeric protein. In some embodiments, B and C have different sequences. In some embodiments, B and C are associated to form a heterodimeric protein. In some embodiments, the dimeric protein is a domain-swapped dimer. These two monomeric subunits can be fused to the N-termini of VH and VL of the ABD respectively. During protein expression, the monomeric subunits associate with each other non-covalently to form a homo- or hetero-dimeric protein, thereby joining the N-termini of the VH and VL of the ABD. See, e.g., FIG. 2C.

In some embodiments, the monomeric subunits in an activatable antibody are identical. In some embodiments, the monomeric subunits are different. In some embodiments, each of the monomeric subunits comprises an amino acid sequence selected from the group consisting of SEQ ID NOs: 8-10. In some embodiments, the first monomeric subunit comprises the amino acid sequence of SEQ ID NO: 11 and the second monomeric subunit comprises the amino acid sequence SEQ ID NO: 12, or the second monomeric subunit comprises the amino acid sequence of SEQ ID NO: 11 and the first monomeric subunit comprises the amino acid sequence SEQ ID NO: 12.

In some embodiments, the activatable antibody comprises a first polypeptide comprising the amino acid sequence of SEQ ID NO: 37, and a second polypeptide comprising the amino acid sequence of SEQ ID NO: 38. In some embodiments, the activatable antibody comprises a first polypeptide comprising the amino acid sequence of SEQ ID NO: 41, and a second polypeptide comprising the amino acid sequence of SEQ ID NO: 42.

Any of the known dimeric proteins in the art can be used in the present application, including, but not limited to those listed in Table 4 below. In some embodiments, the dimeric protein is selected from the group consisting of HIV protease, relaxin-2, Myo10, STIL, Troponin C, defensin-5, IL-10. DHBN domain of human BLM helicase, Insulin, human copper chaperone, KIX domain of human RECQL5, galectin-1, TNF-alpha, human neutrophil peptide 1, CXCL5, CXCL4, ILT1-immunoglobulin-like transcript, and IL-12. See, for example, Zdanov et al. 1995. Structure. 3: 591-601.

TABLE 4

Exemplary monomeric subunits of protein dimers.

| SEQ ID NO | Source | Sequence |
|---|---|---|
| 8 | IL-10 | SPGQGTQSENSCTHFPGNLPNMLRDLRDAFSRVKTFFQMKDQLDNLL LKESLLEDFKGYLGCQALSEMIQFYLEEVMPQAENQDPDIKAHVNSL GENLKTLRLRLRRCHRFLPCENKSKAVEQVKNAFNKLQEKGIYKAMS EFDIFINYIEAYMTMKIRN |
| 9 | CXCLR | EAEEDGDLQCLCVKTTSQVRPRHITSLEVIIKAGPHCPTAQLIATLKNG RKICLDLQAPLYKKIIKKLLES |
| 10 | CXCL5 | AGPAAAVLRELRCVCLQTTQGVHPKMISNLQVFAIGPQCSKVEVVAS LKNGKEICLDPEAPFLKKVIQKILDGGNKEN |
| 11 | IL-12 | MCPARSLLLVATLVLLDHLSLARNLPVATPDPGMFPCLHHSQNLLRA VSNMLQKARQTLEFYPCTSEEIDHEDITKDKTSTVEACLPLELTKNES CLNSRETSFITNGSCLASRKTSFMMALCLSSIYEDLKMYQVEFKTMNA KLLMDPKRQIFLDQNMLAVIDELMQALNFNSETVPQKSSLEEPDFYK TKIKLCILLHAFRIRAVTIDRVMSYLNAS (Subunit A) |
| 12 | | MCHQQLVISWFSLVFLASPLVAIWELKKDVYVVELDWYPDAPGEMV VLTCDTPEEDGITWTLDQSSEVLGSGKTLTIQVKEFGDAGQYTCHKG GEVLSHSLLLLHKKEDGIWSTDILKDQKEPKNKTFLRCEAKNYSGRFT CWWLTTISTDLTFSVKSSRGSSDPQGVTCGAATLSAERVRGDNKEYE YSVECQEDSACPAAEESLPIEVMVDAVHKLKYENYTSSFFIRDIIKPDP PKNLQLKPLKNSRQVEVSWEYPDTWSTPHSYFSLTFCVQVQGKSKRE KKDRVFTDKTSATVICRKNASISVRAQDRYYSSSWSEWASVPCS (Subunit B) |

3. Complementary Binding Peptides

In some embodiments, B and C are complementary binding peptides. In some embodiments, B and C are associated to form a parallel coiled-coil homodimers. In some embodiments, B and C are associated to form an anti-parallel coiled-coil heterodimers. In some embodiments, B and C are associated to form a leucine zipper. In some embodiments, B and C have the same sequence. In some embodiments, B and C have different sequences. The two complementary binding peptides can be fused to the N-termini of VH and VL of the ABD respectively. During protein expression, the complementary binding peptides associate with each other non-covalently to form a homo- or hetero-dimer complex, thereby joining the N-termini of the VH and VL of the ABD. See, e.g., FIG. 2D.

In some embodiments, the first complementary binding peptide and the second complementary binding peptide are identical. In some embodiments, the first complementary binding peptide and the second complementary binding peptide are different. In some embodiments, each of the first complementary binding peptide and the second complementary binding peptide comprises an amino acid sequence selected from the group consisting of SEQ ID NOs: 13-15. In some embodiments, the first complementary binding peptide comprises the amino acid sequence of SEQ ID NO: 16 and the second complementary binding peptide comprises the amino acid sequence SEQ ID NO: 17, or the second complementary binding peptide comprises the amino acid sequence of SEQ ID NO: 16 and the first complementary binding peptide comprises the amino acid sequence SEQ ID NO: 17. In some embodiments, the activatable antibody comprises a first polypeptide comprising the amino acid sequence of SEQ ID NO: 43, and a second polypeptide comprising the amino acid sequence of SEQ ID NO: 44.

Any of the known complementary binding peptides in the art can be used in the present application, including, but not limited to those listed in Table 5 below.

the N-termini of VH and VL of the ABD, either in the form of VH2-VL1 and VL2-VH1, or VH2-VH1 and VL2-VL1. In some embodiments, each of B and C comprises a cysteine, and wherein B and C are conjugated to each other via a disulfide bond. Fv fusions to antibodies, including those with disulfide enhancement for the Fv domains are known in the art to provide multispecific antibodies, in which the Fv domain does not block the antigen binding sites of the antibodies. See, e.g., DVD-Igs described in WO2007024715. While the fusion techniques known for DVD-Igs are applicable to the present application, the Fv in the activatable antibodies described herein sterically blocks antigen binding of the ABD. This can be achieved by shortening or omitting any peptide linkers between the second VH or VL and the N-terminus of the VH or VL of the ABD. In some embodiments, one or more (such as 1, 2, 3, 4, or 5) native N-terminal residues of the FR1 region of VH and/or VL of the ABD are deleted to enhance the steric hindrance of the Fv on the antigen binding site.

In some embodiments, the second VH comprises the amino acid sequence of SEQ ID NO: 35, and the second VL comprises the amino acid sequence of SEQ ID NO: 36. In some embodiments, the activatable antibody comprises a first polypeptide comprising the amino acid sequence of SEQ ID NO: 45, and a second polypeptide comprising the amino acid sequence of SEQ ID NO: 46. In some embodiments, disruption (e.g., cleavage) of DS1 and/or DS2 unblocks the binding of the ABD to its target. In some embodiments. DS1 and/or DS2 comprises a peptide substrates specific for an enzyme (e.g., protease) that is expressed at a diseased site. In some embodiments, DS1 and/or DS2 comprises a pH-sensitive protein or peptide. In some embodiments, the Fv is a therapeutic agent.

The VH and VL of any suitable Fv fragments can be used in the present application. In some embodiments, the second

TABLE 5

Exemplary complementary binding peptides that form coiled coils.

| SEQ ID NO | Source | Sequence |
|---|---|---|
| 13 | Myo10 | ENKQVEEILRLEKEIEDLQRMKEQQELSLT |
| 14 | JIP3 | GAMDPEFTKNALNVVKNDLIAKVDQLSGEQEVLRGELEAAKQAK VKLENRIKELEEELKRV |
| 15 | KIF21A | GSMTISNMEADMNRLLKQREELTKRREKLSKRREKIVKENGEGD KNVANINEEMESLTANIDYINDSISDCQANIMQMEE |
| 63 | | KLEALEGKLEALEKLEALEGKLEALEGKLEALEG GSDYEFLKSWTVEDLQKRLLALDPMMEQEIEEIRQKYQSKRQPIL |
| 16 | MSTI- | DAIEAK (Part A) |
| 17 | RASSF5 SARAH | GSEVEWDAFSIPELQNFLTILEKEEQDKIQQVQKKYDKFRQKLEEA LRESQGKPG (Part B) |
| 64 | E. coli ProP | DNIEQKIDDIDHEIADLQAKRTRKVQQHPR |
| 65 | 468-497 | RPHQQVLRTRKAQLDAIEHDIDDIKQEIND |
| 66 | | RRRRRRRRRR |
| 67 | | EEEEEEEEEE |

4. Fv Fragments

In some embodiments, one of B and C comprises a second VH, and the other comprises a second VL, and wherein B and C are associated to form an Fv. In some embodiments, B comprises a second VH and C comprises a second VL. In some embodiments, B comprises a second VL and C comprises a second VH. The second VH and VL can be fused to VH and second VL are derived from the L19 antibody as shown in Table 6. In some embodiments, the Fv is a therapeutic agent. In some embodiments, the Fv targets any one of the molecules listed in Table 8. In some embodiments, the Fv is derived from any one of the known therapeutic antibodies in the art, such as those listed in Table 9.

TABLE 6

Exemplary VH and VL sequences of therapeutic Fv.

| SEQ ID NO | Target | Sequence |
|---|---|---|
| 35 | ED-B | EVQLLESGGGLVQPGGSLRLSCAASGFTFSSFSMSWVRQAPGKGL EWVSSISGSSGTTYYADSVKGRFTISRDNSKNTLYLQMNSLRAED TAVYYCAKPFPYFDYWGQGTLVTV (VH) |
| 36 | | EIVLTQSPGTLSLSPGERATLSCRASQSVSSSYLAWYQQKPGQAPR LLIYYASSRATGIPDRFSGSGSGTDFTLTISRLEPEDFAVYYCQQTG RIPPTFGQGTKVEI (VL) |

5. Glycan-Binding Protein-Glycan Complex

In some embodiments, one of B and C is a glycan linked to a glycosylation peptide sequence, and the other is a glycan-binding protein. In some embodiments, the glycan-binding protein is a lectin, ficolin, or ERGIC-53. Both the glycosylation peptide sequence and the lectin can be genetically fused to the N-termini of the VH and VL of the ABD. During expression of the antibody in mammalian cells or other cells (e.g., yeast) expressing engineered glycosylases, the glycosylation peptide sequence is glycosylated, allowing formation of a glycan-binding protein-glycan complex to sterically block the antigen binding site of the ABD. In some embodiments, the conformation of the glycan-binding protein is sensitive to change in pH, such as acidic pH. Thus, the glycan-binding protein can serve as DS1 or DS2. For example, at acidic pH environment in a tumor tissue, the glycan-binding protein has a conformational change, thereby releasing the glycan, and disrupting the steric shield. In some embodiments, DS1 and/or DS2 comprise disease-specific protease substrates, which allow cleavage and release of the glycan-binding protein-glycan complex from the antigen-binding site.

In some embodiments, the glycan-binding protein is a lectin, ficolin, or ERGIC-53. In some embodiments, the glycan-binding protein is M-ficolin, such as an engineered M-ficolin monomer, and the glycan is GlcNAc. In some embodiments, the glycan-binding protein comprises the amino acid sequence of SEQ ID NO: 20. In some embodiments, the glycosylation peptide sequence comprises the amino acid sequence of SEQ ID NO: 18. In some embodiments, the glycan-binding protein is M-ficolin. In some embodiments, the activatable antibody comprises a first polypeptide comprising the amino acid sequence of SEQ ID NO: 47, and a second polypeptide comprising the amino acid sequence of SEQ ID NO: 48. In some embodiments, the activatable antibody comprises a first polypeptide comprising the amino acid sequence of SEQ ID NO: 49, and a second polypeptide comprising the amino acid sequence of SEQ ID NO: 50.

Any suitable glycan-binding protein-glycan pair known in the art can be used in the present application. In some embodiments, the glycan-binding protein is a lectin, ficolin, or ERGIC-53. In some embodiments, the glycosylation peptide sequence comprises one or more (such as any of 1, 2, 3, or more) glycosylation sites. In some embodiments, one or more (such as any of 1, 2, 3, or more) glycans are added to the glycosylation peptide sequence. In some embodiments, the glycosylation peptide sequence comprises an N-glycosylation site. In some embodiments, the glycosylation peptide sequence comprises an O-glycosylation site. Exemplary glycosylation peptide sequences are listed in Table 7. In some embodiments, the glycosylation peptide sequence has an amino acid sequence selected from SEQ ID NOs: 18, and 68-73.

In some embodiments, the glycans are added during expression of the fusion antibody in mammalian cells or other cells (e.g., yeast) expressing engineered glycosylases. In some embodiments, the glycans are added to the expressed fusion antibody in vitro by treating the fusion antibody with a glycosylase. In some embodiments, the antibody carrying the N-terminal glycosylation peptide sequence has its native glycosylation site(s) mutated to abolish the native glycosylation sites. For example, an amino acid substitution at residue Asn297 can be introduced to the antibody.

TABLE 7

| Exemplary glycosylation tag and glycan-binding protein sequences. | | |
|---|---|---|
| SEQ ID NO | Source | Sequence |
| 68 | N-glycosylation tag | NXS/T/C, where X is any amino acid with exception of P |
| 18 | SLC6A1 | SNYSMVNTTNMTSA |
| 69 | ABCB11 | VNNTIVWTNSSLNQNMTNGT |
| 70 | FactorX | FNQTQPERGDNNLTR |
| 71 | CFTR | GNSTHSRNNSY |
| 72 | IgG | EEQYNSTYR |
| 73 | IgG | EEQYNSTFR |

TABLE 7-continued Exemplary glycosylation tag and glycan-binding protein sequences.

| SEQ ID NO | Source | Sequence |
|---|---|---|
| 20 | Monomeric M-Ficolin with site-specific mutation (bold letter) | QSCATGPRNCKDLLDRGYFRSGWHTIYLPDCRPLTVLCDMDTDGGG WTVFQRRMDGSVDFYRDWAAYKQGFGSQLGEFWLGNDNIHALTAQ GSSELRTDLVDFEGNHQFAKYKSFKVADEAEKYKLVLGAFVGGSAGN SLTGHNNNFFSTKDQDNDVSSSNCAEKFQGAWWYADCHASNLNGLY LMGPHESYANGINWSAAKGYKYSYKVSEMKVRPA |

C. Disease-Sensing Releasable Moieties

S1 and/or S2 comprises a disease-sensing releasable moiety. In some embodiments, S comprises DS1 but S2 does not comprise DS2. In some embodiments, S2 comprises DS2 but S1 does not comprise DS1. In some embodiments, S1 comprises DS1 and S2 comprises DS2. In some embodiments, DS1 is identical to DS2. In some embodiments. DS1 is different from DS2.

As used herein, "disease-sensing releasable moiety" refers to polypeptides or chemical groups that are sensitive to a specific chemical or physical element present in a diseased tissue. For example, many diseased tissues are known to differ from normal tissue by pH, oxygen level, and expression of enzymes such as disease-specific proteases. The disease-sensing releasable moiety is disrupted, such as cleaved or undergone conformational changes, by the chemical or physical element in the diseased tissue, thereby releasing the steric shield and unblocking the antigen binding site. Each of DS1 and DS2 can sense one or more chemical or physical elements specific to the diseased tissue. For example, each of DS1 and DS2 may comprise a single disease-specific protease substrate, or two or more substrates that respond to different disease-specific proteases. In some embodiments, DS1 and/or DS2 can respond to acidic pH and be cleaved by a disease-specific protease. In some embodiments. DS1 and DS2 sense the same specific chemical or physical element in a diseased tissue. In some embodiments, DS1 and DS2 sense different chemical or physical elements in a diseased tissue. For example, one of DS1 and DS2 is a pH sensor, and the other is a protease-cleavable sensor. A skilled person in the art would readily appreciate that the different disease-sensing releasable moieties described herein can be mixed and matched to provide activatable antibodies with different activation mechanisms and dynamics.

In some embodiments, DS1 and/or DS2 comprises at least two (such as any of 2, 3, 4, 5, or more) peptide substrates each specific for an enzyme that is expressed at a diseased site. In some embodiments, DS1 and/or DS2 comprises a peptide linker, such as a flexible peptide linker that connects between the various peptide substrates.

In some embodiments, DS1 and/or DS2 is a tumor-sensing releasable moiety. Tumors differ from normal tissues in several physiological and micro-environmental characteristics. For example, hypoxia and extracellular acidity are hallmark of malignant tumors. Tumor hypoxia indicates that within tumors significant areas have lower oxygen tension that found in normal tissues. pH of extracellular compartment in tumors is lower than commonly observed in normal tissues.

1. Disease-Specific Protease Sensors

In some embodiments, DS1 and/or DS2 is a protease substrate cleavable by a disease-specific protease, such as a tumor-specific protease. In some embodiments, the tumor-specific protease express at elevated levels in diseased tissues, such as tumor tissues, compared to normal tissues. For example, studies have shown that tumor tissues exhibit increased activity of specific proteases and decreased activity of the opposing endogenous inhibitors (Sevenich L and Joyce J A. Genes & Dev. 2014. 28: 2331-2347. 2014). In some embodiments, tumor-specific protease is selected from the group consisting of matriptase (MTSP1), urinary-type plasminogen activator (uPA), legumain, PSA (also called KLK3, kallikrein-related peptidase-3), matrix metalloproteinase-2 (MMP-2), matrix metalloproteinase-9 (MMP9), human neutrophil elastase (HNE), proteinase 3 (Pr3), cathepsin B and cathepsin K.

In some embodiments, DS1 and/or DS2 comprises a peptide substrate of matriptase. Any known matriptase cleavage sequence can be used, for example, RQARVV (SEQ ID NO: 147); X1SGRSA (SEQ ID NO: 148), wherein X1 is G or K; LSGRSX1NH (SEQ ID NO: 154) wherein X1 is D, V or A; X1X2X3X4X5X6X7X8 (SEQ ID NO: 149), wherein X1 is R, X2 and X3 are any amino acid, X4 is R, X5 is K, X6 is V, X7 is any amino acid, X8 is G; X9X10X11X12X13 (SEQ ID NO: 150), wherein X9 is K or R, X10 is R, K, H or Q, X11 is G, A or S, X12 is R or K, X13 is A; X14X15X16X7X8X19X20X21 (SEQ ID NO: 151), wherein X14 is L, I, A or K, X15 is S, G, or Q, X16 is K, L, A, G, or S, X17 is R, X18 is S, K, G, A or V, X19 is A, V or L, X20 is N, X21 is H, G, V, or L; X22X23X24X25X26 (SEQ ID NO: 152), wherein X22 is R or K, X23 is non-basic amino acid (G,A,S,T,C,V,L,I, M,P, F,Y,W,D,E,N, or Q), X24 is S, X25 is R, X26 is A; or X27X28X29X30X31 (SEQ ID NO: 153), wherein X27 is non-basic amino acid (G,A,S,T,C,V,L,I, M,P,F,Y,W,D,E,N, Q), X28 is R or K, X29 is S, X30 is R, X31 is A.

In some embodiments, DS1 and/or DS2 comprises a peptide substrate of legumain. Any known legumain cleavage sequence can be used, for example, LSGRSX1NH (SEQ ID NO: 154), wherein X1 is D, V or A; X1X2X3X4X5X6X7X8 (SEQ ID NO: 155), wherein X1, X2, X3 are any amino acid, X4 is N, X5, X6, X7, X8 are any amino acid; AANL (SEQ ID NO: 156); ATNL (SEQ ID NO: 157); or X9X10X11X12X13X14X15X16 (SEQ ID NO: 158), wherein X9 is L, I, A or K, X10 is S, G, or Q, X11 is K, L, A, G, or S, X12 is R, X13 is S, K, G, A or V, X14 is A, V or L, X15 is N, X16 is H, G, V, or L.

In some embodiments, DS1 and/or DS2 comprises a peptide substrate of uPA (Urinary-type plasminogen activator). Any known uPA cleavage sequence can be used, for example, X1SGRSA (SEQ ID NO: 159), wherein X1 is G or K; LSGRSX1NH (SEQ ID NO: 154) wherein X1 is D, V or A; X1X2X3X4X5X6X7X8 (SEQ ID NO: 160), wherein X1 is any amino acid, X2 is S, X3 is G or S, X4 is R or K, X5 is any amino acid, X6 is R or V, X7 is any amino acid, X8 is any amino acid; SGRSA (SEQ ID NO: 161); X9X10X11X12X3X14X15X6 (SEQ ID NO: 162) wherein X9 is L, I, A or K, X10 is S, G, or Q, X11 is K, L, A, G, or S, X12 is R, X13 is S, K, G, A or V, X14 is A, V or L, X15 is N, X16 is H, G, V, or L; or RKSSIIIRMRDWL (SEQ ID NO: 163).

In some embodiments, DS1 and/or DS2 comprises a peptide substrate of Pro-urokinase. Any known Pro-uPA cleavage sequence can be used, for example, PRFX1IIGG (SEQ ID NO: 164), wherein X1 is K or R.

In some embodiments, DS1 and/or DS2 comprises a peptide substrate of matrix metalloprotease. Any known matrix metalloprotease cleavage sequence can be used, for example, SRPLALR (SEQ ID NO: 165); SRPANLR (SEQ ID NO: 166); or X1X2X3X4X5X6X7 (SEQ ID NO: 167), wherein X1 is S, V or R, X2 is any amino acid, X3 is P or A, X4 is L, M, A, R or Y, X5 is A, S, N, G, H or M, X6 is L, X7 is R, L, Q or M.

In some embodiments, DS1 and/or DS2 comprises a peptide substrate of MMP1 (Human fibroblast collagenase). Any known MMP1 cleavage sequence can be used, for example, DVAQFVLT (SEQ ID NO: 168); or X1X2X3X4X5X6X7X8 (SEQ ID NO: 169), wherein X1 is any amino acid, X2 is P or A, X3 and X4 are any amino acids, X5 is L or I, X6, X7, X8 are any amino acids.

In some embodiments, DS1 and/or DS2 comprises a peptide substrate of MMP2. Any known MMP2 cleavage sequence can be used, for example, HRPRGX1TN (SEQ ID NO: 170), wherein X1 is V or W; X1X2X3X4X5X6X7X8 (SEQ ID NO: 171), wherein X1 is any amino acid, X2 is P, X3 and X4 are any amino acids, X5 is L or I, X6, X7 and X8 are any amino acids; or PLGLAG (SEQ ID NO: 172).

In some embodiments, DS1 and/or DS2 comprises a peptide substrate of MMP9. Any known MMP9 cleavage sequence can be used, for example, HRPRGX1TN (SEQ ID NO: 173), wherein X1 is V or W; X1X2X3X4X5X6X7X8 (SEQ ID NO: 174), wherein X1 is G, X2 is P or A, X3 is any amino acids, X4 is G or A, X5 is L, X6 is any amino acid, X7 is G, X8 is any amino acid; GPLGIAGQ (SEQ ID NO: 175); PVGLIG (SEQ ID NO: 176); or HPVGLLAR (SEQ ID NO: 177).

In some embodiments, DS1 and/or DS2 comprises a peptide substrate of Gelatinase. Any known Gelatinase cleavage sequence can be used, for example, PLGLWA (SEQ ID NO: 178); or X1X2X3X4X5X6X7 (SEQ ID NO: 179), wherein X1 Is H, K, R or V, X2 is R, M, T, V, Y, or A, X3 is P or V, X4 is R, S or A, X5 is G, A, S, N or W, X6 is V, W, L or Y, X7 is T, R, Y, I.

In some embodiments, DS1 and/or DS2 comprises a peptide substrate of PSA. Any known PSA cleavage sequence can be used, for example, SSKLQ (SEQ ID NO: 180); SRKSQQY (SEQ ID NO: 181); GQKGQHY (SEQ ID NO: 182); KGISSQY (SEQ ID NO: 183); X1X2X3X4X5X6X7X8 (SEQ ID NO: 184), wherein X is S or I, X2 is S or Q, X3 is any amino acid, X4 is Y, Q, or E, X5 is S, X6 is S, X7 and X8 are any amino acid; or SSX1YSX2 (SEQ ID NO: 185), wherein X1 is Y or F and X2 is G or S.

In some embodiments, DS1 and/or DS2 comprises a peptide substrate of human neutrophil elastase. Any known human neutrophil elastase cleavage sequence can be used, for example, X1X2X3X4X5X6X7X8 (SEQ ID NO: 186), wherein X1, X2 and X3 are any amino acid, X4 are V, I, A or T, X5, X6, X7, X8 are any amino acids; X9EX10VVY (SEQ ID NO: 187), wherein X9 is R or M, X10 is A or H; VADCAQ (SEQ ID NO: 188); APEEIMDRQ (SEQ ID NO: 189); IVSARMAPEEIIMDRQ (SEQ ID NO: 190); or GIATFCMLMPEQ (SEQ ID NO: 191).

In some embodiments, DS1 and/or DS2 comprises a peptide substrate of proteinase 3. Any known proteinase 3 cleavage sequence can be used, for example, X1X2X3X4X5X6X7X8 (SEQ ID NO: 192), wherein X1 is any amino acid X2 is Y, X3 is Y, X4 is V, T or A, X5, X6, X7, X8 are any amino acids: VADCAQ (SEQ ID NO: 193); APEEIMDRQ (SEQ ID NO: 194); IVSARMAPEEIIMDRQ (SEQ ID NO: 195); or GIATFCMLMPEQ (SEQ ID NO: 196).

In some embodiments, DS1 and/or DS2 comprises a peptide substrate of Factor Xa. Any known Factor Xa cleavage sequence can be used, for example, IEGR (SEQ ID NO: 197); IDGR (SEQ ID NO: 198); GGSIDGR (SEQ ID NO: 199); or X1X2X3X4X5X6X7X8 (SEQ ID NO: 200), wherein X is A or I, X2 is any amino acid, X3 is G, P or F, X4 is R, X5 is T, S or I, X6 is V or F, X7 is any amino acid, X8 is G.

In some embodiments, DS1 and/or DS2 comprises a peptide substrate of cathepsin B. Any known cathepsin B cleavage sequence can be used, for example, X1X2X3GX4GX5 (SEQ ID NO: 201), wherein X1, X2, X3, X4 and X5 are any amino acid.

In some embodiments, DS1 and/or DS2 comprises a peptide substrate of cathepsin K. Any known cathepsin K cleavage sequence can be used, for example, X1X2X3X4X5X6X7X8 (SEQ ID NO: 202), wherein X1, X2, X5, X6. X7 and X8 are any amino acids, and X3 is L, P or V, and X4 is E or A.

In some embodiments, DS1 and/or DS2 comprise a single peptide substrate cleavable by a disease-specific protease, such as any one of SEQ ID NOs: 147-202. In some embodiments, DS1 and/or DS2 comprises two or more copies (such as any one of 2, 3, 4, 5, or more) of a peptide substrate cleavable by a disease-specific protease. In some embodiments, DS1 and/or DS2 comprises a peptide substrate that can be cleaved by more than one (e.g., any of 2, 3, 4, or more) disease-specific proteases. In some embodiments, DS1 and/or DS2 comprises two or more (e.g., any of 2, 3, 4, or more) peptide substrates cleavable by one or more (e.g., any of 2, 3, 4, or more) disease-specific proteases. Any of the protease peptide substrate sequences disclosed herein (e.g., SEQ ID NOs: 19 and 147-202) can be mixed and matched to provide a disease-sensing releasable moiety with optimal mechanism and dynamics for release of the steric shield in a diseased site. The different protease substrate sequences or copies thereof can be fused to each other via peptide linkers to provide suitable disease-sensing releasable moieties.

In some embodiments, DS1 and/or DS2 comprises the amino acid sequence of LSGRSDNH (SEQ ID NO: 19). The protease substrate LSGRSDNH (SEQ ID NO: 19) is sensitive to numerous proteases that are activated and/or upregulated in a variety of human carcinomas, including matriptase, urinary-type plasminogen activator (uPA), and legumain. In some embodiments, DS1 and/or DS2 comprises the amino acid sequence of PLGLAG (SEQ ID NO: 172). The protease substrate PLGLAG (SEQ ID NO: 172) is sensitive to matrix metalloproteases that are activated and/or upregulated in a variety of human carcinomas. In some embodiments, DS1 and/or DS2 comprises the amino acid sequence of KSRTTNG (SEQ ID NO: 240) or KGSRTTNG (SEQ ID NO: 241). The protease substrates KSRTTNG (SEQ ID NO: 240) and KGSRTING (SEQ ID NO: 241) are sensitive to matriptase and legumain.

In some embodiments, DS1 and/or DS2 comprises a peptide with unnatural amino acids that can be cleaved by a disease-specific protease. In some embodiments, DS1 and/or DS2 comprises valine-citrulline (SEQ ID NO: 204), which can be cleaved by cathepsin B.

2. pH Sensors.

In some embodiments, DS1 and/or DS2 is a pH sensing moiety. In some embodiments, DS1 and/or DS2 is disrupted by low pH. Studies have shown that tumor cell mediated oncogenic metabolism generates a large amount of lactic acid and protons, leading to the reduction in the extracellular pH values to as low as 6 in tumor tissue (Icard et al., Biochim. Biophys. Acta. 1826:423-433, 2012). Thus, in the healthy tissues where pH concentration is higher, the N-termini of activatable antibodies have a low-pH sensor as DS1 and/or DS2 remain linked, while in the diseased tissue, under acidic pH conditions. DS1 and/or DS2 is cleaved, thereby releasing the steric shield and unblocking the antigen biding sites.

In some embodiments, DS1 and/or DS2 are proteins that undergo conformational changes as pH shifts from neutral towards acidic. For example, histidines within proteins can act as pH sensor and thus mediate pH-controlled structural changes. In some embodiments, the association moieties B and/or C are pH-sensitive proteins, and thus also serve as disease-sensing releasable moieties.

In some embodiments, one of each of DS1 and DS2 are pH-sensitive peptides. Any known pH-sensitive peptides can be used in the present application, for example, the GALA comprising the amino acid sequence of WEAALAEA-LAEALAEHLAEALAEALEALAA (SEQ ID NO: 203), coiled-coil domain of macrophage scavenger receptor (Doi et al. 1994. J. Biol. Chem. 269: 25598-25604), or coiled-coil domains of Emp46p and Emp47p (Ishi K et al. 2015. PLoS ONE 10(10): e014028).

D. Peptide Linkers

In some embodiments, S1 and/or S2 comprises one or more peptide linkers that connect between the various components in the activatable antibody. In some embodiments, the N-terminus of the VH is fused to the C-terminus of S1 via a peptide linker. In some embodiments, the N-terminus of the VL is fused to the C-terminus of S2 via a peptide linker. In some embodiments, DS1 is fused to B via a peptide linker. In some embodiments, DS2 is fused to C via a peptide linker. In some embodiments, different protease substrate sequences within DS1 are linked to each other via a peptide linker.

The peptide linker can have any suitable sequences and of any suitable length. In some embodiments, the peptide linker is about any one of 1, 2, 3, 4, 5, 6, 7, 8, 9, 10, 12, 15, 20 amino acids long. In some embodiments, the peptide linker is about 1-12 amino acids long. In some embodiments, the peptide linker is a flexible peptide linker containing flexible amino acid residues, such as glycine and serine. In some embodiments, the peptide linker comprises a motif. e.g., multiple or repeating motifs, of GS, GGS (SEQ ID NO: 205), GGGGS (SEQ ID NO: 206), GGSG (SEQ ID NO: 207). SGGG (SEQ ID NO: 208), or GSGGGS (SEQ ID NO: 226). In some embodiments, the peptide linker comprises 1 to 12 amino acids including motifs of GS, e.g., GS, GSGS (SEQ ID NO: 209), GSGSGS (SEQ ID NO: 210), GSGSGSGS (SEQ ID NO: 211), GSGSGSGSGS (SEQ ID NO: 212), or GSGSGSGSGSGS (SEQ ID NO: 213). In some embodiments, the peptide linker comprises 3 to 12 amino acids including motifs of GGS (SEQ ID NO: 205), e.g., GGS (SEQ ID NO: 205), GGSGGS (SEQ ID NO: 214), GGSGGSGGS (SEQ ID NO: 215), or GGSGGSGGSGGS (SEQ ID NO: 216). In some embodiments, the peptide linker comprises 4 to 12 amino acids including motifs of GGSG (SEQ ID NO: 207), e.g., GGSG (SEQ ID NO: 207). GGSGGGSG (SEQ ID NO: 217), GGSGGGSGGGSG (SEQ ID NO: 218).

In some embodiments, the peptide linker comprises repeating motifs of (GGGGS)n (SEQ ID NO: 219), wherein n is an integer from 1 to 10. In some embodiments, the peptide linker does not comprise a motif. Other exemplary peptide linkers that can be used herein include, but are not limited to, GG, GGGS (SEQ ID NO: 223), PAS (SEQ ID NO: 220), A(EAAAK)n (SEQ ID NO: 221), wherein n is an integer from 1 to 10, or (XP)n (SEQ ID NO: 222) wherein X is any amino acid, preferably Ala, Lys, or Glu and n is an integer from 1 to 10.

E. Antibody

The activatable antibodies described herein comprise an antibody that is capable of specifically binding to one or more targets on a diseased cell (such as tumor) when the antigen-binding sites are not blocked by the association of the polypeptide shields (i.e., the steric shield). The antibodies contemplated herein include any suitable antibody formats having a heavy chain and a light chain, including antigen-binding fragments and antibody-drug conjugates.

In some embodiments, the antibody is a single-domain antibody fragment, such as Fv or Fab. In some embodiments, the antibody comprises two or more (such as any of 2, 3, 4, 5, or more) antigen binding domains. In some embodiments, each of the antigen binding domains are fused to polypeptide shield moieties. In some embodiments, polypeptide shield moieties are fused to the N-terminal of VH and VL where one or more (e.g., 1, 2, 3, 4, or 5) amino acids at the N-terminal of the nativeVH and VL are removed. In some embodiments, the antibody is a full length antibody. In some embodiments, the antibody described herein is a monoclonal antibody, polyclonal antibody, a human antibody, a mouse antibody, a rat antibody, a monkey antibody, humanized antibody, a chimeric antibody, a bispecific antibody, or a multispecific antibody.

In some embodiments, the antibody comprises an Fc region. In some embodiments, the antibody is an IgG. In some embodiments, the IgG is selected from the group consisting of IgG1, IgG2, IgG3, IgG4. In some embodiments, the antibody is an IgA, IgE, IgD, or IgM.

In some embodiments, the antibody has one or more amino acid substitutions compared to the native antibody. In some embodiments, the antibody has one or more amino acid additions to the N-terminus of the native heavy chain and/or the native light chain. In some embodiments, the antibody has one or more amino acid deletions in the N-terminal residues (such as any one or more of residues 1-5) of the native FR1 region in the heavy chain and/or the native light chain. In some embodiments, the antibody has one or more amino acid substitutions in the N-terminal residues (such as any one or more of residues 1-5) of the native FR1 region in the heavy chain and/or the native light chain.

In some embodiment, the antibody has one antigen binding domain (ABD) directed against a single target. In some embodiments, the antibody is monovalent. In some embodiments, the antibody is in the form of a Fab, Fab', or an Fv fragment.

In some embodiments, the antibody has two or more antigen binding domains (ABDs), such as any one of 2, 3, 4, 5, 6, or more ABDs. In some embodiments, the ABDs specifically bind to the same target. In some embodiments, the ABDs specifically bind to the same epitope. In some embodiments, the ABDs specifically bind to different epitopes of the same target. In some embodiments, the antibody is multivalent, such as bivalent, trivalent, or tetravalent. In some embodiments, the ABDs specifically bind to different targets. In some embodiments, the antibody is multispecific, such as bispecific, trispecific, or tetraspecific.

The antibody (or the ABD) can be directed against any targets of interest that are expressed on a diseased cell or in a diseased tissue. In some embodiments, the antibody (or the ABD) is directed against a target that is over-expressed on a diseased cell (or in a diseased tissue) compared to a normal cell (or in a normal tissue). In some embodiments, the antibody (or the ABD) is directed against a target that is expressed at a substantially similar level on a diseased cell (or in a diseased tissue) compared to a normal cell (or in a normal tissue). In some embodiments, the antibody (or the ABD) is directed to a target expressed on a tumor cell. In some embodiments, the antibody (or the ABD) is directed to a target expressed in a tumor tissue. In some embodiments, the antibody (or the ABD) is directed to a target expressed on a tumor stromal cell. In some embodiments, the antibody (or the ABD) is directed to a target expressed on a blood vessel cell in a tumor tissue. In some embodiments, the antibody (or the ABD) is directed to a tumor antigen, such as a tumor-specific antigen or a tumor-associated antigen.

Suitable targets of the antibody (or the ABD) include, but are not limited to the molecules listed in Table 8 below. In some embodiments, the antibody (or the ABD) is capable of binding to EGFR, CTLA-4, PD-1, CD-71 or PD-L1.

TABLE 8

Exemplary targets of the activatable antibody.

| | | | | | |
|---|---|---|---|---|---|
| a-4 integrin | CD22 | CD 125 | CXCR4 | GAL3STI | IgE Receptor (FceRI) |
| a-V integrin | CD24 | CD 132 (IL-2RG) | CYR61 | G-CSF | IGF |
| a-4-b-1 integrin | CD25 | CD133 | DL44 | G-CSFR | IGF1R |
| a-4-b-7 integrin | CD27 | CD137 | DLK1 | GD2 | IL1B |
| AGR2 | CD28 | CD138 | DLL4 | GITR | IL1R |
| Anti-Lewis_Y | CD30 | CD166 | DPP-4 | GLUT1 | IL2 |
| Apelin J receptor | CD40 | CD172A | DSG1 | GLUT4 | IL2R |
| APRIL | CD40L | CD248 | EGFR | GM-CSF | IL4 |
| B7-H3 | CD41 | CDH6 | EGFRVIII | GM-CSFR | IL4R |
| B7-H4 | CD44 | CEACM5 (CEA) | Endothelin b receptor (ETBR) | GPIIb/IIIa receptor | IL6 |
| BCMA | CD44v6 | CEACAM6 (NCA-90) | ENPP3 | Gp130 | IL6R |
| BTLA | CD47 | CLAUDIN-3 | EPCAM | GPIIB/IIIA | IL11 |
| C5 complement | CD51 | CLAUDIN-4 | EPHA2 | GPNMB | IL12 |
| C-242 | CD52 | cMet | EPHB2 | GRP78 | IL12p40 |
| CA9 | CD56 | Collagen | ERBB3 | HER-2/neu | IL12R |
| CA19-9 (Lewis a) | CD64 | Cripto | F protein of RSV | HGF | IL12Rb1 |
| Carbonic anhydrase 9 | CD70 | CSFR | FAP | hGH | IL13 |
| CD2 | CD71 | CSFR-1 | FGF-2 | HVEM | IL13R |
| CD3 | CD74 | CTLA-4 | FGF-8 | Hyaluronidase | IL15 |
| CD6 | CD80 | CTFG | FGFR-1 | ICOS | IL17 |
| CD9 | CD81 | CXCL10 | FGFR-2 | INFa | IL18 |
| CD11a | CD86 | CXCL13 | FGFR-3 | INFb | IL21 |
| CD19 | CD95 | CXCR1 | FGFR-4 | INFg | IL23 |
| CD20 | CD117 | CXCR2 | Folate receptor | IgE | IL23R |
| IL27 | MCSP | OX-40L | RAGE | TLR9 | VEGF-B |
| IL27R (wsx1) | Mesothelin | OX-40R | SLC44A4 | TMEM31 | VEGF-C |
| IL29 | MRP4 | PAR2 | TNFa | Sphingosine 1 Phosphate | VEGF-D |
| IL31 | MUC1 | PDGF-AA | STEAP1 | TNFR | VEGFR1 |
| IL31R | Mucin-16 (CA-125) | PDGF-BB | STEAP2 | TNFRS12A | VEGFR2 |
| Insulin Receptor | Na/K ATPase | PDGFRa | TAG-72 | TRAIL-R1 | VEGFR3 |
| Jagged-1 | Neutrophil elastase | PDGFRb | TAPA1 | TRAIl-R2 | VISTA |
| Jagged-2 | NGF | PD-1 | TGFb | Transferrin | WISP-1 |
| KIR | Nicastrin | PD-L1 | TIGIT | Transferrin Receptor | WISP-1 |
| LAG-3 | NOTCH1 | PD-L2 | TIM3 | TRK-A | WISP-2 |
| LIF-R | NOTHC2 | Phospahtidylserine | TLR2 | TRK_B | WISP-3 |
| Lewis X | NOTHC3 | P1GF | TLR4 | uPAR | |
| LIGHT | NOTCH4 | PSCA | TLR6 | VCAM-1 | |
| LRP4 | NOV | PSMA | TLR7 | VEGF | |
| LRRC26 | OSM-R | RAAG12 | TLR8 | VEGF-A | |

In some embodiments, the antibody is a therapeutic antibody. In some embodiments, the antibody is derived from one or more known therapeutic antibodies known in the art. Exemplary suitable therapeutic antibodies include, but are not limited to the antibodies listed in Table 9 below. In some embodiments, the activatable antibody comprises an antibody derived from Cetuximab, Trastuzumab, Tremelimumab, Ipilimumab, Nivolumab, Pembmrlizumab, or Atezolizumab.

In some embodiments, the activatable antibody comprises an ADB comprising a heavy chain variable domain (VH) comprising three CDRs of the amino acid sequence of SEQ ID NO: 228, and a light chain variable domain (VL) comprising three CDRs of the amino acid sequence of SEQ ID NO: 229. In some embodiments, the activatable antibody comprises an ADB comprising a VH comprising an amino acid sequence having at least about 90%, 91%, 92%, 93%, 94%, 95%, 96%, 97%, 98%, 99%, or 100% sequence identity to the amino acid sequence of SEQ ID NO: 228, and a VL comprising an amino acid sequence having at least about 90%, 91%, 92%, 93%, 94%, 95%, 96%, 97%, 98%, 99%, or 100% sequence identity to the amino acid sequence of SEQ ID NO: 229. In some embodiments, the activatable antibody comprises an antibody derived from Pembrolizumab.

In some embodiments, the activatable antibody comprises an ADB comprising a heavy chain variable domain (VH) comprising three CDRs of the amino acid sequence of SEQ ID NO: 230, and a light chain variable domain (VL) comprising three CDRs of the amino acid sequence of SEQ ID NO: 231. In some embodiments, the activatable antibody comprises an ADB comprising a VH comprising an amino acid sequence having at least about 90%, 91%, 92%, 93%, 94%, 95%, 96%, 97%, 98%, 99%, or 100% sequence identity to the amino acid sequence of SEQ ID NO: 230, and a VL comprising an amino acid sequence having at least about 90%, 91%, 92%, 93%, 94%, 95%, 96%, 97%, 98%, 99%, or 100% sequence identity to the amino acid sequence of SEQ ID NO: 231. In some embodiments, the activatable antibody comprises an antibody derived from Cetuximab.

In some embodiments, the activatable antibody comprises an ADB comprising a heavy chain variable domain (VH) comprising three CDRs of the amino acid sequence of SEQ ID NO: 232, and a light chain variable domain (VL) comprising three CDRs of the amino acid sequence of SEQ ID NO: 233. In some embodiments, the activatable antibody comprises an ADB comprising a VH comprising an amino acid sequence having at least about 90%, 91%, 92%, 93%, 94%, 95%, 96%, 97%, 98%, 99%, or 100% sequence identity to the amino acid sequence of SEQ ID NO: 232, and a VL comprising an amino acid sequence having at least about 90%, 91%, 92%, 93%, 94%, 95%, 96%, 97%, 98%, 99%, or 100% sequence identity to the amino acid sequence of SEQ ID NO: 233. In some embodiments, the activatable antibody comprises an antibody derived from Tremelimumab.

In some embodiments, the activatable antibody comprises an ADB comprising a heavy chain variable domain (VH) comprising three CDRs of the amino acid sequence of SEQ ID NO: 234, and a light chain variable domain (VL) comprising three CDRs of the amino acid sequence of SEQ ID NO: 235. In some embodiments, the activatable antibody comprises an ADB comprising a VH comprising an amino acid sequence having at least about 90%, 91%, 92%, 93%, 94%, 95%, 96%, 97%, 98%, 99%, or 100% sequence identity to the amino acid sequence of SEQ ID NO: 234, and a VL comprising an amino acid sequence having at least about 91%, 91%, 92%, 93%, 94%, 95%, 96%, 97%, 98%, 99%, or 100% sequence identity to the amino acid sequence of SEQ ID NO: 235. In some embodiments, the activatable antibody comprises an antibody derived from Trastuzumab.

In some embodiments, the activatable antibody comprises an ADB comprising a heavy chain variable domain (VH) comprising three CDRs of the amino acid sequence of SEQ ID NO: 236, and a light chain variable domain (VL) comprising three CDRs of the amino acid sequence of SEQ ID NO: 237. In some embodiments, the activatable antibody comprises an ADB comprising a VH comprising an amino acid sequence having at least about 90%, 91%, 92%, 93%, 94%, 95%, 96%, 97%, 98%, 99%, or 100% sequence identity to the amino acid sequence of SEQ ID NO: 236, and a VL comprising an amino acid sequence having at least about 90%, 91%, 92%, 93%, 94%, 95%, 96%, 97%, 98%, 99%, or 100% sequence identity to the amino acid sequence of SEQ ID NO: 237. In some embodiments, the activatable antibody comprises an antibody derived from Ipilimumab.

In some embodiments, the activatable antibody comprises an ADB comprising a heavy chain variable domain (VH) comprising three CDRs of the amino acid sequence of SEQ ID NO: 238, and a light chain variable domain (VL) comprising three CDRs of the amino acid sequence of SEQ ID NO: 239. In some embodiments, the activatable antibody comprises an ADB comprising a VH comprising an amino acid sequence having at least about 90%, 91%, 92%, 93%, 94%, 95%, 96%, 97%, 98%, 99%, or 100% sequence identity to the amino acid sequence of SEQ ID NO: 238, and a VL comprising an amino acid sequence having at least about 90%, 91%, 92%, 93%, 94%, 95%, 96%, 97%, 98%, 99%, or 100% sequence identity to the amino acid sequence of SEQ ID NO: 239. In some embodiments, the activatable antibody comprises an antibody derived from 9D9.

In some embodiments, the antibody comprises a heavy chain variable domain (VH) sequence having at least 90%, 91%, 92%, 93%, 94%, 95%, 96%, 97%, 98%, 99%, or 100% sequence identity to the amino acid sequence of the VH of an antibody of Table 9. In some embodiments, the antibody comprises a light chain variable domain (VL) sequence having at least 90%, 91%, 92%, 93%, 9, 94%, 95%, 96%, 97%, 98%, 99%, or 100% sequence identity to the amino acid sequence of the VL of an antibody of Table 9. In some embodiments, a VH or VL sequence having at least 90%, 91%, 92%, 93%, 94%, 95%, 96%, 97%, 98%, or 99% identity contains substitutions (e.g., conservative substitutions), insertions, or deletions relative to the reference sequence, but the antibody comprising that sequence retains the ability to bind to its target. In some embodiments, substitutions, insertions, or deletions occur in regions outside the HVRs (i.e., in the FRs).

TABLE 9

Exemplary therapeutic antibodies or antibody-drug conjugates.

| Antibody | Target | Antibody | Target |
|---|---|---|---|
| Atezoliaumab (e.g., TECENTRIQ ®) | PD-L1 | Duravalumab | PD-L1 |
| Bevacizumab (e.g., AVASTIN ®) | VEGF-A | Ipilimumab (e.g., YERVOY ®) | CTLA-4 |
| Ranibizumab (e.g., LUCENTIS ®) | VEGF | Tremelimumab | CTLA-4 |
| Cetuximab (e.g., ERBITUX ®) | EGFR | Nivolumab (e.g., OPDIVO ®) | PD1 |
| Panitumumab (e.g., VECTIBIX ®) | EGFR | Pembrolizumab(e.g., KEYTRUDA ®) | PD-1 |
| Infliximab (e.g., REMICADE ®) | TNFa | Utomilumab (PF-05082566) | CD137 |
| Adalimumab (e.g., HUMIRA ®) | TNFa | Hu5F9-G4 | CD47 |
| Natalizumab (e.g., TYSABRI ®) | Integrina4 | Ertumaxomab | CD3/HER-2-neu |
| Basiliximab (e.g., SIMULECT ®) | IL2R | Tanezumab | NGF |
| Eculizumab (e.g., SOLIRIS ®) | Complement C5 | Bavituximab | Phosphatidylserine |
| Efalizumab (e.g., RAPTIVA ®) | CD11a | Zalutumumab | EGFR |
| Tositumomab (e.g., BEXXAR ®) | CD20 | Matuzumab | EGFR |
| Ibritumomab tiuxetan (e.g., ZEVALIN ®) | CD20 | Nimotuzumab | EGFR |
| Rituximab (e.g., RITUXAN ®) | CD20 | Figitumumab | IGF1R |
| Ocrelizumab (e.g., OCREVUS ®) | CD20 | Tocilizumab (e.g., ACTEMRA ®) | IL-6R |
| Ofatumumab (e.g., ARZERRA ®) | CD20 | Mapatumumab (HGS-ETR1) | TRAIL-R1 |
| Obinutuzumab (e.g., GAZYVA ®) | CD20 | Teprotumumab | IGF-1R |
| Daclizumab (e.g., ZENAPAX ®) | CD25 | MDX447 | EGFR/CD64 |
| Brentuximab vedotin (e.g., ADCENTRIS ®) | CD30 | HuJ591 | PSMA |
| Gemtuzumab | CD33 | Denosumab (e.g., PROLIA ®) | RANKL |
| Gemtuzumab ozogamicin (e.g., MYELOTARG ®) | CD33 | Ustekinumab (e.g., STELARA ®) | Il-12/IL-23 |
| Alemtuzumab (e.g., CAMPATH ®) | CD52 | Adecatumumab | EpCAM |
| Abiciximab (e.g., REOPRO ®) | Glycoprotein receptor IIb/IIIa | Abrilumab | integrin α4β7 |
| Omalizumab (e.g., XOLAIR ®) | IgE | Belimumab | BAFF |
| Trastuzumab (e.g., HERCEPTIN ®) | HER-2 | Briakinumab | IL-12; IL-23 |
| Trastuzumab emtansine (e.g., KADCYLA ®) | HER-2 | Lexatumumab | TRAIL-R2 |
| Palivizumab (e.g., SYNAGIS ®) | F protein of RSV | Oxelumab | OX-40 |
| Ruplizumab (Hu5c8) | CD40L | Ziralimumab | CD147 |
| Pertuzumab | HER-2/neu | Inotuzumab ozogamicin | CD22 |
| Avelumab | PD-L1 | | |

F. Binding Affinity

Binding affinity and specificity of the activatable antibodies described herein can be determined experimentally by methods known in the art. Such methods comprise, but are not limited to Western blots. ELISA, RIA, ECL, IRMA, EIA, and BIACORE® based binding assays and peptide scans.

In some embodiments, the $K_D$ of the binding between the activatable antibody having intact S1 and S2 associated with each other and the target of the ABD is no stronger than about any one of $10^{-9}$ M, $10^{-8}$ M, $10^{-7}$ M, $10^{-6}$ M, $10^{-5}$ M, $10^{-4}$ M, $10^{-3}$ M, or less. In some embodiments, the $K_D$ of the binding between the activatable antibody after disruption (e.g., cleavage) of the DS1 and/or DS2 and the target of the ABD is stronger than about any one of $10^{-7}$ M, $10^{-8}$ M, $10^{-9}$ M, $10^{-10}$ M, $10^{-11}$ M, or $10^{-12}$ M. In some embodiments, the $K_D$ of the binding between the activatable antibody and the target of the ABD after disruption (e.g., cleavage) of the DS1 and/or DS2 is at least about any one of 2×, 5×, 10×, 20×, 50×, 100×, 200×, 500×, 1000× or stronger than the $K_D$ of the binding between the activatable antibody having intact S1 and S2 associated with each other and the target of the ABD. In some embodiments, the $K_D$ of the binding between the ABD and the target of the ABD is at least about any one of 2×, 5×, 10×, 20×, 50×, 100×, 200×, 500×, 1000× or stronger than the $K_D$ of the binding between the activatable antibody having intact S1 and S2 associated with each other and the target of the ABD.

In some embodiments, the $K_{on}$ of the binding between activatable antibody having S1 and S2 associated with each other and the target of the ABD is no more than about any one of 1 $M^{-1}s^{-1}$, 10 $M^{-1}s^{-1}$, 100 $M^{-1}s^{-1}$, $10^3$ $M^{-1}s^{-1}$, $10^4$ $M^{-1}s^{-1}$, $10^5$ $M^{-1}s^{-1}$, or $10^6$ $M^{-1}s^{-1}$.

In some embodiments, the $K_{on}$ of the binding between activatable antibody having S1 and S2 associated with each other and the target of the ABD is at least about any one of $10^3$ $s^{-1}$, 100 $s^{-1}$, 10 $s^{-1}$, 1 $s^{-1}$, $10^{-2}$ $s^{-1}$, $10^{-3}$ $s^{-1}$.

In some embodiments, the $EC_{50}$ of the activatable antibody having intact S1 and S2 associated with each other in a cell proliferation assay with a target cell expressing the target of the ABD is more than about any one of 2×, 5×, 10×, 20×, 30×, 40×, 50×, 100×, 200×, 500×, 1000× or more than that of the $EC_{50}$ of the activatable antibody after disruption (e.g., cleavage) of the DS1 and/or DS2 in the same cell proliferation assay.

III. Methods of Preparing Activatable Antibodies

Further provided are methods of preparing the activatable antibodies described herein. As the polypeptide shield moieties (i.e., S1 and S2) of the activatable antibodies are genetically fused to the antibody component in the activatable antibodies, any of the known antibody expression and purification methods in the art can be used to prepare a fusion antibody comprising the polypeptide shield moieties fused to the N-termini of the VH and VL. In some embodiments, an activatable antibody is obtained while the polypeptide shield moieties in the fusion antibody associate with each other during the antibody expression process. In some embodiments, the method further comprises treating the fusion antibody under a condition that allows association of the polypeptide shield moieties, thereby providing the activatable antibody. "Heavy chain" when used in conjunction with the activatable antibody refers to the polypeptide chain comprising the polypeptide shield moiety S1 fused to the N-termini of the VH of the antibody. "Light chain" when used in conjunction with the activatable antibody refers to the polypeptide chain comprising the polypeptide shield moiety S2 fused to the N-termini of the VL of the antibody. "Fusion antibody" refers to the protein complex formed by the heavy chain(s) and the light chain(s) of the activatable antibody, wherein the steric shield may or may not be formed.

A. Nucleic Acid Molecules Encoding Activatable Antibodies

Nucleic acid molecules comprising polynucleotides that encode one or more chains of the activatable antibodies are provided. In some embodiments, there is provided a first nucleic acid encoding a heavy chain comprising S1 fused to the N-terminus of the VH in the activatable antibody, and a second nucleic acid encoding a light chain comprising S2 fused to the N-terminus of the VL in the activatable antibody. In some embodiments, there is provided a nucleic acid encoding a heavy chain comprising S1 fused to the N-terminus of the VH in the activatable antibody, and a second nucleic acid encoding a light chain comprising S2 fused to the N-terminus of the VL in the activatable antibody. In some embodiments, wherein the activatable antibody comprises two non-identical heavy chains and two non-identical light chains, a nucleic acid encoding each of the four chains or a single nucleic acid encoding all four chains is provided. In some embodiments, the nucleic acids encoding the heavy chain(s) and the light chain(s) are operably linked to the same promoter. In some embodiments, the nucleic acids encoding the heavy chain(s) and the light chain(s) are operably linked to different promoters.

In some embodiments, a nucleic acid encoding a heavy chain or light chain of the activatable antibody comprises a nucleotide sequence that encodes a leader sequence, which, when translated, is located at the N terminus of the heavy chain or light chain. The leader sequence may be the native antibody heavy or light chain leader sequence, or may be another heterologous leader sequence.

Nucleic acid molecules may be constructed using recombinant DNA techniques conventional in the art. In some embodiments, a nucleic acid molecule is an expression vector that is suitable for expression in a selected host cell. Vectors comprising polynucleotide(s) that encode the heavy chains and light chain(s) of the activatable antibodies are provided. Such vectors include, but are not limited to, DNA vectors, phage vectors, viral vectors, retroviral vectors, etc. In some embodiments, there is provided a vector comprising: (a) a first nucleic acid encoding a heavy chain comprising S1 fused to the N-terminus of the VH, and (b) a second nucleic acid encoding a light chain comprising S2 fused to the N-terminus of the VL.

In some embodiments, a first vector comprises a first nucleic acid encoding the heavy chain of the activatable antibody and a second vector comprises a second nucleic acid encoding the light chain of the activatable antibody. In some embodiments, the first vector and second vector are transfected into host cells in similar amounts (such as similar molar amounts or similar mass amounts). In some embodiments, a mole- or mass-ratio of between 5:1 and 1:5 of the first vector and the second vector is transfected into host cells. In some embodiments, a mass ratio of between 1:1 and 1:5 for the vector encoding the heavy chain and the vector encoding the light chain is used.

In some embodiments, a vector is selected that is optimized for expression of polypeptides in CHO or CHO-derived cells, or in NSO cells. Exemplary such vectors are described, e.g., in Running Deer et al., Biotechnol. Prig. 20:880-889 (2004).

B. Host Cells

In various embodiments, the heavy chains and/or light chains of the activatable antibodies may be expressed in prokaryotic cells, such as bacterial cells; or in eukaryotic cells, such as fungal cells, yeast cells, plant cells, insect cells, and mammalian cells. Such expression may be carried out, for example, according to procedures known in the art. Exemplary eukaryotic cells that may be used to express polypeptides include, but are not limited to, COS cells, including COS 7 cells: 293 cells, including 293-6E cells; CHO cells, including CHO-S. DG44. Lec13 CHO cells, and FUT8 CHO cells; PER.C6® cells (Crucell); and NSO cells. In some embodiments, a particular eukaryotic host cell is selected based on its ability to make desired post-translational modifications to the activatable antibodies. In some embodiments, a host cell capable of protein glycosylation is provided. For example, in some embodiments, CHO cells produce polypeptides that have a higher level of sialylation than the same polypeptide produced in 293 cells.

Introduction of one or more nucleic acids into a desired host cell may be accomplished by any method, including but not limited to, calcium phosphate transfection, DEAE-dextran mediated transfection, cationic lipid-mediated transfection, electroporation, transduction, infection, etc. Non-limiting exemplary methods are described, e.g., in Sambrook et al., Molecular Cloning, A Laboratory Manual, $3^{rd}$ ed. Cold Spring Harbor Laboratory Press (2001). Nucleic acids may be transiently or stably transfected in the desired host cells, according to any suitable method.

The invention also provides host cells comprising any of the nucleic acids or vectors described herein. In some embodiments, the invention provides a host cell comprising an activatable antibody or a vector encoding the heavy chain(s) and/or light chain(s) of the activatable antibody. Any host cells capable of over-expressing heterologous DNAs can be used for the purpose of isolating the genes encoding the activatable antibody, polypeptide or the corresponding fusion antibodies. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtillis*) and yeast (such as *S. cerevisae, S. pombe*; or *K. lactis*).

In some embodiments, the activatable antibody is produced in a cell-free system. Non-limiting exemplary cell-free systems are described, e.g., in Sitaraman et al., *Methods Mol. Biol.* 498: 229-44 (2009): Spirin, *Trends Biotechnol.* 22: 538-45 (2004): Endo et al., *Biotechnol. Adv.* 21: 695-713 (2003).

C. Purification

The activatable antibodies or the corresponding fusion proteins may be purified by any suitable method. Such methods include, but are not limited to, the use of affinity matrices or hydrophobic interaction chromatography. Suitable affinity ligands include the ROR1 ECD and ligands that bind antibody constant regions. For example, a Protein A. Protein G, Protein A/G, or an antibody affinity column may be used to bind the constant region and to purify a full-length activatable antibody. Hydrophobic interactive chromatography, for example, a butyl or phenyl column, may also suitable for purifying some activatable antibodies. Ion exchange chromatography (e.g., anion exchange chromatography and/or cation exchange chromatography) may also suitable for purifying some activatable antibodies. Mixed-mode chromatography (e.g. reversed phase/anion exchange, reversed phase/cation exchange, hydrophilic interaction/anion exchange, hydrophilic interaction/cation exchange, etc.) may also suitable for purifying some activatable antibodies. Many methods of purifying polypeptides are known in the art and may be used to purify the fusion antibody prior to the formation of the steric shield, and/or the activatable antibody after the formation of the steric shield.

D. Formation of Steric Shield

In some embodiments, the steric shield forms, i.e., S1 and S2 associates with each other spontaneously upon expression of the fusion antibody corresponding to the activatable antibody. In some embodiments, there is provided a method of preparing an activatable antibody, comprising: (a) culturing a host cell comprising one or two vectors encoding the heavy chain(s) and the light chain(s) of the activatable antibody under a condition that produces a fusion antibody comprising the heavy chain(s) and the light chain(s); and (b) isolating the fusion antibody, thereby providing the activatable antibody.

In some embodiments, the fusion antibody is subject to an enzymatic or chemical treatment step to conjugate S1 and S2. In some embodiments, the fusion antibody is subject to a chemical treatment step to reform the covalent bond between S1 and S2. In some embodiments, S1 and S2 are conjugated to each other via one or more disulfide bonds.

In some embodiments, there is provided a method of preparing an activatable antibody, wherein S1 and S2 comprise cysteines, and S1 and S2 are conjugated to each other via one or more disulfide bonds, the method comprising: (a) culturing a host cell comprising one or two vectors encoding the heavy chain(s) and the light chain(s) of the activatable antibody under a condition that produces a fusion antibody comprising the heavy chain(s) and the light chain(s); (b) isolating the fusion antibody; and (c) treating the fusion antibody with a reducing agent followed by an oxidation agent, thereby providing the activatable antibody. In some embodiments, the reducing agent is TCEP and the oxidation agent is ascorbic acid. In some embodiments, the molar ratio between the fusion antibody to the TCEP is at least about any one of 10:1, 5:1, 4:1, 3:1, 2:1, 1:1, 1:2, or 1:5. In some embodiments, the molar ratio between the TCEP to ascorbic acid is no more than about any one of 1:1, 1:2, 1:3, 1:4, 1:5, 1:10 or more. In some embodiments, the reducing agent is reduced glutathione, and the oxidation agent is oxidized glutathione. Any other known reducing agents and oxidization agents suitable for protein preparation can also be used.

In some embodiments, there is provided a method of preparing an activatable antibody, wherein one of S1 and S2 comprises an acyl donor residue and the other comprises an acyl acceptor residue, and wherein S1 and S2 are conjugated to each other by a transglutaminase, the method comprising: (a) culturing a host cell comprising a vector encoding the heavy chain(s) and the light chain(s) of the activatable antibody under a condition that produces a fusion antibody comprising the heavy chain(s) and the light chain(s); (b) isolating the fusion antibody; and (c) treating the fusion antibody with the transglutaminase, thereby providing the activatable antibody.

In some embodiments, there is provided a method of preparing an activatable antibody, wherein one of S1 and S2 comprises a glycan-binding protein (such as lectin, ficolin, or ERGIC-53) and the other comprises an glycan attached to a glycosylation residue, the method comprising: (a) culturing a host cell comprising a vector encoding the heavy chain(s) and the light chain(s) of the activatable antibody under a condition that produces a fusion antibody comprising the heavy chain(s) and the light chain(s); (b) isolating the fusion antibody; and (c) treating the fusion antibody with a glycosylase, thereby providing the activatable antibody.

Also provided is a composition comprising the fusion antibody prepared in any one of the methods described above.

IV. Methods of Treatment

The activatable antibodies described herein and compositions thereof (such as pharmaceutical composition) can be used to treat various diseases, such as cancer, including solid tumor or hematological cancer. Thus, in some embodiments, there is provided a method of treating a disease in an individual (such as a human), comprising administering to the individual an effective amount of any one of the activatable antibodies described herein. In some embodiments, the disease is cancer. In some embodiments, the cancer is selected from the group consisting of bladder cancer, brain cancer, breast cancer, cervical cancer, colorectal cancer, esophageal cancer, kidney cancer, leukemia, liver cancer, lung cancer, melanoma, non-Hodgkin's lymphoma, ovarian cancer, pancreatic cancer, prostate cancer, skin cancer, thyroid cancer and uterine cancer.

In some embodiments, there is provided a method of treating a disease (such as cancer) in an individual, comprising administering to the individual an effective amount of an activatable antibody comprising a therapeutic antibody comprising an antigen-binding domain (ABD), wherein the ABD comprises a heavy chain variable region (VH) and a light chain variable region (VL), wherein the N-terminus of the VH is fused to a first polypeptide shield moiety (S1), and the N-terminus of the VL is fused to a second polypeptide shield moiety (S2), wherein S1 comprises a first disease-sensing releasable moiety (DS1) and/or S2 comprises a second disease-sensing releasable moiety (DS2), wherein association of S1 with S2 blocks binding of the ABD to its target, wherein the ABD does not specifically bind to S1, S2, or association thereof, and wherein DS1 and/or DS2 are disrupted (such as cleaved) at a diseased site, thereby unblocking binding of the ABD to its target at the diseased site. In some embodiments, S1 comprises a first association moiety B, and S2 comprises a second association moiety C, wherein B and C associate with each other covalently and/or non-covalently. In some embodiments, DS1 and/or DS2 comprises a peptide substrates specific for an enzyme (e.g., protease) that is expressed at a diseased site. In some embodiments, DS1 and/or DS2 comprise a pH-sensitive protein or peptide. In some embodiments, the disease is a cancer. In some embodiments, the cancer is selected from the group consisting of bladder cancer, brain cancer, breast cancer, cervical cancer, colorectal cancer, esophageal cancer, kidney cancer, leukemia, liver cancer, lung cancer, melanoma, non-Hodgkin's lymphoma, ovarian cancer, pancreatic cancer, prostate cancer, skin cancer, thyroid cancer and uterine cancer.

In some embodiments, there is provided a method of preferentially delivering a therapeutic antibody to a diseased site in an individual in need of treatment with the therapeutic antibody, comprising administering to the individual an effective amount of an activatable antibody comprising the therapeutic antibody comprising an antigen-binding domain (ABD), wherein the ABD comprises a heavy chain variable region (VH) and a light chain variable region (VL), wherein the N-terminus of the VH is fused to a first polypeptide shield moiety (S1), and the N-terminus of the VL is fused to a second polypeptide shield moiety (S2), wherein S1 comprises a first disease-sensing releasable moiety (DS1) and/or S2 comprises a second disease-sensing releasable moiety (DS2), wherein association of S1 with S2 blocks binding of the ABD to its target, wherein the ABD does not specifically bind to S1, S2, or association thereof, and wherein DS1 and/or DS2 are disrupted (such as cleaved) at a diseased site, thereby unblocking binding of the ABD to its target at the diseased site. In some embodiments, S1 comprises a first association moiety B, and S2 comprises a second association moiety C, wherein B and C associate with each other covalently and/or non-covalently. In some embodiments, DS1 and/or DS2 comprises a peptide substrates specific for an enzyme (e.g., protease) that is expressed at a diseased site. In some embodiments, DS1 and/or DS2 comprise a pH-sensitive protein or peptide. In some embodiments, the disease is a cancer. In some embodiments, the cancer is selected from the group consisting of bladder cancer, brain cancer, breast cancer, cervical cancer, colorectal cancer, esophageal cancer, kidney cancer, leukemia, liver cancer, lung cancer, melanoma, non-Hodgkin's lymphoma ovarian cancer, pancreatic cancer, prostate cancer, skin cancer, thyroid cancer and uterine cancer.

In some embodiments, there is provided a method of increasing the effective concentration of a therapeutic antibody at a diseased site in an individual in need of treatment with the therapeutic antibody, comprising administering to the individual an effective amount of an activatable antibody comprising the therapeutic antibody comprising an antigen-binding domain (ABD), wherein the ABD comprises a heavy chain variable region (VH) and a light chain variable region (VL), wherein the N-terminus of the VH is fused to a first polypeptide shield moiety (S1), and the N-terminus of the VL is fused to a second polypeptide shield moiety (S2), wherein S1 comprises a first disease-sensing releasable moiety (DS1) and/or S2 comprises a second disease-sensing releasable moiety (DS2), wherein association of S1 with S2 blocks binding of the ABD to its target, wherein the ABD does not specifically bind to S1, S2, or association thereof, and wherein DS1 and/or DS2 are disrupted (such as cleaved) at a diseased site, thereby unblocking binding of the ABD to its target at the diseased site. In some embodiments, S1 comprises a first association moiety B, and S2 comprises a second association moiety C, wherein B and C associate with each other covalently and/or non-covalently. In some embodiments, DS1 and/or DS2 comprises a peptide substrates specific for an enzyme (e.g., protease) that is expressed at a diseased site. In some embodiments, DS1 and/or DS2 comprises a pH-sensitive protein or peptide. In some embodiments, the disease is a cancer. In some embodiments, the cancer is selected from the group consisting of bladder cancer, brain cancer, breast cancer, cervical cancer, colorectal cancer, esophageal cancer, kidney cancer, leukemia, liver cancer, lung cancer, melanoma, non-Hodgkin's lymphoma, ovarian cancer, pancreatic cancer, prostate cancer, skin cancer, thyroid cancer and uterine cancer. In some embodiments, the effective concentration of the therapeutic antibody is increased by about any of 10%, 20%, 50%, 1×, 2×, 5× or more at the diseased site compared to administration of the therapeutic antibody to the individual at the same effective amount.

In some embodiments, there is provided a method of reducing binding of a therapeutic antibody to a target in normal tissues in an individual having a disease in need of treatment with the therapeutic antibody, comprising administering to the individual an effective amount of an activatable antibody comprising the therapeutic antibody comprising an antigen-binding domain (ABD), wherein the ABD comprises a heavy chain variable region (VH) and a light chain variable region (VL), wherein the N-terminus of the VH is fused to a first polypeptide shield moiety (S1), and the N-terminus of the VL is fused to a second polypeptide shield moiety (S2), wherein S1 comprises a first disease-sensing releasable moiety (DS1) and/or S2 comprises a second disease-sensing releasable moiety (DS2), wherein association of S1 with S2 blocks binding of the ABD to its target, wherein the ABD does not specifically bind to S1, S2, or association thereof, and wherein DS1 and/or DS2 are disrupted (such as cleaved) at a diseased site, thereby unblocking binding of the ABD to its target at the diseased site. In some embodiments, S1 comprises a first association moiety B, and S2 comprises a second association moiety C, wherein B and C associate with each other covalently and/or non-covalently. In some embodiments, DS1 and/or DS2 comprises a peptide substrates specific for an enzyme (e.g., protease) that is expressed at a diseased site. In some embodiments, DS1 and/or DS2 comprises a pH-sensitive protein or peptide. In some embodiments, the disease is a cancer. In some embodiments, the cancer is selected from the group consisting of bladder cancer, brain cancer, breast cancer, cervical cancer, colorectal cancer, esophageal cancer, kidney cancer, leukemia, liver cancer, lung cancer, melanoma, non-Hodgkin's lymphoma, ovarian cancer, pancreatic cancer, prostate cancer, skin cancer, thyroid cancer and uterine cancer. In some embodiments, administration of the activatable antibody reduces binding of the therapeutic antibody to its target on normal cells by about any of 10%, 20%, 30%, 40%, 50%, 60%, 70%, 80%, 90% or more compared to administration of the therapeutic antibody to the individual.

In some embodiments, there is provided a method of reducing toxicity (such as on-target off-tissue toxicity) of a therapeutic antibody to an individual having a disease in need of treatment with the therapeutic antibody, comprising administering to the individual an effective amount of an activatable antibody comprising the therapeutic antibody comprising an antigen-binding domain (ABD), wherein the ABD comprises a heavy chain variable region (VH) and a light chain variable region (VL), wherein the N-terminus of the VH is fused to a first polypeptide shield moiety (S1), and the N-terminus of the VL is fused to a second polypeptide shield moiety (S2), wherein S1 comprises a first disease-sensing releasable moiety (DS1) and/or S2 comprises a second disease-sensing releasable moiety (DS2), wherein association of S1 with S2 blocks binding of the ABD to its target, wherein the ABD does not specifically bind to S1, S2, or association thereof, and wherein DS1 and/or DS2 are disrupted (such as cleaved) at a diseased site, thereby unblocking binding of the ABD to its target at the diseased site. In some embodiments, S1 comprises a first association moiety B, and S2 comprises a second association moiety C, wherein B and C associate with each other covalently and/or non-covalently. In some embodiments, DS1 and/or DS2 comprises a peptide substrates specific for an enzyme (e.g., protease) that is expressed at a diseased site. In some embodiments, DS1 and/or DS2 comprises a pH-sensitive protein or peptide. In some embodiments, the disease is a cancer. In some embodiments, the cancer is selected from the group consisting of bladder cancer, brain cancer, breast cancer, cervical cancer, colorectal cancer, esophageal cancer, kidney cancer, leukemia, liver cancer, lung cancer, melanoma, non-Hodgkin's lymphoma, ovarian cancer, pancreatic cancer, prostate cancer, skin cancer, thyroid cancer and uterine cancer. In some embodiments, administration of the activatable antibody reduces the toxicity of the therapeutic antibody by about any of 10%, 20%, 30%, 40%, 50%, 60%, 70%, 80%, 90% or more compared to administration of the therapeutic antibody at the same effective amount to the individual.

The activatable antibodies described herein can be administered to an individual via various routes, for example, with the same route of administration as the therapeutic antibody that the activatable antibody is based on. Exemplary routes of administration include, but are not limited to parenteral, intravenous, intramuscular, and subcutaneous administration.

The effective amount, suitable dose, and dosing schedule of the activatable antibody administered to an individual can vary depending on the particular composition, the route of administration, and the particular type of disease being treated. In some embodiments, the effective amount of the activatable antibody is the same as the effective amount of the therapeutic antibody. In some embodiments, the effective amount of the activatable antibody is at least about any of 90%, 80%, 70%, 60%, 50%, 40%, 30%, 20%, or less than the effective amount of the therapeutic antibody.

In some embodiments, the individual is a mammal, such as human, rodents, or primates. In some embodiments, the individual is human.

V. Pharmaceutical Compositions, Kits, and Articles of Manufacture

The present application further provides pharmaceutical compositions, kits, and articles of manufacture comprising any one of the activatable antibodies described herein. In some embodiments, there is provided a pharmaceutical composition comprising any one of the activatable antibodies described herein and a pharmaceutically-acceptable carrier. In some embodiments, the composition (such as pharmaceutical composition) further comprises a carrier, diluent, or excipient, which may facilitate administration of the composition to an individual in need thereof. Examples of carriers, diluents, and excipients include, but are not limited to, calcium carbonate, calcium phosphate, various sugars such as lactose, or types of starch, cellulose derivatives, gelatin, vegetable oils, polyethylene glycols and physiologically compatible solvents.

If desired, solutions of the above compositions may be thickened with a thickening agent such as methylcellulose. They may be prepared in emulsified form, either water in oil or oil in water. Any of a wide variety of pharmaceutically acceptable emulsifying agents may be employed including, for example, acacia powder, a non-ionic surfactant (such as a Tween), or an ionic surfactant (such as alkali polyether alcohol sulfates or sulfonates, e.g., a Triton).

The pharmaceutical compositions described herein can be prepared by mixing the ingredients following generally accepted procedures. For example, the selected components may be simply mixed in a blender or other standard device to produce a concentrated mixture which may then be adjusted to the final concentration and viscosity by the addition of water or thickening agent and possibly a buffer to control pH or an additional solute to control tonicity.

Other pharmaceutically acceptable carriers and their formulation are described in standard formulation treatises, e.g., Remington's Pharmaceutical Sciences by E. W. Martin. See also Wang, Y. J, and Hanson, M. A. "Parenteral Formulations of Proteins and Peptides: Stability and Stabilizers," Journal of Parenteral Science and Technology, Technical Report No. 10, Supp. 42:2S (1988).

In some embodiments, the pharmaceutical composition is a liquid suspension. In some embodiments, the pharmaceutical composition is a lyophilized powder. In some embodiments, the pharmaceutical composition is a sterile composition.

Also provided are kits comprising any one of the activatable antibodies described herein. The kits of the invention are in suitable packaging. Suitable packaging includes, but is not limited to, vials, bottles, jars, flexible packaging (e.g., sealed Mylar or plastic bags), and the like. Kits may optionally provide additional components such as buffers and interpretative information. The present application thus also provides articles of manufacture, which include vials (such as sealed vials), bottles, jars, flexible packaging, and the like.

The article of manufacture can comprise a container and a label or package insert on or associated with the container. Suitable containers include, for example, bottles, vials, syringes, etc. The containers may be formed from a variety of materials such as glass or plastic. Generally, the container holds a composition which is effective for treating a disease as described herein, and may have a sterile access port. The label or package insert indicates that the composition is used for treating the particular condition in an individual. The label or package insert will further comprise instructions for administering the composition to the individual.

Package insert refers to instructions customarily included in commercial packages of therapeutic products that contain information about the indications, usage, dosage, administration, contraindications and/or warnings concerning the use of such therapeutic products. In some embodiments, the package insert indicates that the composition is used for treating a disease (such as cancer).

Additionally, the article of manufacture may further comprise a second container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

EXAMPLES

The examples below are intended to be purely exemplary of the invention and should therefore not be considered to limit the invention in any way. The following examples and detailed description are offered by way of illustration and not by way of limitation.

Example 1. Production of Fusion Antibodies

Fusion antibodies that correspond to exemplary activatable antibodies, including those comprising a full-length antibody or Fab fragments, were prepared by expressing nucleic acids encoding the heavy chain and light chain of each activatable antibody.

Briefly, fusion gene constructs were generated using gene synthesis and codon optimized for expression in mammalian cells (DNA2.0). The heavy and light chain genes were cloned into separate mammalian expression vectors, and then co-transfected in EXPI293F™ cells (Thermo Fisher). Antibody expression was carried out in EXPI293F™ Expression Medium (Thermo Fisher). The supernatant was harvested at 5-7 days post transfection.

Fusion antibodies comprising full-length antibodies were purified using MABSELECT™ Sure resin (GE Healthcare Life Sciences). The fusion antibodies were loaded onto the resin in 20 mM sodium phosphate, 150 mM NaCl, pH 7.2 and eluted using 0.1 M sodium citrate, pH 3.5. Fractions were eluted into 1.0 M Tris-HCl, pH 8.0, pooled and buffer exchanged into 1xPBS, pH 7.4 buffer. Size-exclusion data indicated that none of the fusion antibodies was aggregated during expression (data not shown).

In fusion Fab constructs, each of the heavy chains is designed to carry a10x histidine affinity tag, which allows purification of the fusion Fabs using Immobilized Metal Affinity Chromatography (IMAC). Briefly, HIS-TRAP™ Ni Sepharose resin column (GE Healthcare) is first equilibrated with 5 mM imidazole, 20 mM TrisHCl (pH7.4), 500 mM NaCl buffer. The clarified media expressing each fusion Fab is loaded onto HIS-TRAP™ Ni Sepharose excel affinity resin and column washed with 5 mM imidazole, 20 mM TrisHCl (pH7.4), 500 mM NaCl buffer. Then, the column is washed with 40 mM imidazole, 20 mM Tris HCl pH 7.4, 500 mM NaCl buffer and subsequently eluted with 200 mM imidazole, 20 mM Tris HCl pH 7.4 500 mM NaCl buffer. Eluted fractions containing each fusion Fab are pooled and buffer exchanged into 1xPBS buffer, pH 7.4.

Example 2. Design of Exemplary Activatable Antibodies

This example describes the design of various exemplary activatable antibodies (including activatable antibody fragments). The activatable antibodies described herein remain inert until activated locally in a diseased tissue to bind to their antigens. This property will minimize binding of the activatable antibody to its antigen on the surface of non-diseased cells and prevent undesirable "on-target-off-tissue" toxicity. To generate such constructs, exemplary activatable antibodies are designed to carry a releasable steric shield covering their antigen binding sites thus preventing antigen binding. Polypeptide shield moieties S1 and S2 are genetically fused, respectively, to the N-termini of the heavy chain and light chain of a therapeutic antibody. The polypeptide shield moieties interact with each other to provide the steric shield, which does not bind to the antigen binding sites. Rather, the steric shield hoovers over the antigen binding sites at such a distance as to present steric hindrance to antigen binding. A disease-sensing releasable moiety is further incorporated as a part of each polypeptide shield moiety. In the presence of a diseased tissue-specific element (such as an enzyme), the disease-sensing releasable moieties are disrupted. Consequently, the steric shield is either allowed to freely diffuse away from the antibody, or cleaved such that it no longer joins the N-termini of the heavy chain and light chain, but portions of the polypeptide shield moieties remain attached to the antibody.

The fusion antibodies corresponding to the activatable antibodies are produced as described in Example 1, and the steric shields are formed during expression, or by treatment of the fusion antibodies with transglutaminase (transglutaminase-conjugated activatable antibodies), oxidation/reduction agents (Cys-Cys disulfide-conjugated activatable antibodies), or glycosylase (glycan-binding protein-glycan) antibodies, thereby providing the activatable antibodies. Formation of the steric shields is assessed by SDS-PAGE gel analysis. Antigen binding of the activatable antibodies in the presence and absence of the steric shields is evaluated by surface plasmon resonance as described in Example 9.

A. Exemplary Activatable Anti-EGFR Antibody Constructs with Covalently Associated Polypeptide Shield Moieties.

Four exemplary activatable anti-EGFR antibody (referred herein as "activatable EGFR Ab") constructs were prepared. Polypeptide shield moieties were genetically fused to the N-termini of the heavy chain and the light chain of a full-length therapeutic anti-EGFR antibody comprising a VH comprising the amino acid sequence of SEQ ID NO: 230, and a VL comprising the amino acid sequence of SEQ ID NO: 231. The anti-EGFR antibody was modified to carry a point mutation that abolished its native N-glycosylation site in the Fab region to facilitate analysis. The activatable EGFR Ab constructs (and the corresponding fusion antibodies) comprise sequences that are listed in Table 10 below. In each sequence, the polypeptide shield moiety is underlined, including an association moiety (the single underlined portion with bold letters), a disease-sensing releasable moiety (the underlined portion with regular letters, SEQ ID NO: 19) which can be cleaved by disease-specific proteases, and in some cases, a flexible peptide linker (italicized letters with double underlines). Activatable EGFR Ab 1 and 2 had acyl donor (SEQ ID NO: I) and acyl acceptor sequences (SEQ ID NO: 2) to allow transglutaminase-catalyzed conjugation. A skilled person in the art would readily appreciate that other acyl donor and acyl acceptor sequences, cysteine-containing peptides, disease-sensing releasable moieties (such as protease substrate peptides) and therapeutic antibodies described herein can be used to prepare similar activatable antibodies.

The lengths of the polypeptide shield moieties were designed based on the structural models as described in Example 3. In constructs having a transglutaminase-conjugated steric shield (e.g., activatable EGFR Ab 1 and 2), each polypeptide shield was designed to have 11, 12, 15 or 16 amino acids, but other lengths are possible. The total numbers of added amino acid residues to the native N-termini of the anti-EGFR antibody were 12 for the heavy chain and 11 for the light chain in the activatable EGFR Ab 1; and 16 for the heavy and 15 for the light chain in the activatable EGFR Ab 2. After transglutaminase-catalyzed conjugation, the length of the steric shield is 20 and 28 amino acids respectively for the activatable EGFR Ab 1 and 2 respectively.

In constructs having a disulfide-conjugated steric shield (e.g., activatable EGFR Ab 3 and 4), each polypeptide shield was designed to have 12 or 14 amino acids, but other lengths are possible. The total numbers of added amino acid residues to the native N-termini of the anti-EGFR antibody were 12 for the heavy chain and 12 for the light chain in the activatable EGFR Ab 3; and 14 for the heavy and 14 for the light chain in the activatable EGFR Ab 4. After transglutaminase-catalyzed conjugation, the length of the steric shield is 22 and 26 amino acids respectively for the activatable EGFR Ab 3 and 4 respectively.

TABLE 10

Exemplary activatable anti-EGFR antibody constructs.

| No. | Chain (SEQ ID NO) | Sequence |
|---|---|---|
| 1 | Heavy (21) | LLQGLSGRSDNHQVQLKQSGPGLVQPSQSLSITCTVSGFSLTNYGVHW VRQSPGKGLEWLGVIWSGGNTDYNTPFTSRLSINKDNSKSQVFFKMNS LQSEDTAIYYCARALTYYDYEFAYWGQGTLVTVSAASTKGPSVFPLAP SSKSTSGGTAALGCLVKDYFPEPVTVSWNSGALTSGVHTFPAVLQSSG LYSLSSVVTVPSSSLGTQTYICNVNHKPSNTKVDKKVEPKSCDKTHTCP PCPAPELLGGPSVFLFPPKPKDTLMISRTPECTCVVVDCSHEDPEVKFN WYVDGVEVHNAKTKPREEQYNSTYRVVSVLTVLHQDWLNGKEYKC KVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQ QGNVFSCSVMHEALHNHYTQKSLSLSPG |
|  | Light (22) | GKGLSGRSDNHDILLTQSPVILSVSPGERVSFSCRASQSIGTNIHWYQQ RTNGSPRLLIKYASESISGIPSRFSGSGSGTDFTLSINSVESEDIADYYCQ QNNNWPTTFGAGTKLELKRTVAAPSVFIFPPSDEQLKSGTASVVCLIN NFYPREAKVQWKVDNALQSGNSQESVTEQDSKDSTYSLSSTLTLSKA DYEKHKVYACEVTHQGLSSPVTKSFNRGEC |
| 2 | Heavy (23) | LLQGLSGRSDNHGGGSQVQLKQSGPGLVQPSQSLSITCTVSGFSLTNY GVHWVRQSPGKGLEWLGVIWSGGNTDYNTPFTSRLSINKDNSKSQVF FKMNSLQSEDTAIYYCARALTYYDYEFAYWGQGTLVTVSAASTKGPS VFPLAPSSKSTSGGTAALGCLVKDYFPEPVTVSWNSGALTSGVHTFPA VLQSSGLYSLSSVVTVPSSSLGTQTYICNVNHKPSNTKVDKKVEPKSCD KTHTCPPCPAPELLGGPSVFLFPPKPKDTLMISRTPEVTCVVVDVSHED PEVKFNWYVDGVEVHNAKTKPREEQYNSTYRVVSVLTVLHQDWLNG KEYKCKVSNKALPAPIEKTISKAKGQPREPQVYTLPPSRDELTKNQVSL TCLVKGFYPSDIAVEWESNGQPENNYKTTPPVLDSDGSFFLYSKLTVD KSRWQQGNVFSCSVMHEALHNHYTQKSLSLSPG |
|  | Light (24) | GKGLSGRSDNHGGGSDILLTQSPVILSVSPGERVSFSCRASQSIGTNIHW YQQRTNGSPRLLIKYASESISGIPSRFSGSGSGTDFTLSINSVESEDIADY YCQQNNNWPTTFGAGTKLELKRTVAAPSVFIFPPSDEQLKSGTASVVC LLNNFYPREAKVQWKVDNALQSGNSQESVTEQDSKDSTYSLSSTLTLS KADYEKHKVYACEVTHQGLSSPVTKSFNRGEC |
| 3 | Heavy (25) | SCLSGRSDNHGGQVQLKQSGPGLVQPSQSLSITCTVSGFSLTNYGVHW VRQSPGKGLEWLGVIWSGGNTDYNTPFTSRLSINKDNSKSQVFFKMNS LQSEDTAIYYCARALTYYDYEFAYWGQGTLVTVSAASTKGPSVFPLAP SSKSTSGGTAALGCLVKDYFPEPVTVSWNSGALTSGVHTFPAVLQSSG LYSLSSVVTVPSSSLGTQTYICNVNHKPSNTKVDKKVEPKSSDKTHTCP PCPAPELLGGPSVFLFPPKPKDTLMISRTPEVTCVVVDVSHEDPEVKFN WYVDGVEVHNAKTKPREEQYNSTYRVVSVLTVLHQDWLNGKEYKC KVSNKALPAPIEKTISKAKGQPREPQVYTLPPSRDELTKNQVSLTCLVK GFYPSDIAVEWESNGQPENNYKTTPPVLDSDGSFFLYSKLTVDKSRWQ QGNVFSCSVMHEALHNHYTQKSLSLSPG |
|  | Light (26) | SCLSGRSDNHGGDILLTQSPVILSVSPGERVSFSCRASQSIGTNIHWYQQ RTNGSPRLLIKYASESISGIPSRFSGSGSGTDFTLSINSVESEDIADYYCQ QNNNWPTTFGAGTKLELKRTVAAPSVFIFPPSDEQLKSGTASVVCLLN NFYPREAKQWKVDNALQSGNSQESVTEQDSKDSTYSLSSTLTLSKA DYEKHKVYACEVTHQGLSSPVTKSFNRGES |
| 4 | Heavy (27) | SCLSGRSDNHGGGSQVQLKQSGPGLVQPSQSLSITCTVSGFSLTNYGV HWVRQSPGKGLEWLGVIWSGGNTDYNTPFTSRLSINKDNSKSQVFFK MNSLQSEDTAIYYCARALTYYDYEFAYWGQGTLVTVSAASTKGPSVF PLAPSSKSTSGGTAALGCLVKDYFPEPVTVSWNSGALTSGVHTFPAVL QSSGLYSLSSVVTVPSSSLGTQTYICNVNHKPSNTKVDKKVEPKSSDKT HTCPPCPAPELEGGPSVFLPPKPKDTLMISRTPEVTCVVVDVSHEDPE VKFNWYVDGVEVHNAKTKPREEQYNSTYRVVSVLTVLHQDWLNGK EYKCKVSNKALPAPIEKTISKAKGQPREPQVYTLPPSRDELTKNQVSLT CLVKGFYPSDIAVEWESNGQPENNYKTTPPVLDSDGSFFLYSKLTVDK SRWQQGNVFSCSVMHEALHNHYTQKSLSLSPG |
|  | Light (28) | SCLSGRSDNHGGGSDILLTQSPVILSVSPGERVSFSCRASQSIGTNIHWY QQRTNGSPRLLIKYASESISGIPSRFSGSGSGTDFTLSINSVESEDIADYY CQQNNNWPTTFGAGTKLELKRTVAAPSVFIFPPSDEQLKSGTASVVCL LNNFYPREAKVQWKKVDNALQSGNSQESVTEQDSKDSTYSLSSTLTLSK ADYEKHKVYACEVTHQGLSSPVTKSFNRGES |

B. Exemplary Activatable Fabs with Covalently Associated Polypeptide Shield Moieties.

Based on structural models of Example 3, it was discovered that the same polypeptide shield moieties can be engineered into different antigen binding sites to provide steric shields. Exemplary activatable Fabs targeting human HER-2, human CTLA-4, human PD-1, and mouse CTLA-4 are designed and prepared. The activatable Fabs (and the corresponding fusion Fabs) comprise sequences that are shown in Table 11. The exemplary activatable Fabs were further designed to contain a His tag at the C-terminus of the heavy chain. Sequences corresponding to the polypeptide shield moieties S1 and S2 are underlined. A skilled person in the art would readily appreciate that other acyl donor and acyl acceptor sequences, cysteine-containing peptides, disease-sensing releasable moieties (such as protease substrate peptides) and antigen-binding fragments derived from therapeutic antibodies described herein can be used to prepare similar activatable antibodies.

TABLE 11

Exemplary activatable Fabs.

| Target | Chain (SEQ ID NO) | Sequence |
|---|---|---|
| Human HER-2 | Heavy (29) | LLQGLSGRSDNH*GGGS*EVQLVESGGGLVQPGGSLRLSCAASGFNIKDTYIH WVRQAPGKGLEWVARIYPTNGYTRYADSVKGRFTISADTSKNTAYLQMNS LRAEDTAVYYCSRWGGDGFYAMDYWGQGTLVTVSSASTKGPSVFPLAPSS KSTSGGTAALGCLVKDYFPEPVTVSWNSGALTSGVHTFPAVLQSSGLYSLSS VVTVPSSSLGTQTYICNVNHKPSNTKVDKKVEPKSC |
| | Light (30) | GKGLSGRSDNH*GGGS*DIQMTQSPSSLSASVGDRVTITCRASQDVNTAVAWY QQKPGKAPKLLIYSASFLYSGVPSRFSGSRSGTDFTLTISSLQPEDFATYYCQ QHYTFPPTFGQGTKVEIKRTVAAPSVFIFPPSDEQLKSGTASVVCLLNNFYPR EAKVQWKVDNALQSGNSQESVTEQDSKDSTYSLSSTLTLSKADYEKHKVY ACEVTHQGLSSPVTKSFNRGEC |
| Human CTLA-4 | Heavy (31) | LLQGLSGRSDNH*GGGS*QVQLVESGGGVVQPGRSLRLSCAASGFTFSSYTMH WVRQAPGKGLEWVTFISYDGNNKYYADSVKGRFTISRDNSKNTLYLQMNS LRAEDTAIYYCARTGWLGPFDYWGQGTLVTVSSASTKGPSVFPLAPSSKSTS GGTAALGCLVKDYFPEPVTVSWNSGALTSGVHTFPAVLQSSGLYSLSSVVT VPSSSLGTQTYICNVNHKPSNTKVDKRVEPKSC |
| | Light (32) | GKGLSGRSDNH*GGGS*EIVLTQSPGTLSLSPGERATLSCRASQSVGSSYLAWY QQKPGQAPRLLIYGAFSRATGIPDRFSGSGSGTDFTLTISRLEPEDFAVYYCQ QYGSSPWTFGQGTKVEIKRTVAAPSVFIFPPSDEQLKSGTASVVCLLNNFYP REAKVQWKVDNALQSGNSQESVTEQDSKDSTYSLSSTLTLSKADYEKHKV YACEVTHQGLSSPVTKSFNRGEC |
| Human PD-1 | Heavy (33) | LLQGLSGRSDNH*GGGS*QVQLVQSGVEVKKPGASVKVSCKASGYTFTNYYM YWVRQAPGQGLEWMGGINPSNGGTNFNEKFKNRVTLTTDSSTTTAYMELK SLQFDDTAVYYCARRDYRFDMGFDYWGQGTTVTVSSASTKGPSVFPLAPC SRSTSESTAALGCLVKDYFPEPVTVSWNSGALTSGVHTFPAVLQSSGLYSLS SVVTVPSSSLGTKTYTCNVDHKPSNTKVDKRV |
| | Light (34) | GKGLSGRSDNH*GGGS*EIVLTQSPATLSLSPGERATLSCRASKGVSTSGYSYL HWYQQKPGQAPRLLIYLASYLESGVPARFSGSGSGTDFTLTISSLEPEDFAVY YCQHSRDLPLTFGGGTKVEIKRTVAAPSVFIFPPSDEQLKSGTASVVCLLNNF YPREAKVQWKVDNALQSGNSQESVTEQDSKDSTYSLSSTLTLSKADYEKH KVYACEVTHQGLSSPVTKSFNRGEC |
| Mouse CTLA-4 | Heavy (224) | LLQGPLGLAGGS*GGGS*EAKLQESGPVLVKPGASVKMSCKASGYTFTDYYM NWVKQSHGKSLEWIGVINPYNGDTSYNQKFKGKATLTVDKSSSTAYMELN SLTSEDSAVYYCARYYGSWFAYWGQGTLITVSTAKTTPPSVYPLAPGCGDT TGSSVTLGCLVKGYFPESVTVTWNSGSLSSSVHTFPALLQSGLYTMSSSVTV PSSTWPSETVTCSVAHPASSTTVDKKLEP |
| | Light (225) | GKGLSGRSDNH*GGGS*DIVMTQTTLSLPVSLGDQASISCRSSSQSIVHSNGNTY LEWYLQKPGQSPKLLIYKVSNRFSGVPDRFSGSGSGTDFTLKISRVEAEDLG VYYCFQGSHVPYTFGGGTKLEIKRADAAPTVSIFPPSSEQLTSGGASVVCFL NNFYPKDINVKWKIDGSERQNGVLNSWTDQNSKDSTYSMSSTLTLTKDEYE RHNSYTCEATHKTSTSPIVKSFNRNEC |

C. Exemplary Activatable Antibodies with Non-Covalently Associated Polypeptide Shield Moieties.

Exemplary activatable antibodies targeting human EGFR and human CTLA-4 are designed, in which each polypeptide shield moiety comprises protein fragments or complementary binding peptides. Non-covalent binding between the protein fragments or complementary binding peptides result in steric shields that block the antigen binding sites of the therapeutic antibodies. Sequences of the heavy chain and light chain of the exemplary activatable antibodies are shown in Table 12. A skilled person in the art would readily appreciate that other dimeric proteins, split-proteins, complementary binding peptides, and Fv fragments, disease-sensing releasable moieties (such as protease substrate peptides) and therapeutic antibodies described herein can be used to prepare similar activatable antibodies.

Exemplary Activatable Antibodies with a Dimeric Protein as Steric Shield

Exemplary activatable antibodies with a dimeric protein as the steric shield are prepared. The polypeptide shield moieties, which contain monomeric subunits of a protein dimer, are genetically fused to the N-termini of the heavy chain and light chain of a therapeutic antibody via a disease-sensing releasable moiety. The monomeric subunits associate to form a homo- or hetero-dimer, thereby joining the N-termini of the heavy chain and light chain of the therapeutic antibody. In one exemplary construct, an IL-10 monomeric subunit (e.g., SEQ ID NO: 8) is fused to each of the N-termini of the heavy chain and light chain of an exemplary anti-EGFR antibody via a tumor-sensing releasable moiety (e.g., SEQ ID NO: 19). In another exemplary construct, a CXCL4 monomeric subunit (e.g., SEQ ID NO: 9) is fused to each of the N-termini of the heavy chain and light chain of an exemplary anti-EGFR antibody via a tumor-sensing releasable moiety (e.g., SEQ ID NO: 19). In a third exemplary construct, a CXCL5 monomeric subunit (e.g., SEQ ID NO: 10) is fused to each of the N-termini of the heavy chain and light chain of an exemplary anti-EGFR antibody via a tumor-sensing releasable moiety (e.g., SEQ ID NO: 19).

Monomeric subunits of heterodimers can also be used to generate activatable antibodies. For example, IL-12 is hetero-dimer where two monomeric subunits comprising amino acid sequences SEQ ID NO: 11 and SEQ ID NO: 12 respectively. In one exemplary construct, a polypeptide having the amino acid sequence of SEQ ID NO: 11 is genetically fused to the N-terminus of VH of an exemplary anti-EGFR antibody via a tumor-sensing releasable moiety (e.g., SEQ ID NO: 19), and a polypeptide having the amino acid sequence of SEQ ID NO: 12 is genetically fused to the N-terminus of VL of the exemplary anti-EGFR antibody via a tumor-sensing releasable moiety (e.g., SEQ ID NO: 19). Although a large number of protein dimers are suitable as steric shields, IL-10, IL-12, CXCL4 and CXCL5 have been chosen as examples as they could deliver therapeutic benefit on their own once released from the activatable antibodies in a diseased tissue.

Exemplary Activatable Antibodies with a Split-Protein as Steric Shield

Exemplary activatable antibodies with a split-protein as the steric shield are prepared. The split-protein is separated into two polypeptides that associate to form a whole split-protein fused to the N-termini of the heavy chain and light chain of an exemplary anti-EGFR antibody via releasable linker disease-sensor moiety. In an exemplary construct Cub (e.g., SEQ ID NO: 6) is genetically fused to the N-terminus of the heavy chain of an exemplary anti-EGFR antibody via a tumor-sensing releasable moiety (e.g., SEQ ID NO: 19), and Nub (e.g., SEQ ID NO: 7) is genetically fused to the N-terminus of the heavy chain of the exemplary anti-EGFR antibody via a tumor-sensing releasable moiety (e.g., SEQ ID NO: 19). Cub and Nub are complementary half fragments of split ubiquitin (Johnsson, N. & Varshavsky, A. 1994. Proc. Natl. Acad. Sci. USA 91, 10340-10344). Upon expression, the two halves (Nub and Cub) associate to form ubiquitin, thereby joining the N-termini of the heavy and light chains of the exemplary anti-EGFR antibody and sterically blocking its antigen binding sites.

In another exemplary construct, SpyCatcher (e.g., SEQ ID NO: 4) is genetically fused to the N-terminus of the heavy chain of an exemplary anti-EGFR antibody via a tumor-sensing releasable moiety (e.g., SEQ ID NO: 19), and SpyTag (e.g., SEQ ID NO: 5) is genetically fused to the N-terminus of the heavy chain of the exemplary anti-EGFR antibody via a tumor-sensing releasable moiety (e.g., SEQ ID NO: 19). Upon expression, the two halves (SpyCatcher and SpyTag) associate to form ubiquitin, thereby joining the N-termini of the heavy and light chains of the exemplary anti-EGFR antibody and sterically blocking its antigen binding sites.

Exemplary Activatable Antibodies with a Coiled-Coil Complex as Steric Shield

Exemplary activatable antibodies with a coiled-coil complex as the steric shield are prepared. The heavy and light chains of the activatable antibodies carry peptides that bind to each other and form parallel or antiparallel coiled-coils. In an exemplary construct, Myo 10 anti-CC peptide (e.g., SEQ ID NO: 13), JIP3 fragment (e.g., SEQ ID NO: 14) or KIF21A (e.g., SEQ ID NO: 15) is genetically fused to each of the N-termini of the heavy chain and light chain of an exemplary anti-EGFR antibody via a tumor-sensing releasable moiety (e.g., SEQ ID NO: 19).

Heterodimer coiled-coils can also be used as steric shields. In an exemplary construct. MST1-RASSF5 SARAH peptide A (e.g., SEQ ID NO: 16) is genetically fused to the N-terminus of the heavy chain of an exemplary anti-EGFR antibody via a tumor-sensing releasable moiety (e.g., SEQ ID NO: 19), and MST1-RASSF5 SARAH peptide B (e.g., SEQ ID NO: 17) is genetically fused to the N-terminus of the light chain of the exemplary anti-EGFR antibody via a tumor-sensing releasable moiety (e.g., SEQ ID NO: 19).

Exemplary Activatable Antibodies with an Fv as Steric Shield

Exemplary activatable antibodies with an Fv fragment as the steric shield are prepared. For example, Fv (also known as "variable fragment") of an exemplary anti-ED-B antibody comprises a VH having an amino acid sequence of SEQ ID NO: 35, and a VL having an amino acid sequence of SEQ ID NO: 36. The L19 Fv is a previously described human recombinant antibody specific for the ED-B domain of fibronectin isoform B-FN, which targets tumor blood vessels (Tarli L et al. 1999. Blood. 94: 192-8). In an exemplary construct, an activatable anti-CTLA4 antibody is designed. The VH of L19 (e.g., SEQ ID NO: 35) is genetically fused to the N-terminus of the heavy chain of an exemplary anti-CTLA-4 antibody via a tumor-sensing releasable moiety (e.g., SEQ ID NO: 19), and the VL of L19 (e.g., SEQ ID NO: 36) is genetically fused to the N-terminus of the light chain of the anti-CTLA-4 antibody via a tumor-sensing releasable moiety (e.g., SEQ ID NO: 19). Fusion of the L19 Fv to the anti-CTLA-4 antibody prevents binding of the activatable anti-CTLA-4 antibody to its antigen CTLA-4 until L19 Fv is released. The N-termini of the heavy chain and light chain of the parent anti-CTLA-4 antibody have been engineered, with a few amino acid residues deleted from the native sequence to shorten the distance between the two N-termini. The shield moiety L19 Fv has two-fold capacities: 1) to block CTLA-4 binding by the activatable anti-CTLA-4 antibody outside tumor, and 2) to concentrate the activated anti-CTLA-4 antibody in tumor by unblocking the CTLA-4 binding site in the activatable anti-CTLA-4 antibody in tumor tissue only.

TABLE 12

Exemplary activatable antibodies comprising split-proteins, protein dimers and peptide coiled coil as steric shields.

| target | Steric shield | Chain (SEQ ID NO) | Sequence |
| --- | --- | --- | --- |
| Human EGFR | IL-10 dimer | Heavy (37) | SPGQGTQSENSCTHFPGNLPNMLRDLRDAFSRVKTFFQMKDQLDNL LLKESLLEDFKGYLGCQALSEMIQFYLEEVMPQAENQDPDIKAHVN SLGENLKTLRLRLRRCHRFLPCENKSKAVEQVKNAFNKLQEKGIYK AMSEFDIFINYIEAYMTMKIRNLSGRSDNHQVQLKQSGPGLVQPSQS LSITCTVSGFSLTNYGVHWVRQSPGKGLEWLGVIWSGGNTDYNTPF TSRLSINKDNSKSQVFFKMNSLQSEDTAIYYCARALTYYDYEFAYW GQGTLVTVSAASTKGPSVFPLAPSSKSTSGGTAALGCLVKDYFPEPV TVSWNSGALTSGVHTFPAVLQSSGLYSLSSVVTVPSSSLGTQTYICN |

TABLE 12-continued

Exemplary activatable antibodies comprising split-proteins, protein dimers and peptide coiled coil as steric shields.

| target | Steric shield | Chain (SEQ ID NO) | Sequence |
|---|---|---|---|
| | | | VNHKPSNTKVDKKVEPKSCDKTHTCPPCPAPELLGGPSVFLFPPKPK<br>DTLMISRTPEVTCVVVDVSHEDPEVKFNWYVDGVEVHNAKTKPRE<br>EQYNSTYRVVSVLTVLHQDWLNGKEYKCKVSNKALPAPIEKTISKA<br>KGQPREPQVYTLPPSRDELTKNQVSLTCLVKGFYPSDIAVEWESNG<br>QPENNYKTTPPVLDSDGSFFLYSKLTVDKSRWQQGNVFSCSVMHE<br>ALHNHYTQKSLSLSPG |
| | | Light (38) | SPGQGTQSENSCTHFPGNLPNMLRDLRDAFSRVKTFFQMKDQLDNL<br>LLKESLLEDFKGYLGCQALSEMIQFYLEEVMPQAENQDPDIKAHVN<br>SLGENLKTLRLRLRRCHRFLPCENKSKAVEQVKNAFNKLQEKGIYK<br>AMSEFDIFINYIEAYMTMKIRNLSGRSDNHDILLTQSPVILSVSPGER<br>VSFSCRASQSIGTNIHWYQQRTNGSPRLLIKYASESISGIPSRFSGSGS<br>GTDFTLSINSVESEDIADYYCQQNNNWPTTFGAGTKLELKRTVAAP<br>SVFIFPPSDEQLKSGTASVVCLLNNFYPREAKVQWKVDNALQSGNS<br>QESVTEQDSKDSTYSLSSTLTLSKADYEKHKVYACEVTHQGLSSPV<br>TKSFNRGEC |
| | Split ubiquitin (Nub/Cub) | Heavy (39) | MQIFVKTLTGKTITLEVEPSDTIENVKAKIQDKELSGRSDNHQVQLK<br>QSGPGLVQPSQSLSITCTVSGFSLTNYGVHWVRQSTGKGLEWLGVI<br>WSGGNTDYNTPFTSRLSINKDNSKSQVFFKMNSLQSEDTAIYYCAR<br>ALTYYDYEFAYWGQGTLVTVSAASTKGPSVFPLAPSSKSTSGGTAA<br>LGCLVKDYFPEPVTVSWNSGALTSGVHTFPAVLQSSGLYSLSSVVT<br>VPSSSLGTQTYICNVNHKPSNTKVDKKVEPKSCDKTHTCPPCPAPEL<br>LGGPSVFLFPPKPKDTLMISRTPEVTCVVVDVSHEDPEVKFNWYVD<br>GVEVHNAKTKPREEQYNSTYRVVSVLTVLHQDWLNGKEYKCKVS<br>NKALPAPIEKTISKAKGQPREPQVYTLPPSRDELTKNQVSLTCLVKG<br>FYPSDIAVEWESNGQPENNYKTTPPVLDSDGSFFLYSKLTVDKSRW<br>QQGNVFSCSVMHEALHNHYTQKSLSLSPG |
| | | Light (40) LLIKYA | GIPPDQQRLIFAGKQLEDGRTLSDYNIQKESTLHLVLRLRGGLSGRS<br>DNHDILLTQSPVILSVSPGERVSFSCRASQSIGTNIHWYQQRTNGSPR<br>LLIKYASESISGIPSRFSGSGSGTDFTLSINSVESEDIADYYCQQNNNW<br>PTTFGAGTKLELKRTVAAPSVFIFPPSDEQLKSGTASVVCLLNNFYP<br>REAKVQWKVDNALQSGNSQESVTEQDSKDSTYSLSSTLTLSKADYE<br>KHKVYACEVTHQGLSSPVTKSFNRGEC |
| | CXCL4 dimer | Heavy (41) | EAEEDGDLQCLCVKTTSQVRPRHITSLEVIKAGPHCPTAQLIATLKN<br>GRKICLDLQAPLYKKIIKKLLESLSGRSDNHQVQLKQSGPGLVQPSQ<br>SLSITCTVSGFSLTNYGVHWVRQSPGKGLEWLGVIWSGGNTDYNTP<br>FTSRLSINKDNSKSQVFFKMNSLQSEDTAIYYCARALTYYDYEFAY<br>WGQGTLVTVSAASTKGPSVFPLAPSSKSTSGGTAALGCLVKDYFPE<br>PVTVSWNSGALTSGVHTFPAVLQSSGLYSLSSVVTVPSSSLGTQTYI<br>CNVNHKPSNTKVDKKVEPKSCDKTHTCPPCPAPELLGGPSVFLFPPK<br>PKDTLMISRTPEVTCVVVDVSHEDPEVKFNWYVDGVEVHNAKTKP<br>REEQYNSTYRVVSVLTVLHQDWLNGKEYKCKVSNKALPAPIEKTIS<br>KAKGQPREPQVYTLPPSRDELTKNQVSLTCLVKGFYPSDIAVEWES<br>NGQPENNYKTTPPVLDSDGSFFLYSKLTVDKSRWQQGNVFSCSVM<br>HEALHNHYTQKSLSLSPG |
| | | Light (42) | EAEEDGDLQCLCVKTTSQVRPRHITSLEVIKAGPHCPTAQLIATLKN<br>GRKICLDLQAPLYKKIIKKLLESLSGRSDNHDILLTQAPVILSVSPGER<br>VSFSCRASQSIGTNIHWYQQRTNGSPRLLIKYASESISGIPSRFSGSGS<br>GTDFTLSINSVESEDIADYYCQQNNNWPTTFGAGTKLELKRTVAAP<br>SVFIFPPSDEQLKSGTASVVCLLNNFYPREAKVQWKVDNALQSGNS<br>QESVTEQDSKDSTYSLSSTLTLSKADYEKHKVYACEVTHQGLSSPV<br>TKSFNRGEC |
| | Myo10 anti-parallel coiled coil | Heavy (43) | ENKQVEEILRLEKEIEDLQRMKEQQELSLTLSGRSDNHQVQLKQSGP<br>GLVQPSQSLSITCTVSGFSLTNYGVHWVRQSPGKGLEWLGVIWSGG<br>NTDYNTPFTSRLSINKDNSKSQVFFKMNSLQSEDTATYYCARALTYY<br>DYEFAYWGQGTLVTVSAASTKGPSVFPLAPSSKSTSGGTAALGCLV<br>KDYFPEPVTVSWNSGALTSGVHTFPAVLQSSGLYSLSSVVTVPSSSL<br>GTQTYICNVNHKPSNTKVDKKVEPKSCDKTHTCPPCPAPELLGGPS<br>VTLFPPKPKDTLMISRTPEVTCVVVDVSHEDPEVKFNWYVDGVEVH<br>NAKTKPREEQYNSTYRVVSVLTVLHQDWLNGKEYKCKVSNKALP<br>APIEKTISKAKGQPREPQVYTLPPSRDELTKNQVSLTCLVKGFYPSDI<br>AVEWESNGQPENNYKTTPPVLDSDGSFFLYSKLTVDKSRWQQGNV<br>FSCSVMHEALHNHYTQKSLSLSPG |
| | | Light (44) | ENKQVEEILRLEKEIEDLQRMKEQQELSLTLSGRSDNHDILLTQSPVI<br>LSVSPGERVSFSCRASQSIGTNIHWYQQRTNGSPRLLIKYASESISGIP<br>SRFSGSGSGTDFTLSINSVESEDIADYYCQQNNNWPTTFGAGTKLEL<br>KRTVAAPSVFIFPPSDEQLKSGTASVVCLLNNFYPREAKVQWKVDN<br>ALQSGNSQESVTEQDSKDSTYSLSSTLTLSKADYEKHKVYACEVTH<br>QGLSSPVTKSFNRGEC |

TABLE 12-continued

Exemplary activatable antibodies comprising split-proteins, protein dimers and peptide coiled coil as steric shields.

| target | Steric shield | Chain (SEQ ID NO) | Sequence |
|---|---|---|---|
| Human CTLA-4 | L19Fv | Heavy (45) | EVQLLLESGGGLVQPGGSLRLSCAASGFTFSSFSMSWVRQAPGKGLE WVSSISGSSGTTYYADSVKGRFTISRDNSKNTLYLQMNSLRAEDTA VYYCAKPFPYFDYWGQGTVTVLSGRSDNHVQLVESGGGVVQPGR SLRLSCAASGFTFSSYGMHWVRQAPGKGLEWVAVIWYDGSNKYY ADSVKGRFTISRDNSKNTLYLQMNSLRAEDTAVYYCARDPRGATL YYYYYGMDVWGQGTTVTVSSASTKGPSVFPLAPCSRSTSESTAALG CLVKDYFPEPVTVSWNSGALTSGVHTFPAVLQSSGLYSLSSVVTVPS SNFGTQTYTCNVDHKPSNTKVDKTVERKCCVECPPCPAPPVAGPSV FLFPPKPKDTLMISRTPEVTCVVVDVSHEDPEVQFNWYVDGVEVHN AKTKPREEQFNSTFRVVSVLTVVHQDWLNGKEYKCKVSNKGLPAPI EKTISKTKGQPREPQVYTLPPSREEMTKNQVSLTCLVKGFYPSDIAV EWESNGQPENNYKTTPPMLDSDGSFFLYSKLTVDKSRWQQGNVFS CSVMHEALHNHYTQKSLSLSPGK |
| | | Light (46) | EIVLTQSPGTLSLSPGERATLSCRASQSVSSSYLAWYQQKPGQAPRL LIYYASSRATGIPDRFSGSGSGTDFTLTISRLEPEDFAVYYCQQTGRIP PTFGQGTKVEILSGRSDNHIQMTQSPSSLSASVGDRVTITCRASQSIN SYLDWYQQKPGKAPKLLIYAASSLQSGVPSRFSGSGSGTDFTLTISSL QPEDFATYYCQQYYSTPFTFGPGTKVEIKRTVAAPSVFIFPPSDEQLK SGTASVVCLLNNFYPREAKVQWKVDNALQSGNSQESVTEQDSKDS TYSLSSTLTLSKADYEKHKVYACEVTHQGLSSPVTKSFNRGEC |

D. Exemplary Activatable Anti-EGFR Ab Constructs with a pH-Sensing or Protease-Sensing Steric Shield Comprising a Glycan-Binding Protein-Glycan Complex.

Some proteins undergo conformational changes as pH shifts from neutral towards acidic. For example, histidines within proteins can act as pH sensor and thus mediate pH-controlled structural changes. Tumor tissues are known to have lower extracellular pH than normal tissues, thus shield moiety wherein peptide shield moieties S1 and S2 are associated at normal tissue pH (e.g. ~pH 7.4), and dissociated at tumor tissue pH (e.g, ~pH 6.5 or lower) is designed.

M-ficolin is a human lectin that binds to N-acetylglucosamine (GlcNAc), where binding of M-ficolin to N-acetylglucosamine (GlcNAc) is subject to a pH-sensitive conformational switch. M-ficolin binds GlcNAc at normal physiological pH, but affinity starts to decrease at ~pH 6.5 (Garlatti V. et al. 2008. J. Biol. Chem. 282: 35814-35820, Tanio M et al. J. Synchrotron Rad. 2008, 15, 243-245. Gout E. et al. 2010. J. Biol. Chem. 285: 6612-6622). Therefore, pH activatable anti-EGFR antibodies are designed. An engineered M-ficolin monomer (e.g., SEQ ID NO: 20) is directly fused to the N-terminus of the heavy chain of an exemplary anti-EGFR antibody, and an N-glycosylation sequence tag is directly fused to the N-terminus of the light chain of the anti-EGFR antibody, as shown in Table 13. The N-glycosylation tag is glycosylated during expression of the fusion antibody in mammalian cell lines, and the glycans added to the glycosylation tag binds to M-ficolin at normal tissue pH thus providing a steric shield in the activatable anti-EGFR antibody. At lower than normal pH (e.g., in a tumor tissue), M-ficolin changes its conformation and releases the glycan, thereby releasing the steric shield and allowing the antigen binding site to bind its antigen, EGFR. In another exemplary construct, the engineered M-ficolin monomer (e.g., SEQ ID NO: 20) is genetically fused to the N-terminus of the heavy chain of the anti-EGFR antibody via a tumor-specific protease substrate (e.g., SEQ ID NO: 19), and the N-glycosylation sequence tag is genetically fused to the N-terminus of the heavy chain of anti-the EGFR antibody via a tumor-specific protease substrate (e.g., SEQ ID NO: 19). Cleavage of the tumor-specific protease substrate (i.e., disease-sensing releasable moieties) release the M-ficolin-glycan complex, thereby unblocking the antigen binding site for EGFR.

TABLE 13

Exemplary activatable anti-EGFR antibody constructs comprising a glycan binding protein-glycan steric shield and a pH-sensing releasable moiety or protease-cleavable disease-sensing releasable moiety.

| DS | Chain (SEQ ID NO) | Sequence |
|---|---|---|
| pH-sensing releasable moiety | Heavy (47) | QSCATGPRNCKDLLDRGYFRSGWHTIYLPDCRPLTVLCDMDTDGGGWTV FQRRMDGS TABLE 13-continued Exemplary activatable anti-EGFR antibody constructs comprising a glycan binding protein-glycan steric shield and a pH-sensing releasable moiety or protease-cleavable disease-sensing releasable moiety.

| DS | Chain (SEQ ID NO) | Sequence |
|---|---|---|
|  | Light (48) | SNYSMVNTTNMTSDILLTQSPVILSVSPGERVSFSCRASQSIGTNIHWYQQRTN GSPRLLIKYASESISGIPSRFSGSGSGTDFTLSINSVESEDIADYYCQQNNNWPTT FGAGTKLELKRTVAAPSVFIFPPSDEQLKSGTASVVCLLNNFYPREAKVQWKV DNALQSGNSQESVTEQDSKDSTYSLSSTLTLSKADYEKHKVYACEVTHQGLSS PVTKSFNRGEC |
| Disease-specific protease substrate | Heavy (49) | QSCATGPRNCKDLLDRGYFRSGWHTIYLPDCRPLTVLCDMDTDGGGWTV FQRRMDGSVDFYRDWAAYKQGFGSQLGEFWLGNDNIHALTAQGSSELRT DLVDFEGNHQFAKYKSFKVADEAEKYKLVLGAFVGGSAGNSLTGHNNNF FSTKDQDNDVSSSNCAEKFQGAWWYADCHASNLNGLYLNGPHESYANGI NWSAAKGYKYSYKVSEMKVRPALSGRSDNHQVQLKQSGPGLVQPSQSLSIT CTVSGFSLTNYGVHWVRQSPGKGLEWLGVIWSGGNTDYNTPFTSRLSINKDNS KSQVFFKNNSLQSEDTAIYYCARALTYYDYEFAYWGQGTLVTVSAASTKGPS VFPLAPSSKSTSGGTAALGCLVKDYFPEPVTVSWNSGALTSGVHTFPAVLQSS GLYSLSSVVTVPSSSLGTQTYICNVNHKPSNTKVDKKVEPKSCDKTHTCPPCPA PELLGGPSVFLFPPKPKDTLMISRTPEVTCVVVDVSHEDPEVKFNWYVDGVEV HNAKTKPREEQYNSTYRVVSVLTVLHQDWLNGKEYKCKVSNKALPAPIEKTIS KAKGQPREPQVYTLPPSRDELTKNQVSLTCLVKGFYPSDIAVEWESNGQPENN YKTTPPVLDSDGSFFLYSKLTVDKSRWQQGNVFSCSVMHEALHNHYTQKSLS LSPG |
|  | Light (50) | SNYSMVNTTNMTSLSGRSDNHDILLTQSPVILSVSPGERVSFSCRASQSIGTNIH WYQQRTNGSPRLLIKYASESISGIPSRFSGSGSGTDFTLSINSVESEDIADYYCQQ NNNWPTTFGAGTKLELKRTVAAPSVFIFPPSDEQLKSGTASVVCLLNNFYPREA KVQWKVDNALQSGNSQESVTEQDSKDSTYSLSSTLTLSKADYEKHKVYACEV THQGLSSPVTKSFNRGEC |

Example 3. Structural Models of Polypeptide Steric Shields on Four Different Antibodies Structural examination of antibodies showed that the N-termini of the heavy chain and light chain are positioned such that if conn

Example 4. Steric Shield Generation by Transglutaminase-Catalyzed Conjugation of Polypeptide Shield Moieties Steric shields were formed on two exemplary activatable anti-EGFR antibodies (referred herein as "activatable EGFR Ab"), constructs 1 and 2 of Table 10, by treating the corresponding fusion antibodies with transglutaminase under different reaction conditions.

Figure 4:
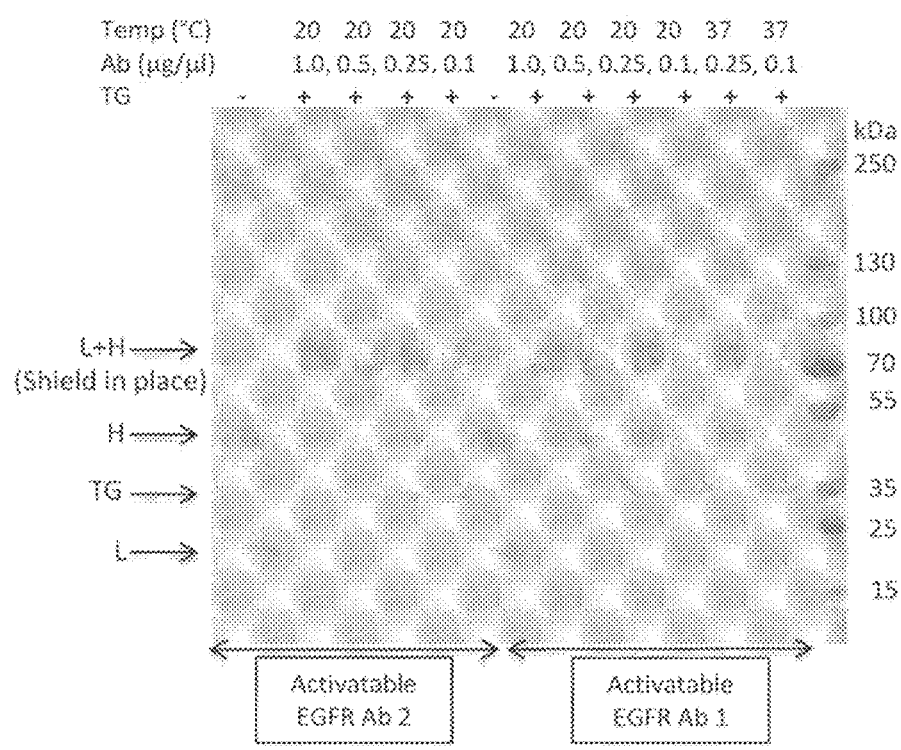
FIG. 4 shows an SDS-PAGE gel demonstrating transglutaminase-mediated steric shield formation in two exemplary activatable antibodies (activatable EGFR Ab 1 and 2) under different reaction conditions.
Figure 5:
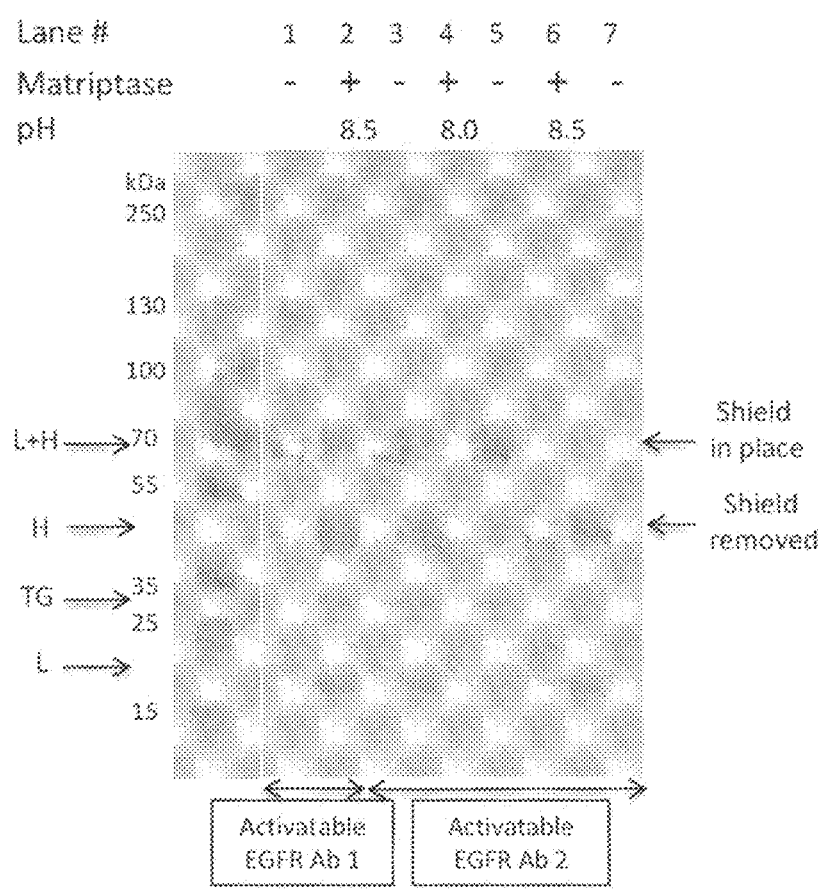
FIG. 5 shows an SDS-PAGE gel demonstrating removal of steric shields via cleavage of the disease-sensing releasable moieties by the protease matriptase from two exemplary antibodies (activatable EGFR Ab 1 and 2) under different reaction conditions.

The following reaction parameters were used: transglutaminase concentration range (0.25, 0.5, 0.75, 1.0, 2.0% wt/v), fusion antibody concentration range (0.1, 0.25, 0.5 and 1.0 mg/ml), NaCl concentration (20, 150 and 300 mM), pH (7.4, 8.0, 8.5) and temperature of reaction (20, 37° C.) for 12 hr. Efficiency of transglutaminase-catalyzed steric shield formation was analyzed using 4-12% Tris-Glycine SDS-PAGE gels. FIG. 4 shows results for a subset of tested conditions. The 4-12% SDS-PAGE gel was ran in the presence of reducing agent (TCEP) so that heavy chain (marked by letter H) and light chain (marked by letter L) in conventional antibodies ran as separate bands, around ~50 and 25 kDa respectively. However, activatable antibodies having conjugated steric shield yielded a band corresponding to conjugated heavy chain and light chain species at about ~75 kDa. On top of the gel image, absence or presence of transglutaminase (TG) in the reaction is marked by minus (–) or plus (+) sign, and fusion antibody concentrations (Ab μg/μl) and reaction temperature for each reaction are indicated.

Notably, in the presence of transglutaminase, the heavy chain and light chain in the activatable antibody were conjugated, and thus ran as the 75 kDa specie (marked as H+L). Thus, this data clearly demonstrates that the polypeptide shield moieties fused to the N-termini of the heavy chain and light chain of the anti-EGFR antibody were conjugated by the transglutaminase, thereby providing a complete steric shield.

Example 5. In Vitro Removal of Transglutaminase-Conjugated Steric Shield by Protease Cleavage of Tumor-Sensing Releasable Moieties In order to determine whether the activatable EGFR Ab 1 and 2 could be activated specifically in tumor tissues, in vitro experiments were performed using proteases uPA and matriptase, which are commonly known to be up-regulated in cancers.

In order to optimize cleavage conditions, activatable EGFR Ab 1 and 2, were each incubated with matriptase or uPA at a protease:antibody concentration ratio of 1:10, 1:100, or 1:1000 (mole:mole) in 50 mM Tris pH 8.5, 0.01% Tween-20 buffer for 18 hrs at 37° C., or at a protease: antibody concentration ratio of 1:100 in 100 mM Tris-HCl pH 8.0, 150 mM NaCl or 100 mM Tris-HCl pH 8.5, 150 mM NaCl buffers. The cleavage reaction was stopped by adding SDS-PAGE sample buffer and heating sample at 95° C. for 5 minutes. Effects of matriptase or uPA-specific digestion were evaluated by running samples on reducing 4-12% Tris-Glycine SDS-PAGE gels (Thermo Fisher) in the presence of the reducing agent TCEP, so that heavy (marked by letter H) and light (marked by letter L) chains ran as separate bands, ~50 and ~25 kDa respectively, unless conjugated (marked as H+L, ~75 kDa specie).

Results are shown in FIG. 5. For samples in lanes 1-6, steric shields were first formed by incubation with a transglutaminase (TG) in separate reactions, followed by removal of the steric shields by cleavage of the tumor-sensing releasable moiety (SEQ ID NO: 19) by matriptase at pH 8.5 or pH 8.0. The minus (−) or plus (+) signs on top of the gel image indicate absence or presence of matriptase in each reaction. Lane 7 shows a control sample in which the antibody was not subjected to transglutaminase treatment, and thus a steric shield was never formed prior to matriptase treatment. As a result, in lane 7, the heavy (H) and light (L) chains ran as separate bands. Notably, in the presence of matriptase, the fraction of conjugated heavy and light chains (H+L; ~75 kDa band) decreased, while the fraction of heavy (H) and light (L) chains that ran as separate bands (~50 kDa and ~25 kDa respectively) increased as the relative concentration of matriptase in the reaction increased. Thus, this data demonstrates that the transglutaminase-conjugated steric shield can be removed via cleavage of the disease-sensing releasable moieties by a disease-specific protease.

Example 6. Steric Shield Generation by Cys-Cys Disulfide Bridge Formation Between Polypeptide Shield Moieties During Expression in Mammalian Cells Eukaryotic protein expression systems support disulfide bond formation in eukaryotic proteins. In particular, mammalian expression systems using HEK293 and CHO cell lines have been extensively used in the art for expression of antibodies with their native disulfide bonds in place. Two exemplary activatable EGFR Abs (constructs 3 and 4 of Table 10) have been designed. The cysteines in B and C were designed to be in the vicinity of each another so that they could form a disulfide bridge during expression in mammalian cells.

The fusion antibody constructs were expressed in Expi293F cells. After protein purification, non-reducing SDS-PAGE gels were used to analyze disulfide bridge mediated steric shield formation during antibody expression in Expi293F cells. FIG. 6 shows 4-12% Tris-Glycine SDS-PAGE gel (ThermoFisher) image ran in the absence of reducing agent, thus Cys-Cys disulfide bridges (shown as black lines in the antibody cartoons) remained intact. Antibody constructs with heavy and light chains SEQ ID NO: 25 and 26, and SEQ ID NO: 27 and 28 are designed to carry Cys/Ser mutation in their heavy (H) and light (L) chains such that native heavy-light (HL) Cys-Cys disulfide bridge could not form, while native heavy-heavy chain (HH) disulfide bridges still formed. Thus, it was expected to observe the following species on non-reducing SDS-PAGE gel: 25 kDa light chain species (in FIG. 6 labeled L and shown as cartoon), ~100 kDa heavy-heavy chain species (in FIG. 6 labeled HH and shown as cartoon) if the steric shield did not form, ~125 kDa species if the Cys-Cys steric shield formed on one of the two antigen-binding-sites (in FIG. 6, labeled HHL and shown as cartoon) and ~150 kDa species if the Cys-Cys steric shield formed on both antigen binding sites (in FIG. 6, labeled HLHL and shown as cartoon).

SDS-PAGE gel showed the presence of four species: ~150 kDa HLHL species (2 steric shields formed); ~125 kDa HLH species (1 steric shield formed); ~100 kDa HH species (no steric shield formed); and ~25 kDa light chain species. Data shown in FIG. 6 demonstrated that Cys-Cys conjugated steric shields formed on both antigen-binding sites or on one of the two antigen binding sites during expression in mammalian cells.

Example 7. Steric Shield Generation by Cys-Cys Disulfide Bridge Formation Between Polypeptide Shield Moieties by Reduction/Oxidation During protein expression, cysteines introduced to the N-termini of antibodies can complex with free cysteine or glutathione amino acids present in the expression media (Junutula J R et al. 2008. Nature Biotech. 26, 925-932), thus blocking said cysteines from forming a disulfide bond with the desired partner(s). Such cysteines can be unconjugated from cysteine or glutathione amino acids by reduction using TCEP followed by oxidation using ascorbic acid (Junutula J R et al. 2008. Nature Biotech. 26, 925-932).

Here, the fusion antibodies (activatable EGFR Ab 3 and 4) expressed in mammalian cells was incubated with TCEP (ThermoFisher) at a range of concentration ratios between the fusion antibody and TCEP including 1:1, 1:3, 1:5, 1:10 or 1:20 (mole:mole) for 30 or 60 min at 20° C. or 4° C. TCEP was removed by dialysis for 3 hr at room temperature in 1×PBS buffer, using SLIDE-A-LYZER™ MINI Dialysis Device (ThermoFisher). The N-terminal Cys-Cys disulfide bond between the polypeptide shield moieties was formed by addition of dihydroascorbic acid (dhAA) (Sigma-Aldrich) to the dialyzed antibodies at TCEP:dhAA ratios (mole:mole) of 1:3 or 1:5 at 20° C. or 4° C. In addition to TCEP/dhAA, other reduction/oxidation reagents can be used, e.g., reduced/oxidized glutathione.

Figure 7:
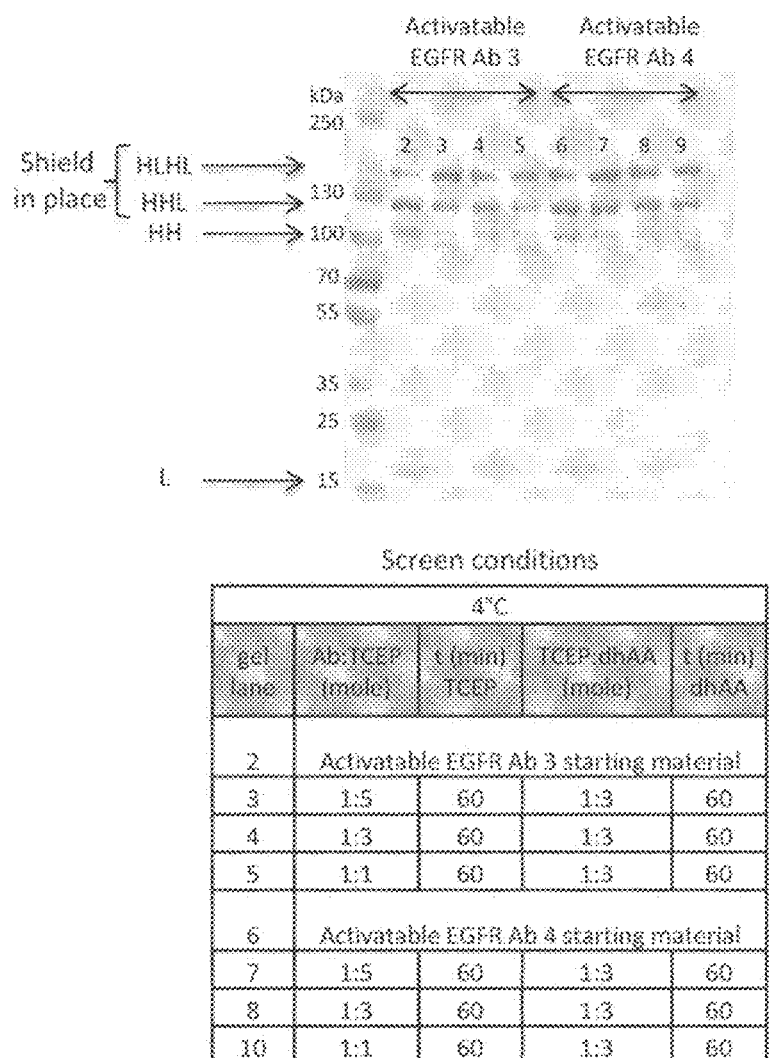
FIG. 7 shows an SDS-PAGE gel demonstrating steric shield formation via a Cys-Cys disulfide bridge by reduction an oxidation of Cys under different conditions, in two exemplary activatable antibodies (activatable EGFR Ab 3 and 4).

Formation of the Cys-Cys disulfide bond in the steric shield after TCEP/dHAA incubation was assessed using non-reducing 4-12% SDS-PAGE gels. Results from a subset of reaction conditions are shown in FIG. 7. As discussed in Example 6, four distinct species may be observed on the SDS-PAGE gel: ~25 kDa light chain (in FIG. 7 labeled L): ~100 kDa heavy-heavy chain species (in FIG. 7 labeled HH), when the steric shield did not form; ~125 kDa species if the steric shield formed on one of the two antigen-binding sites (in FIG. 7, labeled HHL), and 150 kDa species if the steric shield formed on both antigen binding sites (in FIG. 7, labeled HLHL).

Samples in lanes 3-5 and 7-9 were first reduced by incubation with TCEP under conditions listed in the accompanying table in FIG. 7, then TCEP was dialyzed and ascorbic acid (dhAA) added under conditions indicated in the accompanying table in FIG. 7. Comparison of lanes 2 (starting material) and lanes 3-5 for activatable EGFR Ab construct 3 and lanes 6 (starting material) and lanes 7-10 for EGFR Ab construct 4 showed that reduction followed by oxidation with TCEP-dhAA changed the ratio among 3 species: HH (no steric shield), HHL (one steric shield) and HLHL (two steric shields). Fractions of the HH species (no steric shield formed) decreased, while fractions of the HLHL (two steric shields formed) were enriched as the Antibody:TCEP ratio in the reduction step decreased. This data demonstrates that the Cys-Cys disulfide-conjugated steric shield can be re-formed in vitro after expression.

Example 8. In Vitro Removal of Cys-Cys Disulfide-Conjugated Steric Shield by Cleavage of Tumor-Sensing Releasable Moieties In order to determine whether the activatable EGFR Ab 3 and 4 could be activated specifically in tumor tissues, in vitro experiments were performed using proteases uPA and matriptase, which are commonly known to be up-regulated in cancers.

Figure 8:
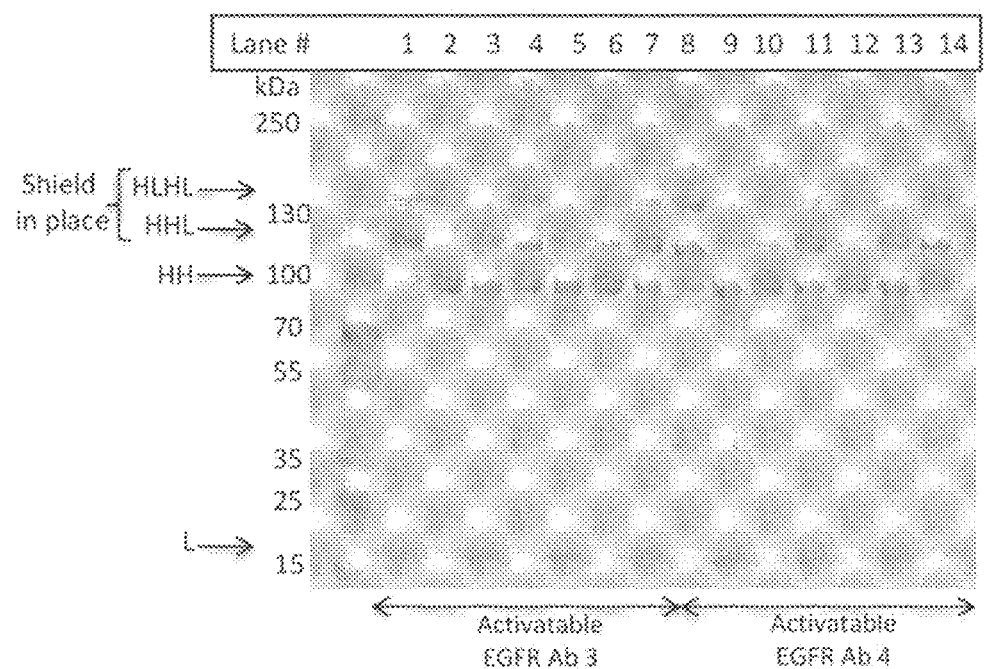
FIG. 8 shows an SDS-PAGE gel demonstrating removal of the steric shields via cleavage of the disease-sensing releasable moieties by the protease matriptase or uPA from two exemplary antibodies (activatable EGFR Ab 3 and 4) under different reaction conditions.

In order to optimize cleavage conditions, activatable EGFR Ab 3 and 4 were incubated with matriptase or uPA at a range of protease:antibody ratios (1:10, 1:100, 1:1000 (mole:mole)) in 50 mM Tris pH 8.5, 0.01% Tween-20 buffer for 18 hrs at 37° C. The cleavage reaction by matriptase or uPA was stopped by adding SDS-PAGE sample buffer, and the samples were subsequently heated at 95° C. for 5 minutes. Effects of matriptase or uPA specific digestion was evaluated by running the samples on non-reducing 4-12% Tris-Glycine SDS-PAGE gels (Thermo Fisher) so that any disulfide-bridges would remain intact. Results are shown in FIG. 8.

Figure 6:
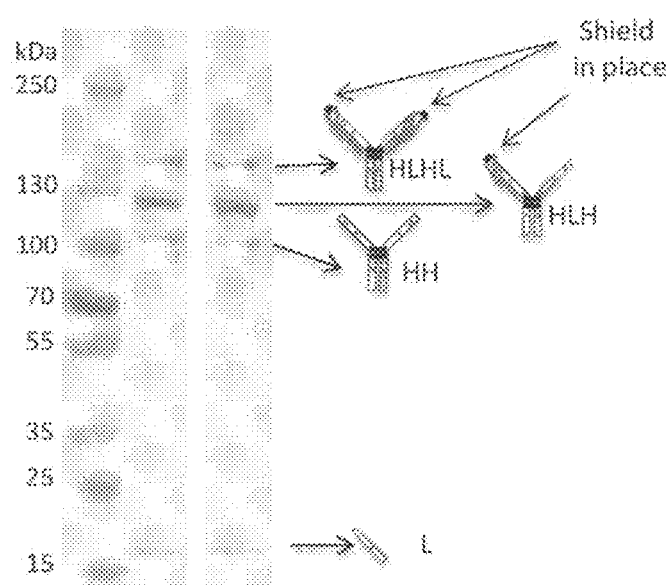
FIG. 6 shows an SDS-PAGE gel demonstrating steric shield formation via a Cys-Cys disulfide bridge during antibody expression in mammalian cells in two exemplary activatable antibodies (activatable EGFR Ab 3 and 4).

Non-reducing SDS-PAGE gel analysis of the starting material (FIG. 6 and FIG. 8 lanes 1 and 8) before treatment with matriptase or uPA showed the ~150 kDa HLHL species and ~125 kDa HHL species, which correspond to activatable antibodies having both or one antigen binding site covered by the Cys-Cys disulfide-conjugated steric shield, respectively. After incubation with matriptase (lanes 2-4 and lanes 9-12) or uPA (lanes 5-7 and lanes 12-14), the ~125 kDa HHL species (one steric shield) and the 150 kDa HLHL species (two steric shields) decreased with increasing protease concentration. This data clearly demonstrates that the activatable EGFR Ab 3 and 4 can be cleaved by matriptase or uPA to release the Cys-Cys conjugated steric shield in vitro. By comparing the amount of the uncleaved activatable antibody (HHL and HLHL species) to that of completely cleaved species (HH), it appears that matriptase was more efficient than uPA to cleave the activatable antibodies, i.e., resulting in more complete cleavage.

Example 9. Antigen Binding to Activatable Antibodies in the Presence and Absence of Steric Shields Binding of human EGFR to activatable EGFR Ab 1, 2, 3, and 4 that either did or did not have steric shields in place (i.e., conjugation between S1 and S2 were formed or not formed), and protease-treated activatable antibodies were analyzed on a PROTEON™ XPR36 Surface Plasmon Resonance (SPR) Instrument (BioRad) using phosphate buffered saline (pH 7.4) supplemented with 0.01% Tween-20 as running buffer.

Figure 11A:
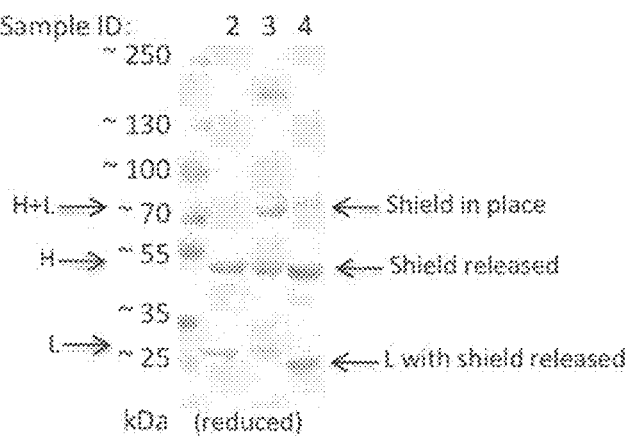
FIG. 11A shows an SDS-PAGE gel demonstrating transglutaminase-mediated steric shield formation on activatable EGFR Ab 1, and demonstrating shield release by cleavage of disease-sensing releasable moieties by protease matriptase. Activatable EGFR Ab 1 samples shown here were used for SPR studies shown in FIG. 11B.

For transglutaminase-catalyzed shield formation, 1.0 and 0.5 mg/ml of fusion antibody comprising SEQ ID NOs: 21 and 22 (activatable EGFR Ab 1) or fusion antibody comprising SEQ ID NOs: 23 and 24 (activatable EGFR Ab 2) was incubated with 0.75% wt/v transglutaminase enzyme in 100 mM Tris-HCl pH 8.5, 150 mM NaCl buffer for 12 hrs at 18° C. Afterwards, transglutaminase was removed from activatable EGFR Ab 1 or EGFR Ab 2 by protein A affinity chromatography. Representative results of shield formation of activatable EGFR Ab 1 is shown on a reduced SDS-PAGE gel in FIG. 11A (lane labeled sample ID 3). Reducing SDS-PAGE gel analysis of the starting (lane labeled sample ID 2) and transglutaminase cross-linked material (lane labeled sample ID 3) clearly demonstrates formation of 70 kDa HL species with conjugated heavy and light chains as discussed in Example 4.

For Cys-Cys disulfide bridge mediated shield formation, the Cys-Cys disulfide bridge on activatable EGFR Ab 3 and 4 was reformed post-expression as described in Example 7, and purified using chromatography. For the shown SPR data incubation conditions with TCEP/dhAA, Ab:TCEP ratios were 1:10 and 1:20 for 30 min at 20° C., and 1:5 for 60 min at 4° C., followed by TCEP:dhAA of 1:3 for 60 or 180 min.

After steric shield formation, for in vitro shield removal (FIGS. 11A-11B), activatable EGFR Ab 1 with shield moiety in place was incubated with matriptase protease at protease:antibody ratio of 1:50 (mole:mole) in 50 mM Tris pH 8.5, 0.01% Tween-20 buffer for 18 hrs at 37° C. Representative result of shield removal of activatable EGFR Ab 1 is shown on a reduced SDS-PAGE gel in FIG. 11A (lane labeled sample ID 4). Reducing SDS-PAGE el analysis of the starting and matriptase treated material (lane labeled sample ID 3 and lane labeled sample ID 4) clearly demonstrates that activatable EGFR Ab 1 cleaved by matriptase releases the transglutaminase conjugated steric shield in vitro, as discussed in Example 5.

Figure 12A:
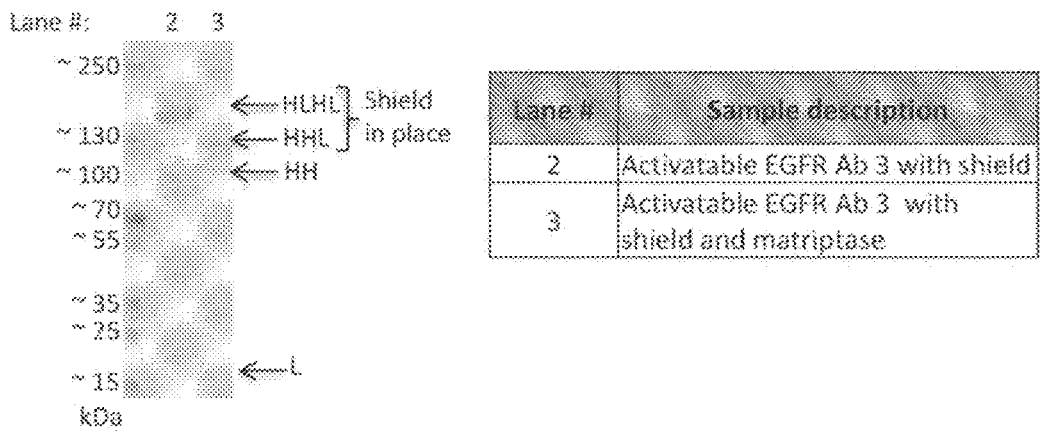
FIG. 12A shows an SDS-PAGE gel demonstrating steric shield formation via a Cys-Cys disulfide bridge by reduction and oxidation of Cys under different conditions in exemplary activatable EGFR Ab 3, and demonstrating shield release by cleavage of disease-sensing releasable moieties by protease matriptase. Activatable EGFR Ab 3 samples shown here were used for SPR studies shown in FIG. 12B.

In another experiment (FIGS. 12A-12C), activatable EGFR Ab 3 with shield moiety in place was incubated with matriptase protease at protease:antibody ratio of 1:50 (mole:mole) in PBS pH 7.4 for 18 hr at 37° C. FIG. 12A shows a non-reducing 4-12% Tris-Glycine SDS-PAGE gel demonstrating Cys-Cys disulfide bridge formation (lane labeled as sample ID: 2), and results of subsequent shield removal mediated by matriptase cleavage of the tumor-sensing moieties (SEQ ID NO: 19). Non-reducing SDS-PAGE gel analysis of the starting material (FIG. 12A lane labeled SAMPLE ID 2 before treatment with matriptase) shows that the majority of sample were the ~150 kDa HLHL species and ~125 kDa HHL species, which correspond to activatable antibodies having both or one antigen binding site covered by the Cys-Cys disulfide-conjugated steric shield, respectively. After incubation with matriptase (FIG. 12A lane labeled SAMPLE ID 3) the ~125 kDa HHL species (one steric shield) and the ~150 kDa HLHL species (two steric shields) decreased, while the ~100 kDa HH species (no steric shield) increased. This data clearly demonstrates that the activatable EGFR Ab 3 cleaved by matriptase releases the Cys-Cys conjugated steric shield in vitro, as discussed in Example 8.

Figure 9A:
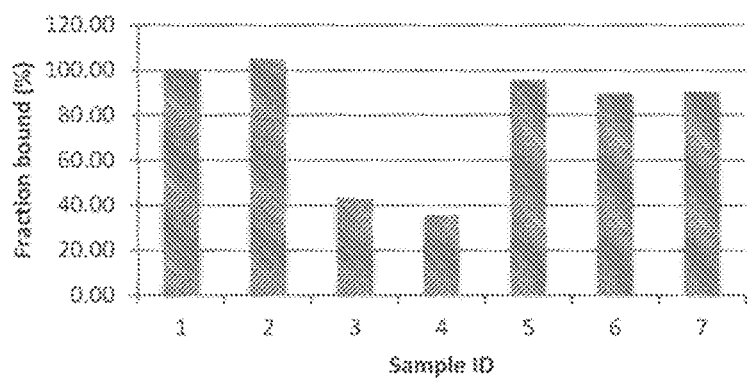
FIG. 9A shows a bar graph of surface plasmon resonance (SPR) data illustrating EGFR binding to an exemplary activatable anti-EGFR antibody (activatable EGFR Ab 2). The data demonstrated that the steric shields formed via transglutaminase catalysis in the activatable antibody substantially reduced its EGFR binding activity, and removal of the steric shields from the activatable antibody restored its EGFR binding activity.

In the experiments shown in FIGS. 9A-9B, activatable EGFR Ab 2-4 with shield moiety in place were incubated with either matriptase or uPA protease at protease:antibody ratio of 1:15 (mole:mole) in 50 mM Tris pH 8.5, 0.01% Tween-20 buffer for 18 hrs at 37° C.

Activatable EGFR Ab constructs and the native anti-EGFR antibody were attached to chips via Protein G, and binding to their antigen, EGFR, was measured. The amount of EGFR-binding by the activatable EGFR Abs was normalized to EGFR binding by the parent anti-EGFR antibody, and shown as bar graphs. EGFR-binding efficiency was evaluated before steric shield formation (activatable EGFR Ab 1-2), after shield formation, and after protease-specific shield removal (activatable EGFR Ab 1-4).

Figure 11B:
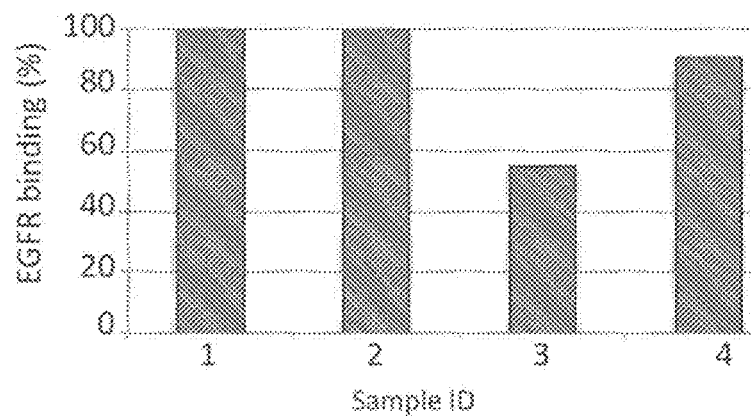
FIG. 11B shows a bar graph of SPR data illustrating EGFR binding of activatable EGFR Ab 1. The data demonstrates that steric shield formation on activatable EGFR Ab 1 substantially reduces its EGFR binding activity and removal of the steric shields from the activatable antibody restores its EGFR binding activity.

FIGS. 9A and 11B show bar graphs illustrating differences in binding activity of activatable EGFR Ab 2 and activatable EGFR Ab 1, respectively, to its target, EGFR, before and after shield moiety formation via transglutamination, and before and after in vitro release of the steric shield via cleavage of the tumor sensing releasable moiety by protease. The results demonstrate: 1) the presence of unconjugated polypeptide shield moieties at the N-termini of the anti-EGFR antibody did not hinder EGFR binding since the fraction of the fusion antibody bound to EGFR was similar to that of its parent antibody; (2) formation of the steric shield effectively blocked EGFR binding as steric shield formation by transglutamination under two different experimental conditions reduced the fraction of the activatable antibodies bound to EGFR compared to the parent antibody; and (3) following steric shield release by protease cleavage of the tumor-sensing releasable moiety SEQ ID NO: 19 (matriptase or uPA), EGFR binding was restored to levels similar to that of parent antibody.

Figure 12B:
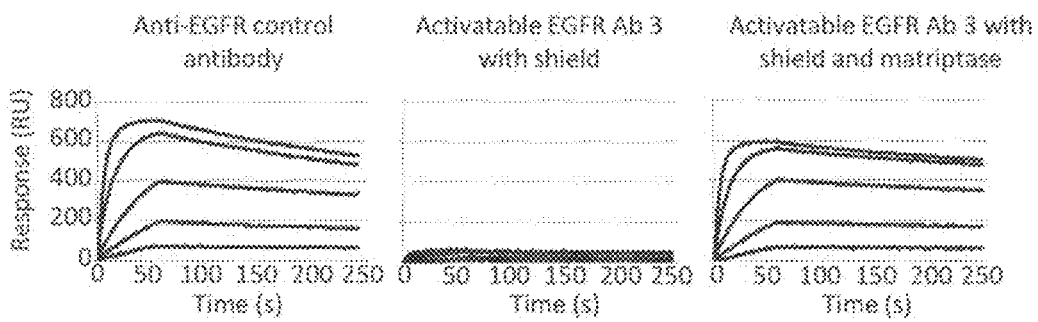
FIG. 12B shows SPR sensograms data illustrating EGFR binding of activatable EGFR Ab 3. The data demonstrates that steric shield formation on activatable EGFR Ab 3 substantially reduces its EGFR binding activity and that matriptase mediated shield release by cleavage of disease-sensing releasable moieties restores EGFR binding activity.
Figure 12C:
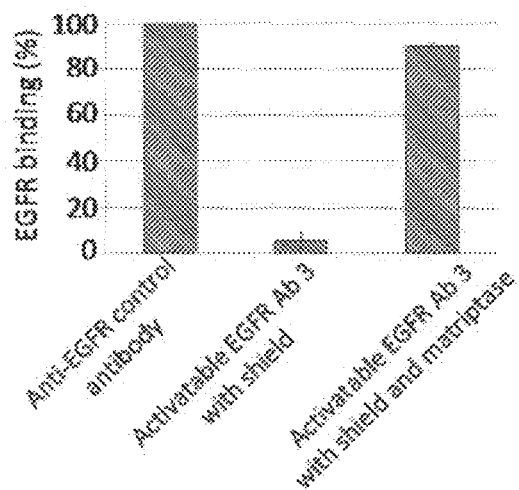
FIG. 12C shows a bar graph of SPR data illustrating EGFR binding of activatable EGFR Ab 3. The data demonstrates that steric shield formation on activatable EGFR Ab 3 substantially reduces its EGFR binding activity and that activation by matriptase mediated shield release by cleavage of disease-sensing releasable moieties restores EGFR binding activity.

FIG. 12B shows representative SPR sensograms of EGFR binding to parent anti-EGFR antibody and activatable EGFR Ab 3 with shield in place, and with shield removed by protease matriptase. FIGS. 9B and 12B show bar graphs illustrating differences in binding activities of activatable EGFR Ab 3 and 4 to the target, EGFR, before and after shield moiety formation via Cys-Cys disulfide bridge, and before and after in vitro release of the steric shield via cleavage of the tumor sensing releasable moiety by protease. The results demonstrate: (1) formation of the steric shield effectively blocked EGFR binding as steric shield formation via Cys-Cys disulfide conjugation under two different experimental conditions and for two different polypeptide shield moiety sequences reduced the fraction of the activatable antibodies bound to EGFR compared to the parent antibody; (2) following steric shield release by protease cleavage of the tumor-sensing releasable moieties (matriptase or uPA), EGFR binding was restored to levels similar to that of parent antibody.

Example 10. In Vitro Efficacy of Activatable EGFR Ab 2-4

The in vitro efficacy of activatable EGFR Ab 2, 3, and 4 was evaluated by cell proliferation assays. H292 human lung cancer cell line NCI-H292 (ATCC, USA) and human colon cancer cell line SW48 (ATCC, USA) were used because proliferation of H292 and SW48 cells is sensitive to EGFR inhibition. H292 and SW48 cells were maintained at 37° C. (5% $CO_2$) in RPMI-1640 medium (Gibco, USA) supplemented with 15% fetal bovine serum (FBS) (Hyclone, USA). For the proliferation assay of SW48 cell line, cells were seeded at 1680 cells per well in a 384-well plate under low serum conditions (RPMI containing 2% FBS). For the proliferation assay of H292 cell line, cell were seeded at 850 cells per well in a 384 well plate under low serum condition (RPMI containing 2% FBS). After 24 hrs, parent anti-EGFR antibody, activatable EGFR Ab 2, 3 and 4 with a shield in place, or matriptase-treated activatable EGFR Ab 2, 3 and 4 (activated activatable EGFR Ab) were each respectively added to the cancer cells at 2 fold serial dilutions. Cell viability was measured 96 hrs later using a CELLTITER-GLO™ kit (Promega) according to the manufacturer's instructions.

Figure 15A:
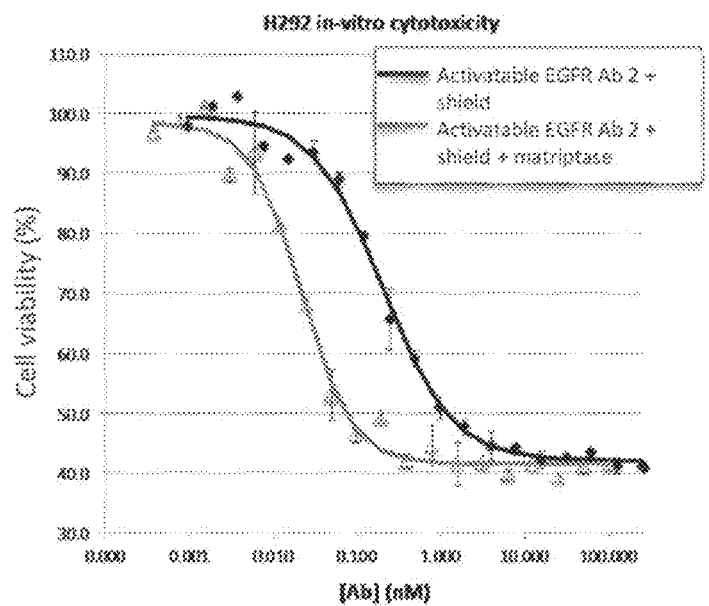
FIG. 15A shows in vitro cytotoxicity of activatable EGFR Ab 2 with shield or with shield released by protease matriptase against an EGFR-sensitive human lung carcinoma cell line H292. This data demonstrates that the presence of shield decreases binding of the activatable EGFR Ab 2 to EGFR on H292, and shield removal by matriptase increases binding to EGFR on H292.

FIG. 15A shows representative results of H292 cell proliferation in the presence of activatable EGFR Ab 2 carrying a steric shield and active activatable EGFR Ab 2 with shield released by matriptase cleavage of the disease-sensing moieties. The data shows that the anti-proliferation activity of activatable EGFR Ab 2 carrying a steric shield is reduced relative to that of activated activatable EGFR Ab 2, demonstrating the shielding effect. Error bars represent standard errors of the mean (SEM).

Figure 15B:
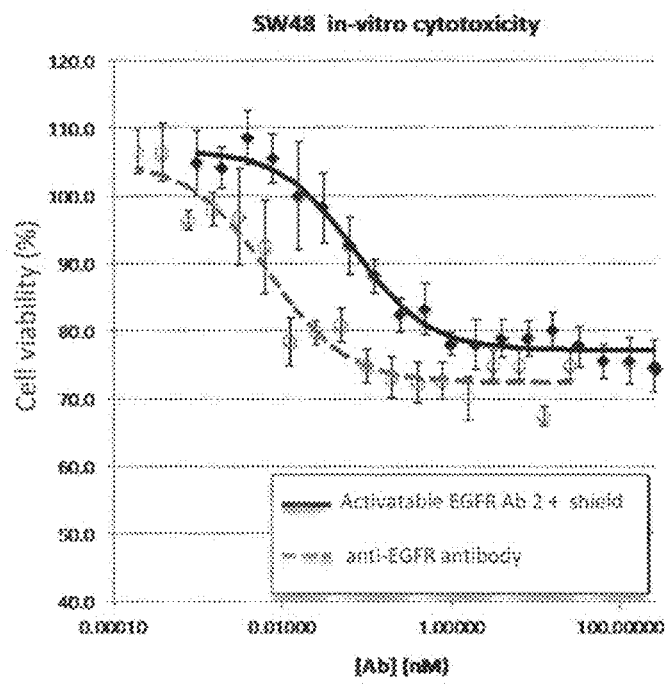
FIG. 15B shows in vitro cytotoxicity of activatable EGFR Ab 2 with shield or with shield released by protease matriptase against an EGFR-sensitive human colorectal adenocarcinoma cell line SW48. This data demonstrates that the presence of shield decreases binding of the activatable EGFR Ab 2 to EGFR on SW48, and shield removal by matriptase increases binding to EGFR on SW48.

FIG. 15B shows representative results of SW48 cell proliferation in the presence of activatable EGFR Ab 2 carrying a steric shield and EGFR Ab. The data shows that the anti-proliferation activity of activatable EGFR Ab 2 carrying a steric shield is reduced relative to that of the parent anti-EGFR antibody, demonstrating the shielding effect.

Figure 16A:
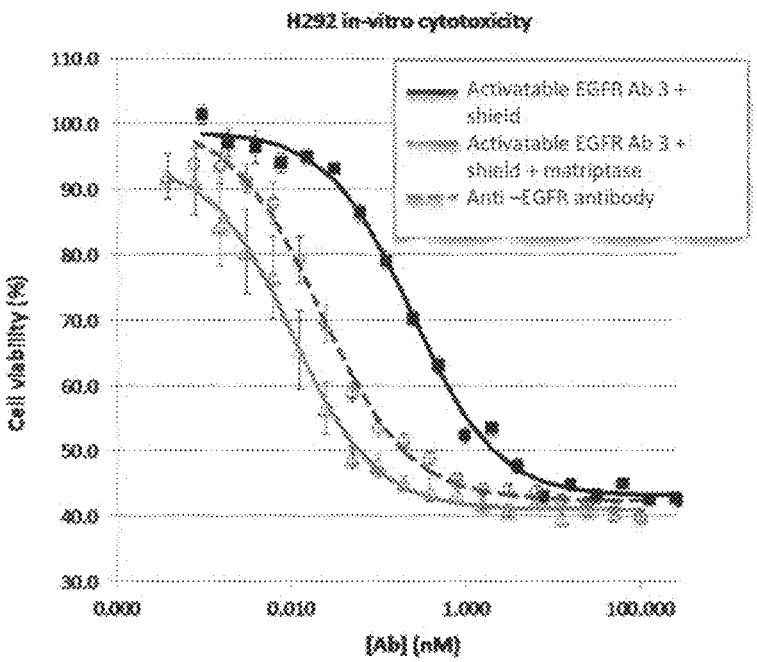
FIG. 16A shows in vitro cytotoxicity of activatable EGFR Ab 3 with shield or with shield released by protease matriptase, or parent anti-EGFR antibody against an EGFR-sensitive human lung carcinoma cell line H292.

FIG. 16A shows representative results of H292 cell proliferation in the presence of activatable EGFR Ab 3 carrying a steric shield, active activatable EGFR Ab 3 with shield released by matriptase cleavage of the disease-sensing moieties, and EGFR Ab. The data shows that the anti-proliferation activity of activatable EGFR Ab 3 carrying a steric shield is reduced relative to that of activated activatable EGFR Ab 3 and EGFR Ab, demonstrating the shielding effect. In addition, this data shows that the anti-proliferation activity of activatable EGFR Ab 3 with the tumor-sensing releasable moieties cleaved by matriptase is similar to that of the parent anti-EGFR antibody.

Figure 16B:
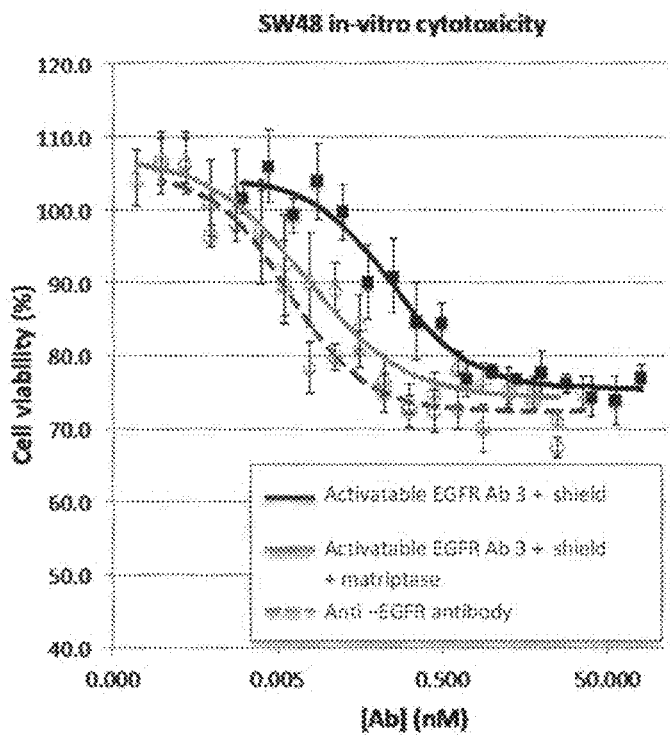
FIG. 16B shows in vitro cytotoxicity of activatable EGFR Ab 3 with shield or with shield released by protease matriptase, or parent anti-EGFR antibody against an EGFR-sensitive human colorectal adenocarcinoma cell line SW48.

FIG. 16B shows representative results of SW48 cell proliferation in the presence of activatable EGFR Ab 3 carrying a steric shield, active activatable EGFR Ab 3 with shield released by matriptase cleavage of the disease-sensing moieties, and parent anti-EGFR antibody. The data shows that the anti-proliferation activity of activatable EGFR Ab 3 carrying a steric shield is reduced relative to that of activated activatable EGFR Ab 3 and the parent antibody, demonstrating the shielding effect. In addition, this data shows that the anti-proliferation activity of activatable EGFR Ab 3 with the tumor-sensing releasable moieties cleaved by matriptase is nearly identical to that of the parent anti-EGFR antibody.

Figure 17A:
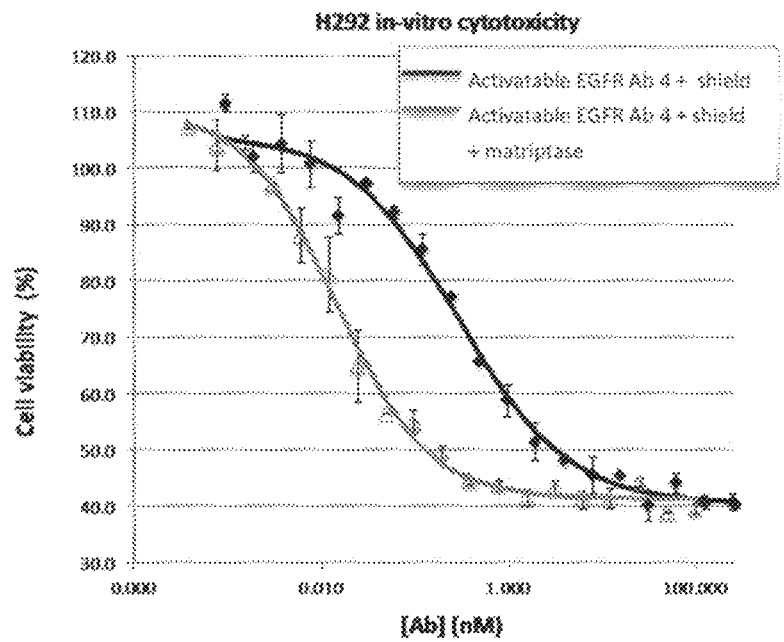
FIG. 17A shows in vitro cytotoxicity of activatable EGFR Ab 4 with shield or with shield released by protease matriptase against an EGFR-sensitive human lung carcinoma cell line H292.

FIG. 17A shows representative results of H292 cell proliferation in the presence of activatable EGFR Ab 4 carrying a steric shield and active activatable EGFR Ab 4 with shield released by matriptase cleavage of the disease-sensing moieties. The data shows that the anti-proliferation activity of activatable EGFR Ab 4 carrying a steric shield is reduced relative to that of activated activatable EGFR Ab 4, demonstrating the shielding effect.

Figure 17B:
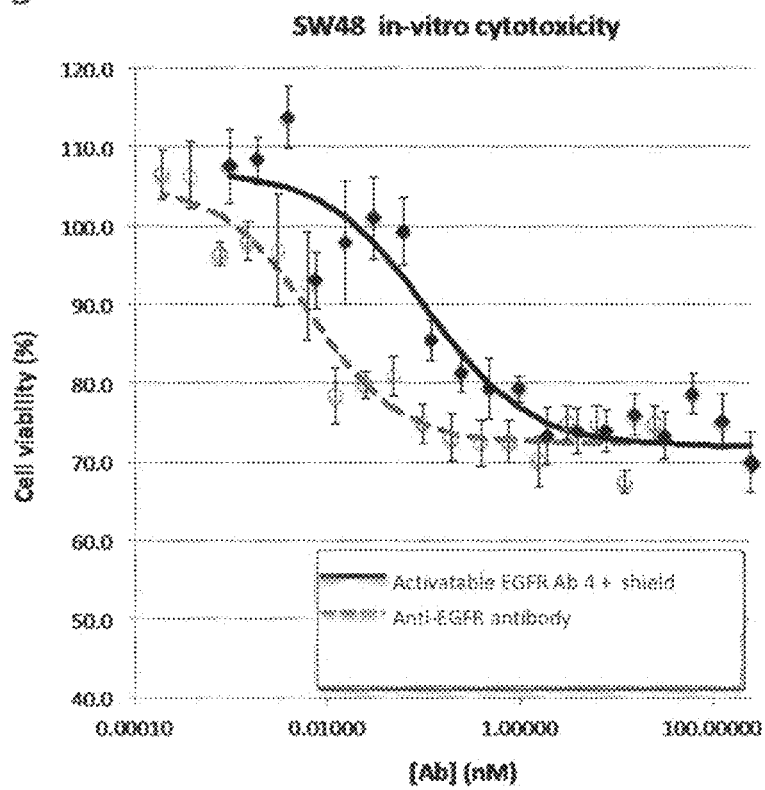
FIG. 17B shows in vitro cytotoxicity of activatable EGFR Ab 4 with shield or parent anti-EGFR antibody against an EGFR-sensitive human colorectal adenocarcinoma cell line SW48.

FIG. 17B shows representative results of SW48 cell proliferation in the presence of activatable EGFR Ab 4 carrying a steric shield and parent anti-EGFR antibody. The data shows that the anti-proliferation activity of activatable EGFR Ab 4 carrying a steric shield is reduced relative to that of the parent antibody, demonstrating the shielding effect.

The data in FIGS. 15A-17B suggests that activatable EGFR Ab 2-4 carrying a steric shield would have improved safety profile compared to the parent anti-EGFR antibody. At the same time, activatable EGFR Ab 2-4 would have comparable efficacy as the parent antibody after release of the steric shield mediated by cleavage of the disease-sensing releasable moieties (such as in the tumor environment).

Example 11. In Vivo Efficacy of an Exemplary Activatable Anti-EGFR Antibody

The in vivo efficacy of activatable EGFR Ab 2 is assessed in a human H292 lung xenograft model in nude mice. H292 xenografts are established by subcutaneous injection of $5\times10^6$ (NCI-H292) cells mixed 1:1 in MATRIGEL® into the left flank of each mouse. Tumor cells are allowed to reach 200 to 400 mm$^3$ for the study before randomization into three treatment groups, with 10 mice per group. Parent anti-EGFR antibody, activatable EGFR Ab 2 with an intact steric shield (i.e., treated with transglutaminase), or matriptase-treated activatable EGFR Ab 2 (i.e. steric shield released) is injected subcutaneously into the animals weekly at 25 mg/kg. Animals are sacrificed once the tumor volume reached 2000 mm$^3$ or at the end of the study (21 days).

At the 25 mg/kg dose, activatable EGFR Ab 2 and the parent anti-EGFR antibody show comparable efficacy at suppressing tumor growth in the H292 model. This data shows that activatable EGFR Ab with intact steric shield can be activated in the tumor environment and achieve comparable efficacy to the parent anti-EGFR antibody.

Example 12. Exemplary Activatable Anti-HER-2 Fab and Activatable Anti-Mouse CTLA-4 Fab Constructs with Polypeptide Shield Moieties Exemplary anti-mouse CTLA-4 activatable Fabs (referred herein as "activatable mCTLA-4 Fab") and an exemplary anti-HER-2 activatable Fab (referred herein as "activatable hHER-2 Fab") were prepared. The corresponding heavy chain and light chain sequences of the activatable hHER-2 Fab and activatable mCTLA-4 Fab (and the corresponding fusion Fabs) are shown in Table 11. Sequences corresponding to the polypeptide shield moieties S1 and S2 are underlined. The parent anti-HER-2 antibody comprises a VH comprising the amino acid sequence of SEQ ID NO: 234 and a VL comprising the amino acid sequence of SEQ ID NO: 235. The parent anti-mouse CTLA-4 antibody comprises a VH comprising the amino acid sequence of SEQ ID NO: 238 and a VL comprising the amino acid sequence of SEQ ID NO: 239.

Design of Activatable Fabs

In order to illustrate that the same shield moieties can form shield on antigen binding sites specific for different antigens, activatable hHER-2 Fab was designed to carry S1 and S2 shield moieties with the same sequences as the S1 and S2 shield moieties on anti-EGFR activatable EGFR Ab 2 (SEQ ID NOs: 142 and 143). The activatable hHER-2 Fab was designed such that the sequence of disease sensing moieties in the shield moieties S1 and S2 are the same, LSGRSDNH (SEQ ID NO: 19), which is substrate(s) of the same protease(s). Thus, in the presence of a specific protease, steric shields can be released from both the S1 and S2 disease sensing moieties. Anti-mouse CTLA-4 activatable mCTLA-4 Fab was designed to carry a S2 shield moiety (SEQ ID NO: 143) with the same sequence as S2 moiety on activatable EGFR Ab 2 and activatable hHER-2 Fab, and an S1 shield moiety (SEQ ID NO: 227) with the same association moiety, same number of amino acids, but different disease-sensing moiety compared to the S2 shield moiety on activatable EGFR Ab 2 and on activatable hHER-2 Fab. The activatable mCTLA-4 Fab was designed such that sequences of the disease sensing moieties in shield moieties S11 and S2 are different, PLGLAG (SEQ ID NO: 172) and LSGRSDNH (SEQ ID NO: 19). In this case, the presence of protease(s) specific for only one disease-sensing moiety (e.g., S1-specific) can release the steric shield by cleavage of only one disease-sensing moiety (e.g., S1 disease sensing moiety or S2 disease sensing moiety).

Steric Shield Generation by Transglutaminase-Catalyzed Conjugation

Steric shields were formed on the activatable hHER-2 Fab, and the activatable mCTLA-4 Fab by treating the corresponding fusion antibodies with a transglutaminase under different reaction conditions. The following reaction parameters were used: transglutaminase (Ajinomoto, Japan) concentration range (0.5, 0.75, 2.0% wt/v), fusion antibody concentration range (0.05, 0.5 and 6 mg/ml), NaCl concentration 150, pH 7.4 and 8.5 and temperature of reaction (20, 37° C.) for 12 hr. Efficiency of transglutaminase-catalyzed steric shield formation was analyzed using reduced 4-12% Tris-Glycine SDS-PAGE gels (ThermoFisher, USA).

Figure 13A:
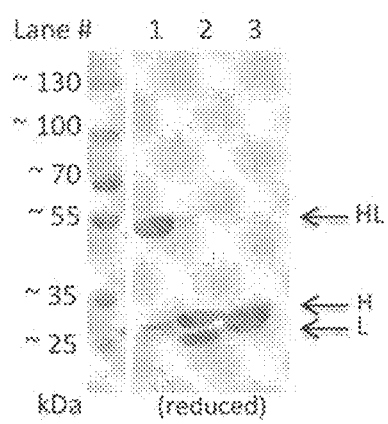
FIG. 13A shows an SDS-PAGE gel demonstrating trans-glutaminase-mediated steric shield formation in an exemplary activatable Fab (activatable hHER-2 Fab) and shield release by cleavage of disease-sensing releasable moieties by protease matriptase. Activatable hHER-2 Fab samples shown here were used for SPR studies shown in FIGS. 13B-13D.
Figure 14A:
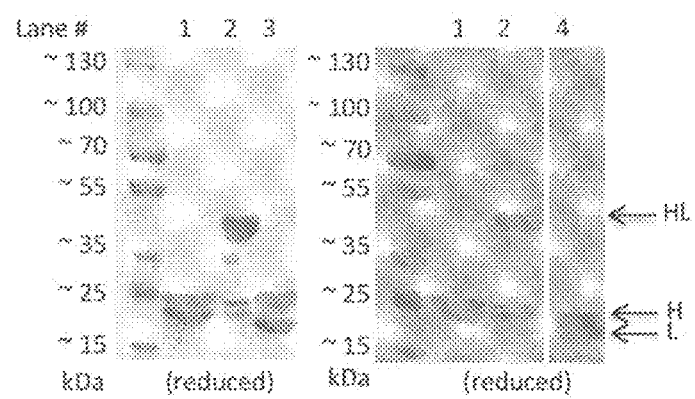
FIG. 14A shows an SDS-PAGE gel demonstrating trans-glutaminase-mediated steric shield formation in an exemplary activatable Fab (activatable mCTLA-4 Fab) and shield release by cleavage of disease-sensing releasable moieties by proteases matriptase and MMP9. Activatable mCTLA-4 Fab samples shown here were used for SPR studies shown in FIGS. 14B-14D.

FIGS. 13A and 14A show representative results of a subset of tested conditions for activatable hHER-2 Fab and activatable mCTLA-4 Fab, respectively. Both activatable hHER-2 Fab and activatable mCTLA-4 Fab were designed with a C-terminal His-tag, which allowed separation of the product from transglutaminase using Ni-NTA affinity chromatography after the reaction was complete. After elution with 300 mM imidazole, activatable hHER-2 Fab and activatable mCTLA-4 Fab were buffer-exchanged into PBS pH 7.4 buffer. Various samples were run on a 4-12% SDS-PAGE gel in the presence of a reducing agent (TCEP) so that heavy chains (marked by letter H) and light chains (marked by letter L) in conventional Fabs would run as separate bands, both around 25 kDa. However, activatable antibodies having conjugated steric shield would yield a band corresponding to the conjugated heavy chain and light chain Fab species at about ~50 kDa. Notably, in the presence of a transglutaminase, the heavy chain and light chain in the activatable Fab constructs were conjugated, and thus ran as the 50 kDa species (marked as H+L). Thus, this data clearly demonstrates that the polypeptide shield moieties fused to the N-termini of the heavy chain and light chain of activatable hHER-2 Fab and activatable mCTLA-4 Fab were conjugated by the transglutaminase, thereby providing a complete shield.

In Vitro Removal of Transglutaminase-Conjugated Steric Shield by Protease Cleavage In order to determine whether the activatable hHER-2 Fab and activatable mCTLA-4 Fab could be activated specifically in tumor tissues, in vitro experiments were performed using proteases matriptase and MMP9, which are up-regulated in cancers.

After steric shield formation, for in vitro shield removal, activatable hHER-2 Fab and activatable mCTLA-4 Fab with shield moiety in place were incubated with matriptase at a protease:antibody ratio of 1:100 (mole:mole) in 50 mM Tris pH 8.5, 0.01° % Tween-20 buffer for 18 hrs at 37° C. In addition, in a separate reaction, activatable mCTLA-4 Fab with shield moiety in place was incubated with MMP9 protease in PBS, pH 7.4 with 10 mM $CaCl_2$. Effects of matriptase or MMP9-specific digestion were evaluated by running samples on reducing 4-12% Tris-Glycine SDS-PAGE gels (ThermoFisher) in the presence of the reducing agent TCEP, so that heavy (marked by letter H) and light (marked by letter L) chains would run as separate bands ~25 kDa respectively, unless conjugated (marked as H+L, ~50 kDa species).

Results are shown in FIGS. 13A (activatable hHER-2 Fab) and 14A (activatable mCTLA-4 Fab). The steric shield was first formed by incubation with a transglutaminase in separate reactions (sample lane indicated in the figure legend), followed by removal of the steric shields by cleavage of the tumor-sensing releasable moiety (SEQ ID NO: 19) by matriptase, and tumor shield moiety (SEQ ID NO: 172) by MMP9 (respective sample lanes are indicated in the figure legend). Also shown are control samples in which the activatable Fabs were not subject to the transglutaminase treatment, and thus a steric shield was never formed prior to matriptase or MMP9 treatment. As a result, the heavy (H) and light (L) chains ran as separate bands (~25 kDa). Notably, in the presence of matriptase or MMP9, the fraction of conjugated heavy and light chains Fab (H+L; ~50 kDa band) decreased, while the fraction of heavy (H) and light (L) chains that ran as separate bands (~25 kDa) increased. Thus, this data demonstrates that the transglutaminase-conjugated steric shield on activatable hHER-2 Fab and activatable mCTLA-4 Fab can be removed via cleavage of the disease-sensing releasable moieties by a disease-specific protease.

Antigen Binding to Activatable Antigen Binding Fragment (Fab)

Binding of human HER-2 to activatable hHER-2 Fab and mouse CTLA-4 to activatable mCTLA-4 Fab before shield formation (i.e., conjugation of S1 and S2), after shield formation, and after protease-specific shield removal was assessed using a PROTEON™ XPR36 Surface Plasmon Resonance (SPR) Instrument (BioRad). Antigens, recombinant human HER-2-Fc (R&D Systems, USA) and recombinant mouse CTLA-4-Fc (R&D Systems. USA) were respectively attached to chips via Protein G, and binding of respective anti-HER-2 and anti-mouse CTLA-4 activatable Fabs was measured. Phosphate buffered saline (PBS, pH 7.4) supplemented with 0.01% Tween-20 was used as the running buffer.

Figure 13B:
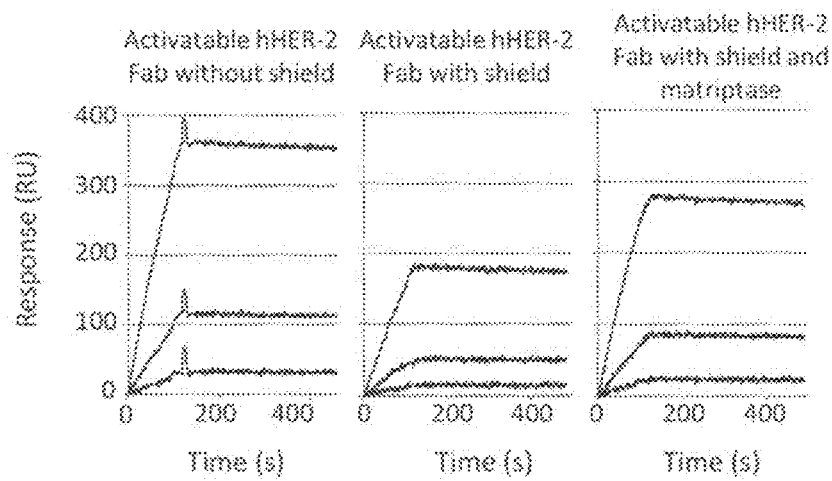
FIG. 13B shows SPR sensograms illustrating HER-2 binding of an activatable hHER-2 Fab. The data demonstrates that steric shield formation on activatable hHER-2 Fab substantially reduces its HER-2 binding activity and that activation by matriptase mediated shield release by cleavage of disease-sensing releasable moieties restores HER-2 binding activity.
Figure 14B:
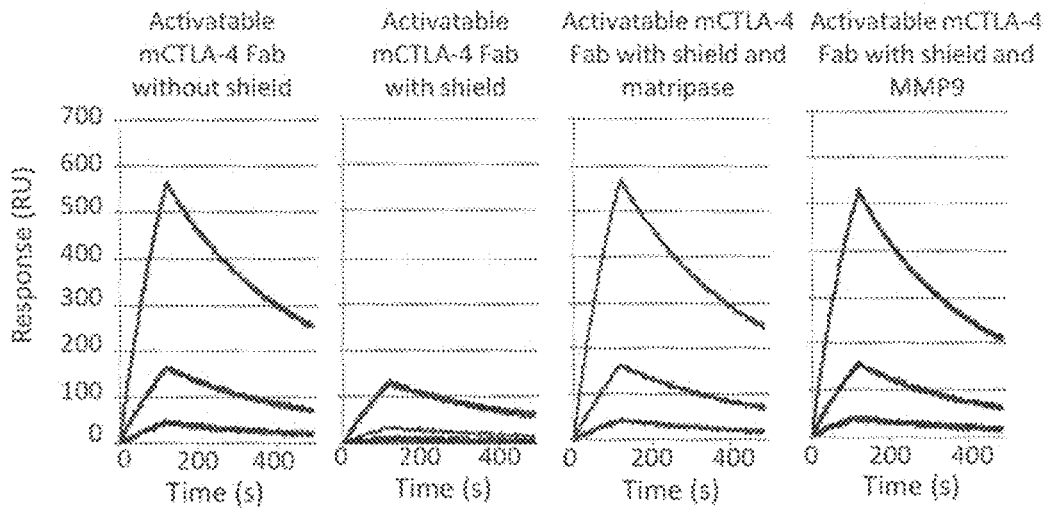
FIG. 14B shows SPR sensograms illustrating binding to mouse CTLA-4 of activatable mCTLA-4 Fab. The data demonstrates that steric shield formation on activatable mCTLA-4 Fab substantially reduces its CTAL4 binding activity and that matriptase mediated shield release by cleavage of disease-sensing releasable moieties restores mouse CTLA-4 binding.
Figure 14C:
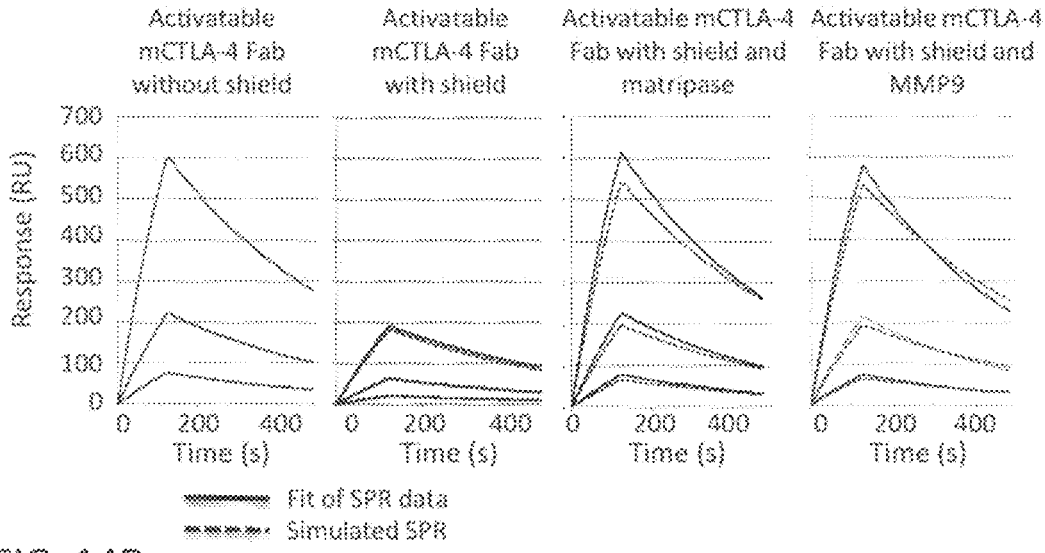
FIG. 14C shows SPR sensograms shown in FIG. 14B fitted against simulated sensograms based on fractions of active Fab (Fab without shield) and inactive Fab (Fab with shield) present in the SPR experiment. Simulated sensograms demonstrate that decrease in mouse CTLA-4 binding observed in the SPR sensograms of activatable mCTLA-4 Fab with shield can be attributed to the inactive activatable mCTLA-4 Fab (Fab with shield).
Figure 14D:
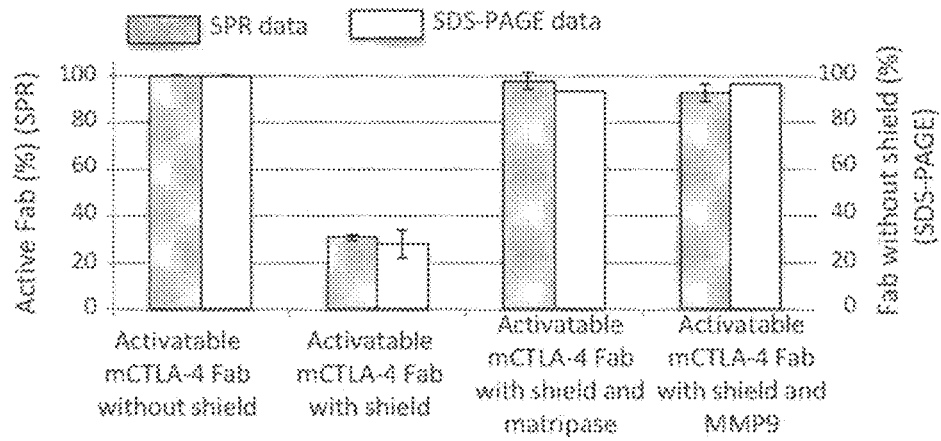
FIG. 14D shows a bar graph illustrating comparison between the fractions of active activatable mCTLA-4 Fab that binds mouse CTLA-4 (estimated from the simulated sensograms of FIG. 14C) and the fractions of Fab without shield (estimated from SDS-PAGE gel data in FIG. 14A). This data demonstrates a positive correlation between the fraction of activatable mCTLA-4 Fab without shield and the fraction of active activatable mCTLA-4 Fab that binds mouse CTLA-4.

FIG. 13B shows representative sensograms of activatable hHER-2 Fab without shield, with shield, and with shield removed when binding to its antigen, human HER-2. FIG. 14B shows representative sensograms of activatable mCTLA-4 Fab without shield, with shield, and with shield removed when binding to its antigen, mouse CTLA-4. The data demonstrates that the presence of the steric shield on activatable hHER-2 Fab and activatable mCTLA-4 Fab suppresses binding to their targets, i.e., HER-2 and CTLA-4 respectively; removal of the steric shield by cleavage of the tumor-sensing releasable moiety SEQ ID NO: 19 (a matriptase substrate) or SEQ ID NO: 172 (an MMP2/9 substrate) recovers antigen binding efficiency.

Figure 13C:
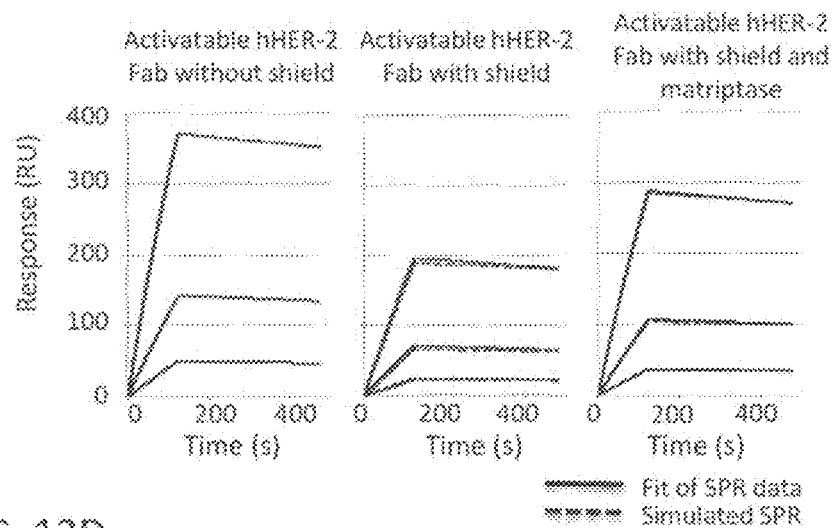
FIG. 13C shows SPR sensograms shown in FIG. 13B fitted against simulated sensograms based on fractions of active Fab (Fab without shield) and inactive Fab (Fab with shield) present in the SPR experiment. Simulated sensograms demonstrate that decrease in HER-2 binding observed in the SPR sensograms of the activatable hHER-2 Fab with shield can be attributed to the inactive activatable hHER-2 Fab (Fab with shield).

In order to estimate the fraction of the Fab population with shield in place in the binding experiments, we simulated SPR curves with different inactive fractions utilizing the experimentally determined parameters ($k_a$, $k_d$, $R_{max}$) and determined the best fit across the concentration range. In this analysis, activatable Fab without shield is assumed to bind at 100% with the same binding kinetics, while Fab with shield does not bind to the target. Representative experimental sensograms are shown in FIGS. 13B and 14B. Simulated sensograms (dashed lines) overlaid on experimental SPR fits (black lines) are shown in FIGS. 13C (activatable hHER-2 Fab) and 14C (activatable mCTLA-4 Fab).

Figure 13D:
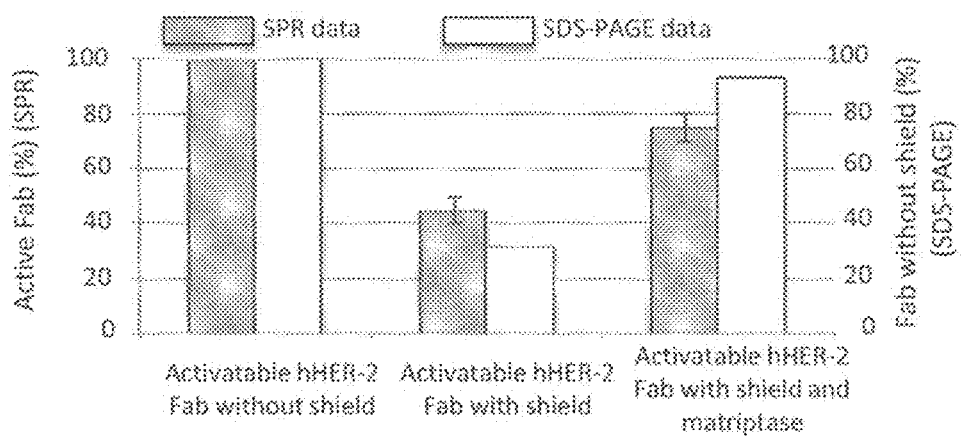
FIG. 13D shows a bar graph illustrating comparison between fractions of active activatable hHER-2 Fab (estimated from simulated sensograms of FIG. 13C) and fractions of activatable hHER-2 Fab without shield in place (estimated from the SDS-PAGE gel data of FIG. 13A). This data demonstrates a positive correlation between the fraction of activatable hHER-2 Fab without shield and the fraction of active hHER-2 Fab that binds HER-2.

Results showing fractions of active (i.e. without shield) Fab species before shield formation, after shield formation, and after shield removal by proteases are shown as bar graphs in FIGS. 13D (activatable hHER-2 Fab) and 14D (activatable mCTLA-4 Fab). The gray bars are based on SPR data, and the white bars are based on integration of pixels of corresponding bands on SDS-PAGE gels (Image J software). Error bars are standard deviations from two to three data sets.

The results demonstrate: (1) formation of the steric shield effectively blocked antigen binding as steric shield formation by transglutamination of shield peptides in two different activatable Fabs, activatable hHER-2 Fab and activatable mCTLA-4 Fab, reduced the fraction of the activatable Fabs bound to their respective antigens; (2) the fractions of activatable hHER-2 Fab and activatable mCTLA-4 Fab carrying a shield (as estimated from analysis of SDS-PAGE gels) and the fractions of activatable hHER-2 Fab and activatable mCTLA-4 Fab that were not able to bind to their respective antigens (i.e., inactive species in the SPR experiments) are similar and positively correlated, which suggests that the presence of the shield prevents antigen binding; (3) following steric shield release by protease cleavage of the tumor-sensing releasable moieties (matriptase or MMP9), respective antigen binding was restored to levels similar to that of an activatable Fab with unconjugated polypeptide shield moieties; (4) S1 and S2 steric shield moieties having the same sequence and/or length can be conjugated to form a shield on activatable antigen binding domains specific for different antigens (e.g., HER-2, CTLA-4 and EGFR); (5) release of the conjugated shield moiety by cleavage of one but not both tumor-sensing moieties (i.e., matriptase or MMP9-mediated shield release on activatable mCTLA-4 Fab), does not hinder antigen binding.

What is claimed is:

1. An activatable antibody comprising an antigen-binding domain (ABD), wherein the ABD comprises a heavy chain variable region (VH) and a light chain variable region (VL), wherein the N-terminus of the VH is fused to a first polypeptide shield moiety (S1), and the N-terminus of the VL is fused to a second polypeptide shield moiety (S2), wherein each of S1 and S2 is a polypeptide no more than about 50 amino acids long,
  wherein association of S1 with S2 blocks binding of the ABD to its target,
  wherein the ABD does not specifically bind to S1, S2, or association thereof,
  wherein S1 comprises a first association moiety (B), and S2 comprises a second association moiety (C), wherein B and C are conjugated to each other by an isopeptide bond, and wherein S1 comprises the amino acid sequence of any one of SEQ ID NOs: 140, 142 and 227, and wherein S2 comprises the amino acid sequence of any one of SEQ ID NOs: 141 and 143; or wherein S1 comprises the amino acid sequence of any one of SEQ ID NOs: 141 and 143, and wherein S2 comprises the amino acid sequence of any one of SEQ ID NOs: 140, 142 and 227.

2. The activatable antibody of claim 1, wherein B and C are conjugated to each other by a transglutaminase.

3. The activatable antibody of claim 1, wherein the antibody is a bispecific antibody.

4. The activatable antibody of claim 1, wherein the antibody is a Fab, a (Fab)2, an Fv, or a full-length antibody.

5. The activatable antibody of claim 1, wherein the antibody is an antibody-drug conjugate (ADC).

6. The activatable antibody of claim 1, wherein the ABD specifically binds to EGFR, CTLA-4, PD-1, CD-71, PD-L1, HER2, CD3, a-4 integrin, a-V integrin, a-4-b-1 integrin, a-4-b-7 integrin, AGR2, Anti-Lewis_Y, Apelin J receptor, APRIL, B7-H3, B7-H4, BCMA, BTLA, C5 complement, C-242, CA9, CA19-9, Carbonic anhydrase 9, CD2, CD3, CD6, CD9, CD11a, CD19, CD20, IL27, IL27R, IL29, IL31, IL31R, Insulin Receptor, Jagged-1, Jagged-2, KIR, LAG-3, LIF-R, Lewis X, LIGHT, LRP4, LRRC26, CD22, CD24, CD25, CD27, CD28, CD30, CD40, CD40L, CD41, CD44, CD44v6, CD47, CD51, CD52, CD56, CD64, CD70, CD71, CD74, CD80, CD81, CD86, CD95, CD117, MCSP, Mesothelin, MRP4, MUC1, Mucin-16, Na/K ATPase, Neutrophil elastase, NGF, Nicastrin, NOTCH1, NOTCH2, NOTCH3, NOTCH4, NOV, OSM-R, CD125, CD132, CD133, CD137, CD138, CD166, CD172A, CD248, CDH6, CEACM5, CEACAM6, CLAUDIN-3, CLAUDIN-4, cMet, Collagen, Cripto, CSFR, CSFR-1, CTLA-4, CTFG, CXCL10, CXCL13, CXCR1, CXCR2, OX-40L, OX-40R, PAR2, PDGF-AA, PDGF-BB, PDGFRa, PDGFRb, PD-1, PD-L1, PD-L2, Phospahtidyl-serine, P1GF, PSCA, PSMA, RAAG12, CXCR4, CYR61, DL44, DLK1, DLL4, DPP-4, DSG1, EGFR, EGFRVIII, Endothelin b receptor (ETBR), ENPP3, EPCAM, EPHA2, EPHB2, ERBB3, F protein of RSV, FAP, FGF-2, FGF-8, FGFR-1, FGFR-2, FGFR-3, FGFR-4, Folate receptor, RAGE, SLC44A4, TNFa, STEAP1, STEAP2, TAG-72, TAPA1, TGFb, TIGIT, TIM3, TLR2, TLR4, TLR6, TLR7, TLR8, GAL3STI, G-CSF, G-CSFR, GD2, GITR, GLUT1, GLUT4, GM-CSF, GM-CSFR, GPIIb/IIIa receptor, Gp130, GPNIVIB, GRP78, HER-2/neu, HGF, hGH, HVEM, Hyaluronidase, ICOS, INFa, INFb, INFg, IgE, TLR9, TMEM31, Sphingosine 1, Phosphate, TNFR, TNFRS12A, TRAIL-R1, TRAIL-R2, Transferrin, Transferrin Receptor, TRK-A, TRK B, uPAR, VCAM-1, VEGF, VEGF-A, IgE Receptor, IGF, IGF1R, IL1B, IL1R, IL2, IL2R, IL4, IL4R, IL6, IL6R, IL11, IL12, IL12p40, IL12R, IL12Rbl, IL13, IL13R, IL15, IL17, IL18, IL21, IL23, IL23R, VEGF-B, VEGF-C, VEGF-D, VEGFR1, VEGFR2, VEGFR3, VISTA, WISP-1, WISP-2, or WISP-3.

7. A pharmaceutical composition comprising the activatable antibody of claim 1 and a pharmaceutically acceptable carrier.

8. The activatable antibody of claim 1, wherein S1 and/or S2 further comprises a glycosylation peptide sequence.

9. The activatable antibody of claim 8, wherein the glycosylation peptide sequence comprises the amino acid sequence of SEQ ID NO: 18.

* * * * *